(12) United States Patent
Roth et al.

(10) Patent No.: US 9,340,510 B2
(45) Date of Patent: May 17, 2016

(54) TETRAHYDROISOQUINOLINE DERIVATIVES, PHARMACEUTICAL COMPOSITIONS AND USES THEREOF

(71) Applicant: Boehringer Ingelheim International GmbH, Ingelheim am Rhein (DE)

(72) Inventors: Gerald Juergen Roth, Biberach an der Riss (DE); Martin Fleck, Warthausen (DE); Peter Wilhelm Haebel, Mittelbiberach (DE); Annekatrin Heimann, Biberach an der Riss (DE); Niklas Heine, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/855,668

(22) Filed: Sep. 16, 2015

(65) Prior Publication Data
US 2016/0075657 A1 Mar. 17, 2016

(30) Foreign Application Priority Data
Sep. 17, 2014 (EP) ..................... 14185224

(51) Int. Cl.
*C07D 217/18* (2006.01)
*C07D 417/12* (2006.01)
*A61K 31/47* (2006.01)

(52) U.S. Cl.
CPC ............ *C07D 217/18* (2013.01); *C07D 417/12* (2013.01)

(58) Field of Classification Search
None
See application file for complete search history.

(56) References Cited

FOREIGN PATENT DOCUMENTS

| WO | 0068202 A1 | 11/2000 |
|----|------------|---------|
| WO | 2006058628 A2 | 6/2006 |
| WO | 2010127212 A1 | 11/2010 |

OTHER PUBLICATIONS

International Search Report and Written Opinion for corresponding application, PCT/EP2015/070741, date of mailing Oct. 22, 2105.

*Primary Examiner* — Zinna Northington Davis
(74) *Attorney, Agent, or Firm* — Michael P. Morris; Alan R. Stempel

(57) ABSTRACT

The invention relates to new pyrrolidine derivatives of the formula

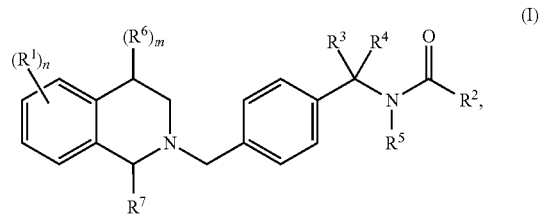

wherein $R^1$ to $R^6$, n and m are as defined in the description and claims, to their use as medicaments, to methods for their therapeutic use and to pharmaceutical compositions containing them.

11 Claims, No Drawings

TETRAHYDROISOQUINOLINE DERIVATIVES, PHARMACEUTICAL COMPOSITIONS AND USES THEREOF

FIELD OF THE INVENTION

This invention relates to new compounds, in particular tetrahydroisoquinoline derivatives, to processes for preparing such compounds, to their use as inhibitors of acetyl-CoA carboxylase(s), to methods for their therapeutic use, in particular in diseases and conditions mediated by the inhibition of acetyl-CoA carboxylase(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairment of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in Japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers, Diabetes 2011; 60:306-14; P Ebeling, B Essen-Gustaysson, J A Tuominen and V A Koivisto, Diabetologia, 41: 111-115; K J Nadeau, J G Regensteiner, T A Bauer, M S Brown, J L Dorosz, A Hull, P Zeitler, B Draznin, J E B. Reusch, J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao, Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao, Front Biosci 2010; 2:515-26).

Furthermore in central nervous system disorders including but not limited to Alzheimer's disease, Parkinson disease and epilepsy, impairments in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (ST Henderson, Neurotherapeutics 2008, 5:470-480; L C Costantini, L J Barr, J L Vogel, S T Henderson BMC Neurosci. 2008, 9 Suppl 2:S16; K W Barañano, A L Hartman, Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson, BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft, Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson, BMC Neurosci. 2008, 9 Suppl 2:S16; K W Barañano, A L Hartman, Curr Treat Options Neurol. 2008; 10:410-9).

Furthermore, the potential of ACC inhibitors as antifungal agents and as antibacterial agents is well documented (L Tong, H J Harwood Jr., Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (J Munger, B D Bennett, A Parikh, X J Feng, J McArdle, H A Rabitz, T Shenk, J D Rabinowitz, *Nat Biotechnol.* 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

Aim of the Present Invention

The aim of the present invention is to provide new compounds, in particular new tetrahydroisoquinoline derivatives, which are active with regard to acetyl-CoA carboxylase(s).

Another aim of the present invention is to provide new compounds, in particular new tetrahydroisoquinoline derivatives, which are active with regard to ACC2.

A further aim of the present invention is to provide new compounds, in particular new tetrahydroisoquinoline derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new tetrahydroisoquinoline derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of various diseases, for example of obesity, diabetes, cancer, viral infections, Parkinson's disease, Alzheimer's disease, hypoxia, ischemia, amyotrophic lateral sclerosis and/or glioma.

Another aim of the present invention is to provide effective ACC inhibitors for the treatment of metabolic disorders such as obesity and diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular tetrahydroisoquinoline derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

In a first aspect the present invention provides a compound of general formula

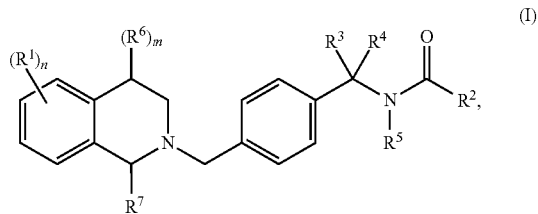

wherein
$R^1$ is selected from the group $R^1$-G1 consisting of:
  halogen, CN, OH, $C_{1-6}$-alkyl, $C_{3-7}$-cycloalkyl, —($C_{1-3}$-alkyl)-($C_{3-7}$-cycloalkyl), —O—($C_{1-6}$-alkyl), —O—($C_{3-7}$-cycloalkyl), —O—($C_{1-3}$-alkyl)-($C_{3-7}$-cycloalkyl), —O-phenyl, —O—($C_{1-3}$-alkyl)-phenyl, —COOH, —COO($C_{1-4}$-alkyl), —CO—NH—($C_{1-3}$-alkyl)-phenyl, —CO—NH—($C_{1-6}$-alkyl), —NH—($C_{1-6}$-alkyl), —NH—($C_{3-7}$-cycloalkyl), —NH—[($C_{1-3}$-alkyl)-($C_{3-7}$-cycloalkyl)] and NH—($C_{1-3}$-alkyl)-phenyl,
  wherein each alkyl and cycloalkyl is optionally substituted with one or more substituents selected from F and $CF_3$; and
  wherein the hydrogen atom in each NH group is optionally replaced with $C_{1-6}$-alkyl;
or, if two $R^1$-groups are attached to adjacent carbon atoms of the phenyl moiety of the tetrahydroisoquinolinyl group, they may be linked with each other and together form a $C_{3-5}$-alkylene bridging group in which 1 or 2 —$CH_2$-groups may independently of each other be replaced by —O—, —C(=O)—, —S—, —S(=O)—, —S(=O)$_2$—, —NH— or —N($C_{1-4}$-alkyl)-;
n is 0, 1, 2 or 3;
$R^2$ is selected from the group $R^2$-G1 consisting of: H, $C_{1-6}$-alkyl, $C_{3-7}$-cycloalkyl, $NH_2$, —NH—($C_{1-6}$-alkyl), —N($C_{1-6}$-alkyl)$_2$, —O—($C_{1-6}$-alkyl), heterocyclyl, 5-membered heteroaryl containing 1 or 2 heteroatoms selected from O, S, N and NH, 6-membered heteroaryl containing one or two nitrogen atoms, and —($C_{1-3}$-alkyl)-(6-membered heteroaryl containing one or two nitrogen atoms);
  wherein each alkyl group is optionally substituted with one or more substituents selected from F, CN, CO—$NH_2$, CO—NH($C_{1-3}$-alkyl), CO—N($C_{1-3}$-alkyl)$_2$, $NH_2$ and OH, wherein each cycloalkyl group is optionally substituted with one or more substituents selected from F, CN, OH, —NH—COO($C_{1-6}$-alkyl), $C_{1-3}$-alkyl and $CF_3$, wherein each heteroaryl group is optionally substituted with one or more substituents selected from F, Cl, $C_{1-3}$-alkyl, $NH_2$ and —NH—CO)—($C_{1-3}$-alkyl), and wherein the heterocyclyl group is selected from a group consisting of 2-oxo-pyrrolidinyl, 2-oxo-dihydrofuranyl and morpholinyl;

$R^3$ is selected from the group $R^3$-G1 consisting of: H and $C_{1-4}$-alkyl;

$R^4$ is selected from the group $R^4$-G1 consisting of: H and $C_{1-4}$-alkyl;

$R^5$ is selected from the group $R^5$-G1 consisting of: H and $C_{1-3}$-alkyl;

$R^6$ is selected from the group $R^6$-G1 consisting of: F, OH, and —O—($C_{1-4}$-alkyl);

or, if m is 2, both $R^6$ groups together with the carbon atom, to which they are attached, may form a carbonyl group; and $R^7$ is selected from the group $R^7$-G1 consisting of: H, $C_{1-4}$-alkyl, —COOH and —COO($C_{1-4}$-alkyl), and m is 0, 1 or 2;

wherein each of the above-mentioned alkyl and —O-alkyl groups may be substituted by one or more F;

a tautomer or stereoisomers thereof, or a salt thereof, or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for use in a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$, $R^3$, $R^4$, $R^5$, $R^6$, $R^7$, m and n, are defined as above and hereinafter. If residues, substituents or groups occur several times in a compound, as for example $R^1$ and $R^6$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore and hereinafter.

$R^1$-G2:

In another embodiment the group $R^1$ is independently of one another selected from the group $R^1$-G2 consisting of:

F, Cl, Br, $C_{1-3}$-alkyl, —O—($C_{1-6}$-alkyl), —O—($C_{3-7}$-cycloalkyl), —O—($C_{1-3}$-alkyl)-($C_{3-7}$-cycloalkyl), —O—($C_{1-3}$-alkyl)-phenyl, —COOH, —COO($C_{1-4}$-alkyl), and —CO—NH—($C_{1-3}$-alkyl)-phenyl, wherein each alkyl and cycloalkyl is optionally substituted with one to three F or one $CF_3$; and wherein the hydrogen atom in each NH group is optionally replaced with $C_{1-4}$-alkyl;

or, if two $R^1$-groups are attached to adjacent carbon atoms of the phenyl moiety of the tetrahydroisoquinolinyl group, they may be linked with each other and together form a $C_{3-5}$-alkylene bridging group in which 1 or 2 —$CH_2$-groups may independently of each other be replaced by —O—.

$R^1$-G3:

In another embodiment the group $R^1$ is selected from the group $R^1$-G3 consisting of: F, Cl, Br, $CF_3$, —O—($C_{1-5}$-alkyl), —O—($C_{3-5}$-cycloalkyl), —O—($C_{1-2}$-alkyl)-($C_{3-5}$-cycloalkyl), —O—($C_{1-2}$-alkyl)-phenyl, —COO($C_{1-2}$-alkyl), and —CO—NH—($C_{1-2}$-alkyl)-phenyl, wherein each alkyl and cycloalkyl is optionally substituted with one to three F or one $CF_3$; and wherein the hydrogen atom in each NH group is optionally replaced with $C_{1-3}$-alkyl;

or, if two $R^1$-groups are attached to adjacent carbon atoms of the phenyl moiety of the tetrahydroisoquinolinyl group, they may be linked with each other and together form a —O—$CH_2$—$CH_2$—O-bridge.

$R^1$-G4:

In another embodiment the group $R^1$ is selected from the group $R^1$-G4 consisting of: F, Cl, Br, $CF_3$, —O—($C_{1-4}$-alkyl), —O-cyclobutyl, —O—($C_{1-2}$-alkyl)-($C_{3-4}$-cycloalkyl), —O—$CH_2$-phenyl, —$COOCH_3$, and —CO—NH—$CH_2$-phenyl, wherein each alkyl and cycloalkyl is optionally substituted with one to three F or one $CF_3$;

or, if two $R^1$-groups are attached to adjacent carbon atoms of the phenyl moiety of the tetrahydroisoquinolinyl group, they may be linked with each other and together form a —O—$CH_2$—$CH_2$—O-bridge.

$R^1$-G4a:

In another embodiment the group $R^1$ is selected from the group $R^1$-G4a consisting of: Cl, $CF_3$, —O—($C_{3-4}$-alkyl), —O-cyclobutyl, —O—($C_{1-2}$-alkyl)-($C_{3-4}$-cycloalkyl), —O—$CH_2$-phenyl, —$COOCH_3$, and —CO—NH—$CH_2$-phenyl, wherein each alkyl and cycloalkyl is optionally substituted with one to three F or one $CF_3$;

or, if two $R^1$-groups are attached to adjacent carbon atoms of the phenyl moiety of the tetrahydroisoquinolinyl group, they may be linked with each other and together form a —O—$CH_2$—$CH_2$—O-group;

or, if n is 2, the second $R^1$ group is selected from the group consisting of F, Cl, Br, and —$OCH_3$.

Preferably, n is 1 or 2.

Preferably, the first $R^1$ group is situated in position 5 or 6 of the tetrahydroisoquinolinyl group, and the second $R^1$ group is situated in position 5 of the tetrahydroisoquinolinyl group.

More preferably, the first $R^1$ group is situated in position 6 of the tetrahydroisoquinolinyl group, and the second $R^1$ group is situated in position 5 of the tetrahydroisoquinolinyl group.

$R^1$-G5:

In another embodiment the group $R^1$ is selected from the group $R^1$-G5 consisting of: Cl, Br, $CF_3$, —O—($C_{3-4}$-alkyl), —O-cyclobutyl, —O—($C_{1-2}$-alkyl)-($C_{3-4}$-cycloalkyl), and —O—$CH_2$-phenyl, wherein each alkyl and cycloalkyl is optionally substituted with one to three F or one $CF_3$.

$R^1$-G5a:

In another embodiment the group $R^1$ is selected from the group $R^1$-G5a consisting of: Cl, $CF_3$, —O—($C_{3-4}$-alkyl), —O-cyclobutyl, —O—($C_{1-2}$-alkyl)-($C_{3-4}$-cycloalkyl), and —O—$CH_2$-phenyl, wherein each alkyl and cycloalkyl is optionally substituted with one to three F or one $CF_3$;

or, if n is 2, the second $R^1$ group is selected from the group consisting of Cl, Br, and —$OCH_3$.

Preferably, n is 1 or 2.

Preferably, the first $R^1$ group is situated in position 5 or 6 of the tetrahydroisoquinolinyl group, and the second $R^1$ group is situated in position 5 of the tetrahydroisoquinolinyl group.

More preferably, the first $R^1$ group is situated in position 6 of the tetrahydroisoquinolinyl group, and the second $R^1$ group is situated in position 5 of the tetrahydroisoquinolinyl group.

$R^1$-G6:

In another embodiment the group $R^1$ is selected from the group $R^1$-G6 consisting of: Cl, Br, $CF_3$, —O—$CH_3$, $R^1$-G6a:

In another embodiment the group $R^1$ is selected from the group $R^1$-G6a consisting of: Cl, $CF_3$, or, if n is 2, the second $R^1$ group is selected from the group consisting of Cl, Br and —O—$CH_3$.

Preferably, n is 1 or 2.

Preferably, the first $R^1$ group is situated in position 5 or 6 of the tetrahydroisoquinolinyl group, and the second $R^1$ group is situated in position 5 of the tetrahydroisoquinolinyl group.

More preferably, the first $R^1$ group is situated in position 6 of the tetrahydroisoquinolinyl group, and the second $R^1$ group is situated in position 5 of the tetrahydroisoquinolinyl group.

n n is 0, 1, 2 or 3.
Preferably, n is 1, 2 or 3.
More preferably, n is 1 or 2.
In one embodiment, n is 2.
In another embodiment, n is 1.

$R^2$ $R^2$-G1:
The group $R^2$ is preferably selected from the group $R^2$-G1 as defined hereinbefore and hereinafter.

$R^2$-G2:
In another embodiment the group $R^2$ is selected from the group $R^2$-G2 consisting of: $C_{1-3}$-alkyl, $C_{3-5}$-cycloalkyl, —O—($C_{1-3}$-alkyl), $NH_2$, —NH—($C_{1-3}$-alkyl), —N($C_{1-3}$-alkyl)$_2$, —($C_{1-2}$-alkyl)-pyrimidinyl, pyrimidinyl, 2-oxo-pyrrolidinyl, 2-oxo-dihydrofuranyl, morpholinyl and a heteroaryl group selected from the group consisting of oxazolyl, isoxazolyl, thiazolyl, isothiatolyl, imidazolyl and 1H-pyrazolyl;
  wherein each alkyl group is optionally substituted with one to three substituents selected from F, CN, —CONH$_2$, —CONH(CH$_3$), —CON(CH$_3$)$_2$, NH$_2$ and OH;
  wherein each cycloalkyl group is optionally substituted with one or two substituents selected from F, CN, OH, —NH—COO(C$_{1-4}$-alkyl), C$_{1-3}$-alkyl and CF$_3$;
  wherein each heteroaryl group is optionally substituted with one or more substituents selected from Cl, CH$_3$, NH$_2$ and —NH—C(O)—(C$_{1-2}$-alkyl).

$R^2$-G2a:
In another embodiment the group $R^2$ is selected from the group $R^2$-G2a consisting of: $C_{1-3}$-alkyl, which is optionally substituted with one to three substituents selected from F, CN, —CONH$_2$, —CO—NH(CH$_3$), —CO—N(CH$_3$)$_2$, NH$_2$ and OH.

$R^2$-G2b:
In another embodiment the group $R^2$ is selected from the group $R^2$-G2b consisting of: $C_{3-5}$-cycloalkyl, which is optionally substituted with one or two substituents selected from F, CN, OH, NH$_2$, —NH—COO(C$_{1-4}$-alkyl), C$_{1-3}$-alkyl and CF$_3$.

$R^2$-G2c:
In another embodiment the group $R^2$ is selected from the group $R^2$-G2c consisting of: oxazolyl, isoxazolyl, thiazolyl, isothiatolyl, imidazolyl and 1H-pyrazolyl, wherein each of said groups is optionally substituted with one or more substituents selected from Cl, CH$_3$, NH$_2$ and —NH—COO (C$_{1-4}$-alkyl).

$R^2$-G3:
In another embodiment the group $R^2$ is selected from the group $R^2$-G3 consisting of: $C_{1-2}$-alkyl, $C_{3-4}$-cycloalkyl, —O—CH$_3$, —NH—(C$_{1-2}$-alkyl), —N(C$_{1-2}$-alkyl)$_2$, —CH$_2$-pyrimidinyl, pyrimidinyl, 2-oxo-pyrrolidinyl, 2-oxo-dihydrofuranyl, morpholinyl and a heteroaryl group selected from the group consisting of oxazolyl, isoxazolyl, thiazolyl, isothiazolyl, imidazolyl and 1H-pyrazolyl;
  wherein each alkyl group is optionally substituted with one to three substituents selected from F, CN, —CO—NH$_2$, —CO—NH(CH$_3$), —CO—N(CH$_3$)$_2$, NH$_2$ and OH;
  wherein each cycloalkyl group is optionally substituted with one or two substituents selected from F, CN, OH, NH$_2$, —NH—COO—C(CH$_3$)$_3$, CH$_3$ and CF$_3$;
  wherein each heteroaryl group is optionally substituted with one or more substituents selected from Cl, CH$_3$, NH$_2$ and —NH—CO—(C$_{1-2}$-alkyl).

$R^2$-G4:
In another embodiment, the group $R^2$ is selected from the group $R^2$-G4 consisting of:

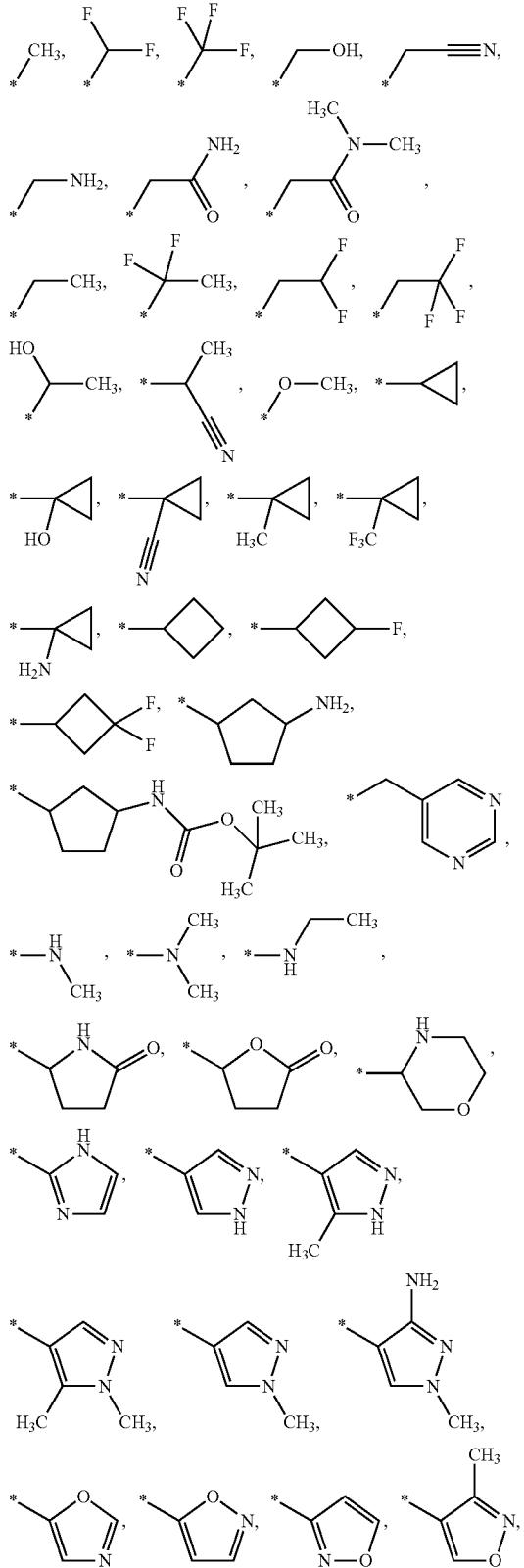

R²-G5:

In another embodiment, the group R² is selected from group R²-G5 consisting of: [structures shown]

R²-G6:

In another embodiment, the group R² is selected from the group R²-G6 consisting of $CH_3$, $CH_2CH_3$, $CH_2CN$, $CH_2OH$, cyclopropyl, cyclobutyl and [structure shown].

R²-G7:

In another embodiment, the group R² is selected from the group R²-G7 consisting of $CH_3$.

R²-G8:

In another embodiment, the group R² is selected from the group R²-G8 consisting of $CH_2CN$.

R³:

R³-G1:
The group R³ is preferably selected from the group R³-G1 as defined hereinbefore and hereinafter.

R³-G2:
In one embodiment the group R³ is selected from the group R³-G2 consisting of H and $C_{1-2}$-alkyl.

R³-G3:
In another embodiment the group R³ is selected from the group R³-G3 consisting of H and $CH_3$.

R³-G4:
In another embodiment the group R³ is selected from the group R³-G4 consisting of H.

R⁴:

R⁴-G1:
The group R⁴ is preferably selected from the group R⁴-G1 as defined hereinbefore and hereinafter.

R⁴-G2:
In one embodiment the group R⁴ is selected from the group R⁴-G2 consisting of H and $C_{1-2}$-alkyl.

R⁴-G3:
In another embodiment the group R⁴ is selected from the group R⁴-G3 consisting of H and $CH_3$.

R⁴-G4:
In another embodiment the group R⁴ is selected from the group R⁴-G4 consisting of $CH_3$.

R⁵:

R⁵-G1:
The group R⁵ is preferably selected from the group R⁵-G1 as defined hereinbefore and hereinafter.

R⁵-G2:
In one embodiment the group R⁵ is selected from the group R⁵-G2 consisting of of H and $C_{1-2}$-alkyl.

R⁵-G3:
In another embodiment the group R⁵ is selected from the group R⁵-G3 consisting of H.

R⁶:

R⁶-G1:
The group R⁶ is preferably selected from the group R⁶-G1 as defined hereinbefore and hereinafter.

R⁶-G2:
In one embodiment the group R⁶ is selected from the group R⁶-G2 consisting of: F, OH and —O—($C_{1-3}$-alkyl), or, if m is 2, both R⁶ groups together with the carbon atom, to which they are attached, may form a carbonyl group.

$R^6$-G3:

In one embodiment the group $R^6$ is selected from the group $R^6$-G3 consisting of: F, OH and —O—$CH_3$,
or, if m is 2, both $R^6$ groups together with the carbon atom, to which they are attached, may form a carbonyl group.

$R^6$-G4:

In one embodiment the group $R^6$ is selected from the group $R^6$-G4 consisting of: F, OH and —O—$CH_3$, if m is 1, or, if m is 2, each of the $R^6$ groups is F or both $R^6$ groups together with the carbon atom, to which they are attached, may form a carbonyl group.

$R^6$-G5:
a) In one embodiment, $R^6$ is F, and m is 1 or 2,
b) In another embodiment, $R^6$ is F, and m is 1,
c) In another embodiment, $R^6$ is F, and m is 2, m m is 0, 1 or 2.
In one embodiment, m is 0.
In another embodiment, m is 1 or 2.
In another embodiment, m is 1.
In another embodiment, m is 0 or 1.
In another embodiment, m is 0 or 2.
In still another embodiment, m is 2.
In one embodiment, the sum of n and m does not exceed 3.

$R^7$:

$R^7$-G1:

The group $R^7$ is preferably selected from the group $R^7$-G1 as defined hereinbefore and hereinafter.

$R^7$-G2:

In one embodiment the group $R^7$ is selected from the group $R^7$-G2 consisting of: H, $C_{1-2}$-alkyl, —COOH and —COO($C_{1-2}$-alkyl).

$R^7$-G3:

In one embodiment the group $R^7$ is selected from the group $R^7$-G3 consisting of: H, $CH_3$, —COOH and —COO($CH_3$).

$R^7$-G4:

In one embodiment the group $R^7$ is selected from the group $R^7$-G4 consisting of: H and $CH_3$.

$R^7$-G5:

In one embodiment the group $R^7$ is selected from the group $R^7$-G5 consisting of: H.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| No. | $R^1$ | $R^2$ | $R^3$ | $R^4$ | $R^5$ | $R^6$ | $R^7$ | n | m |
|---|---|---|---|---|---|---|---|---|---|
| 1 | $R^1$-G1 | $R^2$-G1 | $R^3$-G1 | $R^4$-G1 | $R^5$-G1 | $R^6$-G1 | $R^7$-G1 | 0, 1, 2 or 3 | 0, 1 or 2 |
| 2 | $R^1$-G1 | $R^2$-G1 | $R^3$-G2 | $R^4$-G2 | $R^5$-G2 | $R^6$-G1 | $R^7$-G1 | 1 or 2 | 0, 1 or 2 |
| 3 | $R^1$-G1 | $R^2$-G1 | $R^3$-G3 | $R^4$-G3 | $R^5$-G3 | $R^6$-G1 | $R^7$-G1 | 1 or 2 | 0, 1 or 2 |
| 4 | $R^1$-G1 | $R^2$-G1 | $R^3$-G4 | $R^4$-G4 | $R^5$-G3 | $R^6$-G2 | $R^7$-G2 | 1 or 2 | 0, 1 or 2 |
| 5 | $R^1$-G1 | $R^2$-G1 | $R^3$-G4 | $R^4$-G4 | $R^5$-G3 | — | $R^7$-G5 | 1 or 2 | 0 |
| 6 | $R^1$-G1 | $R^2$-G1 | $R^3$-G4 | $R^4$-G4 | $R^5$-G3 | — | $R^7$-G5 | 1 | 0 |
| 7 | $R^1$-G2 | $R^2$-G1 | $R^3$-G4 | $R^4$-G4 | $R^5$-G3 | $R^6$-G2 | $R^7$-G2 | 1 or 2 | 0, 1 or 2 |
| 8 | $R^1$-G2 | $R^2$-G2 | $R^3$-G4 | $R^4$-G4 | $R^5$-G3 | $R^6$-G2 | $R^7$-G2 | 1 or 2 | 0, 1 or 2 |
| 9 | $R^1$-G3 | $R^2$-G2 | $R^3$-G4 | $R^4$-G4 | $R^5$-G3 | $R^6$-G2 | $R^7$-G2 | 1 or 2 | 0, 1 or 2 |
| 10 | $R^1$-G4 | $R^2$-G2 | $R^3$-G4 | $R^4$-G4 | $R^5$-G3 | $R^6$-G2 | $R^7$-G2 | 1 or 2 | 0, 1 or 2 |
| 11 | $R^1$-G4 | $R^2$-G3 | $R^3$-G4 | $R^4$-G4 | $R^5$-G3 | $R^6$-G2 | $R^7$-G2 | 1 or 2 | 0, 1 or 2 |
| 12 | $R^1$-G4a | $R^2$-G2 | $R^3$-G4 | $R^4$-G4 | $R^5$-G3 | $R^6$-G2 | $R^7$-G2 | 1 or 2 | 0, 1 or 2 |
| 13 | $R^1$-G5 | $R^2$-G2 | $R^3$-G4 | $R^4$-G4 | $R^5$-G3 | $R^6$-G2 | $R^7$-G2 | 1 or 2 | 0, 1 or 2 |
| 14 | $R^1$-G5a | $R^2$-G3 | $R^3$-G4 | $R^4$-G4 | $R^5$-G3 | $R^6$-G2 | $R^7$-G2 | 1 or 2 | 0, 1 or 2 |
| 15 | $R^1$-G6 | $R^2$-G2 | $R^3$-G4 | $R^4$-G4 | $R^5$-G3 | $R^6$-G2 | $R^7$-G2 | 1 or 2 | 0, 1 or 2 |
| 16 | $R^1$-G6a | $R^2$-G3 | $R^3$-G4 | $R^4$-G4 | $R^5$-G3 | $R^6$-G2 | $R^7$-G2 | 1 or 2 | 0, 1 or 2 |
| 17 | $R^1$-G2 | $R^2$-G4 | $R^3$-G4 | $R^4$-G4 | $R^5$-G3 | $R^6$-G2 | $R^7$-G2 | 1 or 2 | 0, 1 or 2 |
| 18 | $R^1$-G2 | $R^2$-G5 | $R^3$-G4 | $R^4$-G4 | $R^5$-G4 | $R^6$-G4 | $R^7$-G4 | 1 or 2 | 0, 1 or 2 |
| 19 | $R^1$-G2 | $R^2$-G6 | $R^3$-G4 | $R^4$-G4 | $R^5$-G4 | $R^6$-G4 | $R^7$-G4 | 1 or 2 | 0, 1 or 2 |
| 20 | $R^1$-G4a | $R^2$-G3 | $R^3$-G4 | $R^4$-G4 | $R^5$-G3 | $R^6$-G2 | $R^7$-G3 | 1 or 2 | 0, 1 or 2 |
| 21 | $R^1$-G4a | $R^2$-G5 | $R^3$-G4 | $R^4$-G4 | $R^5$-G3 | $R^6$-G2 | $R^7$-G2 | 1 or 2 | 0, 1 or 2 |
| 22 | $R^1$-G4a | $R^2$-G6 | $R^3$-G4 | $R^4$-G4 | $R^5$-G3 | $R^6$-G2 | $R^7$-G2 | 1 or 2 | 0, 1 or 2 |

The following preferred embodiments of compounds of the formula (I) are described using generic formulae (I.1) to (I.6b), wherein any tautomers and stereoisomers, solvates, hydrates and salts thereof, in particular the pharmaceutically acceptable salts thereof, are encompassed.

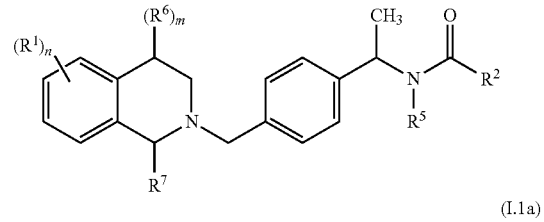

(I.1)

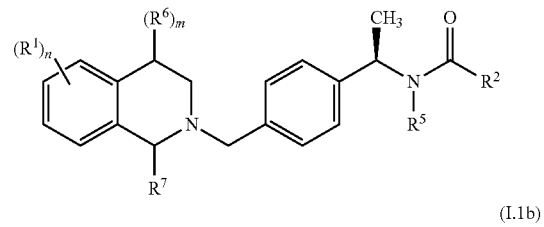

(I.1a)

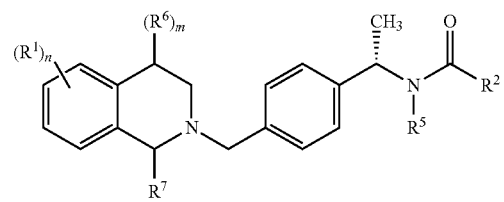

(I.1b)

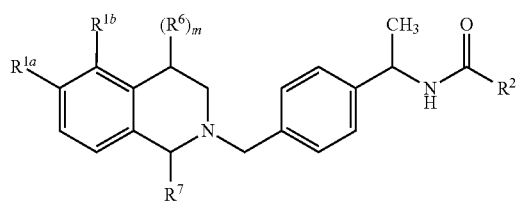
(I.2)
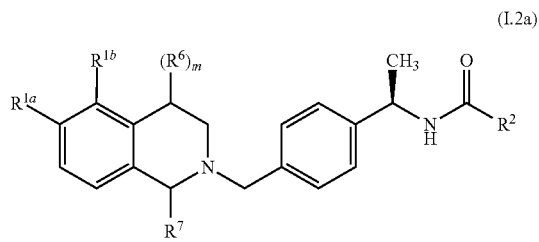
(I.2a)
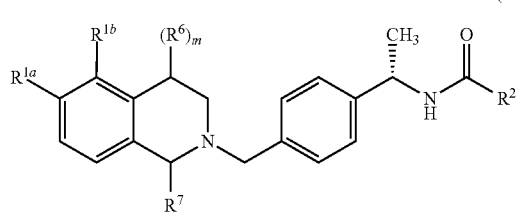
(I.2b)
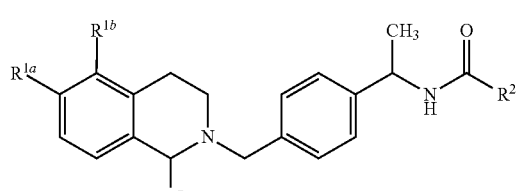
(I.3)
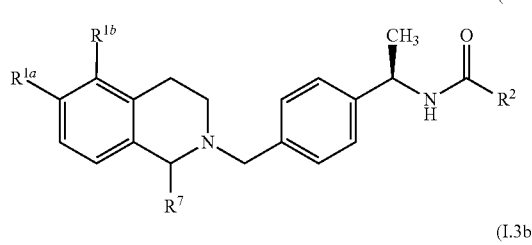
(I.3a)
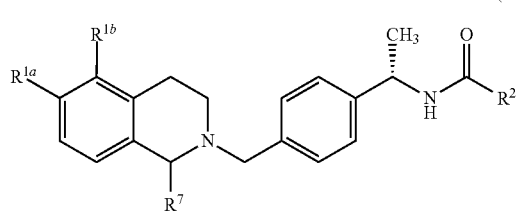
(I.3b)
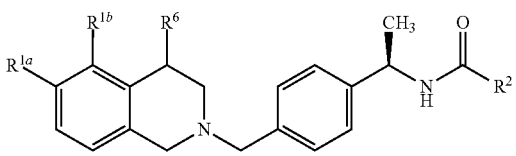
(I.4)
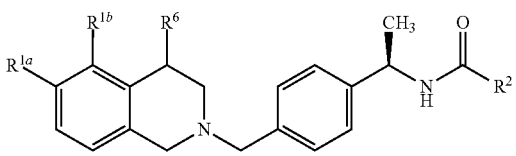
(I.4a)
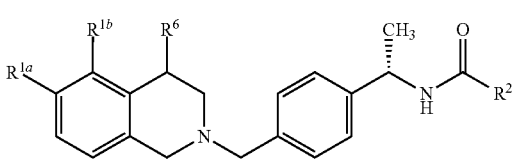
(I.4b)
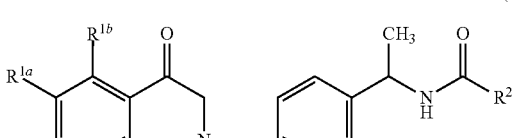
(I.5)
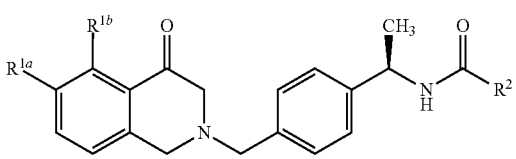
(I.5a)
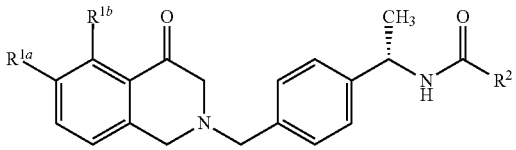
(I.5b)
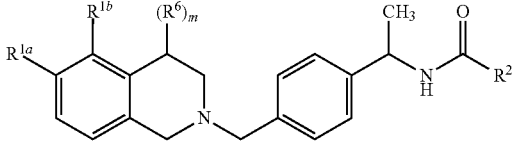
(I.6)
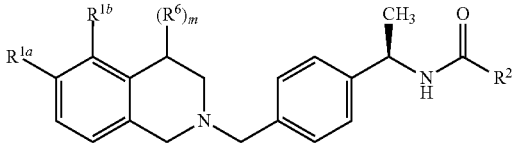
(I.6a)
(I.6b)

wherein in each of the above formulae (I.1) to (I.6b), the groups $R^1, R^2, R^6, R^7$, m and n are defined as hereinbefore and hereinafter and $R^{1a}$ and $R^{1b}$ are as defined hereinbefore and hereinafter for $R^1$. Preferably, $R^{1a}$ is as defined hereinbefore and hereinafter for the first $R^1$-group, as $R^{1b}$ is is as defined hereinbefore and hereinafter for the optional second $R^1$-group.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Formula | $R^1$ | $R^{1a}$ and $R^{1b}$ | $R^2$ | $R^6$ | $R^7$ | n | m |
|---|---|---|---|---|---|---|---|---|
| E-1 | (I.1) | $R^1$-G2 | — | $R^2$-G2 | $R^6$-G2 | $R^7$-G2 | 1 or 2 | 0, 1 or 2 |
| E-2 | (I.1) | $R^1$-G2 | — | $R^2$-G2 | $R^6$-G3 | $R^7$-G3 | 1 or 2 | 0, 1 or 2 |
| E-3 | (I.1) | $R^1$-G2 | — | $R^2$-G2 | $R^6$-G4 | $R^7$-G4 | 1 or 2 | 0, 1 or 2 |
| E-4 | (I.1) | $R^1$-G5 | — | $R^2$-G4 | $R^6$-G4 | $R^7$-G4 | 1 or 2 | 0, 1 or 2 |
| E-5 | (I.2) | — | $R^1$-G4a | $R^2$-G2 | $R^6$-G2 | $R^7$-G2 | — | 0, 1 or 2 |
| E-6 | (I.2) | — | $R^1$-G4a | $R^2$-G2 | $R^6$-G3 | $R^7$-G3 | — | 0, 1 or 2 |
| E-7 | (I.2) | — | $R^1$-G4a | $R^2$-G2 | $R^6$-G4 | $R^7$-G4 | — | 0, 1 or 2 |
| E-8 | (I.2) | — | $R^1$-5a | $R^2$-G4 | $R^6$-G4 | $R^7$-G4 | — | 0, 1 or 2 |
| E-9 | (I.3) | — | $R^1$-G4a | $R^2$-G2 | $R^6$-G2 | $R^7$-G2 | — | 0 or 1 |
| E-10 | (I.3) | — | $R^1$-G4a | $R^2$-G3 | $R^6$-G3 | $R^7$-G3 | — | 0 or 1 |
| E-11 | (I.3) | — | $R^1$-G4a | $R^2$-G4 | $R^6$-G4 | $R^7$-G4 | — | 0 or 1 |
| E-12 | (I.3) | — | $R^1$-G5a | $R^2$-G4 | $R^6$-G4 | $R^7$-G4 | — | 0 or 1 |
| E-13 | (I.3) | — | $R^1$-G6a | $R^2$-G4 | $R^6$-G4 | $R^7$-G4 | — | 0 or 1 |
| E-14 | (I.4) | — | $R^1$-G4a | $R^2$-G2 | $R^6$-G3 | $R^7$-G3 | — | 0 or 1 |
| E-15 | (I.4) | — | $R^1$-G4a | $R^2$-G3 | $R^6$-G3 | $R^7$-G3 | — | 0 or 1 |
| E-16 | (I.4) | — | $R^1$-G4a | $R^2$-G2 | $R^6$-G4 | $R^7$-G4 | — | 0 or 1 |
| E-17 | (I.4) | — | $R^1$-G5a | $R^2$-G3 | $R^6$-G4 | $R^7$-G4 | — | 0 or 1 |
| E-18 | (I.4) | — | $R^1$-G6a | $R^2$-G3 | $R^6$-G4 | $R^7$-G4 | — | 0 or 1 |
| E-19 | (I.5) | — | $R^1$-G4a | $R^2$-G2 | $R^6$-G2 | $R^7$-G2 | — | 2 |
| E-20 | (I.5) | — | $R^1$-G4a | $R^2$-G3 | $R^6$-G2 | $R^7$-G2 | — | 2 |
| E-21 | (I.5) | — | $R^1$-G5a | $R^2$-G3 | $R^6$-G2 | $R^7$-G2 | — | 2 |
| E-22 | (I.5) | — | $R^1$-G5a | $R^2$-G4 | $R^6$-G2 | $R^7$-G2 | — | 2 |
| E-23 | (I.5) | — | $R^1$-G6a | $R^2$-G2 | $R^6$-G2 | $R^7$-G2 | — | 2 |
| E-24 | (I.5) | — | $R^1$-G6a | $R^2$-G4 | $R^6$-G2 | $R^7$-G2 | — | 2 |
| E-25 | (I.2) | — | $R^1$-G4a | $R^2$-G7 | $R^6$-G2 | $R^7$-G2 | — | 0, 1 or 2 |
| E-26 | (I.2) | — | $R^1$-G4a | $R^2$-G8 | $R^6$-G2 | $R^7$-G2 | — | 0, 1 or 2 |

In case the formula or the table contain an entry for $R^{1a}$ and $R^{1b}$, $R^{1a}$ is the first or normal substituent $R^1$, while $R^{1b}$ is the "second" group $R^1$.

A preferred embodiment of the present invention concerns compounds of general formula (I.2)

wherein
$R^{1a}$ is selected from the group consisting of Cl, $CF_3$, —O—($C_{3-4}$-alkyl), —O-cyclo-butyl, —O—($C_{1-2}$-alkyl)-($C_{3-4}$-cycloalkyl), —O—$CH_2$-phenyl, —$COOCH_3$, and —CO—NH—$CH_2$-phenyl,
  wherein each alkyl and cycloalkyl is optionally substituted with one to three F or one $CF_3$;
$R^{1b}$ is H, F, Cl, Br or —$OCH_3$;
$R^2$ is selected from the group consisting of:
  $C_{1-2}$-alkyl, $C_{3-4}$-cycloalkyl, —O—$CH_3$, —NH—($C_{1-2}$-alkyl), —N($C_{1-2}$-alkyl)$_2$, —$CH_2$-pyrimidinyl, pyrimidinyl, 2-oxo-pyrrolidinyl, 2-oxo-dihydrofuranyl, morpholinyl and a heteroaryl group selected from the group consisting of oxazolyl, isoxazolyl, thiazolyl, isothiatolyl, imidazolyl and 1H-pyrazolyl;

wherein each alkyl group is optionally substituted with one to three substituents selected from F, CN, —CO—$NH_2$, —CO—NH($CH_3$), —CO—N($CH_3$)$_2$, $NH_2$ and OH;

wherein each cycloalkyl group is optionally substituted with one or two substituents selected from F, CN, OH, $NH_2$, —NHCO)—O—C($CH_3$)$_3$, $CH_3$ and $CF_3$;

wherein each heteroaryl group is optionally substituted with one or more substituents selected from Cl, $CH_3$, $NH_2$ and —NH—C(O)—($C_{1-2}$-alkyl);

$R^6$ is selected from the group consisting of: F, OH, and —O—$CH_3$, or, if m is 2, both $R^6$ groups together with the carbon atom, to which they are attached, may form a carbonyl group;

$R^7$ is selected from the group consisting of: H, $CH_3$, —COOH and —$COOCH_3$; and m is 0, 1 or 2;

or a salt thereof.

Another preferred embodiment of the present invention concerns compounds of one of the formulae (I.3)

-continued

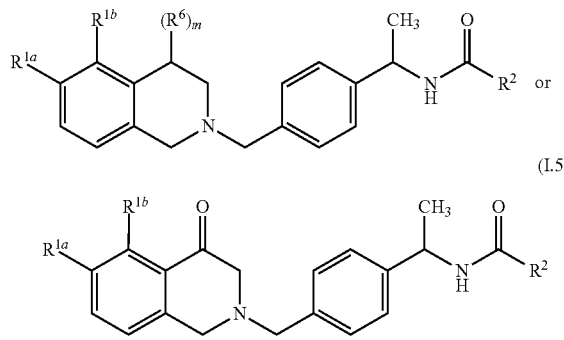

wherein
$R^{1a}$ is Cl, $CF_3$, —O—($C_{3-4}$-alkyl), —O-cyclobutyl, —O—($C_{1-2}$-alkyl)-($C_{3-4}$-cycloalkyl) or —O—$CH_2$-phenyl,
  wherein each alkyl and cycloalkyl is optionally substituted with one to three F or one $CF_3$;
$R^{1b}$ is H, Cl, Br or —$OCH_3$;
$R^2$ is selected from the group consisting of:

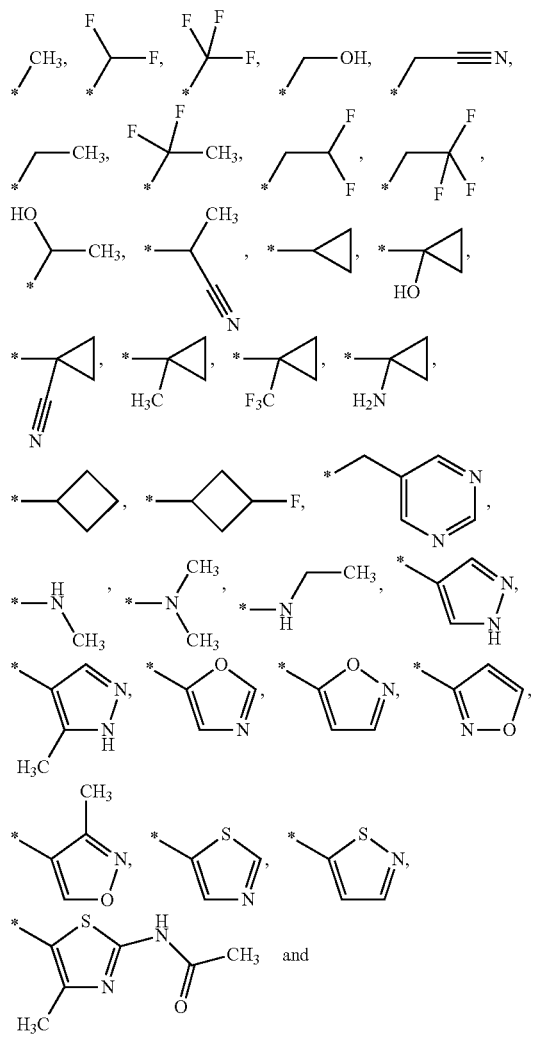

-continued and
$R^6$ is H, F, —OH, or —$OCH_3$;
m is 0 or 1 or, if $R^6$ is F, m may also be 2;
$R^7$ is H or —$CH_3$;
or a pharmaceutically acceptable salt thereof.
  Preferred compounds of the invention include:

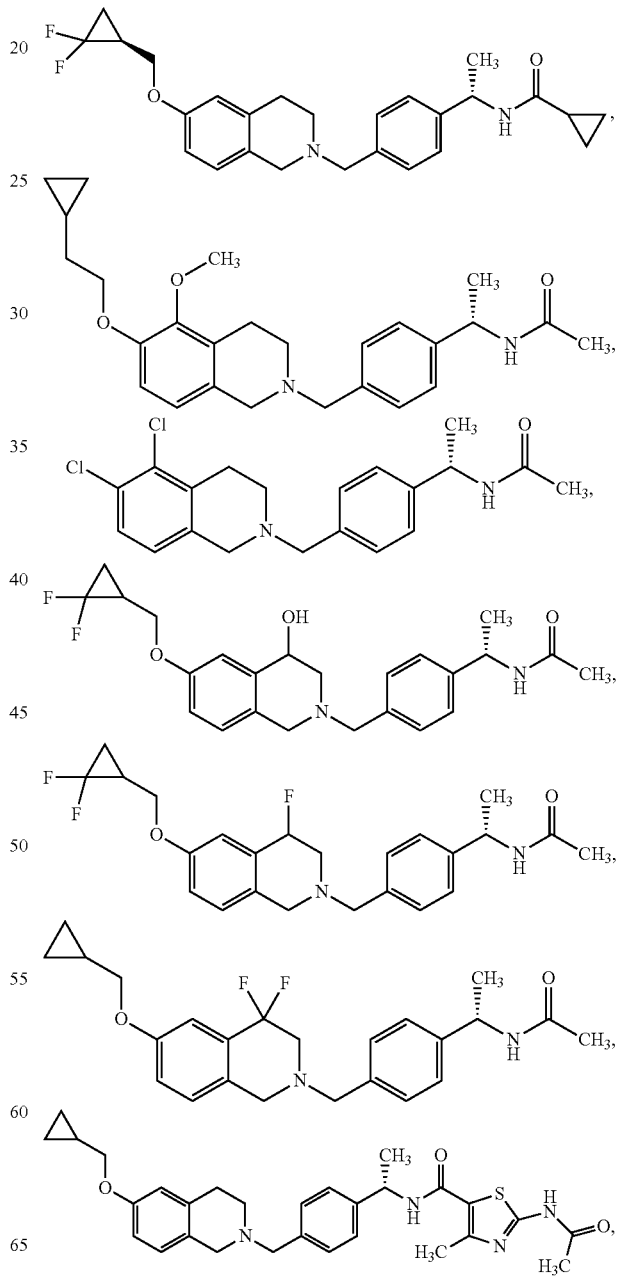

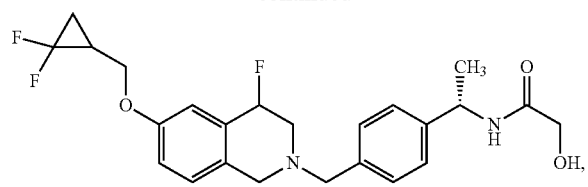
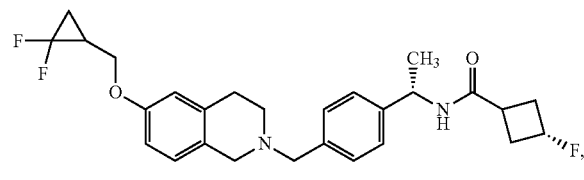
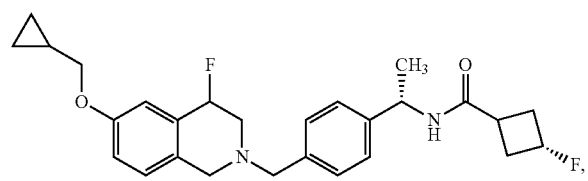
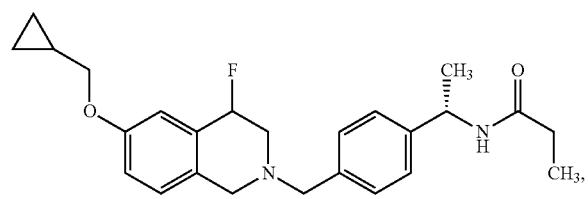
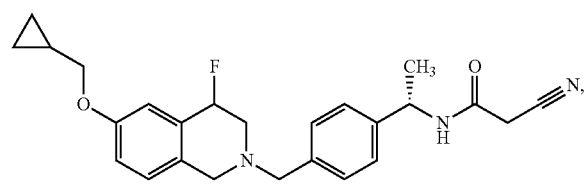
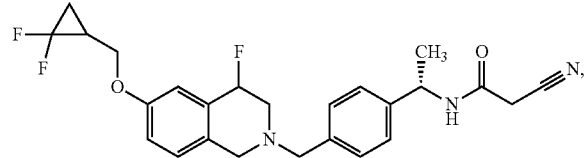
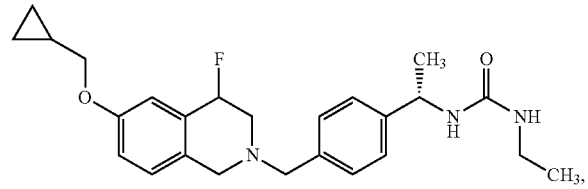
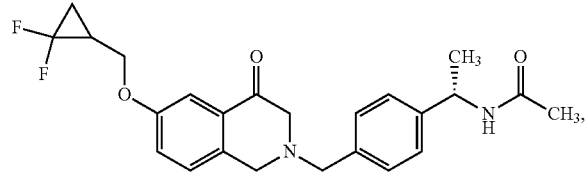
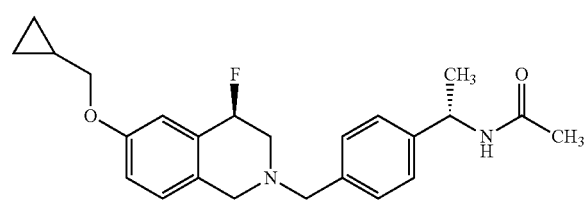

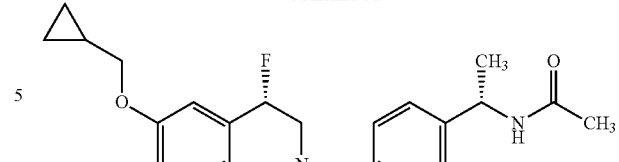
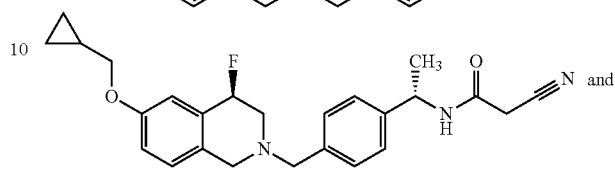
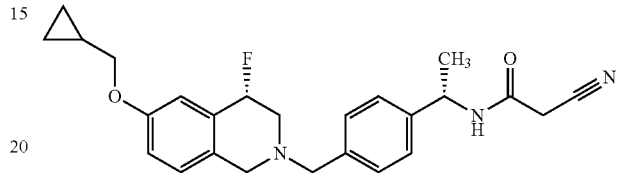

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

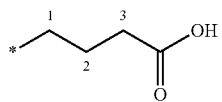

wherein the carboxy group is attached to the third carbon atom of the propyl group. The terms "1-methylpropyl-", "2,2-dimethylpropyl-" or "cyclopropylmethyl-" group represent the following groups:

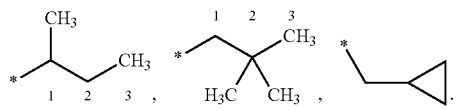

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as solvates thereof such as for instance hydrates.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—$ CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "C$_{1-n}$-alkylene" wherein n is an integer 1 to n, either alone or in combination with another radical, denotes an acyclic, straight or branched chain divalent alkyl radical containing from 1 to n carbon atoms. For example the term C$_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "C$_{2-n}$-alkenyl", is used for a group as defined in the definition for "C$_{1-n}$-alkyl" with at least two carbon atoms, if at least two of those carbon atoms of said group are bonded to each other by a double bond. For example the term C$_{2-3}$-alkenyl includes —CH=CH$_2$, —CH=CH—CH$_3$, —CH$_2$—CH=CH$_2$.

The term "C$_{2-n}$-alkenylene" is used for a group as defined in the definition for "C$_{1-n}$-alkylene" with at least two carbon atoms, if at least two of those carbon atoms of said group are bonded to each other by a double bond. For example the term C$_{2-3}$-alkenylene includes —CH=CH—, —CH=CH—CH$_2$—, —CH$_2$—CH=CH—.

The term "C$_{2-n}$-alkynyl", is used for a group as defined in the definition for "C$_{1-n}$-alkyl" with at least two carbon atoms, if at least two of those carbon atoms of said group are bonded to each other by a triple bond. For example the term C$_{2-3}$-alkynyl includes —C≡CH, —C≡C—CH$_3$, —CH$_2$—C≡CH.

The term "C$_{2-n}$-alkynylene" is used for a group as defined in the definition for "C$_{1-n}$-alkylene" with at least two carbon atoms, if at least two of those carbon atoms of said group are bonded to each other by a triple bond. For example the term C$_{2-3}$-alkynylene includes —C≡C—, —C≡C—CH$_2$—, —CH$_2$—C≡C—.

The term "C$_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term C$_{3-10}$-carbocyclyl includes C$_{3-10}$-cycloalkyl, C$_{3-10}$-cycloalkenyl, octahydro-pentalenyl, octahydroindenyl, decahydronaphthyl, indanyl, tetrahydronaphthyl. Most preferably, the term C$_{3-n}$-carbocyclyl denotes C$_{3-n}$-cycloalkyl, in particular C$_{3-7}$-cycloalkyl.

The term "C$_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "C$_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term C$_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably, the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably, the term "heterocyclyl" as used herein, either alone or in combination with another radical, means a saturated or unsaturated, even more preferably, a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

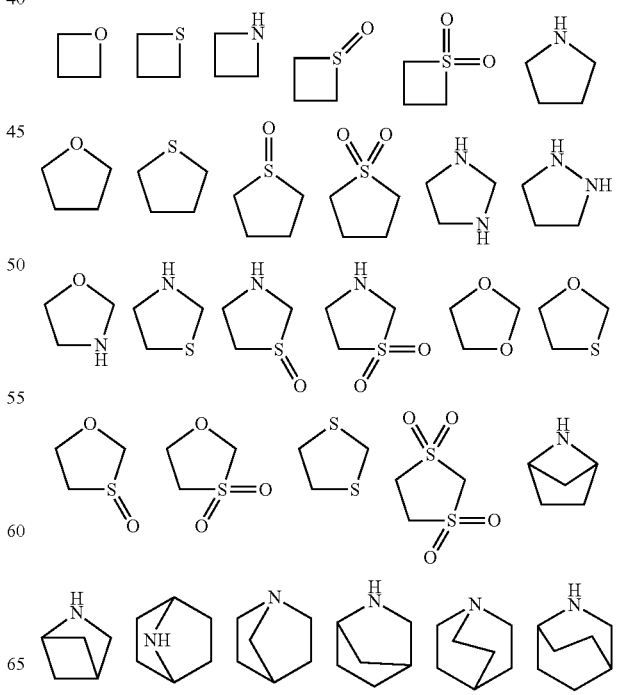

-continued
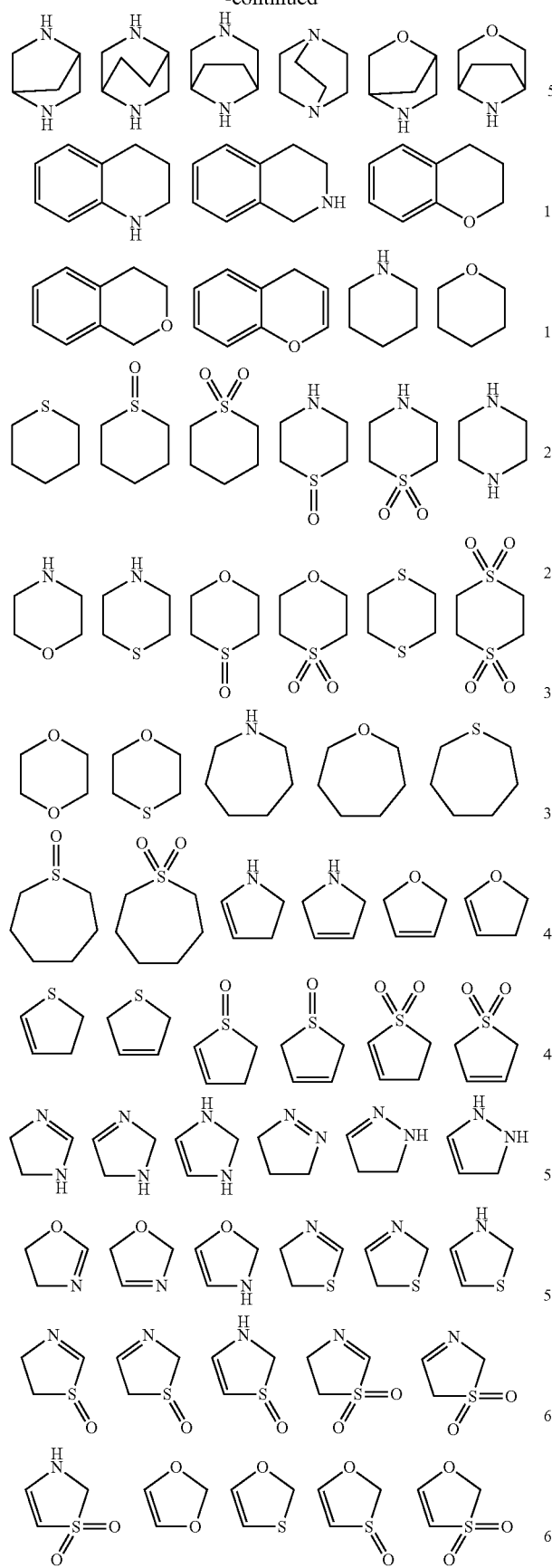
-continued
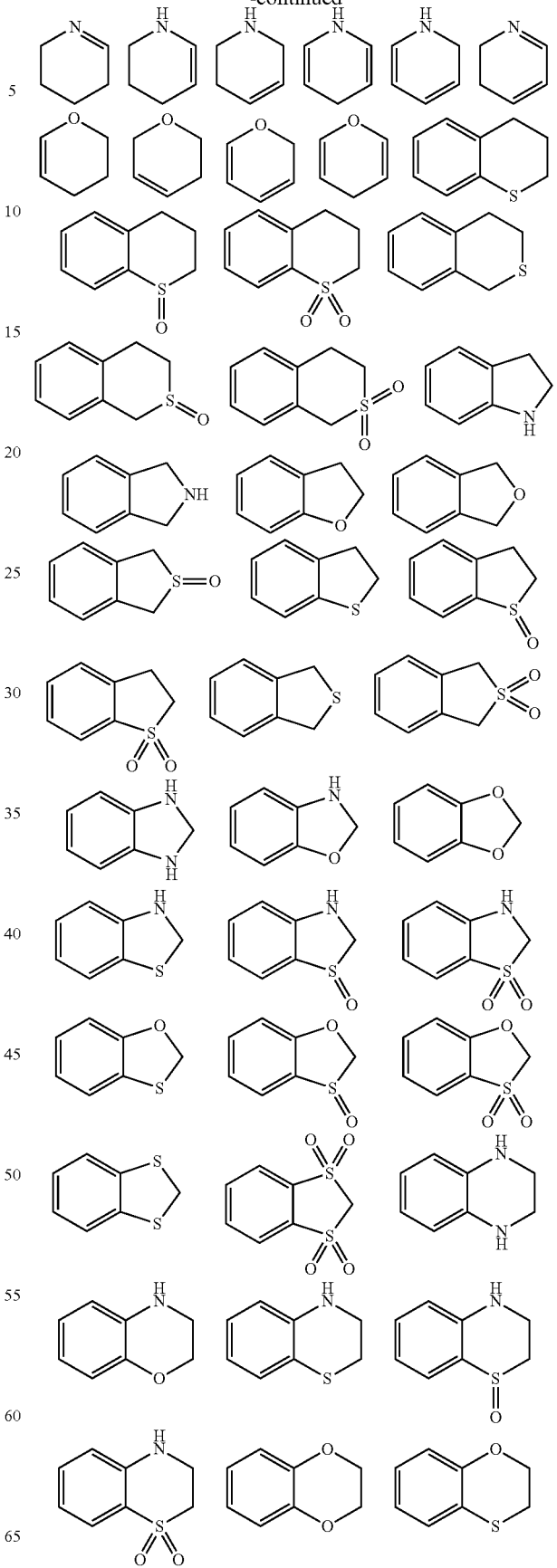

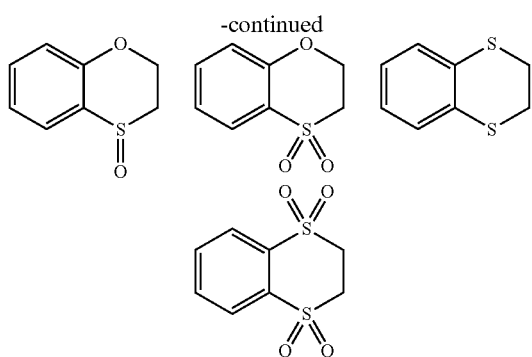

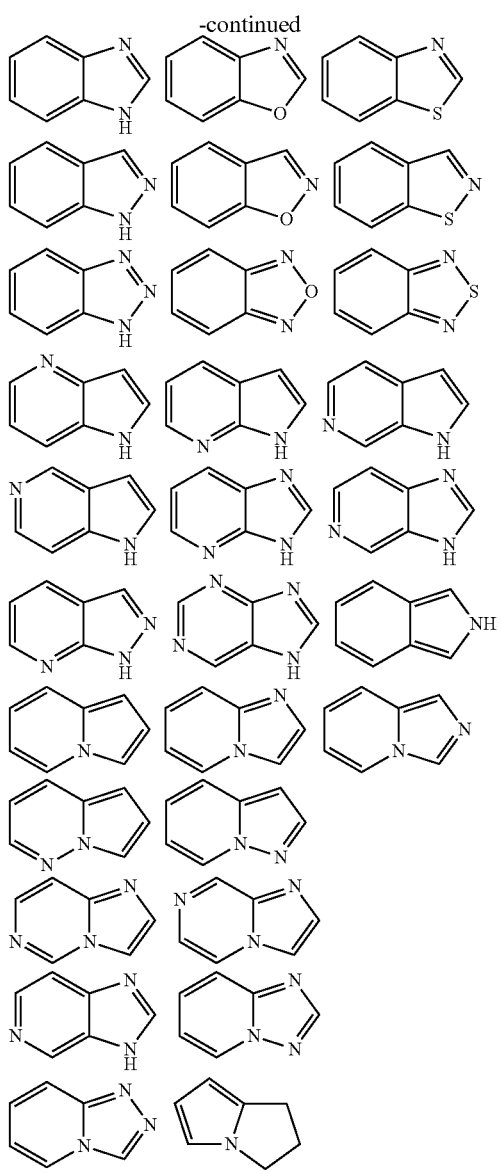

The term "heteroaryl" means a mono- or polycyclic, preferably mono- or bicyclic-ring system containing one or more heteroatoms selected from N, O or $S(O)_r$ with r=0, 1 or 2 wherein at least one of the heteroatoms is part of an aromatic ring, and wherein said ring system may have a carbonyl group. More preferably, the term "heteroaryl" as used herein, either alone or in combination with another radical, means a mono- or bicyclic-ring system containing 1, 2, 3 or 4 heteroatoms selected from N, O or $S(O)_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

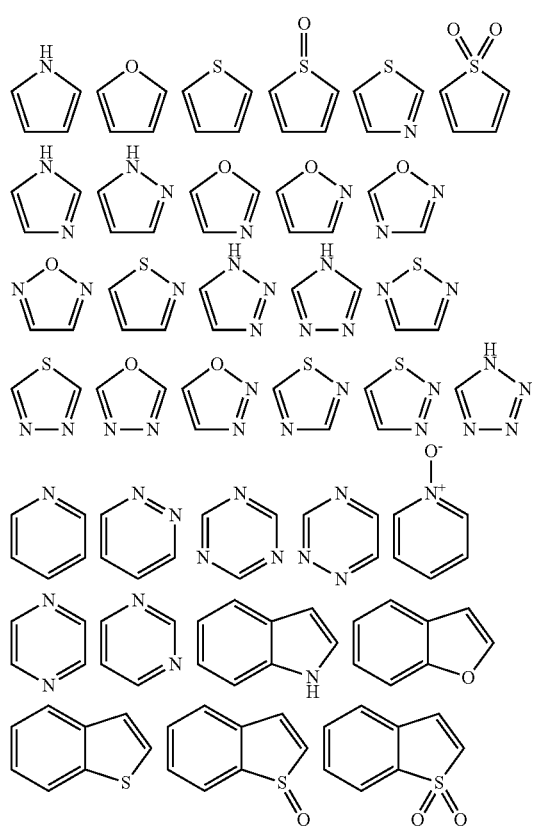

Many of the terms given above may be used repeatedly in the definition of a formula or group and in each case have one of the meanings given above, independently of one another.

All rests and substituents as defined hereinbefore and hereinafter may be substituted with one or more F atoms.

Pharmacological Activity

The activity of the compounds of the invention may be demonstrated using the following ACC2 assay:

Spectrophotometric 384 Well Assay

Malonyl CoA formation by acetyl CoA carboxylases is stoichiometrically linked to the consumption of ATP. ACC2 activity is measured in a 0-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM KHCO$_3$, 10 mM MgCl$_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 2000 f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For IC$_{50}$ value determination, the sample slope in the presence of the test compound after subtraction of the low controls (S(compound)−S('LOW')) are used.

An IC$_{50}$ value is derived from the compound slopes at different dosages after subtraction of the low controls (S(compound)-S('LOW')) by non-linear regression curve fitting (equation y=(A+((B−A)/(1+((C/x)^D))))).

The compounds of general formula (I) according to the invention for example have IC$_{50}$ values below 5000 nM, particularly below 1000 nM, preferably below 300 nM, most preferably below 100 nM.

In the following table the activity expressed as IC$_{50}$ (μM) of compounds according to the invention is presented wherein the IC$_{50}$ values are determined in the ACC2 assay as described hereinbefore. The term "Example" refers to the example numbers according to the following experimental section.

| Example | IC$_{50}$ [μM] |
|---|---|
| 1.001 | 0.293 |
| 1.002 | 0.524 |
| 1.003 | 0.265 |
| 1.004 | 0.206 |
| 1.005 | 0.252 |
| 1.006 | 0.878 |
| 1.007 | 0.291 |
| 1.008 | 0.492 |
| 1.009 | 0.102 |
| 1.010 | 0.614 |
| 1.011 | 0.067 |
| 1.012 | 0.052 |
| 1.013 | 0.146 |
| 1.014 | 0.095 |
| 1.015 | 0.047 |
| 1.016 | 0.273 |
| 1.017 | 0.060 |
| 1.018 | 0.407 |
| 1.019 | 0.326 |
| 1.020 | 0.110 |
| 1.021 | 0.110 |
| 1.022 | 0.126 |
| 1.023 | 0.133 |
| 1.024 | 0.415 |
| 1.025 | 0.049 |
| 1.026 | 0.043 |
| 1.027 | 0.699 |
| 1.028 | 0.789 |
| 1.029 | 0.228 |
| 1.030 | 0.058 |
| 1.031 | 0.076 |
| 1.032 | 0.263 |
| 1.033 | 0.044 |
| 1.034 | 0.054 |
| 1.035 | 0.061 |
| 1.036 | 0.101 |
| 1.037 | 0.080 |
| 1.038 | 0.218 |
| 1.039 | 0.057 |
| 1.040 | 0.135 |
| 1.041 | 0.057 |
| 1.042 | 0.065 |
| 1.043 | 0.180 |
| 1.044 | 0.193 |
| 1.045 | 0.083 |
| 1.046 | 0.163 |
| 1.047 | 0.071 |
| 1.048 | 0.139 |
| 1.049 | 0.063 |
| 1.050 | 0.120 |
| 1.051 | 0.031 |
| 1.052 | 0.024 |
| 1.053 | 0.142 |
| 1.054 | 0.269 |
| 1.055 | 0.041 |
| 1.056 | 0.051 |
| 1.057 | 0.102 |
| 1.058 | 0.137 |
| 1.059 | 0.058 |
| 1.060 | 0.029 |
| 1.061 | 0.140 |
| 1.062 | 0.055 |
| 1.063 | 0.045 |
| 1.064 | 0.104 |
| 1.065 | 0.211 |
| 1.066 | 0.111 |
| 1.067 | 0.233 |
| 1.068 | 0.070 |
| 1.069 | 0.418 |
| 1.070 | 0.145 |
| 1.071 | 0.340 |
| 1.072 | 0.141 |
| 1.073 | 0.040 |
| 1.074 | 0.079 |
| 1.075 | 0.055 |
| 1.076 | 0.068 |
| 1.077 | 0.040 |
| 1.078 | 0.067 |
| 1.079 | 0.136 |
| 1.080 | 0.396 |
| 1.081 | 0.232 |
| 1.082 | 0.039 |
| 1.083 | 0.449 |
| 1.084 | 0.263 |
| 1.085 | 0.280 |
| 1.086 | 0.227 |
| 1.087 | 0.189 |
| 1.088 | 0.012 |
| 1.089 | 0.089 |
| 1.090 | 0.065 |
| 1.091 | 0.130 |
| 1.092 | 0.016 |
| 1.093 | 0.020 |
| 1.094 | 0.296 |
| 1.095 | 0.494 |
| 1.096 | 0.315 |
| 1.097 | 0.038 |
| 1.098 | 0.392 |
| 1.099 | 0.421 |
| 1.100 | 0.030 |
| 1.101 | 0.055 |
| 2.001 | 0.135 |
| 2.002 | 0.237 |
| 2.003 | 0.157 |
| 2.004 | 0.184 |
| 2.005 | 0.105 |

| Example | IC$_{50}$ [μM] |
|---|---|
| 2.006 | 0.085 |
| 2.007 | 0.104 |
| 2.008 | 0.100 |
| 2.009 | 0.249 |
| 2.010 | 0.179 |
| 2.011 | 0.194 |
| 2.012 | 0.097 |
| 2.013 | 0.166 |
| 2.014 | 0.144 |
| 2.015 | 0.038 |
| 2.016 | 0.299 |
| 2.017 | 0.038 |
| 2.018 | 0.047 |
| 2.019 | 0.057 |
| 2.020 | 0.028 |
| 2.021 | 0.168 |
| 2.022 | 0.082 |
| 2.023 | 0.082 |
| 2.024 | 0.150 |
| 2.025 | 0.089 |
| 2.026 | 0.081 |
| 2.027 | 0.130 |
| 2.028 | 0.217 |
| 2.029 | 0.329 |
| 2.03 | 0.459 |
| 2.031 | 0.447 |
| 2.032 | 0.034 |
| 2.033 | 0.039 |
| 2.034 | 0.055 |
| 2.035 | 0.259 |
| 2.036 | 0.408 |
| 2.037 | 0.806 |
| 2.038 | 0.819 |
| 2.039 | 0.565 |
| 2.04 | 0.450 |
| 2.041 | 0.600 |
| 2.042 | 0.624 |
| 2.043 | 0.428 |
| 2.044 | 0.446 |
| 3.001 | 0.035 |
| 3.002 | 0.029 |
| 3.003 | 0.091 |
| 3.004 | 0.046 |
| 3.005 | 0.059 |
| 3.006 | 0.038 |
| 3.007 | 0.050 |
| 3.008 | 0.068 |
| 3.009 | 0.059 |
| 3.010 | 0.025 |
| 3.011 | 0.052 |
| 3.012 | 0.122 |
| 3.013 | 0.040 |
| 3.014 | 0.103 |
| 3.015 | 0.024 |
| 3.016 | 0.162 |
| 3.017 | 0.037 |
| 3.018 | 0.208 |
| 3.019 | 0.028 |
| 3.020 | 0.033 |
| 3.021 | 0.198 |
| 3.022 | 0.028 |
| 3.023 | 0.045 |
| 3.024 | 0.022 |
| 3.025 | 0.026 |
| 3.026 | 0.049 |
| 3.027 | 0.038 |
| 3.028 | 0.046 |
| 3.029 | 0.045 |
| 3.03 | 0.095 |
| 3.031 | 0.077 |
| 3.032 | 0.058 |
| 3.033 | 0.358 |
| 3.034 | 0.115 |
| 3.035 | 0.143 |
| 3.036 | 0.518 |
| 3.037 | 0.060 |
| 3.038 | 0.198 |
| 3.039 | 0.136 |
| 3.040 | 0.189 |
| 3.041 | 0.490 |
| 3.042 | 0.072 |
| 3.043 | 0.354 |
| 3.044 | 0.062 |
| 3.045 | 0.231 |
| 3.046 | 0.056 |
| 3.047 | 0.308 |
| 3.048 | 0.059 |
| 3.049 | 0.448 |
| 3.050 | 0.306 |
| 3.051 | 0.604 |
| 3.052 | 0.153 |
| 3.053 | 0.213 |
| 3.054 | 0.245 |
| 3.055 | 0.055 |
| 3.056 | 0.886 |
| 3.057 | 0.357 |
| 3.058 | 0.266 |
| 3.059 | 0.047 |
| 3.060 | 0.132 |
| 3.061 | 0.090 |
| 3.062 | 0.102 |
| 3.063 | 0.266 |
| 3.064 | 0.052 |
| 4.001 | 0.037 |
| 4.002 | 0.053 |
| 4.003 | 0.025 |
| 5.001 | 0.076 |
| 5.002 | 0.059 |
| 5.003 | 0.020 |
| 5.004 | 0.017 |
| 5.005 | 0.155 |
| 5.006 | 0.872 |
| 5.007 | 0.049 |
| 5.008 | 0.369 |
| 5.009 | 0.116 |
| 6.001 | 0.022 |
| 6.002 | 0.173 |
| 7.001 | 0.192 |
| 7.002 | 0.104 |
| 7.003 | 0.026 |
| 7.004 | 0.148 |
| 7.005 | 0.058 |
| 7.006 | 0.551 |
| 7.007 | 0.185 |
| 7.008 | 0.140 |
| 7.009 | 0.050 |
| 8.001 | 0.715 |
| 9.000 | 0.190 |
| 10.000 | 0.806 |
| 11.000 | 0.013 |
| 11.000 | 0.048 |
| 12.000 | 0.215 |
| 12.000 | 0.513 |
| 13.000 | 0.511 |
| 13.000 | 1.931 |
| 14.000 | 0.084 |
| 14.000 | 0.510 |
| 15.000 | 0.050 |
| 15.000 | 0.156 |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance.

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, including preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;

B. hepatic disorders and conditions related thereto, including: fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;

C. skin disorders and conditions and those associated with polyunsaturated fatty acids, such as
   eczema, acne, sebaceous gland diseases, psoriasis, keloid scar formation or prevention, other diseases related to mucous membrane fatty acid composition;

D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);

E. diseases or conditions related to neoplastic cellular proliferation, for example benign or malignant tumors, cancer, neoplasias, metastases, carcinogenesis;

F. diseases or conditions related to neurological, psychiatric or immune disorders or conditions;

G. other diseases or conditions in which inflammatory reactions, cell differentiation and/or other ACC-mediated aspects may for example be involved are:
   atherosclerosis such as, for example (but not restricted thereto), coronary sclerosis including angina pectoris or myocardial infarction, stroke, ischemic, stroke and transient ischemic attack (TIA),
   peripheral occlusive disease,
   vascular restenosis or reocclusion,
   chronic inflammatory bowel diseases such as, for example, Crohn's disease and ulcerative colitis,
   pancreatitis,
   sinusitis,
   retinopathy, ischemic retinopathy,
   adipose cell tumors,
   lipomatous carcinomas such as, for example, liposarcomas,
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
   tumors in which ACC is up regulated,
   acute and chronic myeloproliferative disorders and lymphomas, angiogenesis
   neurodegenerative disorders including Alzheimer's disease, multiple sclerosis, Parkinson's disease, epilepsy,
   erythemato-squamous dermatoses such as, for example, psoriasis,
   acne vulgaris,
   other skin disorders and dermatological conditions which are modulated by PPAR,
   eczemas and neurodermatitis,
   dermatitis such as, for example, seborrheic dermatitis or photodermatitis,
   keratitis and keratoses such as, for example, seborrheic keratoses, senile keratoses, actinic keratoses, photo-induced keratoses or keratosis follicularis, keloids and keloid prophylaxis,
bacterial infections,
fungal infections,
warts, including condylomata or condylomata acuminata
viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia,
papular dermatoses such as, for example, lichen planus,
skin cancer such as, for example, basal-cell carcinomas, melanomas or cutaneous T-cell lymphomas,
localized benign epidermal tumors such as, for example, keratoderma, epidermal naevi,
chilblains;
high blood pressure,
polycystic ovary syndrome (PCOS),
asthma,
cystic fibrosis,
osteoarthritis,
lupus erythematosus (LE) or inflammatory rheumatic disorders such as, for example rheumatoid arthritis,
vasculitis,
wasting (cachexia),
gout,
ischemia/reperfusion syndrome,
acute respiratory distress syndrome (ARDS)
viral diseases and infections
lipodystrophy and lipodystrophic conditions, also for treating adverse drug effect;
myophathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent.

According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPY Y5 antagonists), $PY_{Y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose cotransporter (SGLT) inhibitors, 11beta-hydroxy steroid dehydrogenase-1 (11beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

Synthesis Schemes

Compounds of general formula (I) may be prepared by reductive amination reactions of cyclic amines (II) with aldehydes (III) under acidic, basic or neutral conditions applying hydrogen donating reagents such as sodium borohydride, lithium borohydride, sodium triacetoxy borohydride, lithium aluminum hydride, or hydrogen.

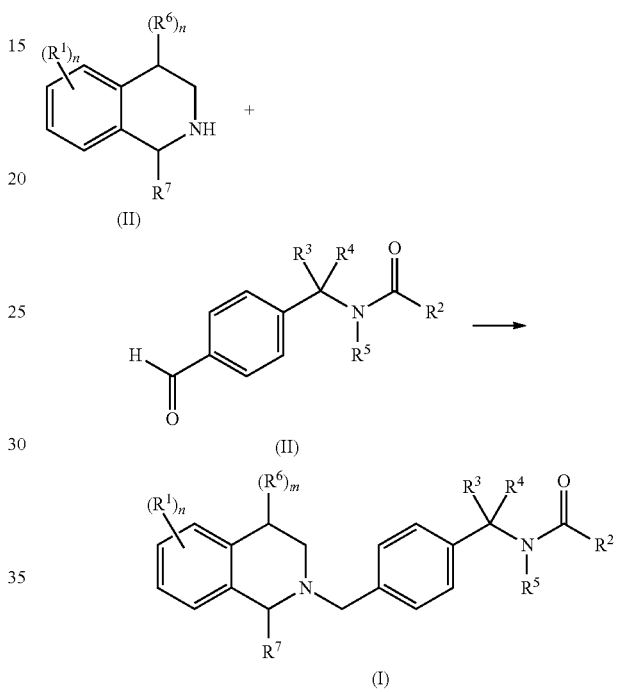

Compounds of general formula (I) may alternatively be prepared by amide coupling reactions of carboxylic acids (V) with amines (IV) mediated by coupling reagents such as for example 2-(1H-benzotriazol-1-yl)-1,1,3,3-tetramethyluronium tetrafluoroborat (TBTU), O-(7-azabenzotriazol-1-yl)-N,N,N',N'-tetramethyluroniumhexafluoro-phosphate (HATU), 1-chloro-N,N-2-trimethylpropenylamine, benzotriazol-1-yloxy)tripyrrolidino-phosphonium hexafluorophosphate and 2-chloro-1,3-dimethyl-2-imidazolinium hexafluorophosphate (CIP).

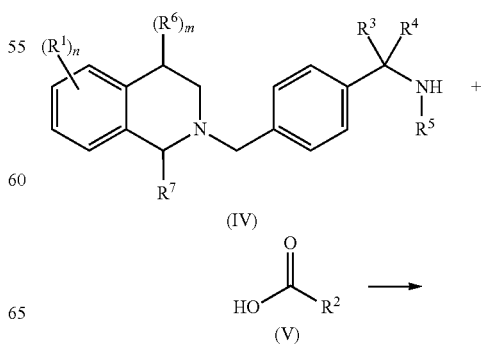

-continued

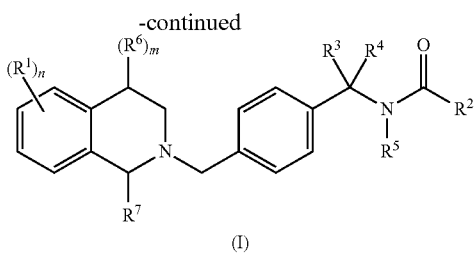

(I)

Compounds of general formula (I) may alternatively be prepared by reactions of carbonyl chlorides or anhydrides (VI) with amines (IV), wherein Z denotes Cl or O(C$_{1-3}$-alkyl).

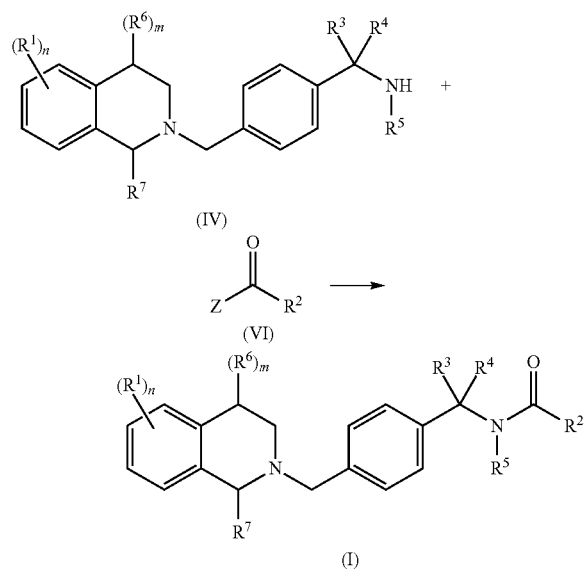

Compounds of general formula (VII) may be prepared by reactions of amines (VIII) with amines (IV) utilizing urea forming reagents such as 1,1'-carbonyldiimidazole or 1,1'-carbonyldi(1,2,4-triazole).

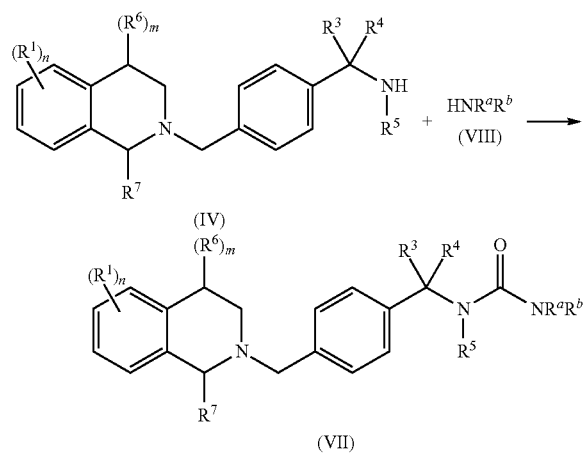

Compounds of general formula (VII) may alternatively be prepared by reactions of carbamoyl chlorides (IX) with amines (IV). N-Succinimidyl-N-alyklcarbamates can be used instead of carbamoyl chlorides.

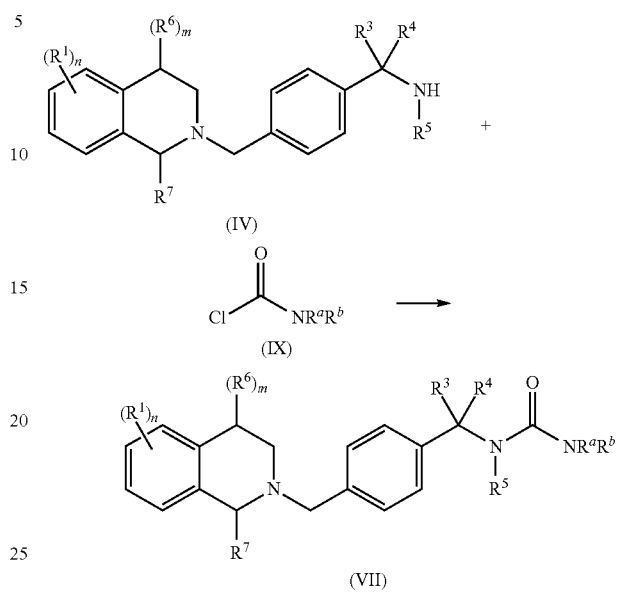

Compounds of general formula (XI) may be prepared by reactions of isocyanates (X) with amines (IV).

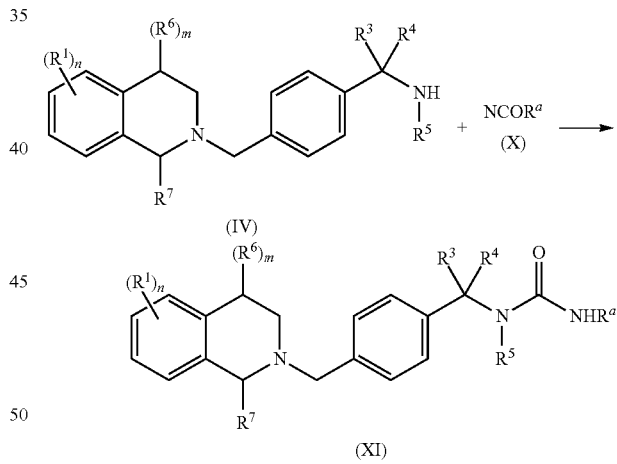

Compounds of general formula (XII) may be prepared by amide coupling reactions of carboxylic acids (XIII) with amines (XIV) mediated by coupling reagents such as for example 2-(1H-benzotriazol-1-yl)-1,1,3,3-tetramethyluronium tetrafluoroborat (TBTU), O-(7-azabenzotriazol-1-yl)-N,N,N',N'-tetramethyluroniumhexafluoro-phosphate (HATU), 1-chloro-N,N-2-trimethylpropenylamine, benzotriazol-1-yloxy)tripyrrolidino-phosphonium hexafluorophosphate and 2-chloro-1,3-dimethyl-2-imidazolinium hexafluorophosphate (CIP).

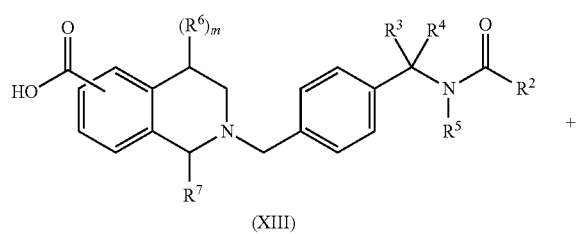

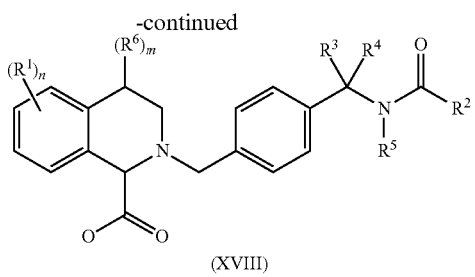

Compounds of general formula (XX) may be prepared by reactions of chloro formates (XXI) with amines (IV).

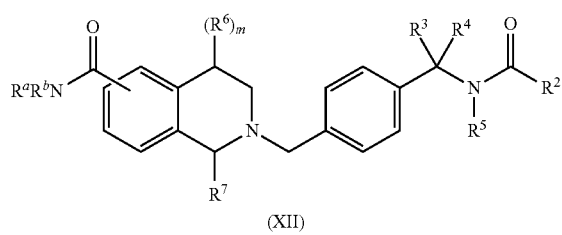

Compounds of general formula (XV) may be prepared by alkylation reactions of alcohols (XVI) with alyklhalides (XVII) wherein Z denotes a leaving group such as a halogen atom or a sulfonate or triflate group.

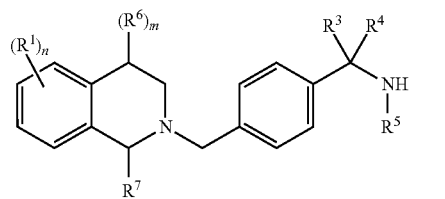

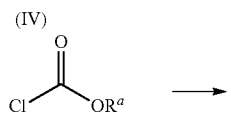

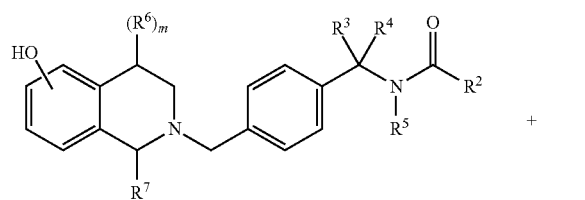

Carboxylic acids of general formula (XVIII) may be prepared by hydrolysis of esters (XIX) under aqueous conditions either using acidic or basic conditions wherein Y is an alkyl group such as methyl or ethyl.

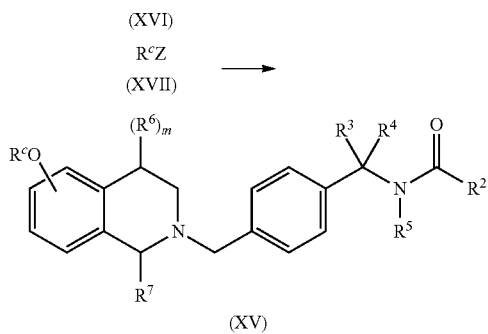

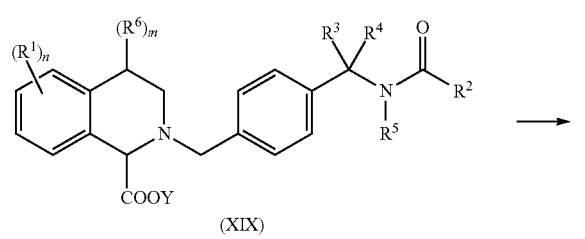

The synthetic routes presented may rely on the use of protecting groups. For example, reactive groups present, such as hydroxy, carbonyl, carboxy, amino, alkylamino or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

Experimental Part

The Examples that follow are intended to illustrate the present invention without restricting it. The terms "ambient temperature" and "room temperature" are used interchangeably and designate a temperature of about 20° C.

ABBREVIATIONS

| | |
|---|---|
| aq. | aqueous |
| ACN | acetonitrile |
| AcOH | acetic acid |
| BOC | tert-butoxy-carbonyl- |
| CDI | 1,1'-carbonyldiimidazole |
| CDT | 1,1'-carbonyldi(1,2,4-triazole) |
| CIP | 2-chloro-1,3-dimethyl-2-imidazolinium hexafluorophosphate |
| DAST | diethylaminosulfur trifluoride |
| DCM | dichloro methane |
| Dess-Martin periodinane | 1,1,1-Tris(acetyloxy)-1,1-dihydro-1,2-benziodoxol-3-(1H)-one |
| DIPE | diisopropyl ether |
| DIPEA | N,N-diisopropylethylamine |
| DMA | N,N-dimethylacetamide |
| DMF | N,N-dimethylformamide |
| EtOAc | ethyl acetate |
| EtOH | ethanol |
| Et$_2$O | diethyl ether |
| Ex | example |
| HATU | O-(7-azabenzotriazol-1-yl)-N,N,N',N'-tetramethyluroniumhexafluorophosphate |
| MeOH | methanol |
| Pd/C | palladium on activated carbon |
| r.t. | room temperature (about 20° C.) |
| sat. | saturated |
| SFC | supercritical fluid chromatography |
| TEA | triethylamine |
| TFA | trifluoroacetic acid |
| THF | tetrahydrofuran |
| THP | tetrahydropyran |
| TBTU | 2-(1H-benzotriazol-1-yl)-1,1,3,3-tetramethyluronium tetrafluoroborate |

Preparation of Starting Compounds

Example I

N-(1-(4-Formylphenyl)ethyl)acetamide

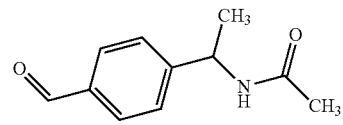

Described in U.S. Pat. No. 6,455,528, 2002.

Example II

[(S)-1-(4-Formyl-phenyl)-ethyl]-carbamic acid tert-butyl ester

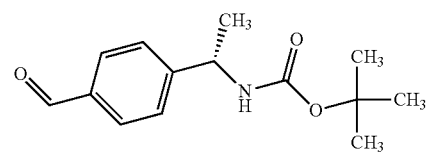

Described in WO 2008/81910.

Example III (S)—N-(1-(4-Formylphenyl)ethyl)acetamide

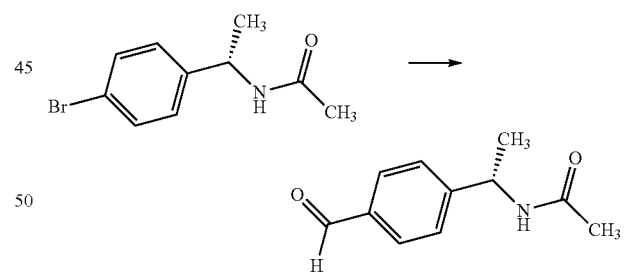

To 20.0 g (74.3 mmol) (S)—N-(1-(4-bromophenyl)ethyl)acetamid (WO 2012/01107) in 300 mL THF are added dropwise 75.0 mL (187 mmol)N-butyllithium (2.5 M in THF) at −78° C. and stirred for 1 h. 10.0 mL (124 mmol) DMF are added dropwise to the mixture at −78° C. and stirred for 2 h. After that aq. NH$_4$Cl solution is added and extracted with EtOAc. The organic layer is dried over Na$_2$SO$_4$, filtered and concentrated by evaporation. The residue is purified by column chromatography (silica gel, MeOH:DCM).

$C_{11}H_{13}NO_2$ (M=191.2 g/mol)

ESI-MS: 192 [M+H]$^+$

R$_f$: 0.50 (silica gel, MeOH:DCM, 1:0)

Example IV (S)-Cyclopropanecarboxylic acid [1-(4-formyl-phenyl)-ethyl]-amide

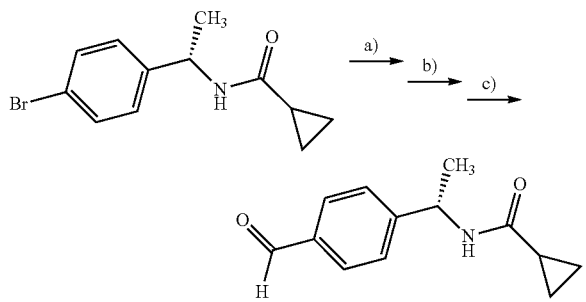

a) To 5.0 g (19 mmol) (S)-cyclopropanecarboxylic acid [1-(4-bromo-phenyl)-ethyl]-amide (WO 2012/01107) in 40 mL MeOH are added 125 mg (0.600 mmol) palladium-(II)-acetate, 620 mg (1.10 mmol) 1,1'-bis(diphenylphosphino)-ferrocene and 4.6 g (56 mmol) sodium acetate. The mixture is stirred at 100° C. and 5 bar CO atmosphere over night. After that time, the mixture is filtered over celite and the filtrate is concentrated by evaporation. The residue is purified by column chromatography (silica gel; gradient hexane/EtOAc 1:0→1:4) to yield the desired product.

$C_{14}H_{17}NO_3$ (M=247.2 g/mol),
ESI-MS: 248 [M+H]$^+$
$R_t$ (HPLC): 0.72 min (method A)

b) To 1.95 g (7.89 mmol) 4-[1-(S)-(cyclopropanecarbonyl-amino)-ethyl]-benzoic acid methyl ester in 20 mL THF are added slowly 685 mg (31.6 mmol) lithium borhydride and stirred at 50° C. over night. The reaction is quenched by the addition of a sat. aq. NaHCO$_3$-solution and extracted three times with EtOAc. The organic layers are combined, dried over MgSO$_4$, filtered and the solvent is removed in vacuo.

$C_{13}H_{17}NO_2$ (M=219.3 g/mol)
ESI-MS: 220 [M+H]$^+$
$R_t$ (HPLC): 0.74 min (method B)

c) To 1.20 g (5.47 mmol) (S)-cyclopropanecarboxylic acid [1-(4-hydroxymethyl-phenyl)-ethyl]-amide in 20 mL acetone are added 2.38 g (27.4 mmol) manganese dioxide and stirring is continued at r.t. over night. The mixture is filtered over celite and the filtrate is concentrated by evaporation to yield the desired product.

$C_{13}H_{15}NO_2$ (M=217.3 g/mol)
ESI-MS: 218 [M+H]$^+$
$R_t$ (HPLC): 0.65 min (method B)

Example V

4-Methyl-2-propionylamino-thiazole-5-carboxylic acid

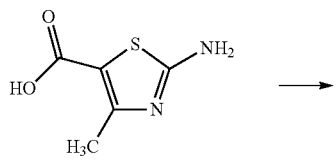

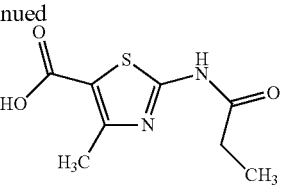

13.4 g (84.7 mmol) 2-Amino-4-methyl-thiazole-5-carboxylic acid and 35.8 mL (279 mmol) propionic anhydride in 90 mL propionic acid are stirred at 100° C. over night. The resulting mixture is cooled to r.t., 200 mL water are added and stirred for 30 min. The precipitate is filtered off and treated with 200 mL water. After stirring for 30 min the precipitate is filtered off, washed with water and dried at 50° C.

$C_8H_{10}N_2O_3S$ (M=214.2 g/mol)
ESI-MS: 215 [M+H]$^+$
$R_t$ (HPLC): 0.68 min (method J)

Example VI (R)-2,2-Difluoro-cyclopropanecarboxylic acid

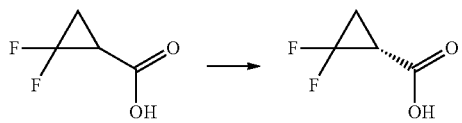 [SMILES: O=C(O)C1CC1(F)F ; O=C(O)[C@H]1CC1(F)F]

40 mL (0.27 mol) (R)-1-(4-Methoxyphenyl)ethylamine are added to 33 g (0.27 mol) 2,2-difluorocyclopropanecarboxylic acid in 250 mL ACN. After stirring at r.t. over night the precipitate is filtered off and recrystallised (3×) from ACN. The precipitate is dissolved in 150 mL DCM and extracted with 100 mL aq. HCl solution (c=1 mol/L).

The aq. layer is separated and extracted three times with DCM. The organic layers are combined, dried over Na$_2$SO$_4$, filtered and the solvent is removed in vacuo.

$C_4H_4F_2O_2$ (M=122.1 g/mol)
ESI-MS: 121 [M−H]$^−$
$R_t$ (GC): 26.1 min (method K)

Example VII ((R)-2,2-Difluoro-cyclopropyl)-methanol

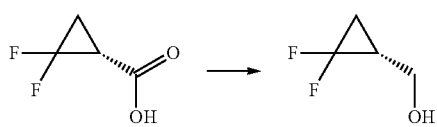

7.2 g (59 mmol) (R)-2,2-Difluoro-cyclopropanecarboxylic acid in 100 mL THF are cooled to 0° C. and 35 mL (77 mmol) lithium aluminum hydride solution (2.2 M in 2-methyltetrahydrofuran) are added dropwise. After stirring over night at r.t. the reaction mixture is cooled to 0° C. and slowly quenched by the addition of 3 mL water and 3 mL aq. NaOH solution (c=4 mol/L). The resulting mixture is stirred for 30 min, filtered, washed with THF and the filtrate is concentrated by evaporation. The residue is added to Et$_2$O, dried over Na$_2$SO$_4$, filtered and the solvent is removed in vacuo.

$C_4H_4F_2O$ (M=108.1 g/mol)
$R_t$ (GC): 15.4 min (method K)

Example VIII (S)-2,2-Difluoro-cyclopropanecarboxylic acid

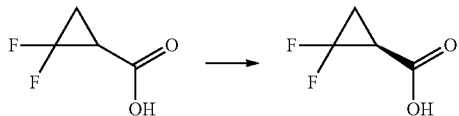 [SMILES: O=C(O)C1CC1(F)F ; O=C(O)[C@@H]1CC1(F)F]

14.9 g (98.3 mmol) (S)-4-Methoxy-alpha-methylbenzylamine are added to 12.0 g (98.3 mmol) 2,2-difluorocyclopropanecarboxylic acid in 120 mL ACN. After stirring over night at r.t. the precipitate is filtered off and recrystallised (3×) from ACN. The precipitate is added to 60 mL DCM, and extracted with 31 mL aq. HCl solution (c=1 mol/L). The aq. layer is separated and extracted three times with DCM, the organic layers are combined, dried over $Na_2SO_4$, filtered and the solvent is removed in vacuo.

$C_4H_4F_2O_2$ (M=122.1 g/mol)
ESI-MS: 121 [M−H]$^-$
$R_t$ (GC): 27.3 min (method K)

Example IX ((S)-2,2-Difluoro-cyclopropyl)-methanol

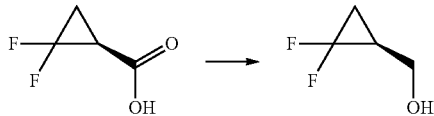 [SMILES: O=C(O)[C@@H]1CC1(F)F ; OC[C@@H]1CC1(F)F]

3.6 g (29 mmol) (S)-2,2-Difluoro-cyclopropanecarboxylic acid in 10 mL THF are cooled to 0° C. 38 mL (38 mmol) lithium aluminum hydride solution (1.0 M in THF) are added slowly. After stirring over night at r.t. the reaction mixture is cooled to 0° C. and quenched by the addition of 2 mL water, 2 mL aq. NaOH solution (c=4 mol/L) and 8 mL water. The resulting mixture is stirred for 30 min, filtered over celite/$Na_2SO_4$ and the filtrate is concentrated by evaporation.

$C_4H_4F_2O$ (M=108.1 g/mol)
$R_t$ (GC): 15.7 min (method K)

Example X

1-Benzyloxy-2-methoxy-3-(2-nitro-vinyl)-benzene

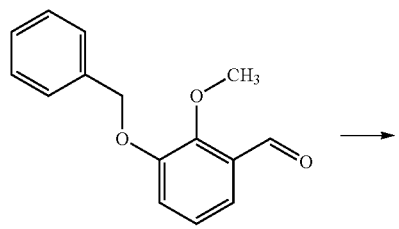

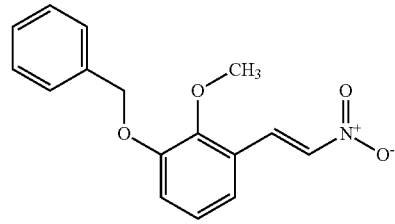

4.46 g (18.4 mmol) 3-Benzyloxy-2-methoxy-benzaldehyde (see CN 102451178), 2.96 mL (55.2 mmol) nitromethane and 1.42 g (18.4 mmol) ammonium acetate in 30 mL AcOH are stirred at 100° C. over night. The reaction mixture is cooled to r.t. and quenched by the addition of 20 mL MeOH and 6 mL water. After stirring at r.t. for 1 h, the precipitate is filtered off and dried at 40° C.

$C_{16}H_{15}NO_4$ (M=285.3 g/mol)
ESI-MS: 286 [M+H]$^+$
$R_t$ (HPLC): 1.01 min (method A)

Example XI (3-Benzyloxy-2-methoxy-phenyl)-acetonitrile

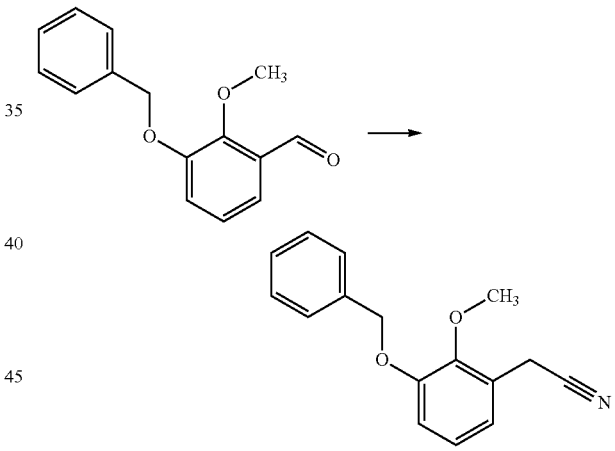

9.3 g (83 mmol) Potassium tert-butoxide in 30 mL 1,2-dimethoxyethane are cooled to −30° C. 9.1 g (45 mmol) toluene-4-sulfonylmethylisocyanide in 30 mL 1,2-dimethoxyethan are added slowly and the resulting mixture is cooled to −50° C. A mixture of 10.0 g (41.3 mmol) 3-benzyloxy-2-methoxy-benzaldehyde (see CN 102451178) in 80 mL 1,2-dimethoxyethane are added within 30 min and stirred for 2 h at −50° C. After that time 60 mL MeOH are added and stirred for 2 h under reflux. The mixture is cooled to r.t., diluted with water and extracted with DCM. The organic layer is dried over $MgSO_4$, filtered and the solvent is removed in vacuo. The residue is purified by column chromatography (silica gel; cyclohexane/EtOAc 4:1) to yield the desired product.

$C_{16}H_{15}NO_2$ (M=253.3 g/mol)
ESI-MS: 254 [M+H]$^+$
$R_t$ (HPLC): 1.09 min (method B)

Example XII 2-(3-Benzyloxy-2-methoxy-phenyl)-ethylamine

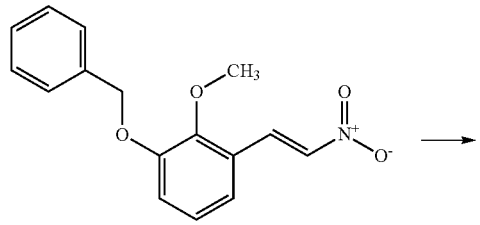

To 13.6 mL (32.6 mmol) lithium aluminum hydride solution (2.4 M in THF) are added dropwise 4.20 g (14.8 mmol) 1-benzyloxy-2-methoxy-3-(2-nitro-vinyl)-benzene (example X) in 20 mL THF at 0° C. After stirring at 0° C. for 2 h the reaction mixture is quenched by the addition of 0.59 mL (33 mmol) water, 8.20 mL (32.6 mmol) aq. NaOH solution (c=4 mol/L) and 1.80 mL (97.9 mmol) water. The resulting mixture is stirred for 20 min and filtered over celite/Na$_2$SO$_4$. The filtrate is concentrated by evaporation and the residue is purified by HPLC (ACN/H$_2$O/NH$_4$OH). After HPLC, ACN is removed in vacuo and the aq. layer is extracted with EtOAc. The organic layer is dried over MgSO$_4$, filtered and the solvent is removed in vacuo.

C$_{16}$H$_{19}$NO$_2$ (M=257.3 g/mol)
ESI-MS: 258 [M+H]$^+$
R$_t$ (HPLC): 0.89 min (method A)

Example XIII 2-(3-Benzyloxy-2-methoxy-phenyl)-ethylamine

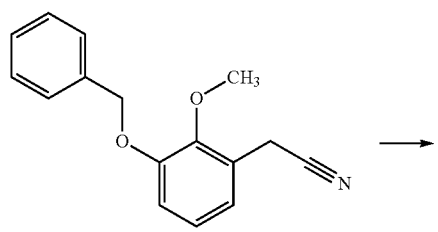

7.7 g (34 mmol) (3-Benzyloxy-2-methoxy-phenyl)-acetonitrile (example XI) in 100 mL methanolic ammonia (c=7 mol/L) are hydrogenated (3 bar, r.t.) using 250 mg Raney-nickel. The reaction mixture is filtered and the solvent is removed in vacuo.

C$_{16}$H$_{19}$NO$_2$ (M=257.3 g/mol)
ESI-MS: 258 [M+H]$^+$
R$_t$ (HPLC): 0.89 min (method A)

Example XIV 2-(3-Benzyloxy-2-methoxy-phenyl)-ethylamine

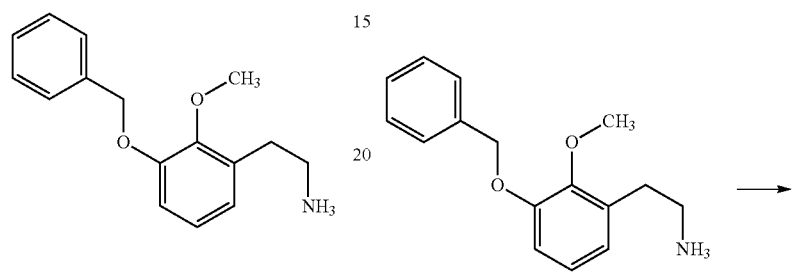

To 7.8 g (30 mmol) 2-(3-benzyloxy-2-methoxy-phenyl)-ethylamine and 3.4 mL (46 mmol) formaldehyde (37% solution in water) in 80 mL DCM are added slowly 4.7 mL (61 mmol) TFA and the resulting mixture is stirred at r.t. over night. The reaction is neutralised by the addition of a sat. aq. NaHCO$_3$ solution and extracted three times with DCM. The organic layers are combined, washed with a sat. aq. NaCl solution, dried over MgSO$_4$, filtered and the solvent is removed in vacuo.

C$_{17}$H$_{19}$NO$_2$ (M=269.3 g/mol)
ESI-MS: 270 [M+H]$^+$
R$_t$ (HPLC): 0.87 min (method A)

Example XV

6-Benzyloxy-5-methoxy-3,4-dihydro-1H-isoquinoline-2-carboxylic acid tert-butyl ester

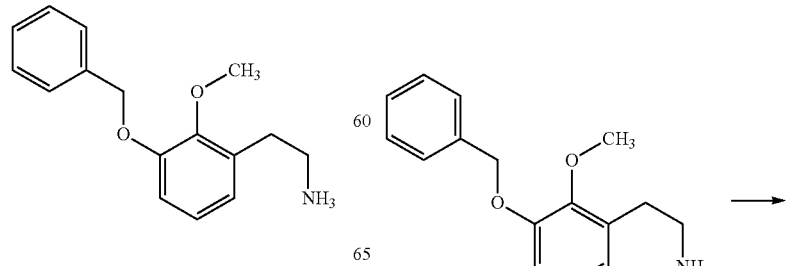

-continued

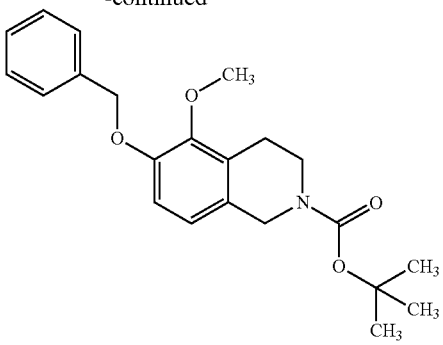

To 8.2 g (30 mmol) 6-benzyloxy-5-methoxy-1,2,3,4-tetrahydro-isoquinoline (example XIV) in 60 mL THF/30 mL water are added 5.1 mL (37 mmol) TEA and 8.0 g (37 mmol) di-tert-butyldicarbonate. The resulting mixture is stirred at r.t. for 4 h. Water is added and the mixture is extracted with EtOAc. The organic layer is separated and dried over MgSO$_4$, filtered and the solvent is removed in vacuo. The residue is purified by column chromatography (silica gel; gradient DCM:MeOH 100:0→95:5) to yield the desired product.

$C_{22}H_{27}NO_4$ (M=369.5 g/mol)
ESI-MS: 314 [M+H-isoButene]$^+$
R$_t$ (HPLC): 1.09 min (method A)

Example XVI

6-Hydroxy-5-methoxy-3,4-dihydro-1H-isoquinoline-2-carboxylic acid tert-butyl ester

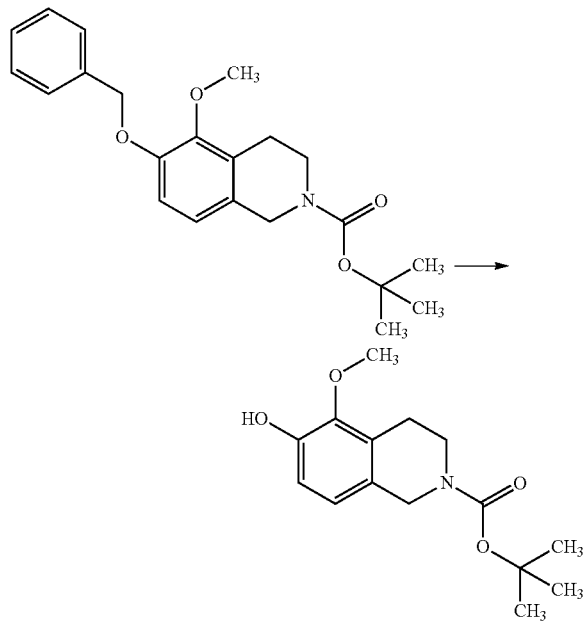

7.8 g (21 mmol) 6-Benzyloxy-5-methoxy-3,4-dihydro-1H-isoquinoline-2-carboxylic acid tert-butyl ester (example XV) in 150 mL THF are hydrogenated (3 bar, r.t.) using 250 mg Pd/C (10%). The reaction mixture is filtered, the solvent is removed in vacuo and the residue is purified by HPLC (ACN/H$_2$O/NH$_3$). After HPLC, ACN is removed in vacuo and the aq. layer is extracted with EtOAc. The organic layer is dried over MgSO$_4$, filtered and the solvent is removed in vacuo.

$C_{15}H_{21}NO_4$ (M=279.3 g/mol)
ESI-MS: 225 [M+H-isoButene]$^+$
R$_t$ (HPLC): 0.82 min (method A)

Example XVII

5-Chloro-6-methoxy-1,2,3,4-tetrahydro-isoquinoline

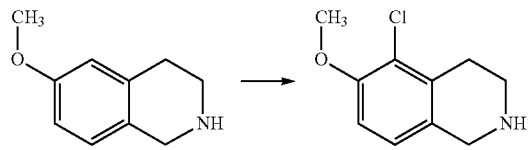

5.0 g (31 mmol) 6-Methoxy-1,2,3,4-tetrahydro-isoquinoline in 30 mL AcOH are cooled to 0° C. and 2.7 mL (34 mmol) sulfuryl chloride are added slowly. The resulting mixture is stirred at r.t. over night. The solvent is removed in vacuo and the residue is treated with toluene/ACN 1:1. The precipitate is filtered off and dried at 40° C. in vacuo.

$C_{10}H_{12}ClNO$ (M=197.7 g/mol)
ESI-MS: 198 [M+H]$^+$
R$_t$ (HPLC): 0.73 min (method A)

Example XVIII

5-Chloro-6-hydroxy-3,4-dihydro-1H-isoquinoline-2-carboxylic acid tert-butyl ester

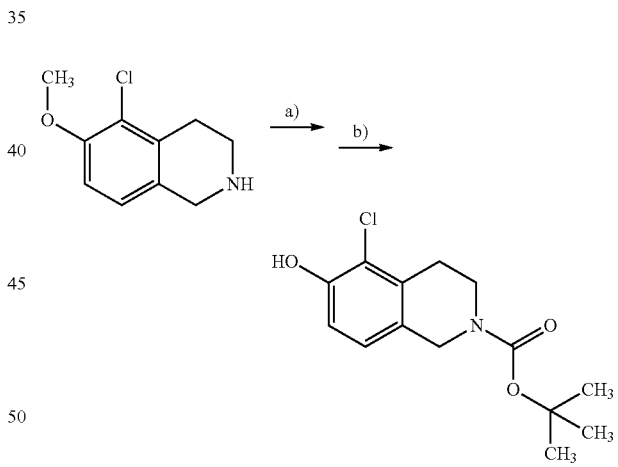

a) 2.7 g (14 mmol) 5-Chloro-6-methoxy-1,2,3,4-tetrahydro-isoquinoline (example XVII) in 20 mL hydrobromic acid (48% solution in water) are stirred at 100° C. over night. The precipitate is filtered off and dried at r.t. over night.

$C_9H_{10}ClNO*HBr$ (M=264.5 g/mol)
ESI-MS: 184 [M+H]$^+$
R$_t$ (HPLC): 0.15 min (method A)

b) To 3.6 g (14 mmol) 5-chloro-1,2,3,4-tetrahydro-isoquinolin-6-ol hydrobromide in 20 mL THF/10 mL water are added 3.8 mL (27 mmol) TEA and 3.6 g (16 mmol) di-tert-butyldicarbonate. The resulting mixture is stirred at r.t. for 4 h. Water is added and the mixture is extracted with EtOAc. The organic layer is separated and dried over MgSO$_4$, filtered and the solvent is removed in vacuo.

$C_{14}H_{18}ClNO_3$ (M=283.8 g/mol)
ESI-MS: 282 [M−H]⁻
$R_t$ (HPLC): 0.71 min (method A)

Example XIX

5-Bromo-6-cyclopropylmethoxy-benzaldehyde

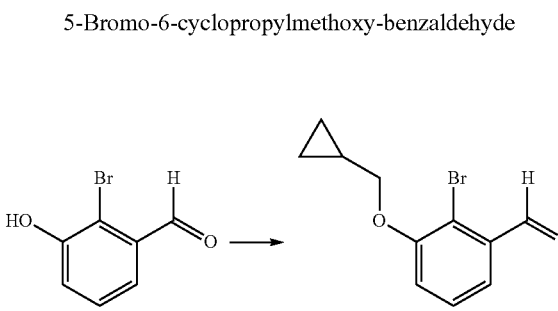

300 mg (1.49 mmol) 2-Bromo-3-hydroxy-benzaldehyde, 302 mg (2.24 mmol) (bromomethyl)cyclopropane and 412 mg (2.99 mmol) $K_2CO_3$ in 3 mL DMF are stirred at 80° C. over night. Afterwards the reaction mixture is diluted with water and extracted with EtOAc. The organic layer is separated and dried over $Na_2SO_4$, filtered and the solvent is removed in vacuo.

$C_{11}H_{11}BrO_2$ (M=255.1 g/mol)
ESI-MS: 255 [M+H]⁺
$R_t$ (HPLC): 0.96 min (method A)

Example XX

2-Bromo-1-cyclopropylmethoxy-3-(2-nitro-vinyl)-benzene

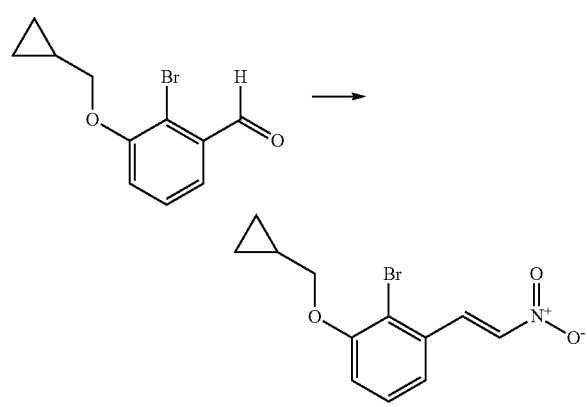

380 mg (1.49 mmol) 5-Bromo-6-cyclopropylmethoxy-benzaldehyde (example XIX), 239 μL (4.47 mmol) nitromethane and 115 mg (1.49 mmol) ammonium acetate in 1.2 mL AcOH are stirred at 100° C. for 2 h. The reaction mixture is cooled to r.t. and quenched by the addition of 4 mL MeOH and 0.9 mL water. After stirring at r.t. for 1 h the precipitate is filtered off and dried at 40° C.

$C_{12}H_{12}BrNO_3$ (M=298.1 g/mol)
ESI-MS: 298 [M+H]⁺
$R_t$ (HPLC): 1.02 min (method A)

Example XXI 2-(2-Bromo-3-cyclopropylmethoxy-phenyl)-ethylamine

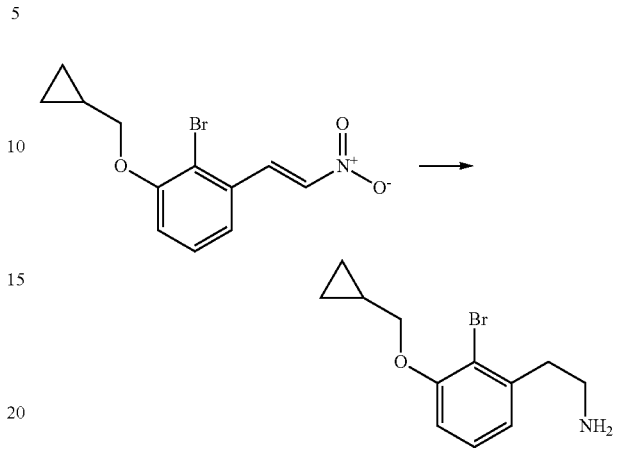

To 0.92 mL (2.2 mmol) lithium aluminum hydride solution (2.4 M in THF) are added dropwise 300 mg (1.01 mmol) 2-bromo-1-cyclopropylmethoxy-3-(2-nitro-vinyl)-benzene (example XX) in 5 mL THF at 0° C. After stirring at 0° C. for 2 h the reaction mixture is quenched by the addition of 36 μL (2.0 mmol) water, 0.50 mL (2.0 mmol) aq. NaOH solution (c=4 mol/L) and 0.11 mL (6.0 mmol) water. The resulting mixture is stirred for 20 min, filtered over celite/$Na_2SO_4$ and the filtrate is concentrated by evaporation. The residue is purified by HPLC (ACN/$H_2O$/$NH_4OH$).

$C_{12}H_{16}BrNO$ (M=270.2 g/mol)
ESI-MS: 270 [M+H]⁺
$R_t$ (HPLC): 0.88 min (method A)

Example XXII

5-Bromo-6-cyclopropylmethoxy-1,2,3,4-tetrahydro-isoquinoline

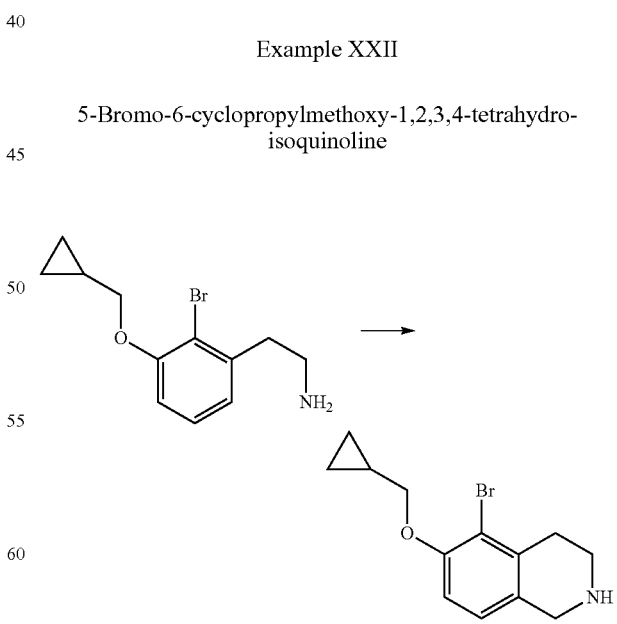

To 40 mg (0.15 mmol) 2-(2-bromo-3-cyclopropylmethoxy-phenyl)-ethylamine (example XXI) and 17 μL (0.22 mmol) formaldehyde (37% solution in water) in 2 mL DCM are added slowly 23 μL (0.30 mmol) TFA and the resulting mixture is stirred at r.t. over night. The reaction mixture is concentrated by evaporation $C_{13}H_{16}BrNO$ (M=282.2 g/mol)
ESI-MS: 282 [M+H]$^+$
$R_t$ (HPLC): 0.90 min (method A)

Example XXIII

5-Bromo-6-isopropoxy-3,4-dihydro-1H-isoquinoline hydrochloride

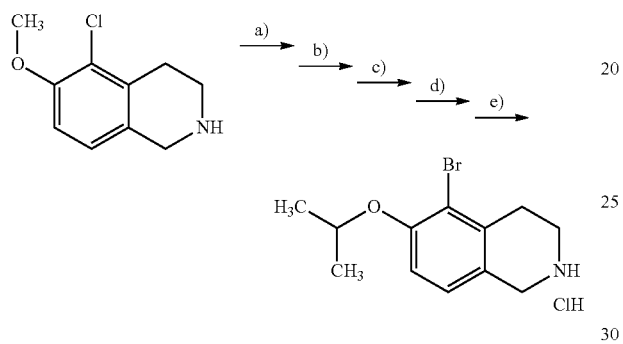

a) To 1.6 g (6.1 mmol) 6-methoxy-1,2,3,4-tetrahydro-isoquinoline in 15 mL AcOH are added 0.34 mL (6.7 mmol) bromine and the mixture is stirred at r.t. for 3 h. The precipitate is filtered off and dried at r.t.

$C_{10}H_{12}BrNO$ (M=242.1 g/mol)
ESI-MS: 242 [M+H]$^+$
$R_t$ (HPLC): 0.74 min (method A)

b) 880 mg (3.64 mmol) 5-Bromo-6-methoxy-1,2,3,4-tetrahydro-isoquinoline in 5 mL hydrobromic acid (48% solution in water) are stirred at 100° C. over night. The resulting mixture is cooled to r.t., the precipitate is filtered off and dried at r.t.

$C_9H_{10}BrNO*HBr$ (M=309.0 g/mol)
ESI-MS: 228 [M+H]$^+$
$R_t$ (HPLC): 0.20 min (method A)

c) To 650 mg (2.10 mmol) 5-bromo-1,2,3,4-tetrahydro-isoquinolin-6-ol hydrobromide in 8 mL THF/4 mL water are added 733 μL (5.26 mmol) TEA and 551 mg (2.53 mmol) di-tert-butyldicarbonate. The resulting mixture is stirred at r.t for 4 h. Water is added and the mixture is extracted with EtOAc. The organic layer is concentrated by evaporation and the residue is purified by HPLC (ACN/H$_2$O/NH$_4$OH).

$C_{14}H_{18}BrNO_3$ (M=328.2 g/mol)
ESI-MS: 272 [M+H-isoButene]$^+$
$R_t$ (HPLC): 0.72 min (method A)

d) 200 mg (0.609 mmol) 5-Bromo-6-hydroxy-3,4-dihydro-1H-isoquinoline-2-carboxylic acid tert-butyl ester, 112 mg (0.914 mmol) 2-bromopropane and 168 mg (1.22 mmol) K$_2$CO$_3$ in 3 mL DMF are stirred at 80° C. over night. After that time the reaction mixture is diluted with water and extracted with DCM. The organic layer is dried over Na$_2$SO$_4$, filtered and the solvent is removed in vacuo. The residue is purified by HPLC (ACN/H$_2$O/NH$_4$OH).

$C_{17}H_{24}BrNO_3$ (M=370.3 g/mol)
ESI-MS: 314 [M+H-isoButene]$^+$
$R_t$ (HPLC): 1.13 min (method A)

e) To 190 mg (0.513 mmol) 5-bromo-6-isopropoxy-3,4-dihydro-1H-isoquinoline-2-carboxylic acid tert-butyl ester in 5 mL dioxane are added 513 μL (2.05 mmol) HCl solution in dioxane (c=4 mol/L). After stirring at r.t. over night the reaction mixture is treated with DIPE, the precipitate is filtered off and dried at 40° C.

$C_{12}H_{16}BrNO*HCl$ (M=306.6 g/mol)
ESI-MS: 270 [M+H]$^+$
$R_t$ (HPLC): 0.88 min (method A)

Example XXIV

5-Bromo-6-(2,2-difluoro-cyclopropylmethoxy)-1,2,3,4-tetrahydro-isoquinoline hydrochloride

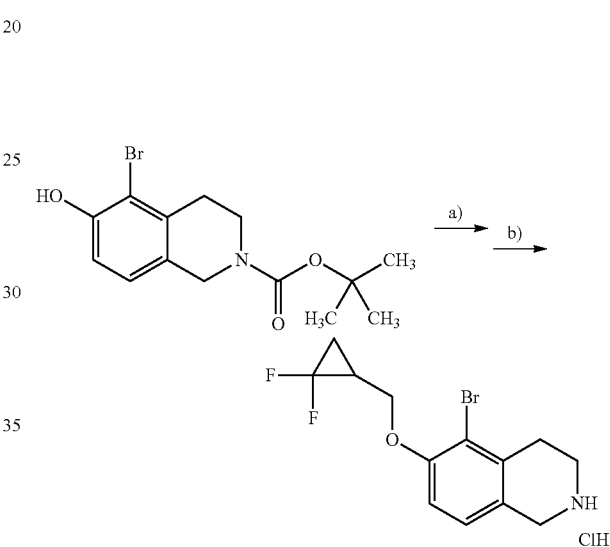

a) 180 mg (0.548 mmol) 5-Bromo-6-hydroxy-3,4-dihydro-1H-isoquinoline-2-carboxylic acid tert-butyl ester (see under Example XIII), 94 mg (0.91 mmol) 1-bromomethyl-2,2-difluorocyclopropane and 152 mg (1.10 mmol) K$_2$CO$_3$ in 3 mL DMF are stirred at 80° C. over night. After that time the reaction mixture is diluted with water and extracted with EtOAc. The organic layer is dried over Na$_2$SO$_4$, filtered and the solvent is removed in vacuo. The residue is purified by HPLC (ACN/H$_2$O/NH$_4$OH).

$C_{18}H_{22}BrF_2NO_3$ (M=418.3 g/mol)
ESI-MS: 362 [M+H-isoButene]$^+$
$R_t$ (HPLC): 1.09 min (method A)

b) To 165 mg (0.394 mmol) 5-bromo-6-(2,2-difluoro-cyclopropylmethoxy)-3,4-dihydro-1H-isoquinoline-2-carboxylic acid tert-butyl ester in 3 mL dioxane are added 394 μL (1.58 mmol) HCl solution in dioxane (c=4 mol/L). After stirring at r.t. over night the reaction mixture is treated with DIPE, the precipitate is filtered off and dried at 40° C.

$C_{13}H_{14}BrF_2NO*HCl$ (M=354.6 g/mol)
ESI-MS: 318 [M+H]$^+$
$R_t$ (HPLC): 0.86 min (method A)

Example XXV

6-Hydroxy-5-methoxy-1-methyl-3,4-dihydro-1H-isoquinoline-2-carboxylic acid tert-butyl ester

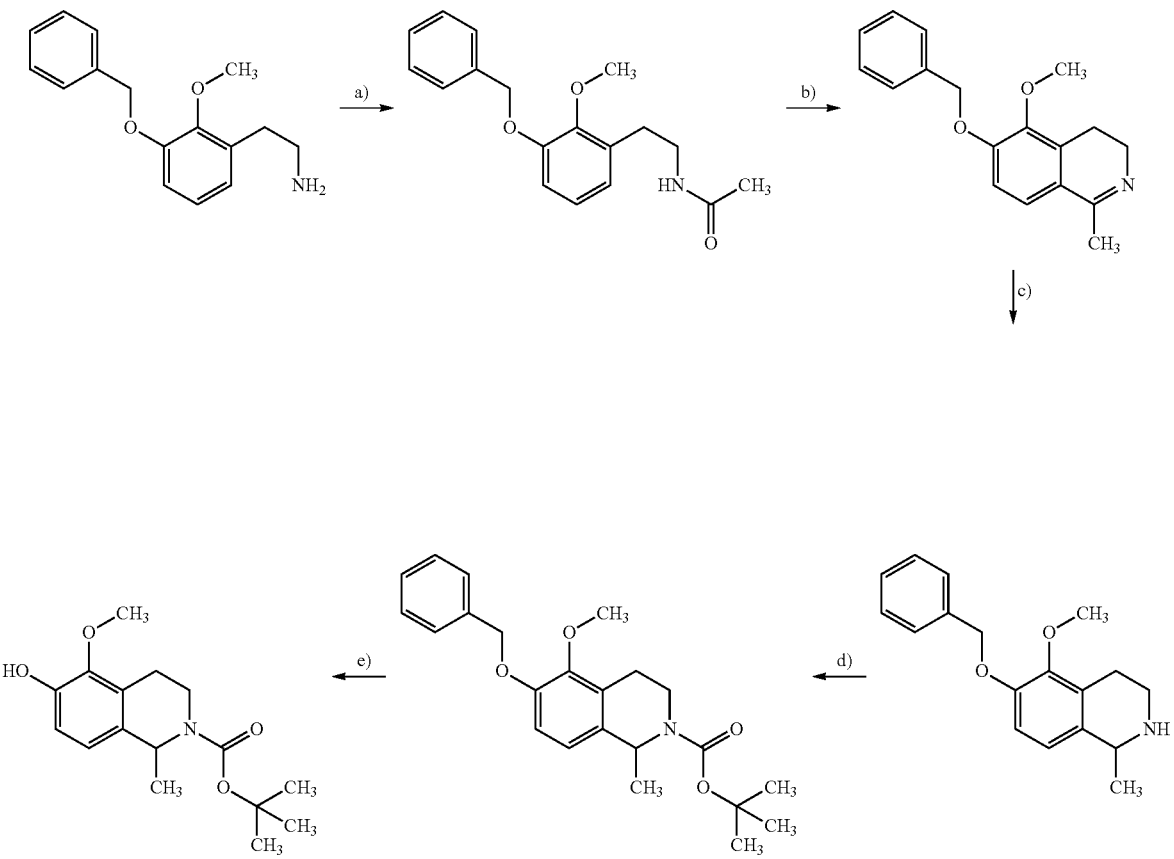

a) To 3.2 g (12 mmol) 2-(3-benzyloxy-2-methoxy-phenyl)-ethylamine (example XIII) and 2.6 mL TEA (19 mmol) in 40 mL DCM are added slowly 1.2 mL (13 mmol) acetic anhydride. After stirring at r.t. for 2 h, the reaction mixture is quenched by addition of water and extracted three times with DCM. The organic layers are combined, dried over MgSO$_4$, filtered and the solvent is removed in vacuo.

$C_{18}H_{21}NO_3$ (M=299.4 g/mol)
ESI-MS: 300 [M+H]$^+$
R$_t$ (HPLC): 0.99 min (method B)

b) To 3.7 g (12 mmol) N-[2-(3-benzyloxy-2-methoxy-phenyl)-ethyl]-acetamide in 40 mL DCM are added 5.7 g (27 mmol) phosphorpentachloride in small portions and the mixture is stirred at r.t. for 2 h. 100 mL water are added and stirring is continued for 30 min. After that time the mixture is extracted three times with DCM and the combined aq. layers are alkalized with aq. NaOH solution (c=4 mol/L). The aq. layer is extracted three times with DCM, the combined organic layers are dried over MgSO$_4$, filtered and the solvent is removed in vacuo.

$C_{18}H_{19}NO_2$ (M=281.3 g/mol)
R$_t$ (HPLC): 0.80 min (method B)

c) To 3.5 g (12 mmol) 6-benzyloxy-5-methoxy-1-methyl-3,4-dihydro-isoquinoline in 40 mL MeOH are added 1.4 g (37 mmol) sodium borhydride in small portions at 0° C. and the mixture is stirred for 2 h. After that time, water is added and the mixture is extracted three times with EtOAc. The organic layers are combined, dried over MgSO$_4$, filtered and the solvent is removed in vacuo.

$C_{18}H_{21}NO_2$ (M=283.4 g/mol)
ESI-MS: 284 [M+H]$^+$
R$_t$ (HPLC): 0.91 min (method A)

d) To 3.0 g (11 mmol) 6-benzyloxy-5-methoxy-1-methyl-1,2,3,4-tetrahydro-isoquinoline in 30 mL THF/15 mL water are added 1.8 mL (13 mmol) TEA and 2.8 g (13 mmol) di-tert-butyldicarbonate. The resulting mixture is stirred at r.t. for 4 h.

Water is added and the mixture is extracted with EtOAc. The organic layer is dried over MgSO$_4$, filtered and the solvent is removed in vacuo. The residue is purified by column chromatography (silica gel; gradient DCM:MeOH 100:0→95:5).

$C_{23}H_{29}NO_4$ (M=383.5 g/mol)
ESI-MS: 328 [M+H-isoButene]$^+$
R$_t$ (HPLC): 1.28 min (method A)

e) 2.4 g (6.3 mmol) 6-Benzyloxy-5-methoxy-1-methyl-3,4-dihydro-1H-isoquinoline-2-carboxylic acid tert-butylester in 150 mL THF are hydrogenated (3 bar, r.t.) using 150 mg Pd/C (10%). The reaction mixture is filtered and the solvent is removed in vacuo.

$C_{16}H_{23}NO_4$ (M=293.4 g/mol)
ESI-MS: 238 [M+H-isoButene]$^+$
R$_t$ (HPLC): 1.05 min (method B)

Example XXVI 6-(2,2-Difluoro-cyclopropylmethoxy)-1-methyl-1,2,3,4-tetrahydro-isoquinoline

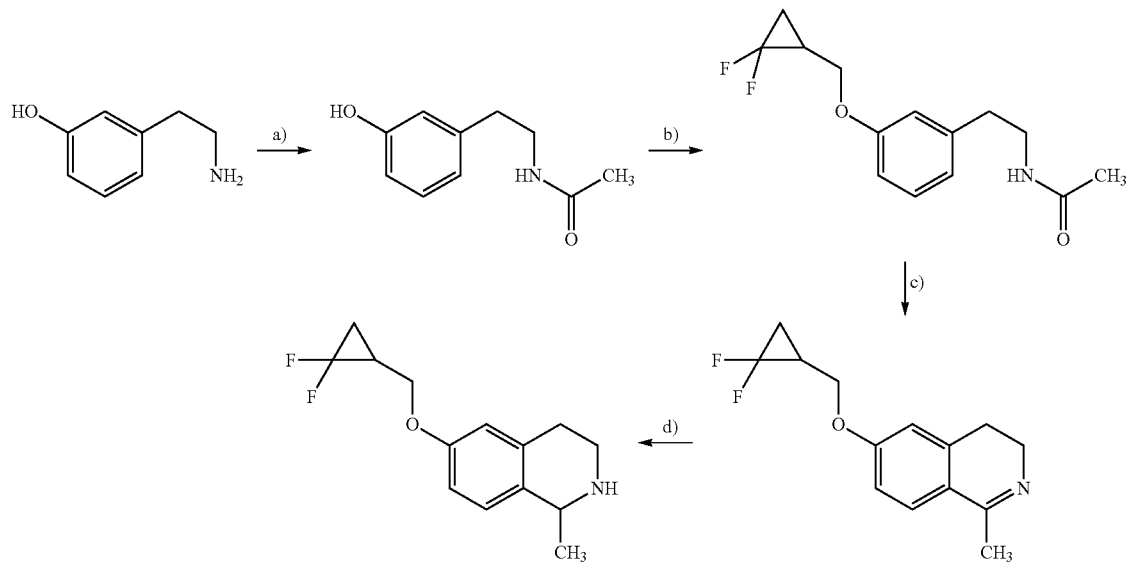

a) To 500 mg (3.65 mmol) 3-(2-amino-ethyl)-phenol and 0.77 mL (5.5 mmol) TEA in 6.7 mL DCM are added slowly 0.36 mL (3.8 mmol) acetic anhydride at 0° C. After stirring for 2 h at r.t., sat. aq. NaHCO$_3$ solution is added and the mixture is extracted with DCM. The organic layer is dried over Na$_2$SO$_4$, filtered and the solvent is removed in vacuo.

$C_{10}H_{13}NO_2$ (M=179.2 g/mol)

ESI-MS: 180 [M+H]$^+$

R$_t$ (HPLC): 0.65 min (method B)

b) 100 mg (0.558 mmol) N-[2-(3-hydroxy-phenyl)-ethyl]-acetamide, 114 mg (0.670 mmol) 1-bromomethyl-2,2-difluorocyclopropane and 154 mg (1.12 mmol) K$_2$CO$_3$ in 1.5 mL DMF are stirred at 80° C. over night. After that time, the reaction mixture is diluted with water and extracted with DCM. The organic layer is dried over Na$_2$SO$_4$, filtered and the solvent is removed in vacuo.

$C_{14}H_{17}F_2NO_2$ (M=269.3 g/mol)

ESI-MS: 270 [M+H]$^+$

R$_t$ (HPLC): 0.78 min (method A)

c) To 100 mg (0.371 mmol) N-{2-[3-(2,2-difluoro-cyclopropylmethoxy)-phenyl]-ethyl}-acetamide in 2 mL DCM are added 170 mg (0.816 mmol) phosphorpentachloride in mall portions and the mixture is stirred at r.t. over night. After that time, the reaction mixture is slowly poured into water and extracted with DCM. The aq. layer is alkalized with aq. NaOH solution (c=4 mol/L) and extracted with DCM. The organic layer is dried over Na$_2$SO$_4$, filtered and the solvent is removed in vacuo.

$C_{14}H_{15}F_2NO$ (M=251.3 g/mol)

ESI-MS: 252 [M+H]$^+$

R$_t$ (HPLC): 0.85 min (method A)

d) To 82 mg (0.33 mmol) 6-(2,2-difluoro-cyclopropylmethoxy)-1-methyl-3,4-dihydro-isoquinoline in 2 mL MeOH are added 35 mg (0.93 mmol) sodium borhydride in small portions at 0° C. and the mixture is stirred for 2 h. After that time, water is added and the mixture is extracted three times with EtOAc. The organic layers are combined, dried over MgSO$_4$, filtered and the solvent is removed in vacuo.

$C_{14}H_{17}F_2NO$ (M=253.3 g/mol)

ESI-MS: 254 [M+H]$^+$

R$_t$ (HPLC): 0.87 min (method A)

Example XXVII

5-Fluoro-6-methoxy-1,2,3,4-tetrahydro-isoquinoline

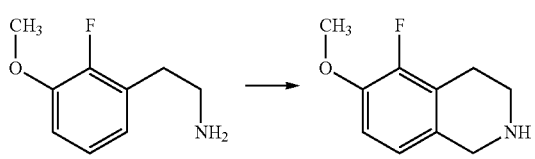

To 1.0 g (5.9 mmol) 2-(2-fluoro-3-methoxy-phenyl)-ethylamine and 0.66 mL (8.9 mmol) formaldehyde (37% solution in water) in 10 mL DCM are added slowly 0.91 mL (12 mmol) TFA and the resulting mixture is stirred at r.t. over night. The reaction mixture is purified by HPLC (ACN/H$_2$O/NH$_4$OH).

$C_{10}H_{12}FNO$ (M=181.2 g/mol)

ESI-MS: 182 [M+H]$^+$

R$_t$ (HPLC): 0.70 min (method A)

Example XXVIII

5-Fluoro-6-methoxy-1-methyl-1,2,3,4-tetrahydro-isoquinoline

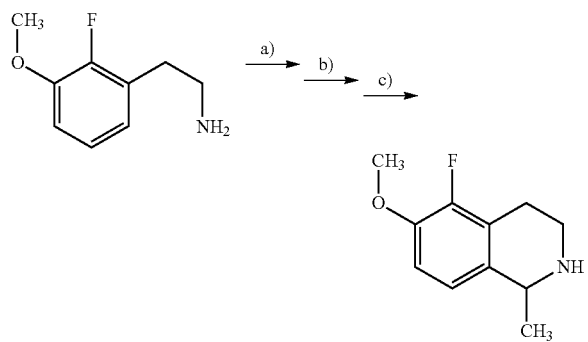

a) To 500 mg (2.96 mmol) 2-(2-fluoro-3-methoxy-phenyl)-ethylamine and 622 μL (3.10 mmol) TEA in 7 mL DCM are added slowly 293 μL (3.83 mmol) acetic anhydride at 0° C. and stirring is continued for 2 h. After that time, the reaction mixture is quenched by the addition of water and extracted three times with DCM. The organic layers are combined, dried over MgSO$_4$, filtered and the solvent is removed in vacuo.

$C_{11}H_{14}FNO_2$ (M=211.2 g/mol)
ESI-MS: 212 [M+H]$^+$
R$_t$ (HPLC): 0.64 min (method A)

b) To 520 mg (2.46 mmol) N-[2-(2-fluoro-3-methoxy-phenyl)-ethyl]-acetamide in 8 mL DCM are added 1.13 g (5.41 mmol) phosphorpentachloride in small portions and the mixture is stirred at r.t. for 2 h. After that time, the reaction mixture is slowly poured into 100 mL water and stirring is continued for 30 min. After that time, the mixture is extracted three times with DCM and the aq. layer is alkalized with aq. NaOH solution (c=4 mol/L). The aq. layer is extracted three times with DCM, the combined organic layers are dried over MgSO$_4$, filtered and the solvent is removed in vacuo.

$C_{11}H_{12}FNO$ (M=193.2 g/mol)
ESI-MS: 194 [M+H]$^+$
R$_t$ (HPLC): 0.61 min (method B)

c) To 320 mg (1.60 mmol) 5-fluoro-6-methoxy-1-methyl-3,4-dihydro-isoquinoline in 5 mL MeOH are added 182 mg (4.81 mmol) sodium borhydride in small portions at 0° C. and stirring is continued for 2 h. The reaction is quenched by the addition of water and the mixture is extracted three times with EtOAc. The organic layers are combined, dried over MgSO$_4$, filtered and the solvent is removed in vacuo.

$C_{11}H_{14}FNO$ (M=195.2 g/mol)
ESI-MS: 196 [M+H]$^+$
R$_t$ (HPLC): 0.71 min (method A)

Example XXIX

Example XXIX.1

5-Difluoromethyl-1,2,3,4-tetrahydro-isoquinoline hydrochloride

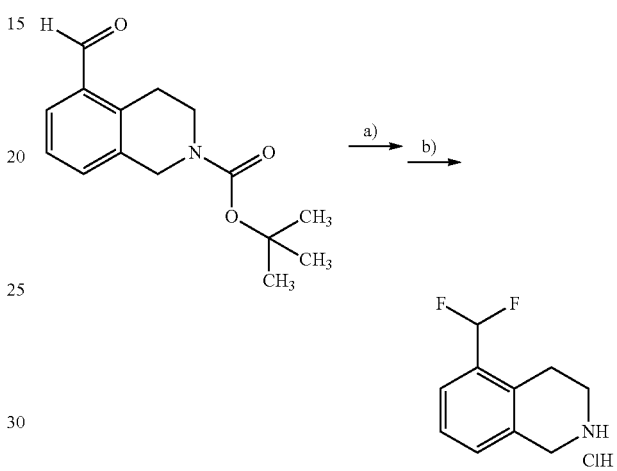

a) To 1.0 g (3.8 mmol) 5-formyl-3,4-dihydro-1H-isoquinoline-2-carboxylic acid tert-butyl ester (Bioorg. Med. Chem. 17, 2009, 7850) in 5 mL DCM are added slowly 853 μL (6.51 mmol) DAST and 44 μL (0.77 mmol) EtOH (reaction in plastic vial). The reaction mixture is stirred at r.t. over night. After that time the reaction mixture is quenched by the addition of sat. aq. NaHCO$_3$ solution and extracted with DCM. The organic layer is dried over MgSO$_4$, filtered, the solvent is removed in vacuo and the residue is purified by HPLC (ACN/H$_2$O/NH$_4$OH).

$C_{15}H_{19}F_2NO_2$ (M=283.3 g/mol)
ESI-MS: 228 [M+H-isoButene]$^+$
R$_t$ (HPLC): 1.00 min (method A)

b) To 550 mg (1.94 mmol) 5-difluoromethyl-3,4-dihydro-1H-isoquinoline-2-carboxylic acid tert-butyl ester in 3 mL dioxane are added 1.94 mL (7.76 mmol) HCl solution in dioxane (c=4 mol/L). After stirring at r.t. over night the reaction mixture is treated with DIPE, the precipitate is filtered off and dried at 40° C.

$C_{10}H_{11}F_2N*HCl$ (M=219.7 g/mol)
ESI-MS: 184 [M+H]$^+$
R$_t$ (HPLC): 0.71 min (method A)

The following compounds are prepared analogously to example XXIX.1

| Ex. | Starting material | Product structure | ESI-MS | HPLC retention time (method) [min] |
|---|---|---|---|---|
| XXIX.1 | [structure: 5-formyl-N-Boc-tetrahydroisoquinoline] | [structure: 5-(difluoromethyl)-1,2,3,4-tetrahydroisoquinoline·HCl] | 184 [M + H]⁺ | 0.71 (A) |
| XXIX.2 | [structure: 6-formyl-N-Boc-tetrahydroisoquinoline] | [structure: 6-(difluoromethyl)-1,2,3,4-tetrahydroisoquinoline·HCl] | 184 [M + H]⁺ | 0.72 (A) |

Example XXX

2,3,5,6,7,8-Hexahydro-1,4-dioxa-7-aza-phenanthrene hydrochloride

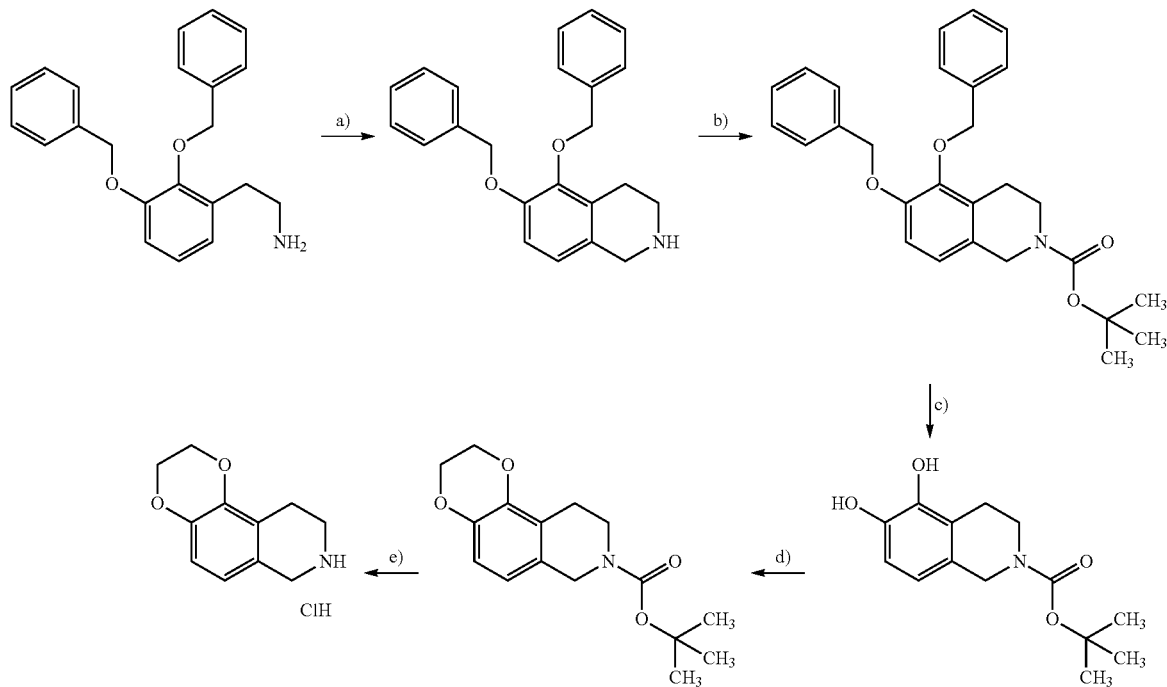

a) To 1.3 g (3.9 mmol) 2-(2,3-bis-benzyloxy-phenyl)-ethylamine (Chimie therapeutique 8, 1973, 308) and 0.44 mL (8.8 mmol) formaldehyde (37% solution in water) in 10 mL DCM are added slowly 0.60 mL (7.8 mmol) TFA and the resulting mixture is stirred at r.t. over night. The reaction is neutralised by the addition of a sat. aq. NaHCO₃ solution and extracted with DCM. The organic layer is dried over MgSO₄, filtered and the solvent is removed in vacuo.

$C_{23}H_{23}NO_2$ (M=345.4 g/mol)
ESI-MS: 346 [M+H]$^+$
$R_t$ (HPLC): 1.05 min (method A)

b) To 1.2 g (3.5 mmol) 5,6-bis-benzyloxy-1,2,3,4-tetrahydro-isoquinoline in 5 mL THF/2.5 mL water are added 0.97 mL (7.0 mmol) TEA and 0.91 g (4.2 mmol) di-tert-butyldicarbonate. The resulting mixture is stirred at r.t. for 4 h. After that time the reaction mixture is quenched by the addition of water and extracted with EtOAc. The organic layer is dried over MgSO$_4$, filtered and the solvent is removed in vacuo.

$C_{28}H_{31}NO_4$ (M=445.6 g/mol)
ESI-MS: 390 [M+H-isoButene]$^+$
$R_t$ (HPLC): 1.18 min (method A)

c) 500 g (1.12 mmol) 5,6-Bis-benzyloxy-3,4-dihydro-1H-isoquinoline-2-carboxylic acid tert-butyl ester in 10 mL THF are hydrogenated (3 bar, r.t.) using 30 mg Pd/C (10%). The reaction mixture is filtered and the solvent is removed in vacuo. The residue is purified by HPLC (ACN/H$_2$O/NH$_4$OH).

$C_{14}H_{19}NO_4$ (M=265.3 g/mol)
ESI-MS: 264 [M−H]$^-$
$R_t$ (HPLC): 0.70 min (method A)

d) 250 mg (0.942 mmol) 5,6-Dihydroxy-3,4-dihydro-1H-isoquinoline-2-carboxylic acid tert-butyl ester, 530 mg (2.83 mmol) 1,2-dibromoethane and 520 mg (3.77 mmol) K$_2$CO$_3$ in 3 mL DMF are stirred at 80° C. over night. After that time, the reaction mixture is diluted with water and extracted with DCM. The organic layer is dried over MgSO$_4$, filtered and the solvent is removed in vacuo. The residue is purified by HPLC (ACN/H$_2$O/NH$_4$OH).

$C_{16}H_{21}NH_4$ (M=291.3 g/mol)
ESI-MS: 236 [M+H-isoButene]$^+$
$R_t$ (HPLC): 0.97 min (method A)

e) To 110 mg (0.378 mmol) 2,3,5,8-tetrahydro-6H-1,4-dioxa-7-aza-phenanthrene-7-carboxylic acid tert-butyl ester in 3 mL dioxane are added 1.94 mL (7.76 mmol) HCl solution in dioxane (c=4 mol/L). After stirring at r.t. over night the reaction mixture is treated with DIPE, the precipitate is filtered off and dried at 40° C.

$C_{11}H_{13}NO_2$*HCl (M=227.7 g/mol)
ESI-MS: 192 [M+H]$^+$
$R_t$ (HPLC): 0.65 min (method A)

Example XXXI

Example XXXI.1 (General Route)

5-Cyclobutoxy-1,2,3,4-tetrahydro-isoquinoline hydrochloride

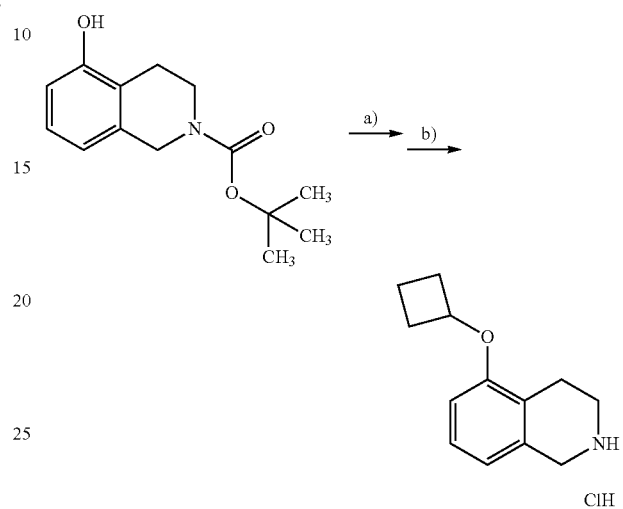

a) 300 mg (1.20 mmol) 5-Hydroxy-3,4-dihydro-1H-isoquinoline-2-carboxylic acid tert-butyl ester, 243 mg (1.81 mmol) cyclobutyl bromide and 332 mg (2.41 mmol) K$_2$CO$_3$ in 5 mL DMF are stirred at 80° C. over night. After that time, the reaction mixture is diluted with water and extracted with EtOAc. The organic layer is dried over MgSO$_4$ and the solvent is removed in vacuo. The residue is purified by HPLC.

$C_{18}H_{25}NO_3$ (M=303.4 g/mol)
ESI-MS: 248 [M+H-isoButene]$^+$
$R_t$ (HPLC): 1.12 min (method A)

b) To 475 mg (1.57 mmol) 5-cyclobutoxy-3,4-dihydro-1H-isoquinoline-2-carboxylic acid tert-butyl ester in 5 mL dioxane are added 1.57 mL (6.26 mmol) HCl solution in dioxane (c=4 mol/L). After stirring over night at r.t. the reaction mixture is treated with DIPE, the precipitate is filtered off and dried at 40° C.

$C_{13}H_{17}NO$*HCl (M=239.7 g/mol)
ESI-MS: 204 [M+H]$^+$
$R_t$ (HPLC): 0.89 min (method A)

The following compounds are prepared analogously to example XXXI.1

| Ex. | Starting material | Starting material | Product structure | ESI-MS | HPLC retention time (method) [min] |
|---|---|---|---|---|---|
| XXXI.1 | (5-hydroxy-tetrahydroisoquinoline-Boc structure) | (cyclobutyl-Br) | (5-cyclobutoxy-tetrahydroisoquinoline·HCl) | 204 [M + H]$^+$ | 0.89 (A) |

-continued
| Ex. | Starting material | Starting material | Product structure | ESI-MS | HPLC retention time (method) [min] |
|---|---|---|---|---|---|
| XXXI.2 | 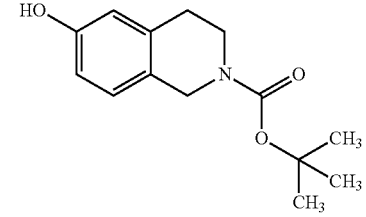 | 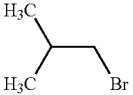 | 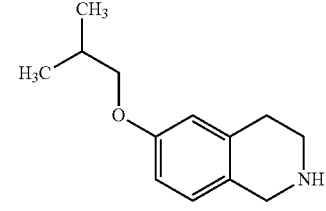 | 206 [M + H]⁺ | 0.93 (A) |
| XXXI.3 | 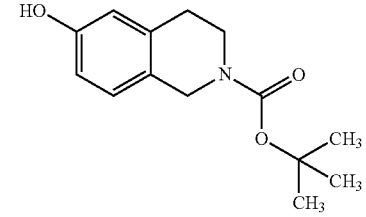 | 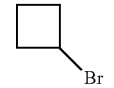 | 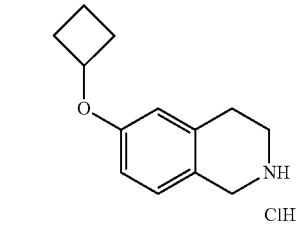 [SMILES: c1cc2c(cc1OC1CCC1)CCNC2 ; Cl] | 204 [M + H]⁺ | 0.74 (B) |
| XXXI.4 | 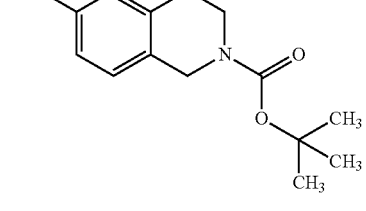 | 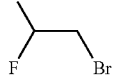 | 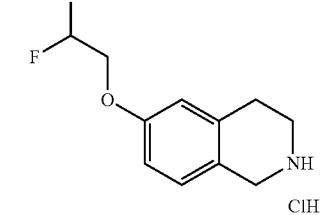 | 214 [M + H]⁺ | 0.74 (A) |
| XXXI.5 | 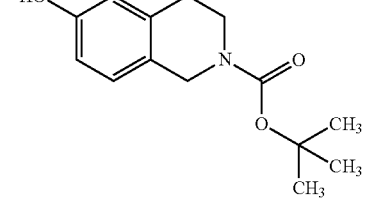 | 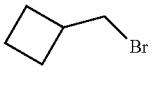 | 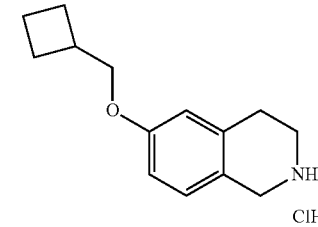 | 218 [M + H]⁺ | 0.95 (A) |
| XXXI.6 | 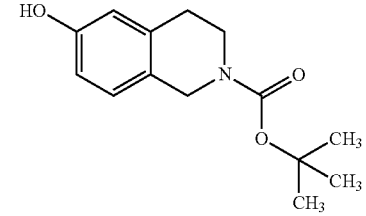 | 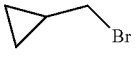 | 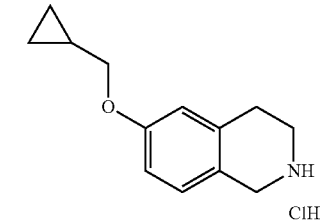 [SMILES: c1cc2c(cc1OCC1CC1)CCNC2 ; Cl] | 204 [M + H]⁺ | 0.82 (A) |
| XXXI.7 | 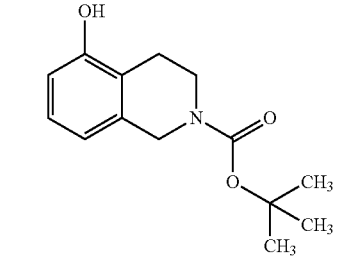 | 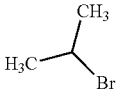 | 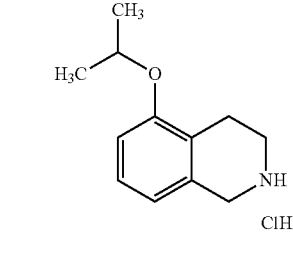 | 192 [M + H]⁺ | 0.83 (A) |

-continued

| Ex. | Starting material | Starting material | Product structure | ESI-MS | HPLC retention time (method) [min] |
|---|---|---|---|---|---|
| XXXI.8 | 5-hydroxy-3,4-dihydroisoquinoline-2(1H)-carboxylic acid tert-butyl ester | 1-bromopropane | 5-propoxy-1,2,3,4-tetrahydroisoquinoline hydrochloride | 192 [M + H]$^+$ | 0.73 (B) |
| XXXI.9 | 5-hydroxy-3,4-dihydroisoquinoline-2(1H)-carboxylic acid tert-butyl ester | (bromomethyl)cyclopropane | 5-(cyclopropylmethoxy)-1,2,3,4-tetrahydroisoquinoline hydrochloride | 204 [M + H]$^+$ | 0.84 (A) |
| XXXI.10 | 6-hydroxy-5-methoxy-3,4-dihydroisoquinoline-2(1H)-carboxylic acid tert-butyl ester | (chloromethyl)cyclopropane | 6-(cyclopropylmethoxy)-5-methoxy-1,2,3,4-tetrahydroisoquinoline hydrochloride | 234 [M + H]$^+$ | 0.73 (B) |
| XXXI.11 | 6-hydroxy-5-methoxy-3,4-dihydroisoquinoline-2(1H)-carboxylic acid tert-butyl ester | 1-(bromomethyl)-2,2-difluorocyclopropane | 6-((2,2-difluorocyclopropyl)methoxy)-5-methoxy-1,2,3,4-tetrahydroisoquinoline hydrochloride | 270 [M + H]$^+$ | 0.74 (B) |
| XXXI.12 | 6-hydroxy-5-methoxy-3,4-dihydroisoquinoline-2(1H)-carboxylic acid tert-butyl ester | bromoethane | 6-ethoxy-5-methoxy-1,2,3,4-tetrahydroisoquinoline hydrochloride | 208 [M + H]$^+$ | 0.75 (A) |

| Ex. | Starting material | Starting material | Product structure | ESI-MS | HPLC retention time (method) [min] |
|---|---|---|---|---|---|
| XXXI.13 | 5-methoxy-6-hydroxy-N-Boc-tetrahydroisoquinoline | isobutyl bromide | 6-isobutoxy-5-methoxy-tetrahydroisoquinoline·HCl | 236 [M + H]⁺ | 0.78 (B) |
| XXXI.14 | 5-methoxy-6-hydroxy-N-Boc-tetrahydroisoquinoline | isopropyl bromide | 6-isopropoxy-5-methoxy-tetrahydroisoquinoline·HCl | 222 [M + H]⁺ | 0.79 (B) |
| XXXI.15 | 5-methoxy-6-hydroxy-N-Boc-tetrahydroisoquinoline | cyclobutyl bromide | 6-cyclobutoxy-5-methoxy-tetrahydroisoquinoline·HCl | 234 [M + H]⁺ | 0.74 (B) |
| XXXI.16 | 5-methoxy-6-hydroxy-N-Boc-tetrahydroisoquinoline | cyclobutylmethyl bromide | 6-(cyclobutylmethoxy)-5-methoxy-tetrahydroisoquinoline·HCl | 248 [M + H]⁺ | 0.80 (B) |
| XXXI.17 | 5-methoxy-6-hydroxy-N-Boc-tetrahydroisoquinoline | n-propyl bromide | 5-methoxy-6-propoxy-tetrahydroisoquinoline·HCl | 222 [M + H]⁺ | 0.73 (B) |

| Ex. | Starting material | Starting material | Product structure | ESI-MS | HPLC retention time (method) [min] |
|---|---|---|---|---|---|
| XXXI.18 | | | | 248 [M + H]⁺ | 0.80 (B) |
| XXXI.19 | | | | 274 [M + H]⁺ | 0.87 (A) |
| XXXI.20 | | | | 238 [M + H]⁺ | 0.89 (A) |
| XXXI.21 | | | | 240 [M + H]⁺ | 0.95 (A) |
| XXXI.22 | | | | 212 [M + H]⁺ | 0.81 (A) |

-continued

| Ex. | Starting material | Starting material | Product structure | ESI-MS | HPLC retention time (method) [min] |
|---|---|---|---|---|---|
| XXXI.23 | | | | 251 [M + H]⁺ | 0.96 (A) |
| XXXI.24 | | | | 252 [M + H]⁺ | 0.94 (A) |
| XXXI.25 | | | | 238 [M + H]⁺ | 0.89 (A) |
| XXXI.26 | | | | 226 [M + H]⁺ | 0.85 (A) |
| XXXI.27 | | | | 222 [M + H]⁺ | 0.71 (B) |

-continued

| Ex. | Starting material | Starting material | Product structure | ESI-MS | HPLC retention time (method) [min] |
|---|---|---|---|---|---|
| XXXI.28 | | | | 284 [M + H]⁺ | 0.75 (B) |
| XXXI.29 | | | | 248 [M + H]⁺ | 0.75 (B) |
| XXXI.30 | | | | 248 [M + H]⁺ | 0.75 (B) |

Example XXXII

Example XXXII.1 (General Route)

6-(2-Cyclopropyl-ethoxy)-1,2,3,4-tetrahydro-iso-quinoline hydrochloride

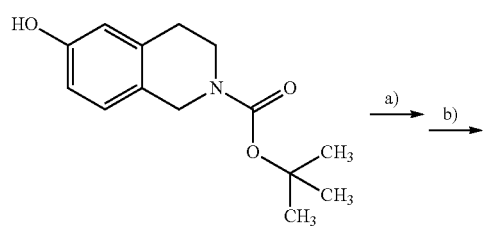

a) ⟶ b)

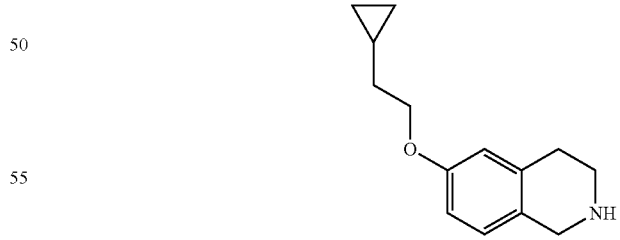

a) 500 mg (2.01 mmol) 6-Hydroxy-3,4-dihydro-1H-iso-quinoline-2-carboxylicacid tert-butyl ester, 173 mg (2.01 mmol) 2-cyclopropylethanol and 526 mg (2.01 mmol) triphenylphosphine in 5 mL THF are stirred at 0° C. under inert gas atmosphere. Then 420 μL (2.01 mmol) diisopropylazodicarboxylate are added slowly and the reaction mixture is stirred at r.t. over night. After that time, the reaction mixture is filtered, concentrated and the residue purified by HPLC.

$C_{19}H_{27}NO_3$ (M=317.4 g/mol)
ESI-MS: 318 [M+H]$^+$
R$_t$ (HPLC): 1.12 min (method A)

b) To 500 mg (1.58 mmol) 6-(2-cyclopropyl-ethoxy)-3,4-dihydro-1H-isoquinoline-2-carboxylic acid tert-butyl ester in 3 mL dioxane are added 1.58 mL (6.30 mmol) HCl solution in dioxane (c=4 mol/L). After stirring over night at r.t. the reaction mixture is treated with DIPE, the precipitate is filtered off and dried at 40° C.

$C_{14}H_{19}NO$*HCl (M=253.8 g/mol)
ESI-MS: 218 [M+H]$^+$
R$_t$ (HPLC): 0.88 min (method A)

The following compounds are prepared analogously to example XXXII.1:

| Ex. | Starting material | Starting material | Product structure | ESI-MS | HPLC retention time (method) [min] |
|---|---|---|---|---|---|
| XXXII.1 | | | | 218 [M + H]$^+$ | 0.88 (A) |
| XXXII.2 | | | | 240 [M + H]$^+$ | 0.81 (A) |
| XXXII.3 | | | | 210 [M + H]$^+$ | 0.74 (A) |
| XXXII.4 | | | | 246 [M + H]$^+$ | 0.81 (A) |
| XXXII.5 | | | | 254 [M + H]$^+$ | 0.85 (A) |

| Ex. | Starting material | Starting material | Product structure | ESI-MS | HPLC retention time (method) [min] |
|---|---|---|---|---|---|
| XXXII.6 | 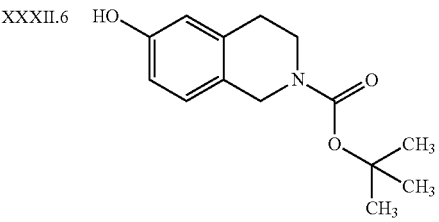 | 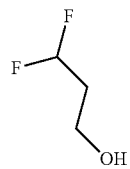 | 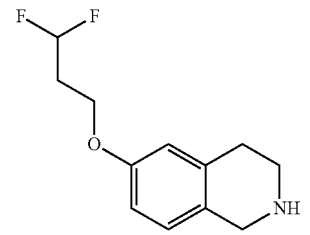 | 228 [M + H]+ | 0.69 (B) |
| XXXII.7 | 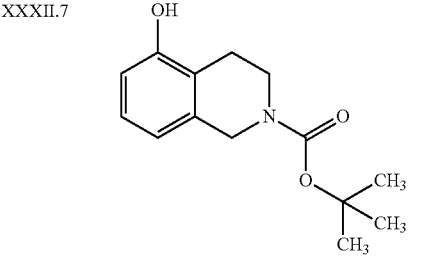 | 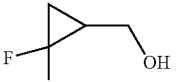 | 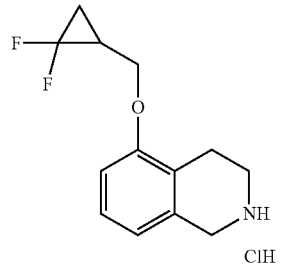 [SMILES: FC1(F)CC1COc1cccc2c1CCNC2 ; Cl] | 240 [M + H]+ | 0.82 (A) |
| XXXII.8 | 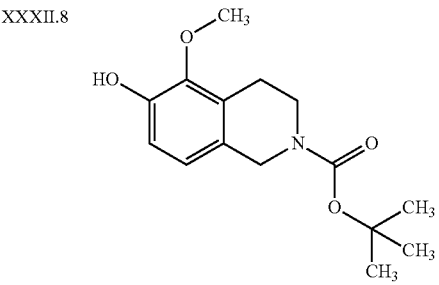 |  | 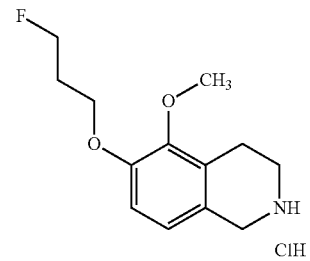 [SMILES: COc1c(OCCCF)ccc2c1CCNC2 ; Cl] | 240 [M + H]+ | 0.67 (B) |
| XXXII.9 | 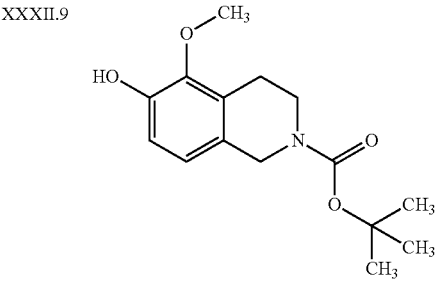 | 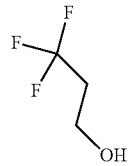 | 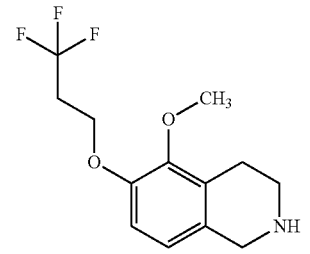 | 276 [M + H]+ | 0.74 (B) |
| XXXII.10 | 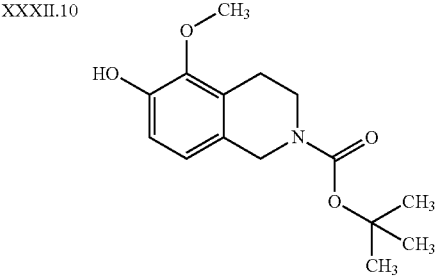 | 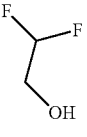 | 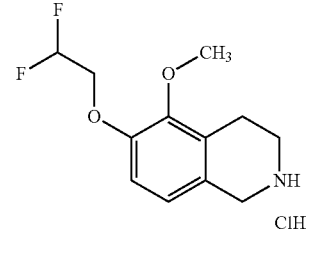 [SMILES: COc1c(OCC(F)F)ccc2c1CCNC2 ; Cl] | 244 [M + H]+ | 0.67 (B) |

-continued

| Ex. | Starting material | Starting material | Product structure | ESI-MS | HPLC retention time (method) [min] |
|---|---|---|---|---|---|
| XXXII.11 | | | | 258 [M + H]+ | 0.72 (B) |
| XXXII.12 | | | | 284 [M + H]+ | 0.77 (B) |
| XXXII.13 | | | | 280 [M + H]+ | 0.86 (A) |
| XXXII.14 | | | | 248 [M + H]+ | 0.78 (A) |
| XXXII.15 | | | | 244 [M + H]+ | 0.80 (A) |

| Ex. | Starting material | Starting material | Product structure | ESI-MS | HPLC retention time (method) [min] |
|---|---|---|---|---|---|
| XXXII.16 | | | | 306 [M + H]⁺ | 0.93 (A) |
| XXXII.17 | | | | 298 [M + H]⁺ | 0.78 (B) |
| XXXII.18 | | | | 240 [M + H]⁺ | 0.80 (A) |
| XXXII.19 | | | | 240 [M + H]⁺ | 0.80 (A) |

Example XXXIII

Example XXXIII.1 (General Route)

(S)-1-{4-[6-(2,2-Difluoro-cyclopropylmethoxy)-3,4-dihydro-1H-isoquinolin-2-ylmethyl]-phenyl}-ethylamine hydrochloride

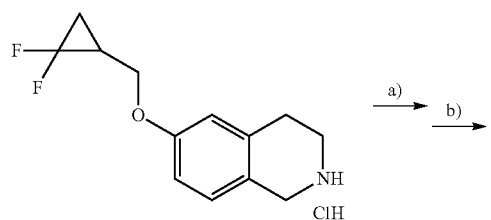

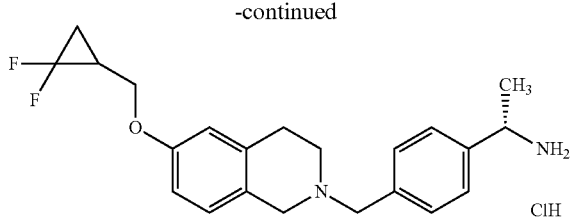

a) To 800 mg (2.94 mmol) 6-(2,2-difluoro-cyclopropylmethoxy)-1,2,3,4-tetrahydro-isoquinoline hydrochloride (example XXXII.2) and 806 mg (3.23 mmol) [(S)-1-(4-formyl-phenyl)-ethyl]-carbamic acid tert-butyl ester (example II) in 8 mL THF are added 504 µL (8.81 mmol) AcOH and the mixture is stirred at r.t. for 10 min. After that time, the resulting mixture is cooled to 0° C. and 934 mg (4.41 mmol)

sodium triacetoxyborohydride are added and the reaction mixture is stirred at r.t. for 2 h. After that time, the reaction is quenched by addition of 500 µl water, the solvent is removed and and the residue is purified by HPLC.

$C_{27}H_{34}F_2N_2O_3$ (M=472.6 g/mol)
ESI-MS: 473 [M+H]$^+$
$R_t$ (HPLC): 1.11 min (method A)

b) To 720 mg (1.52 mmol) ((S)-1-{4-[6-(2,2-difluoro-cyclopropylmethoxy)-3,4-dihydro-1H-isoquinolin-2-ylmethyl]-phenyl}-ethyl)-carbamic acid tert-butyl ester in 3 mL dioxane are added 1.52 mL (6.09 mmol) HCl solution in dioxane (c=4 mol/L). After stirring over night at r.t. the reaction mixture is treated with DIPE, the precipitate is filtered off and dried at 40° C.

$C_{22}H_{26}F_2N_2O$*HCl (M=408.9 g/mol)
ESI-MS: 373 [M+H]$^+$
$R_t$ (HPLC): 0.95 min (method A)

The following compounds are prepared analogously to example XXXIII.1:

| Ex. | Starting material | Product structure | ESI-MS | HPLC retention time (method) [min] |
|---|---|---|---|---|
| XXXIII.1 | | | 373 [M+H]$^+$ | 0.95 (A) |
| XXXIII.2 | | | 297 [M+H]$^+$ | 0.89 (A) |
| XXXIII.3 | | | 335 [M+H]$^+$ | 0.99 (A) |
| XXXIII.4 | | | 345 [M+H]$^+$ | 0.65 (B) |
| XXXIII.5 | | | 337 [M+H]$^+$ | 1.07 (A) |
| XXXIII.6 | | | 387 [M+H]$^+$ | 1.00 (A) |

| Ex. | Starting material | Product structure | ESI-MS | HPLC retention time (method) [min] |
|---|---|---|---|---|
| XXXIII.7 | 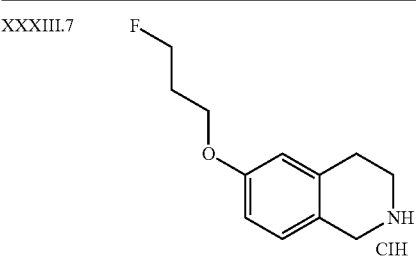 | 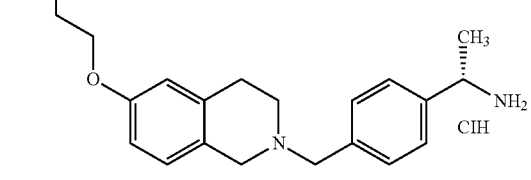 | 343 [M+H]+ | 0.92 (A) |
| XXXIII.8 | 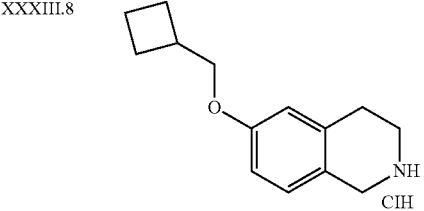 | 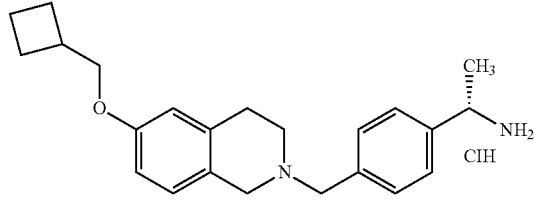 | 351 [M+H]+ | 1.07 (A) |
| XXXIII.9 | 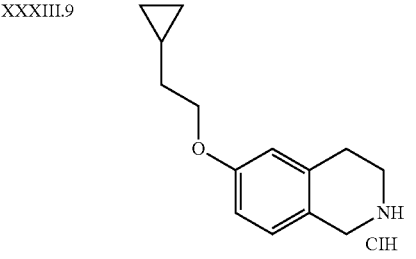 | 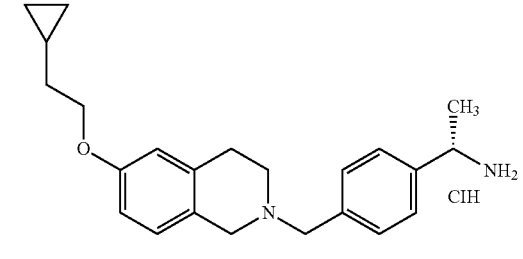 | 351 [M+H]+ | 1.05 (A) |
| XXXIII.10 | 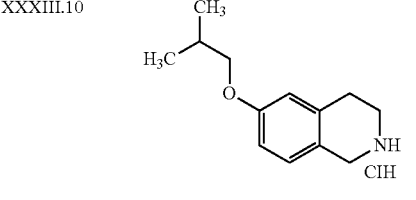 | 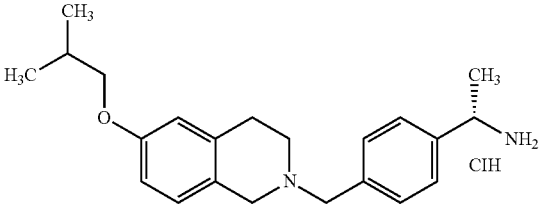 | 339 [M+H]+ | 1.06 (A) |
| XXXIII.11 | 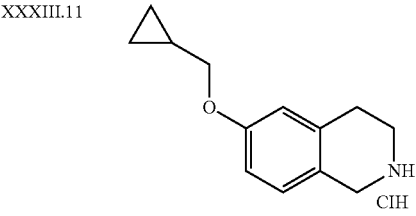 | 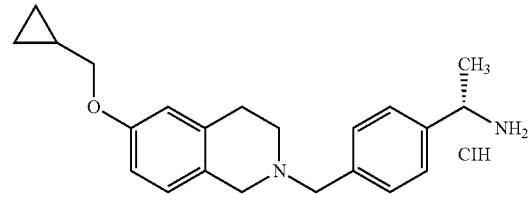 | 339 [M+H]+ | 1.06 (A) |
| XXXIII.12 | 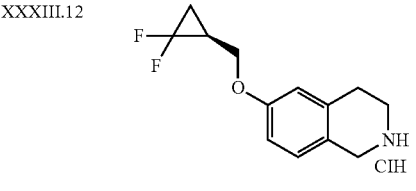 | 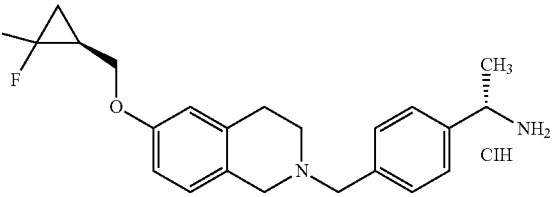 | 373 [M+H]+ | 0.71 (JJ) |

Example XXXIV

2-[4-((S)-1-tert-Butoxycarbonylamino-ethyl)-benzyl]-1,2,3,4-tetrahydro-isoquinoline-5-carboxylic acid methyl ester

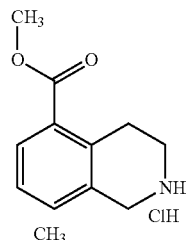

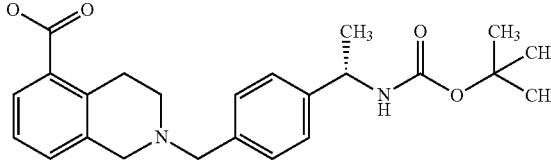

To 600 mg (2.64 mmol) 1,2,3,4-tetrahydro-isoquinoline-5-carboxylic acid methyl ester hydrochloride and 657 mg (2.64 mmol) [(S)-1-(4-formyl-phenyl)-ethyl]-carbamic acid tert-butyl ester (example II) in 5 mL THF are added 452 µL (7.91 mmol) AcOH and the mixture is stirred at r.t. for 10 min. After that time, the resulting mixture is cooled to 0° C., 838 mg (3.95 mmol) sodium triacetoxyborohydride are added and the reaction mixture is stirred at r.t. for 2 h. The reaction is quenched by the addition of 500 µl water and purified by HPLC (ACN/H$_2$O/NH$_3$).

$C_{25}H_{32}N_2O_4$ (M=424.5 g/mol)
ESI-MS: 425 [M+H]$^+$
R$_t$ (HPLC): 1.05 min (method A)

Example XXXV

2-[4-((S)-1-Amino-ethyl)-benzyl]-1,2,3,4-tetrahydro-isoquinoline-5-carboxylic acid methyl ester

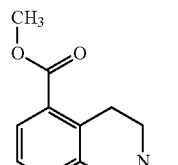

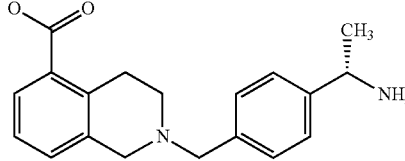

To 630 mg (1.48 mmol) 2-[4-((S)-1-tert-butoxycarbonylamino-ethyl)-benzyl]-1,2,3,4-tetrahydro-isoquinoline-5-carboxylic acid methyl ester (example XXXIV) in 6 mL dioxane are added 1.48 mL (5.94 mmol) HCl solution in dioxane (c=4 mol/L). After stirring over night at r.t. the reaction is neutralised by the addition of a sat. aq. NaHCO$_3$ solution and extracted three times with EtOAc. The organic layers are combined, dried over MgSO$_4$, filtered and the solvent is removed in vacuo.

$C_{20}H_{24}N_2O_2$ (M=324.4 g/mol)
ESI-MS: 325 [M+H]$^+$
R$_t$ (HPLC): 0.88 min (method A)

Example XXXVI

2-[4-((S)-1-Acetylamino-ethyl)-benzyl]-1,2,3,4-tetrahydro-isoquinoline-5-carboxylic acid methyl ester

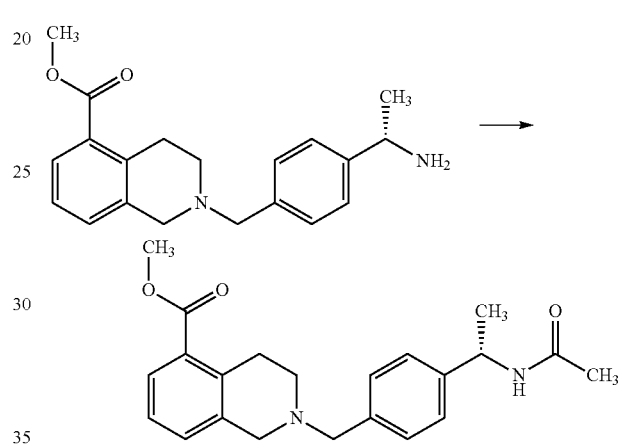

To 475 mg (1.46 mmol) 2-[4-((S)-1-amino-ethyl)-benzyl]-1,2,3,4-tetrahydro-isoquinoline-5-carboxylic acid methyl ester (example XXXV) in 5 mL AcOH are added 152 µL (1.61 mmol) acetic anhydride and the mixture is stirred at r.t. over night. After that time, the reaction mixture is quenched by the addition of a sat. aq. NaHCO$_3$ solution and extracted three times with EtOAc. The organic layers are combined, dried over MgSO$_4$, filtered and the solvent is removed in vacuo.

$C_{22}H_{26}N_2O_3$ (M=366.5 g/mol)
ESI-MS: 367 [M+H]$^+$
R$_t$ (HPLC): 0.85 min (method A)

Example XXXVII

2-[4-((S)-1-Acetylamino-ethyl)-benzyl]-1,2,3,4-tetrahydro-isoquinoline-5-carboxylic acid

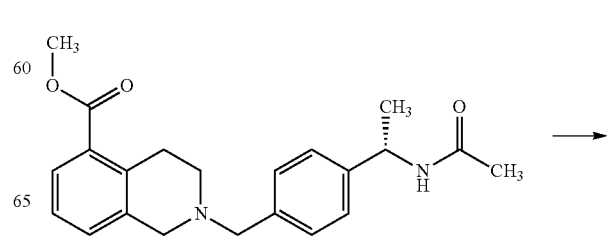

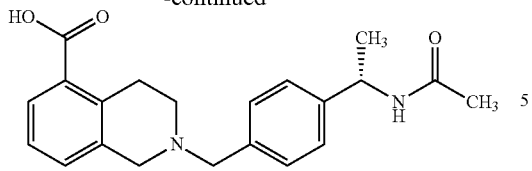

To 560 mg (1.53 mmol) 2-[4-((S)-1-acetylamino-ethyl)-benzyl]-1,2,3,4-tetrahydro-isoquinoline-5-carboxylic acid methyl ester (example XXXVI) in 5 mL MeOH are added 1.68 mL (1.68 mmol) aq. NaOH solution (c=1 mol/L). The reaction mixture is stirred for 1 h at 70° C. After that time, the solvent is partially removed in vacuo and the residue is extracted with DCM. The aq. layer is separated, alkalized with aq. HCl solution (c=1 mol/L) and extracted with EtOAc. The aq. layer was separated and the solvent was removed by lyophilization.

$C_{21}H_{24}N_2O_3$ (M=352.4 g/mol)
ESI-MS: 353 $[M+H]^+$
$R_t$ (HPLC): 0.49 min (method A)

Example XXXVIII

2-[4-((S)-1-Acetylamino-ethyl)-benzyl]-6-hydroxy-1,2,3,4-tetrahydro-isoquinoline-1-carboxylic acid methyl ester

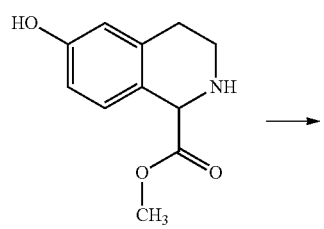

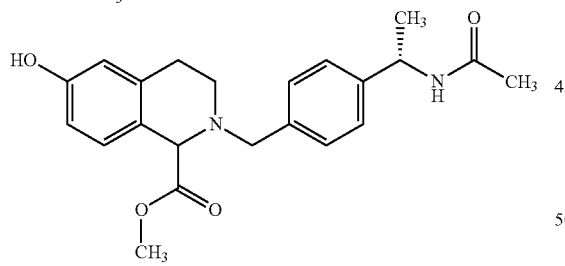

To 200 mg (0.821 mmol) 7-hydroxy-1,2,3,4-tetrahydro-3-isoquinoline-4-carboxylic acid methyl ester hydrochloride and 157 mg (0.821 mmol) (S)—N-(1-(4-formylphenyl)ethyl)acetamide (example III) in 5 mL THF are added 141 μL (2.46 mmol) AcOH and the mixture is stirred at r.t. for 10 min. After that time, the resulting mixture is cooled to 0° C., 261 mg (1.23 mmol) sodium triacetoxyborohydride are added and the reaction mixture is stirred at r.t. for 2 h. After that time, the reaction is quenched by addition of 500 μL water and purified by HPLC (ACN/H$_2$O/NH$_3$).

$C_{22}H_{26}N_2O_4$ (M=382.5 g/mol)
ESI-MS: 383 $[M+H]^+$
$R_t$ (HPLC): 0.71 min (method A)

Example XXXIX

6-Benzyloxy-1,2,3,4-tetrahydro-isoquinolin-4-ol

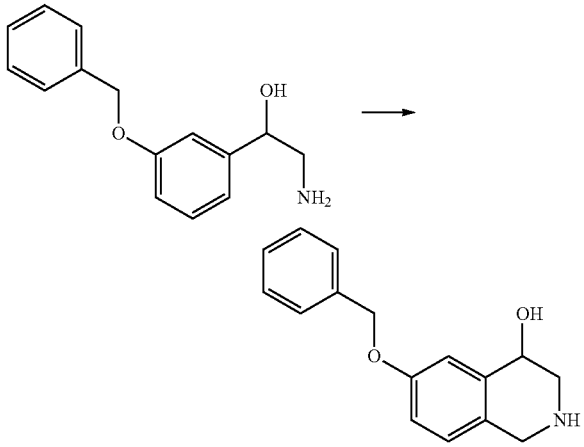

To 10 g (41 mmol) 2-amino-1-[3-(benzyloxy)phenyl]ethan-1-ol and 4.6 mL (62 mmol) formaldehyde (37% solution in water) in 100 mL DCM are added slowly 6.3 mL (82 mmol) TFA and the resulting mixture is stirred at r.t. over night. The reaction is neutralised by the addition of a sat. aq. NaHCO$_3$ solution and extracted with DCM. The organic layer is washed with a sat. aq. NaCl solution, dried over MgSO$_4$, filtered and the solvent is removed in vacuo.

$C_{16}H_{17}NO_2$ (M=255.3 g/mol)
ESI-MS: 256 $[M+H]^+$
$R_t$ (HPLC): 0.74 min (method B)

Example XL

6-Benzyloxy-4-hydroxy-3,4-dihydro-1H-isoquinoline-2-carboxylic acid tert-butyl ester

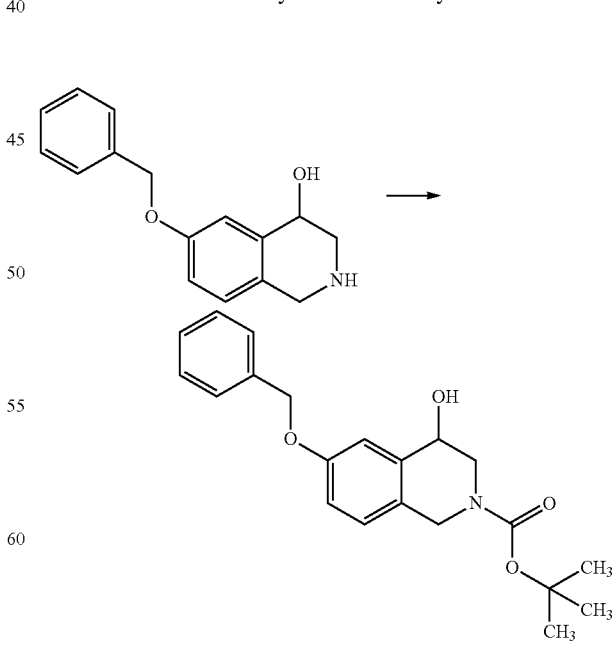

To 5.2 g (20 mmol) 6-benzyloxy-1,2,3,4-tetrahydro-isoquinolin-4-ol (example XXXIX) in 60 mL THF/30 mL water are added 3.4 mL (24 mmol) TEA and 5.3 g (24 mmol) di-tert-butyldicarbonate. The resulting mixture is stirred at r.t. for 4 h. After that time the reaction mixture is quenched by the addition of water and extracted with EtOAc. The organic layer is dried over MgSO$_4$, filtered and the solvent is removed in vacuo. The residue is purified by column chromatography (silica gel; gradient DCM:MeOH 100:0→95:5) to yield the desired product.

$C_{21}H_{25}NO_4$ (M=355.4 g/mol)

ESI-MS: 356 [M+H]$^+$

R$_t$ (HPLC): 0.97 min (method A)

Example XLI

6-Benzyloxy-4-oxo-3,4-dihydro-1H-isoquinoline-2-carboxylic acid tert-butyl ester

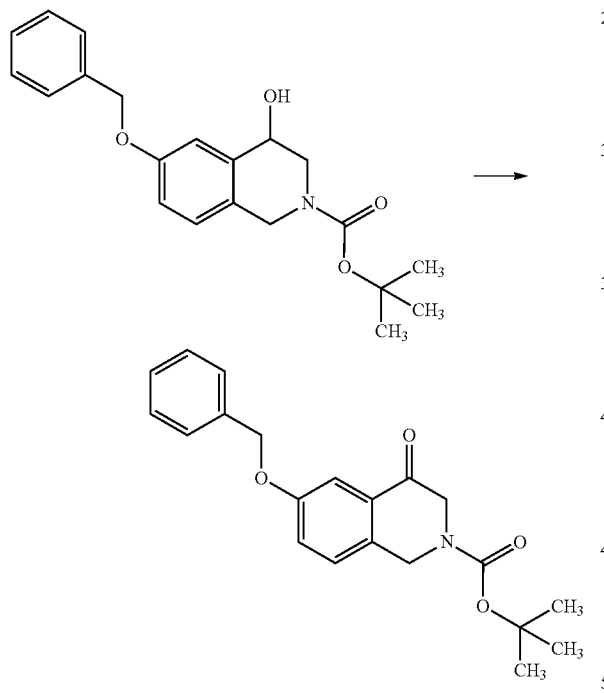

To 500 mg (1.41 mmol) 6-benzyloxy-4-hydroxy-3,4-dihydro-1H-isoquinoline-2-carboxylic acid tert-butyl ester (example XL) in 8 mL DCM are added 618 mg (1.41 mmol) Dess-Martin periodinane and stirred at r.t. over night. After that time, the reaction mixture is diluted with water and extracted with DCM. The organic layer is concentrated by evaporation and the residue is purified by HPLC (ACN/H$_2$O/HCOOH).

$C_{21}H_{23}NO_4$ (M=353.4 g/mol)

ESI-MS: 298 [M+H-isoButene]$^+$

R$_t$ (HPLC): 1.20 min (method B)

Example XLII 4,6-Dihydroxy-3,4-dihydro-1H-isoquinoline-2-carboxylic acid tert-butyl ester 6.0 g (17 mmol) 6-Benzyloxy-4-hydroxy-3,4-dihydro-1H-isoquinoline-2-carboxylic acid tert-butyl ester (example XL) in 80 mL THF are hydrogenated (3 bar, r.t.) using 200 mg Pd/C (10%). The reaction mixture is filtered and the solvent is removed in vacuo.

$C_{14}H_{19}NO_4$ (M=265.3 g/mol)

ESI-MS: 266 [M+H]$^+$

R$_t$ (HPLC): 0.87 min (method B)

Example XLIII

Example XLIII.1 (General Route)

6-Cyclopropylmethoxy-4-hydroxy-3,4-dihydro-1H-isoquinoline-2-carboxylic acid tert-butyl ester

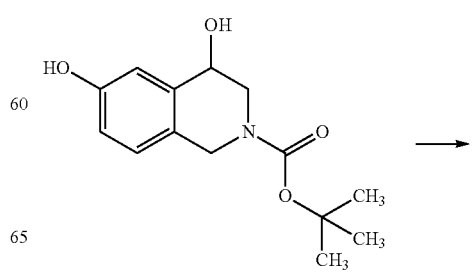

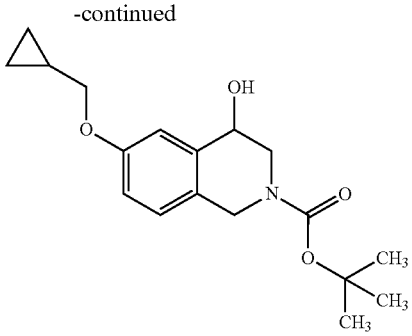

1.50 g (5.65 mmol) 4,6-Dihydroxy-3,4-dihydro-1H-isoquinoline-2-carboxylic acid tert-butyl ester (example XLII), 840 mg (6.22 mmol) (bromomethyl)cyclopropane and 1.60 g (11.3 mmol) $K_2CO_3$ in 10 mL DMF are stirred at 80° C. over night. The reaction mixture is diluted with water and extracted with DCM. The organic layer is concentrated by evaporation and the residue is purified by HPLC.

$C_{18}H_{25}NO_4$ (M=319.4 g/mol)

ESI-MS: 320 $[M+H]^+$ $R_t$ (HPLC): 1.08 min (method B)

The following compounds are prepared analogously to example XLIII.1:

| Ex. | Starting material | Starting material | Product structure | ESI-MS | HPLC retention time (method) [min] |
|---|---|---|---|---|---|
| XLIII.1 | | | | 320 $[M+H]^+$ | 1.08 (B) |
| XLIII.2 | | | | 356 $[M+H]^+$ | 1.15 (B) |
| XLIII.3 | | | | 308 $[M+H]^+$ | 1.02 (A) |

| Ex. | Starting material | Starting material | Product structure | ESI-MS | HPLC retention time (method) [min] |
|---|---|---|---|---|---|
| XLIII.4 | 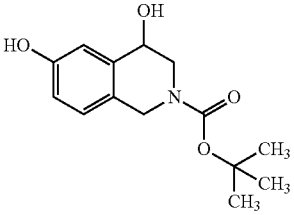 |  | 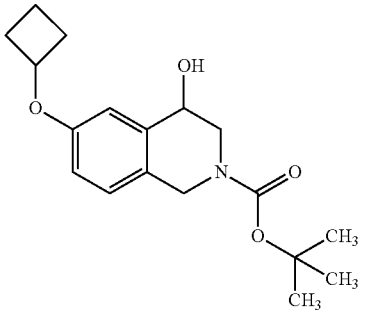 [SMILES: CC(C)(C)OC(=O)N1Cc2ccc(OC3CCC3)cc2C(O)C1] | 320 [M+H]+ | 1.05 (A) |
| XLIII.5 | 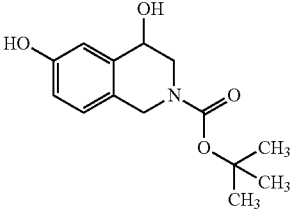 | 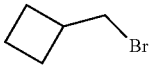 | 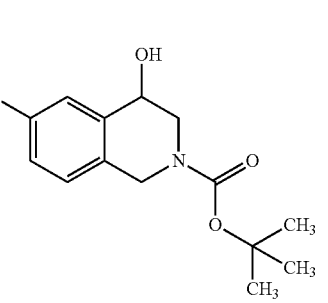 | 334 [M+H]+ | 1.10 (A) |
Example XLIV
Example XLIV.1 (General Route)
6-Cyclopropylmethoxy-4-oxo-3,4-dihydro-1H-isoquinoline-2-carboxylic acid tert-butyl ester
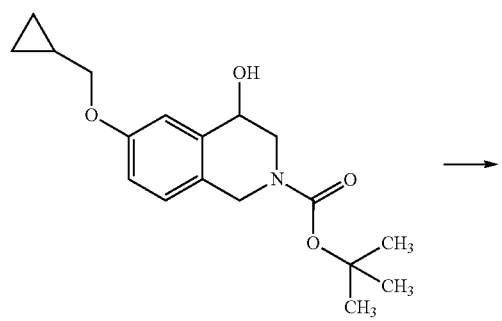
→
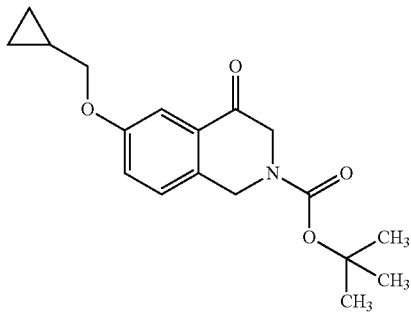 [SMILES: CC(C)(C)OC(=O)N1CC(=O)c2cc(OCC3CC3)ccc2C1]
To 600 mg (1.88 mmol) 6-cyclopropylmethoxy-4-hydroxy-3,4-dihydro-1H-isoquinoline-2-carboxylic acid tert-butyl ester (example XLIII.1) in 6 mL DCM are added 825 mg (1.88 mmol) Dess-Martin periodinane and the resulting mixture is stirred at r.t. over night. The reaction mixture is diluted with water and extracted with DCM. The organic layer is concentrated by evaporation and the residue is purified by HPLC (ACN/H$_2$O/HCOOH).

$C_{18}H_{23}NO_4$ (M=317.4 g/mol)
ESI-MS: 262 [M+H-isoButene]$^+$
R$_f$ (HPLC): 1.17 min (method B)

The following compounds are prepared analogously to example XLIV.1:

| Ex. | Starting material (s) | Product structure | ESI-MS | HPLC retention time (method) [min] |
|---|---|---|---|---|
| XLV.1 | | | 262 [M+H-isoButene]$^+$ | 1.17 (B) |
| XLV.2 | | | 376 [M+Na]$^+$ | 1.15 (JJ) |

Example XLV

Example XLV.1 (General Route)

6-Cyclopropylmethoxy-4-fluoro-3,4-dihydro-1H-isoquinoline-2-carboxylic acid tea-butyl ester

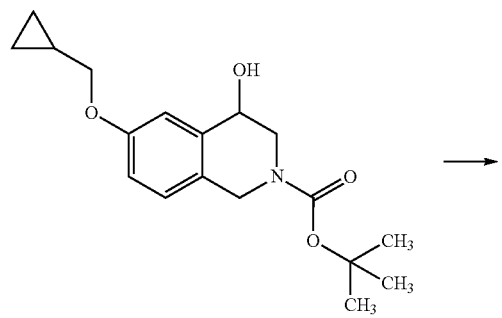

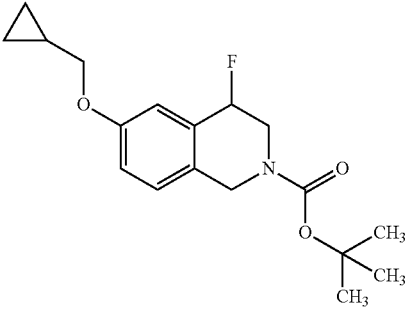 [SMILES: CC(C)(C)OC(=O)N1Cc2ccc(OCC3CC3)cc2C(F)C1]

To 400 mg (3.83 mmol) 6-cyclopropylmethoxy-4-hydroxy-3,4-dihydro-1H-isoquinoline-2-carboxylic acid tert-butyl ester (example XLIII.1) in 5 mL DCM are added slowly 623 µL (1.69 mmol) [bis(2-methoxyethyl)amino]sulfur trifluoride and the resulting mixture is stirred at r.t. for 3 h in a plastic vial. After that time the mixture is cooled to 0° C. and quenched by the addition of 5 mL aq. HCl solution (c=1 mol/L). The aq. layer is extracted three times with DCM, the organic layers are combined and concentrated by evaporation. The residue is purified by HPLC.

$C_{18}H_{24}FNO_3$ (M=321.4 g/mol)
ESI-MS: 322 [M+H]$^+$
R$_t$ (HPLC): 1.20 min (method B)

The following compounds are prepared analogously to example XLV.1:

| Ex. | Starting material(s) | Product structure | ESI-MS | HPLC retention time (method) [min] |
|---|---|---|---|---|
| XLV.1 | | | 322 [M+H]$^+$ | 1.20 (B) |
| XLV.2 | | | 358 [M+H]$^+$ | 1.17 (B) |
| XLV.3 | | | 332 [M+Na]$^+$ | 1.13 (A) |

Example XLVI

6-Cyclopropylmethoxy-4-methoxy-3,4-dihydro-1H-isoquinoline-2-carboxylic acid tert-butyl ester

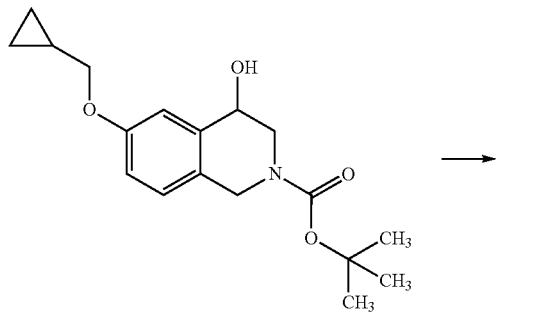

To 200 mg (0.626 mmol) 6-cyclopropylmethoxy-4-hydroxy-3,4-dihydro-1H-isoquinoline-2-carboxylic acid tert-butyl ester (example XLIII.1) in 3 mL THF are added 30 mg (0.69 mmol) NaH (55%) and stirred at r.t. for 30 min. Then 35 μL (0.56 mmol) methyl iodide are added and the reaction mixture is stirred at 80° C. over night. The reaction mixture is quenched by the addition of water and extracted three times with EtOAc. The organic layers are combined, dried over $MgSO_4$, filtered and the solvent is removed in vacuo.

$C_{19}H_{27}NO_4$ (M=333.4 g/mol)
ESI-MS: 334 [M+H]$^+$
$R_t$ (HPLC): 1.19 min (method B)

Example XLVII

Example XLVII.1 (General Route)

6-Cyclopropylmethoxy-4-methoxy-1,2,3,4-tetrahydro-isoquinoline hydrochloride

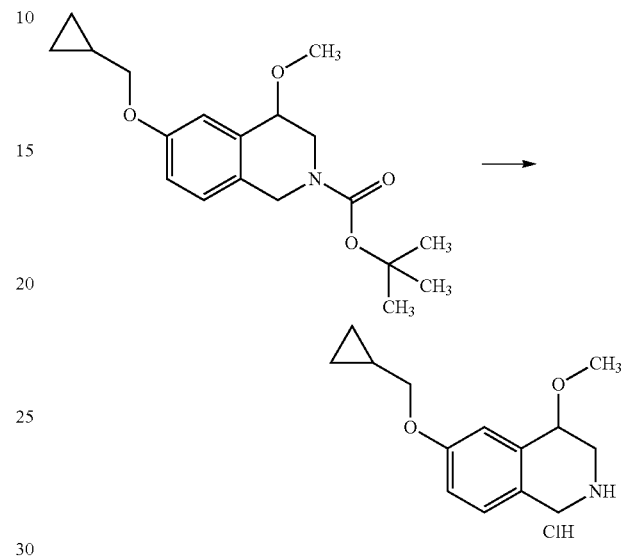

To 200 mg (0.600 mmol) 6-cyclopropylmethoxy-4-methoxy-3,4-dihydro-1H-isoquinoline-2-carboxylic acid tert-butyl ester (example XLVI) in 3 mL dioxane are added 600 μL (2.40 mmol) HCl solution in dioxane (c=4 mol/L). After stirring over night at r.t. the reaction mixture is treated with DIPE, the precipitate is filtered off and dried at 40° C.

$C_{14}H_{19}NO_2$*HCl (M=269.8 g/mol)
ESI-MS: 234 [M+H]$^+$
$R_t$ (HPLC): 0.73 min (method B)

The following compounds are prepared analogously to example XLVII.1:

| Ex. | Starting material(s) | Product structure | ESI-MS | HPLC retention time (method) [min] |
|---|---|---|---|---|
| XLVII.1 | (structure) | (structure) | 234 [M+H]$^+$ | 0.73 (B) |

-continued

| Ex. | Starting material (s) | Product structure | ESI-MS | HPLC retention time (method) [min] |
|---|---|---|---|---|
| XLVII.2 | (cyclopropylmethoxy-substituted 4-hydroxy-3,4-dihydroisoquinoline-2(1H)-carboxylic acid tert-butyl ester) | (cyclopropylmethoxy-substituted 4-hydroxy-1,2,3,4-tetrahydroisoquinoline · HCl) | 220 [M+H]⁺ | 0.68 (B) |
| XLVII.3 | (6-benzyloxy-4-oxo-3,4-dihydroisoquinoline-2(1H)-carboxylic acid tert-butyl ester) | (6-benzyloxy-2,3-dihydroisoquinolin-4(1H)-one · HCl) | 254 [M+H]⁺ | 0.77 (B) |
| XLVII.4 | (6-cyclopropylmethoxy-4-oxo-3,4-dihydroisoquinoline-2(1H)-carboxylic acid tert-butyl ester) | (6-cyclopropylmethoxy-2,3-dihydroisoquinolin-4(1H)-one · HCl) | 218 [M+H]⁺ | 0.72 (B) |
| XLVII.5 | (6-cyclopropylmethoxy-4-fluoro-3,4-dihydroisoquinoline-2(1H)-carboxylic acid tert-butyl ester) | (6-cyclopropylmethoxy-4-fluoro-1,2,3,4-tetrahydroisoquinoline · HCl) | 222 [M+H]⁺ | 0.74 (B) |

| Ex. | Starting material (s) | Product structure | ESI-MS | HPLC retention time (method) [min] |
|---|---|---|---|---|
| XLVII.6 | | | 256 [M+H]+ | 0.70 (B) |
| XLVII.7 | | | 258 [M+H]+ | 0.73 (B) |
| XLVII.8 | | | 254 [M+H]+ | 0.73 (J) |
| XLVII.9 | | | 240 [M+H]+ | 0.81 (J) |

-continued

| Ex. | Starting material (s) | Product structure | ESI-MS | HPLC retention time (method) [min] |
|---|---|---|---|---|
| XLVII.10 | 6-isopropoxy-4-hydroxy-3,4-dihydro-1H-isoquinoline-2-carboxylic acid tert-butyl ester | 6-isopropoxy-1,2,3,4-tetrahydroisoquinolin-4-ol hydrochloride | 208 [M+H]⁺ | 0.76 (A) |
| XLVII.11 | 6-cyclobutoxy-4-hydroxy-3,4-dihydro-1H-isoquinoline-2-carboxylic acid tert-butyl ester | 6-cyclobutoxy-1,2,3,4-tetrahydroisoquinolin-4-ol hydrochloride | 220 [M+H]⁺ | 0.80 (A) |
| XLVII.12 | 4-fluoro-6-isopropoxy-3,4-dihydro-1H-isoquinoline-2-carboxylic acid tert-butyl ester | 4-fluoro-6-isopropoxy-1,2,3,4-tetrahydroisoquinoline hydrochloride | 210 [M+H]⁺ | 0.87 (A) |
| XLVII.13 | 6-(cyclobutylmethoxy)-4-hydroxy-3,4-dihydro-1H-isoquinoline-2-carboxylic acid tert-butyl ester | 6-(cyclobutylmethoxy)-1,2,3,4-tetrahydroisoquinolin-4-ol hydrochloride | 234 [M+H]⁺ | 0.88 (A) |

Example XLVIII

Example XLVIII.1 (General Route)

(S)-1-[4-(6-Cyclopropylmethoxy-4-fluoro-3,4-dihydro-1H-isoquinolin-2-ylmethyl)-phenyl]-ethylamine

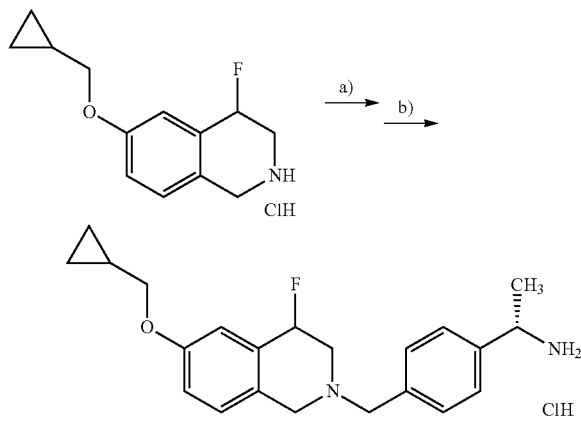

a) To 170 mg (0.660 mmol) 6-cyclopropylmethoxy-4-fluoro-1,2,3,4-tetrahydro-isoquinoline (example XLVII.5) and 164 mg (0.660 mmol) [(S)-1-(4-formyl-phenyl)-ethyl]-carbamic acid tert-butyl ester (example II) in 2 mL THF are added 113 μL (1.98 mmol) AcOH and the mixture is stirred at r.t. for 10 min. The resulting mixture is cooled to 0° C., 210 mg (0.989 mmol) sodium triacetoxyborohydride are added and the reaction mixture is stirred at r.t. for 2 h. The reaction is quenched by the addition of 200 μL water and purified by HPLC (ACN/H$_2$O/NH$_3$).

$C_{27}H_{35}FN_2O_3$ (M=454.6 g/mol)
ESI-MS: 455 [M+H]$^+$
$R_t$ (HPLC): 1.10 min (method B)

b) To 235 mg (0.517 mmol) {(S)-1-[4-(6-cyclopropylmethoxy-4-fluoro-3,4-dihydro-1H-isoquinolin-2-ylmethyl)-phenyl]-ethyl}-carbamic acid tert-butyl ester in 5 mL dioxane are added 517 μL (2.07 mmol) HCl solution in dioxane (c=4 mol/L). After stirring over night at r.t. the reaction mixture is concentrated in vacuo. The residue is treated with MeOH and the solvent is removed in vacuo.

$C_{22}H_{27}FN_2O$*HCl (M=390.9 g/mol)
ESI-MS: 355 [M+H]$^+$
$R_t$ (HPLC): 1.00 min (method A)

The following compounds are prepared analogously to example XLVIII.1:

| Ex. | Starting material | Product structure | ESI-MS | HPLC retention time (method) [min] |
|---|---|---|---|---|
| XLVIII.1 | | | 355 [M+H]$^+$ | 1.00 (A) |
| XLVIII.2 | | | 391 [M+H]$^+$ | 0.76 (B) |
| XLVIII.3 | | | 387 [M+H]$^+$ | 0.75 (J) |
| XLVIII.4 | | | 389 [M+H]$^+$ | 0.71 (J) |

-continued

| Ex. | Starting material | Product structure | ESI-MS | HPLC retention time (method) [min] |
|---|---|---|---|---|
| XLVIII.5 | | | 351 [M+H]⁺ | 0.77 (J) |
| XLVIII.6 | | | 353 [M+H]⁺ | 0.72 (J) |

Example XLIX

6-Cyclopropylmethoxy-4,4-difluoro-3,4-dihydro-1H-isoquinoline-2-carboxylic acid tert-butyl ester

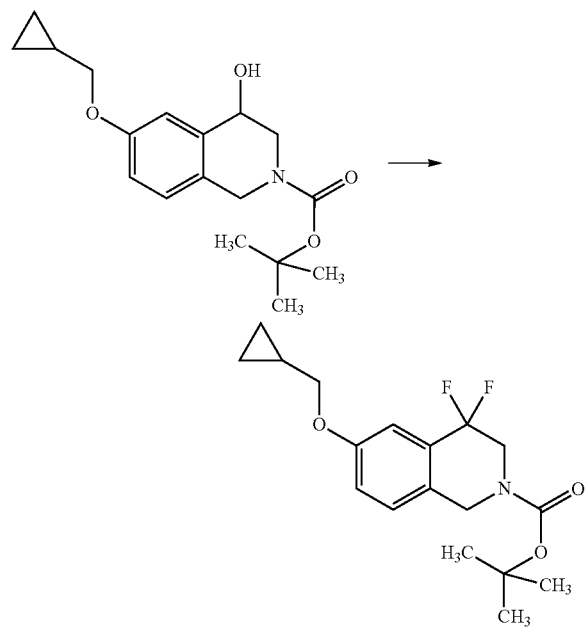

To 460 mg (1.45 mmol) 6-cyclopropylmethoxy-4-oxo-3,4-dihydro-1H-isoquinoline-2-carboxylic acid tert-butyl ester (example XLV.1) in 5 mL DCM are added 2.5 mL (18.9 mmol) diethylaminosulfur trifluoride (DAST) and 5.00 mL (11.8 mmol) bis-(2-methoxyethyl)aminosulfur trifluoride (50% in THF) and the mixture is stirred at 40° C. for 2 weeks. Ethylacetate is added and the mixture is washed with sat. NaHCO₃ solution. The organic layer is concentrated by evaporation and purified by HPLC (ACN/H₂O/TFA).

$C_{18}H_{23}F_2NO_3$ (M=339.4 g/mol)

$R_t$ (HPLC): 0.78 min (method LL)

Preparation of Final Compounds

Example 1

Example 1.1 (General Route)

N-{1-[4-(6-Trifluoromethyl-3,4-dihydro-1H-isoquinolin-2-ylmethyl)-phenyl]-ethyl}-acetamide

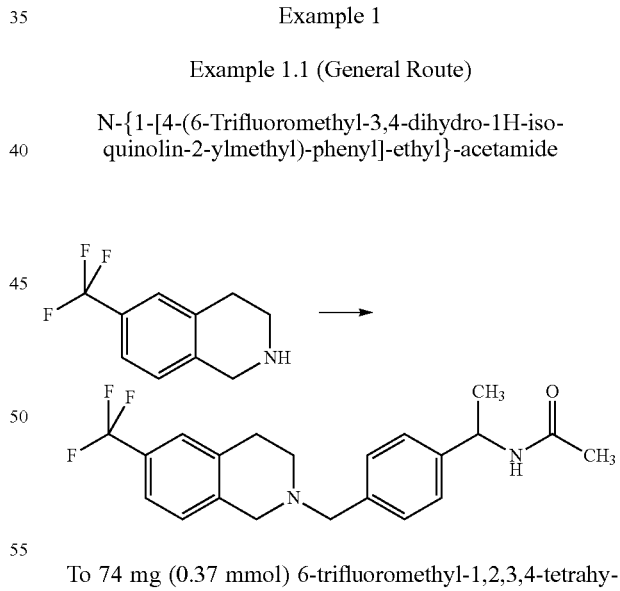

To 74 mg (0.37 mmol) 6-trifluoromethyl-1,2,3,4-tetrahydro-isoquinoline and 70 mg (0.37 mmol) N-(1-(4-Formylphenyl)ethyl)acetamide (example I) in 2 mL THF are added 63 μl (1.1 mmol) AcOH and the reaction mixture is stirred at r.t. for 10 min. The resulting mixture is cooled to 0° C., 117 mg (0.551 mmol) sodium triacetoxyborohydride are added and the reaction mixture is stirred at r.t. for 2 h. After that time, the reaction is quenched by the addition of 200 μL water and purified by HPLC.

$C_{21}H_{23}F_3N_2O$ (M=376.4 g/mol)

ESI-MS: 377 [M+H]⁺

$R_t$ (HPLC): 0.95 min (method A)

The following compounds are prepared according to the general procedure (example 1.1) described above:

| Ex. | Starting materials | | Structure | ESI-MS | HPLC retention time (method) [min] |
|---|---|---|---|---|---|
| 1.1 | 6-Trifluoromethyl-1,2,3,4-tetrahydro-isoquinolin | I | 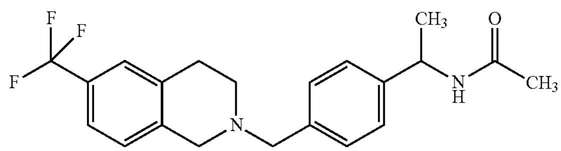 [SMILES: CC(=O)NC(C)c1ccc(CN2CCc3cc(C(F)(F)F)ccc3C2)cc1] | 377 [M+H]⁺ | 0.95 (A) |
| 1.2 | 6-Methoxycarbonyl-1,2,3,4-tetrahydro-isoquinoline hydrochloride | I | 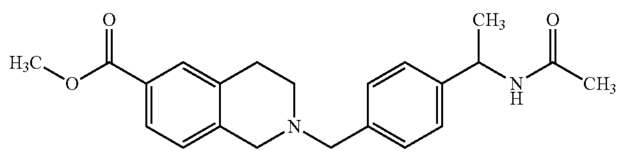 [SMILES: COC(=O)c1ccc2c(c1)CCN(Cc1ccc(C(C)NC(C)=O)cc1)C2] | 367 [M+H]⁺ | 0.85 (A) |
| 1.3 | 6-Bromo-1,2,3,4-tetrahydro-isoquinoline hydrochloride | I | 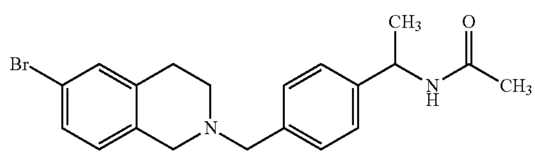 [SMILES: CC(=O)NC(C)c1ccc(CN2CCc3cc(Br)ccc3C2)cc1] | 387 [M+H]⁺ | 0.95 (A) |
| 1.4 | 5-Chloro-1,2,3,4-tetrahydro-isoquinoline hydrochloride | I | 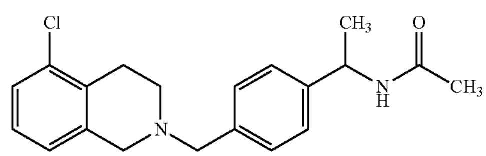 | 343 [M+H]⁺ | 0.93 (A) |
| 1.5 | XXXI.7 | I | 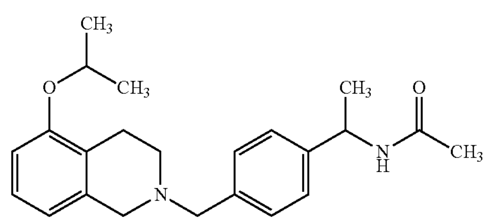 [SMILES: CC(=O)NC(C)c1ccc(CN2CCc3c(cccc3OC(C)C)C2)cc1] | 367 [M+H]⁺ | 0.97 (A) |
| 1.6 | XXXI.9 | I | 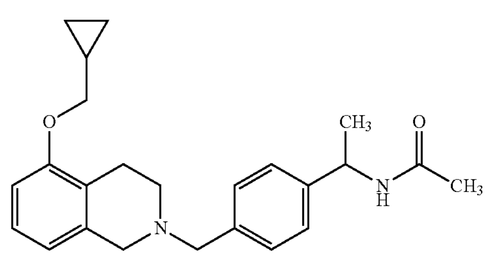 [SMILES: CC(=O)NC(C)c1ccc(CN2CCc3c(cccc3OCC3CC3)C2)cc1] | 379 [M+H]⁺ | 0.98 (A) |
| 1.7 | 6-(Trifluoro-methoxy)-1,2,3,4-tetrahydro isoquinoline | I | 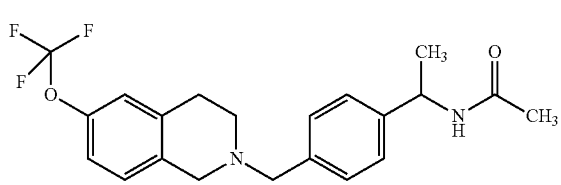 [SMILES: CC(=O)NC(C)c1ccc(CN2CCc3cc(OC(F)(F)F)ccc3C2)cc1] | 393 [M+H]⁺ | 0.97 (A) |

-continued

| Ex. | Starting materials | | Structure | ESI-MS | HPLC retention time (method) [min] |
|---|---|---|---|---|---|
| 1.8 | XXXII.7 | I | 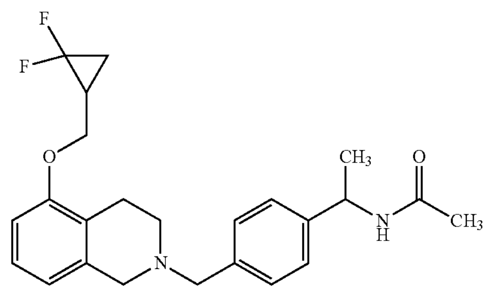 [SMILES: CC(=O)NC(C)c1ccc(CN2CCc3c(cccc3OCC3CC3(F)F)C2)cc1] | 415 [M+H]+ | 0.95 (A) |
| 1.9 | XXXI.2 | I | 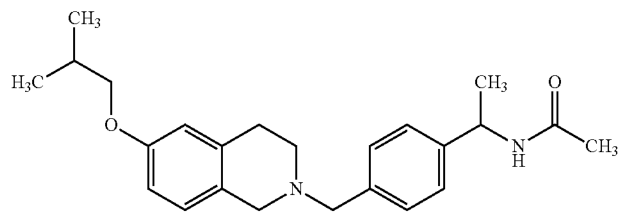 [SMILES: CC(=O)NC(C)c1ccc(CN2CCc3cc(OCC(C)C)ccc3C2)cc1] | 381 [M+H]+ | 1.02 (A) |
| 1.10 | XXXI.4 | I | 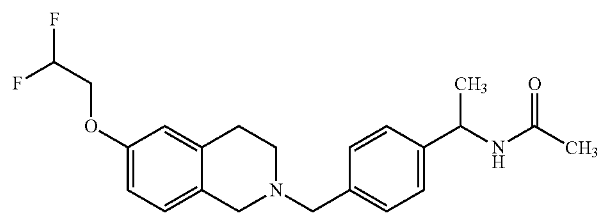 [SMILES: CC(=O)NC(C)c1ccc(CN2CCc3cc(OCC(F)F)ccc3C2)cc1] | 389 [M+H]+ | 0.88 (A) |
| 1.11 | XXXI.5 | I | 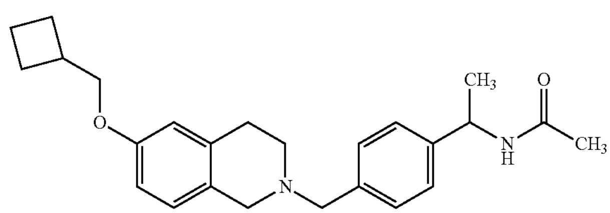 [SMILES: CC(=O)NC(C)c1ccc(CN2CCc3cc(OCC4CCC4)ccc3C2)cc1] | 393 [M+H]+ | 1.03 (A) |
| 1.12 | XXXII.1 | I | 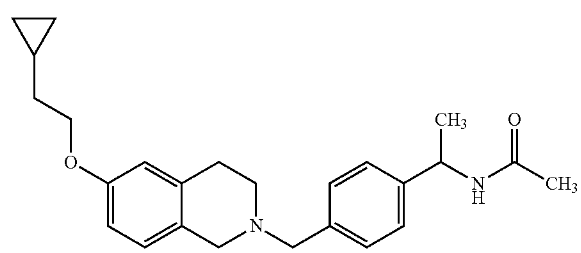 [SMILES: CC(=O)NC(C)c1ccc(CN2CCc3cc(OCCC4CC4)ccc3C2)cc1] | 393 [M+H]+ | 1.00 (A) |
| 1.13 | XXXII.3 | I | 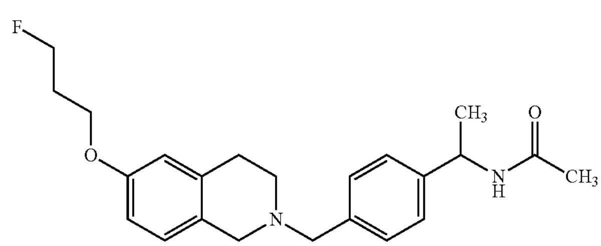 [SMILES: CC(=O)NC(C)c1ccc(CN2CCc3cc(OCCCF)ccc3C2)cc1] | 385 [M+H]+ | 0.89 (A) |

-continued
| Ex. | Starting materials | | Structure | ESI-MS | HPLC retention time (method) [min] |
|---|---|---|---|---|---|
| 1.14 | XXXII.4 | I | 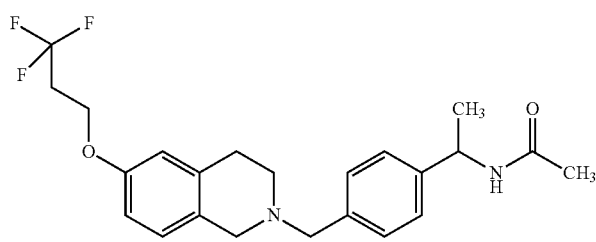 [SMILES: CC(=O)NC(C)c1ccc(CN2CCc3cc(OCCC(F)(F)F)ccc3C2)cc1] | 421 [M+H]+ | 0.94 (A) |
| 1.15 | XXXII.5 | I | 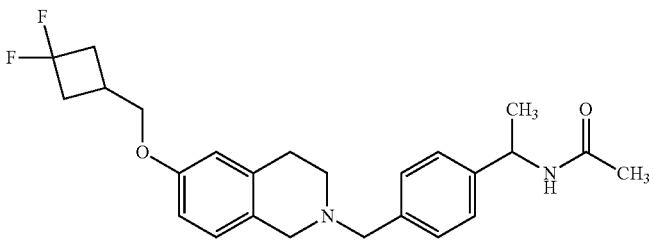 [SMILES: CC(=O)NC(C)c1ccc(CN2CCc3cc(OCC4CC(F)(F)C4)ccc3C2)cc1] | 429 [M+H]+ | 0.97 (C) |
| 1.16 | 6-Ethoxy-1,2,3,4-tetrahydro-isoquinoline | I | 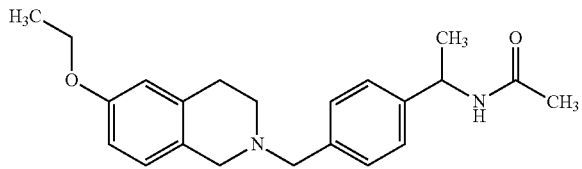 [SMILES: CCOc1ccc2c(c1)CCN(Cc1ccc(C(C)NC(C)=O)cc1)C2] | 353 [M+H]+ | 0.74 (B) |
| 1.17 | 6-Propoxy-1,2,3,4-tetrahydro-isoquinoline | I | 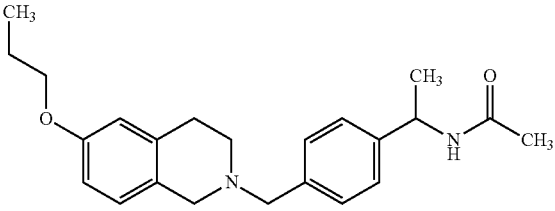 [SMILES: CCCOc1ccc2c(c1)CCN(Cc1ccc(C(C)NC(C)=O)cc1)C2] | 367 [M+H]+ | 0.80 (B) |
| 1.18 | 5-Ethoxy-1,2,3,4-tetrahydro-isoquinoline | I | 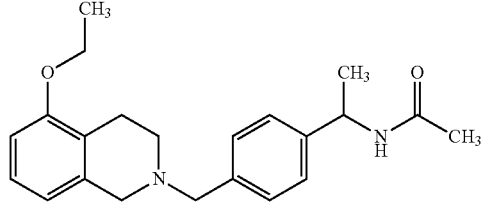 [SMILES: CCOc1cccc2c1CCN(Cc1ccc(C(C)NC(C)=O)cc1)C2] | 353 [M+H]+ | 0.76 (B) |
| 1.19 | XXXI.8 | I | 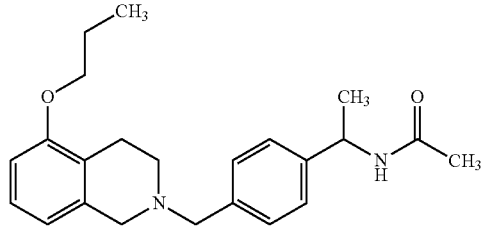 [SMILES: CCCOc1cccc2c1CCN(Cc1ccc(C(C)NC(C)=O)cc1)C2] | 367 [M+H]+ | 0.80 (B) |

| Ex. | Starting materials | | Structure | ESI-MS | HPLC retention time (method) [min] |
|---|---|---|---|---|---|
| 1.20 | XXXI.3 | I | 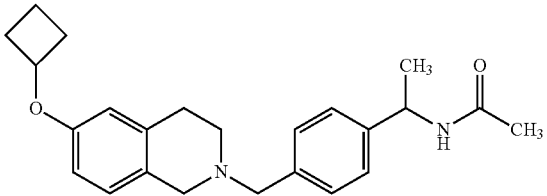 [SMILES: CC(=O)NC(C)c1ccc(CN2CCc3cc(OC4CCC4)ccc3C2)cc1] | 379 [M+H]+ | 0.97 (A) |
| 1.21 | 6-(Propan-2-yloxy)-1,2,3,4-tetrahydro-isoquinoline | I | 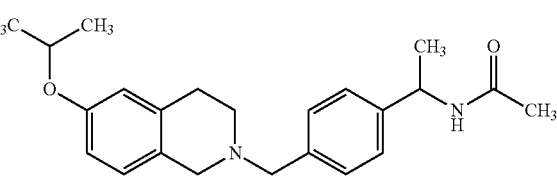 | 367 [M+H]+ | 0.94 (A) |
| 1.22 | XXII | I | 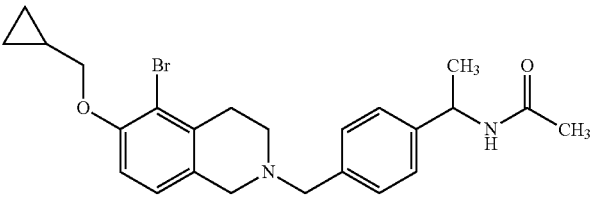 | 457 [M+H]+ | 1.03 (A) |
| 1.23 | XXXI.10 | I | 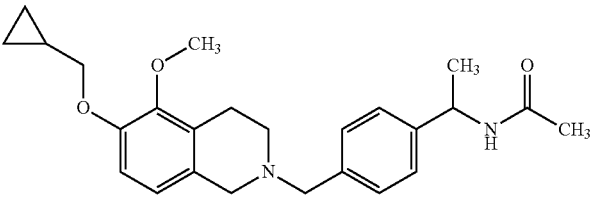 | 409 [M+H]+ | 0.95 (A) |
| 1.24 | XVII | I | 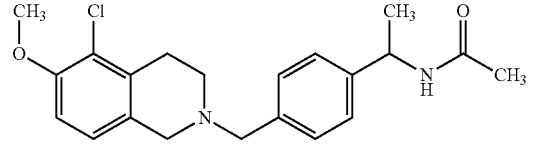 [SMILES: COc1ccc2c(c1Cl)CCN(Cc1ccc(C(C)NC(C)=O)cc1)C2] | 373 [M+H]+ | 0.90 (A) |
| 1.25 | XXXI.19 | I | 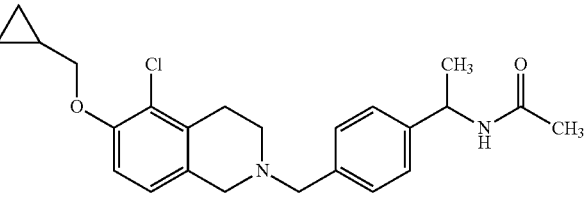 | 449 [M+H]+ | 0.97 (A) |
| 1.26 | XXXI.20 | I | 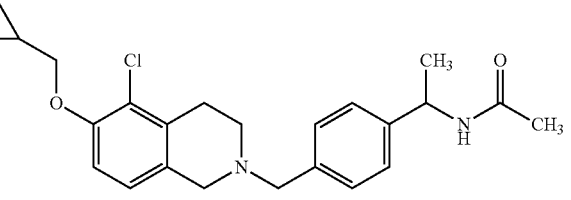 | 413 [M+H]+ | 1.00 (A) |

| Ex. | Starting materials | | Structure | ESI-MS | HPLC retention time (method) [min] |
|---|---|---|---|---|---|
| 1.27 | XXIX.1 | I | 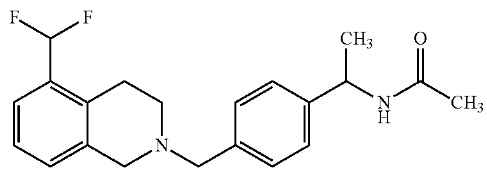 [SMILES: CC(=O)NC(C)c1ccc(CN2CCc3c(cccc3C(F)F)C2)cc1] | 359 [M+H]+ | 0.89 (A) |
| 1.28 | XXIX.2 | I | 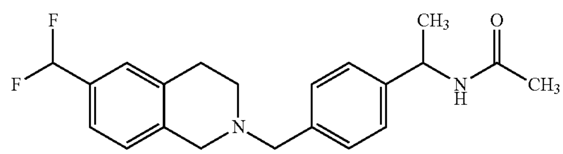 [SMILES: CC(=O)NC(C)c1ccc(CN2CCc3cc(C(F)F)ccc3C2)cc1] | 359 [M+H]+ | 0.88 (A) |
| 1.29 | XXX | I | 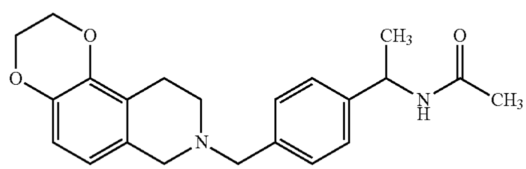 [SMILES: CC(=O)NC(C)c1ccc(CN2CCc3c(ccc4c3OCCO4)C2)cc1] | 367 [M+H]+ | 0.84 (A) |
| 1.30 | XXXI.21 | I | 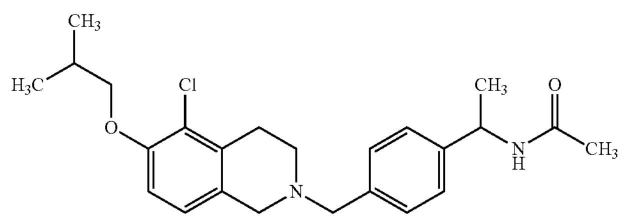 [SMILES: CC(=O)NC(C)c1ccc(CN2CCc3c(ccc(OCC(C)C)c3Cl)C2)cc1] | 415 [M+H]+ | 1.06 (A) |
| 1.31 | XXIV | I | 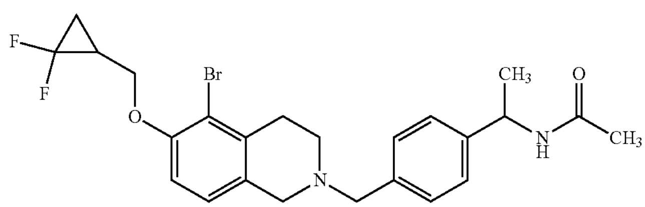 [SMILES: CC(=O)NC(C)c1ccc(CN2CCc3c(ccc(OCC4CC4(F)F)c3Br)C2)cc1] | 493 [M+H]+ | 0.97 (A) |
| 1.32 | XXXI.22 | I | 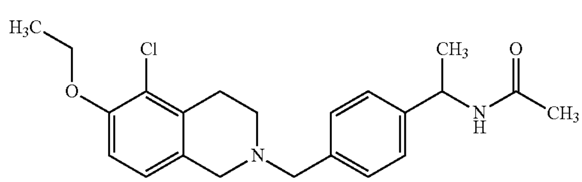 [SMILES: CCOc1ccc2c(c1Cl)CCN(Cc1ccc(C(C)NC(C)=O)cc1)C2] | 387 [M+H]+ | 0.95 (A) |
| 1.33 | XXXI.23 | I | 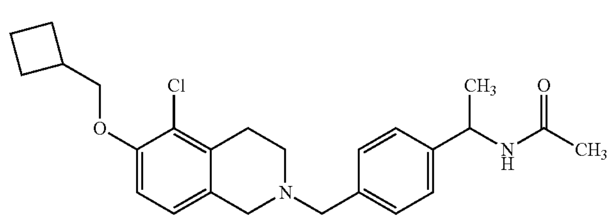 [SMILES: CC(=O)NC(C)c1ccc(CN2CCc3c(ccc(OCC4CCC4)c3Cl)C2)cc1] | 427 [M+H]+ | 1.08 (A) |

-continued
| Ex. | Starting materials | | Structure | ESI-MS | HPLC retention time (method) [min] |
|---|---|---|---|---|---|
| 1.34 | XXXII.13 | I | 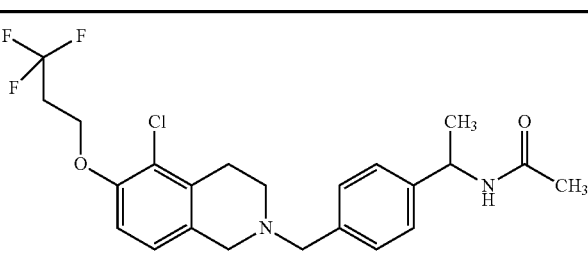 | 455 [M+H]⁺ | 0.98 (A) |
| 1.35 | XXXI.24 | I | 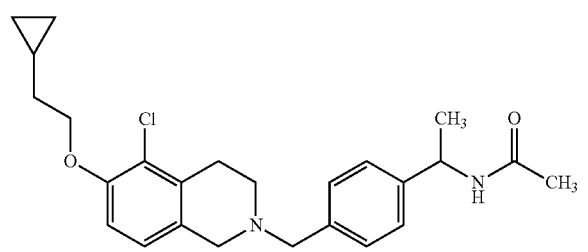 [SMILES: CC(=O)NC(C)c1ccc(CN2CCc3c(ccc(OCCC4CC4)c3Cl)C2)cc1] | 427 [M+H]⁺ | 1.06 (A) |
| 1.36 | XIV | I | 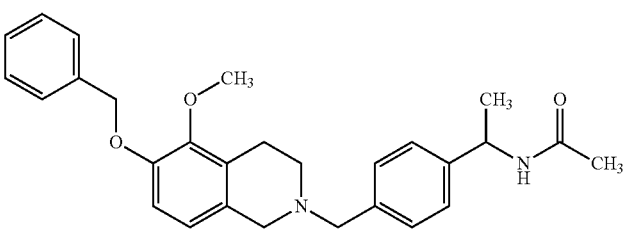 [SMILES: COc1c(OCc2ccccc2)ccc2c1CCN(Cc1ccc(C(C)NC(C)=O)cc1)C2] | 445 [M+H]⁺ | 0.98 (A) |
| 1.37 | XXXI.25 | I | 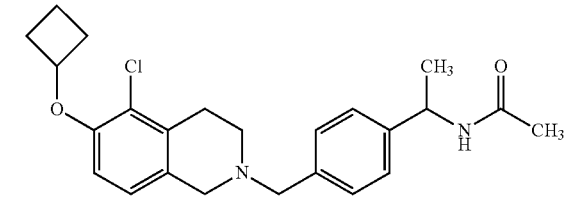 [SMILES: CC(=O)NC(C)c1ccc(CN2CCc3c(ccc(OC4CCC4)c3Cl)C2)cc1] | 413 [M+H]⁺ | 1.02 (A) |
| 1.38 | XXXII.14 | I | 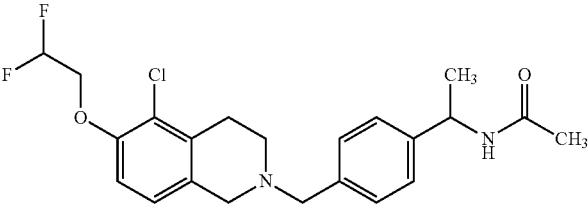 [SMILES: CC(=O)NC(C)c1ccc(CN2CCc3c(ccc(OCC(F)F)c3Cl)C2)cc1] | 423 [M+H]⁺ | 0.92 (A) |
| 1.39 | XXXII.15 | I | 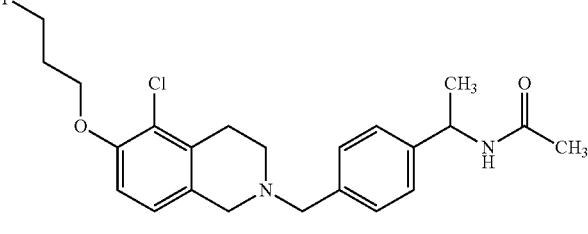 | 419 [M+H]⁺ | 0.94 (A) |

-continued

| Ex. | Starting materials | | Structure | ESI-MS | HPLC retention time (method) [min] |
|---|---|---|---|---|---|
| 1.40 | XXXI.26 | I | (structure: 5-chloro-6-sec-butoxy tetrahydroisoquinoline linked via CH₂ to phenyl-CH(CH₃)-NH-C(O)-CH₃) | 401 [M+H]⁺ | 1.00 (A) |
| 1.41 | 6-Propoxy-1,2,3,4-tetrahydro-isoquinoline | IV | (structure: 6-propoxy tetrahydroisoquinoline linked via CH₂ to phenyl-CH(CH₃)-NH-C(O)-cyclopropyl) | 393 [M+H]⁺ | 0.90 (C) |
| 1.42 | XXXI.6 | IV | (structure: 6-(cyclopropylmethoxy) tetrahydroisoquinoline linked via CH₂ to phenyl-CH(CH₃)-NH-C(O)-cyclopropyl) | 405 [M+H]⁺ | 0.88 (C) |
| 1.43 | 6-Ethoxy-1,2,3,4-tetrahydro-isoquinoline | IV | (structure: 6-ethoxy tetrahydroisoquinoline linked via CH₂ to phenyl-CH(CH₃)-NH-C(O)-cyclopropyl) | 379 [M+H]⁺ | 0.83 (C) |
| 1.44 | XXXI.3 | IV | (structure: 6-cyclobutoxy tetrahydroisoquinoline linked via CH₂ to phenyl-CH(CH₃)-NH-C(O)-cyclopropyl) | 405 [M+H]⁺ | 0.91 (C) |
| 1.45 | XXXII.4 | IV | (structure: 6-(3,3,3-trifluoropropoxy) tetrahydroisoquinoline linked via CH₂ to phenyl-CH(CH₃)-NH-C(O)-cyclopropyl) | 447 [M+H]⁺ | 0.87 (C) |
| 1.46 | XXXI.4 | IV | (structure: 6-(2,2-difluoroethoxy) tetrahydroisoquinoline linked via CH₂ to phenyl-CH(CH₃)-NH-C(O)-cyclopropyl) | 415 [M+H]⁺ | 0.80 (C) |

-continued

| Ex. | Starting materials | | Structure | ESI-MS | HPLC retention time (method) [min] |
|---|---|---|---|---|---|
| 1.47 | 6-(Propan-2-yloxy)-1,2,3,4-tetrahydro-isoquinoline | IV | 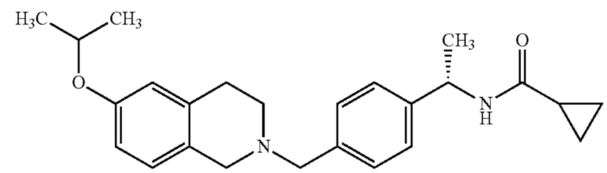 [SMILES: CC(C)Oc1ccc2c(c1)CCN(Cc1ccc([C@H](C)NC(=O)C3CC3)cc1)C2] | 393 [M+H]+ | 1.00 (A) |
| 1.48 | XXXI.10 | IV | 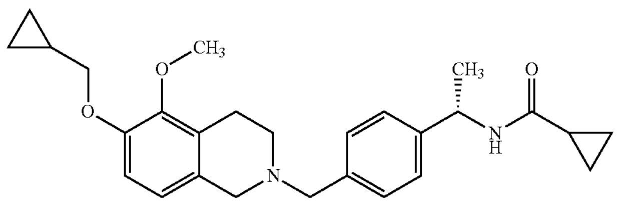 [SMILES: COc1c(OCC2CC2)ccc2c1CCN(Cc1ccc([C@H](C)NC(=O)C3CC3)cc1)C2] | 435 [M+H]+ | 1.00 (A) |
| 1.49 | XXXI.19 | IV | 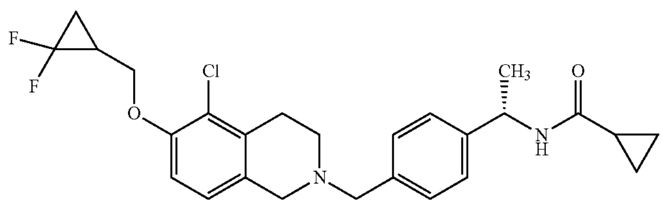 [SMILES: C[C@H](NC(=O)C1CC1)c1ccc(CN2CCc3c(ccc(OCC4CC4(F)F)c3Cl)C2)cc1] | 475 [M+H]+ | 1.02 (A) |
| 1.50 | XXXI.20 | IV | 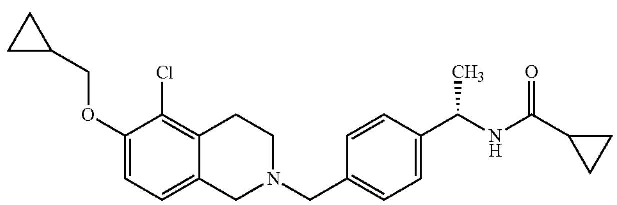 [SMILES: C[C@H](NC(=O)C1CC1)c1ccc(CN2CCc3c(ccc(OCC4CC4)c3Cl)C2)cc1] | 439 [M+H]+ | 1.05 (A) |
| 1.51 | XXXII.19 | IV | 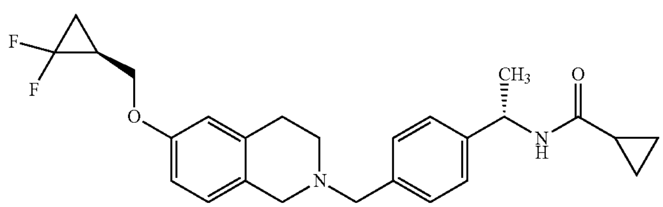 [SMILES: C[C@H](NC(=O)C1CC1)c1ccc(CN2CCc3cc(OC[C@@H]4CC4(F)F)ccc3C2)cc1] | 441 [M+H]+ | 0.98 (A) |
| 1.52 | XXXII.18 | IV | 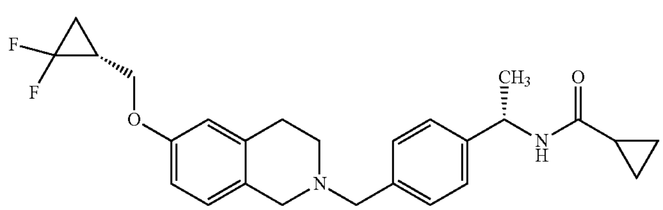 [SMILES: C[C@H](NC(=O)C1CC1)c1ccc(CN2CCc3cc(OC[C@H]4CC4(F)F)ccc3C2)cc1] | 441 [M+H]+ | 0.98 (A) |
| 1.53 | XXXI.11 | IV | 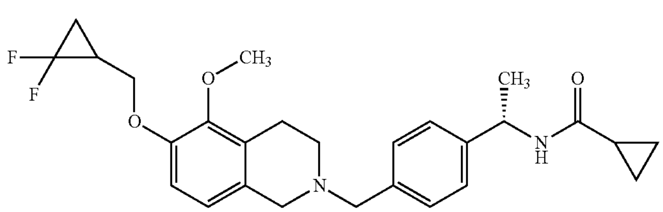 [SMILES: COc1c(OCC2CC2(F)F)ccc2c1CCN(Cc1ccc([C@H](C)NC(=O)C3CC3)cc1)C2] | 471 [M+H]+ | 0.98 (A) |

-continued

| Ex. | Starting materials | | Structure | ESI-MS | HPLC retention time (method) [min] |
|---|---|---|---|---|---|
| 1.54 | XXXII.9 | IV | 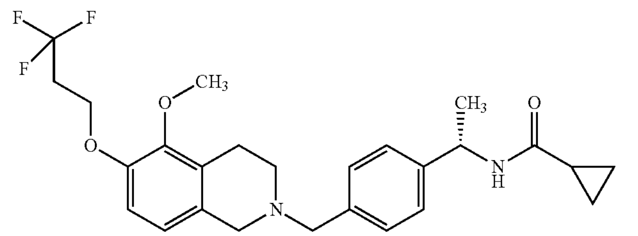 [SMILES: COc1c(OCCC(F)(F)F)ccc2c1CCN(Cc1ccc([C@H](C)NC(=O)C3CC3)cc1)C2] | 477 [M+H]+ | 0.99 (A) |
| 1.55 | XXXI.16 | IV | 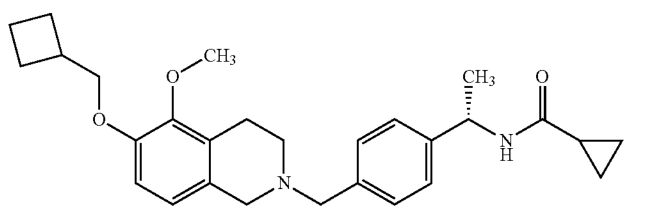 [SMILES: COc1c(OCC2CCC2)ccc2c1CCN(Cc1ccc([C@H](C)NC(=O)C3CC3)cc1)C2] | 449 [M+H]+ | 0.67 (D) |
| 1.56 | XXXII.12 | IV | 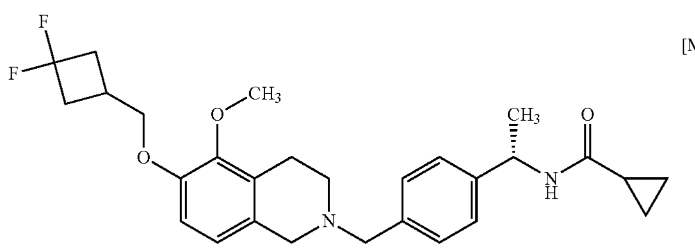 | 485 [M+H]+ | 0.63 (D) |
| 1.57 | XXXI.13 | IV | 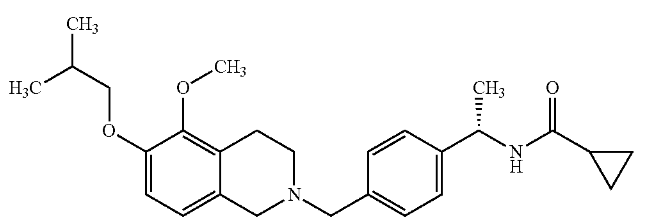 [SMILES: COc1c(OCC(C)C)ccc2c1CCN(Cc1ccc([C@H](C)NC(=O)C3CC3)cc1)C2] | 437 [M+H]+ | 0.65 (D) |
| 1.58 | XXXI.18 | IV | 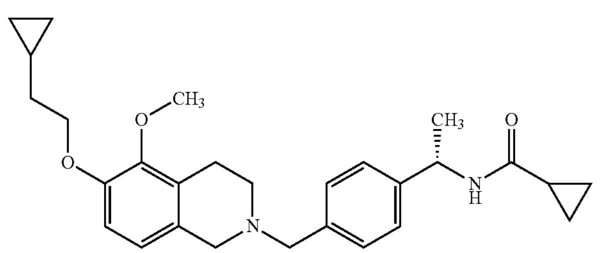 [SMILES: COc1c(OCCC2CC2)ccc2c1CCN(Cc1ccc([C@H](C)NC(=O)C3CC3)cc1)C2] | 449 [M+H]+ | 1.03 (E) |
| 1.59 | XLVII.5 | IV | 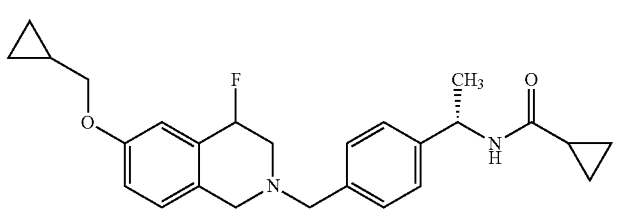 [SMILES: C[C@H](NC(=O)C1CC1)c1ccc(CN2Cc3ccc(OCC4CC4)cc3C(F)C2)cc1] | 423 [M+H]+ | 0.99 (A) |

| Ex. | Starting materials | | Structure | ESI-MS | HPLC retention time (method) [min] |
|---|---|---|---|---|---|
| 1.60 | XLVII.7 | IV | (structure) | 459 [M+H]+ | 0.96 (A) |
| 1.61 | XLVII.6 | IV | (structure) | 457 [M+H]+ | 0.80 (B) |
| 1.62 | XXXII.16 | III | (structure) | 481 [M+H]+ | 1.03 (A) |
| 1.63 | XXXII.6 | III | (structure) | 403 [M+H]+ | 0.78 (B) |
| 1.64 | XXXI.11 | III | (structure) | 445 [M+H]+ | 0.80 (B) |
| 1.65 | XXXII.8 | III | (structure) | 415 [M+H]+ | 0.76 (B) |

| Ex. | Starting materials | | Structure | ESI-MS | HPLC retention time (method) [min] |
|---|---|---|---|---|---|
| 1.66 | XXXII.9 | III | (structure) | 451 [M+H]+ | 0.81 (B) |
| 1.67 | XXXI.12 | III | (structure) | 383 [M+H]+ | 0.89 (A) |
| 1.68 | XXXI.13 | III | (structure) | 411 [M+H]+ | 1.01 (A) |
| 1.69 | XXXI.14 | III | (structure) | 397 [M+H]+ | 0.94 (A) |
| 1.70 | XXXI.15 | III | (structure) | 409 [M+H]+ | 0.92 (E) |
| 1.71 | XXXII.10 | III | (structure) | 419 [M+H]+ | 0.81 (E) |
| 1.72 | XXXII.11 | III | (structure) | 433 [M+H]+ | 0.84 (E) |

-continued

| Ex. | Starting materials | | Structure | ESI-MS | HPLC retention time (method) [min] |
|---|---|---|---|---|---|
| 1.73 | XXXI.16 | III | 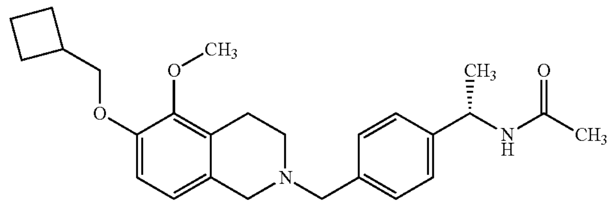 [SMILES: COc1c(OCC2CCC2)ccc2c1CCN(Cc1ccc([C@H](C)NC(C)=O)cc1)C2] | 423 [M+H]⁺ | 0.99 (E) |
| 1.74 | XXXI.17 | III | 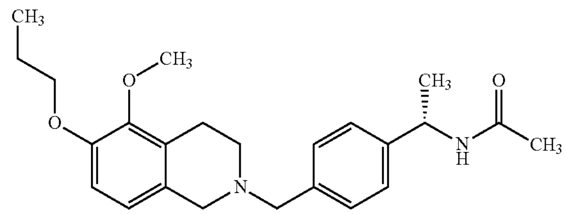 [SMILES: CCCOc1ccc2c(c1OC)CCN(Cc1ccc([C@H](C)NC(C)=O)cc1)C2] | 397 [M+H]⁺ | 0.90 (E) |
| 1.75 | XXXII.12 | III | 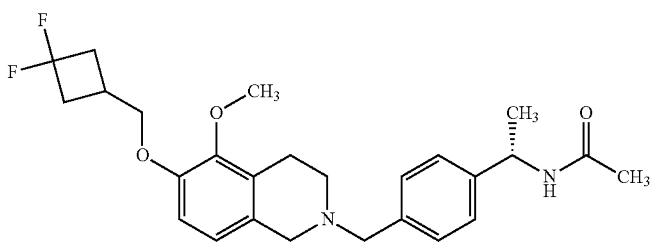 [SMILES: COc1c(OCC2CC(F)(F)C2)ccc2c1CCN(Cc1ccc([C@H](C)NC(C)=O)cc1)C2] | 459 [M+H]⁺ | 0.91 (E) |
| 1.76 | XXXI.10 | III | 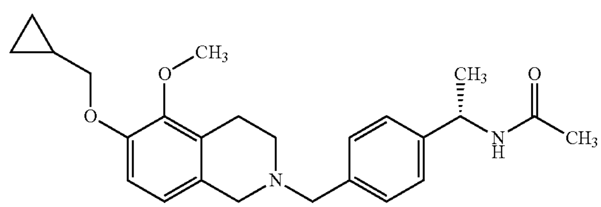 | 409 [M+H]⁺ | 0.57 (D) |
| 1.77 | XXXI.18 | III | 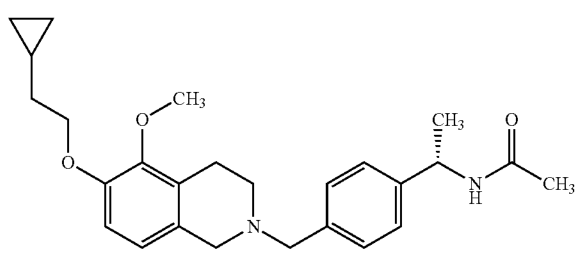 [SMILES: COc1c(OCCC2CC2)ccc2c1CCN(Cc1ccc([C@H](C)NC(C)=O)cc1)C2] | 423 [M+H]⁺ | 0.61 (D) |
| 1.78 | 5,6-Dichloro-1,2,3,4-tetrahydro-isoquinoline hydrochloride | III | 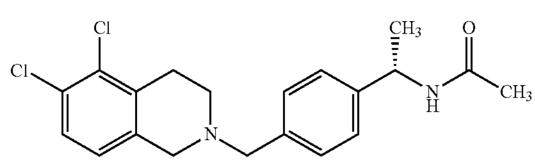 [SMILES: CC(=O)N[C@@H](C)c1ccc(CN2CCc3c(ccc(Cl)c3Cl)C2)cc1] | 377 [M+H]⁺ | 0.99 (A) |
| 1.79 | XXIII | III | 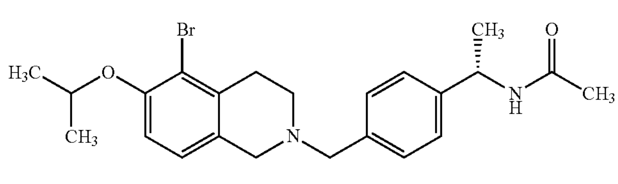 [SMILES: CC(=O)N[C@@H](C)c1ccc(CN2CCc3c(ccc(OC(C)C)c3Br)C2)cc1] | 445 [M+H]⁺ | 1.01 (A) |

-continued

| Ex. | Starting materials | | Structure | ESI-MS | HPLC retention time (method) [min] |
|---|---|---|---|---|---|
| 1.80 | XXVII | III | 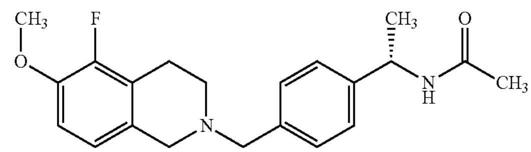 | 357 [M+H]+ | 0.86 (A) |
| 1.81 | 6-Chloro-1,2,3,4-tetrahydro-isoquinoline hydrochloride | III | 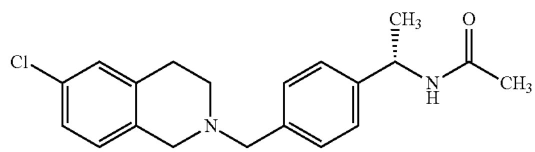 [SMILES: CC(=O)N[C@@H](C)c1ccc(CN2CCc3cc(Cl)ccc3C2)cc1] | 343 [M+H]+ | 0.94 (A) |
| 1.82 | XXVI | III | 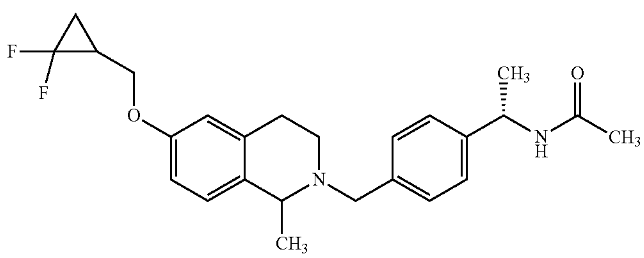 [SMILES: CC(=O)N[C@@H](C)c1ccc(CN2CCc3cc(OCC4CC4(F)F)ccc3C2C)cc1] | 429 [M+H]+ | 0.80 (B) |
| 1.83 | XXXI.27 | III | 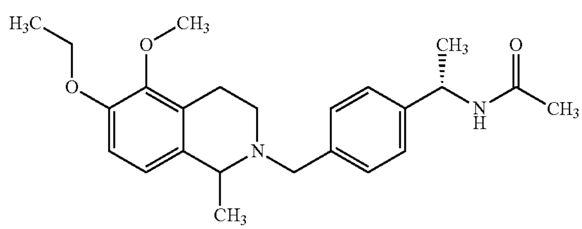 [SMILES: CCOc1ccc2c(c1OC)CCN(Cc1ccc([C@H](C)NC(C)=O)cc1)C2C] | 397 [M+H]+ | 0.38 (F) |
| 1.84 | XXXI.28 | III | 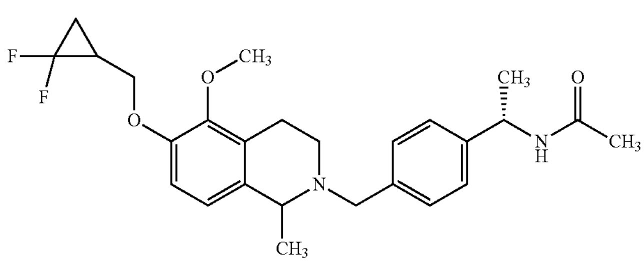 [SMILES: COc1c(OCC2CC2(F)F)ccc2c1CCN(Cc1ccc([C@H](C)NC(C)=O)cc1)C2C] | 459 [M+H]+ | 0.41 (F) |
| 1.85 | XXXI.29 | III | 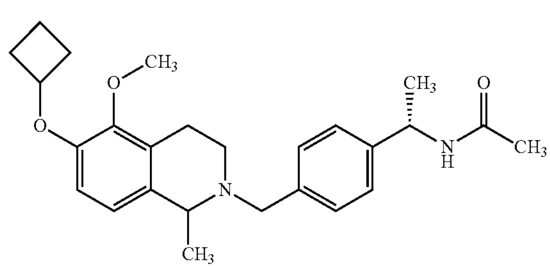 [SMILES: COc1c(OC2CCC2)ccc2c1CCN(Cc1ccc([C@H](C)NC(C)=O)cc1)C2C] | 423 [M+H]+ | 0.42 (F) |

| Ex. | Starting materials | | Structure | ESI-MS | HPLC retention time (method) [min] |
|---|---|---|---|---|---|
| 1.86 | XXXI.30 | III | 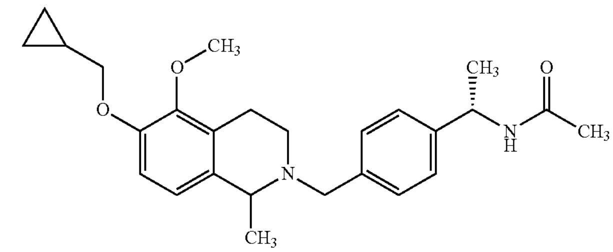 [SMILES: COc1c(OCC2CC2)ccc2c1CCN(Cc1ccc([C@H](C)NC(C)=O)cc1)C2C] | 423 [M+H]+ | 0.42 (F) |
| 1.87 | XXXII.17 | III | 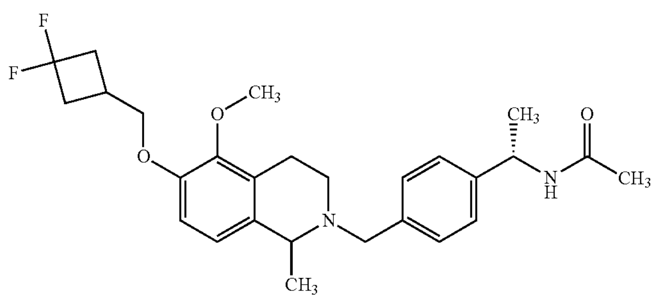 [SMILES: COc1c(OCC2CC(F)(F)C2)ccc2c1CCN(Cc1ccc([C@H](C)NC(C)=O)cc1)C2C] | 473 [M+H]+ | 0.44 (F) |
| 1.88 | XXXI.6 | III | 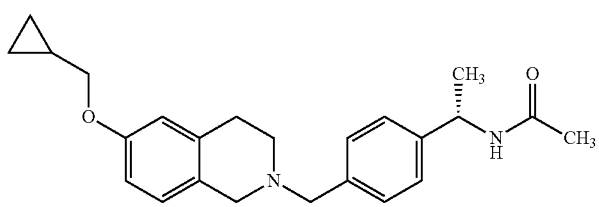 [SMILES: CC(=O)N[C@@H](C)c1ccc(CN2CCc3cc(OCC4CC4)ccc3C2)cc1] | 379 [M+H]+ | 0.55 (D) |
| 1.89 | XLVII.3 | III | 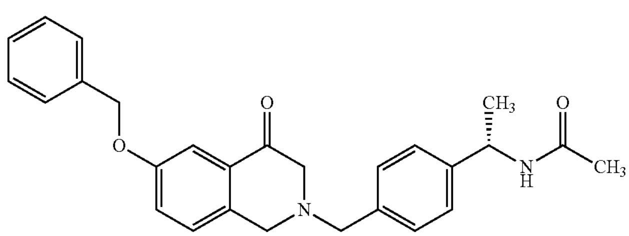 [SMILES: CC(=O)N[C@@H](C)c1ccc(CN2CC(=O)c3cc(OCc4ccccc4)ccc3C2)cc1] | 429 [M+H]+ | 0.88 (E) |
| 1.90 | XLVII.4 | III | 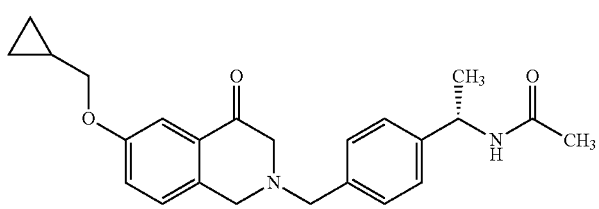 [SMILES: CC(=O)N[C@@H](C)c1ccc(CN2CC(=O)c3cc(OCC4CC4)ccc3C2)cc1] | 393 [M+H]+ | 0.83 (E) |
| 1.91 | XLVII.6 | III | 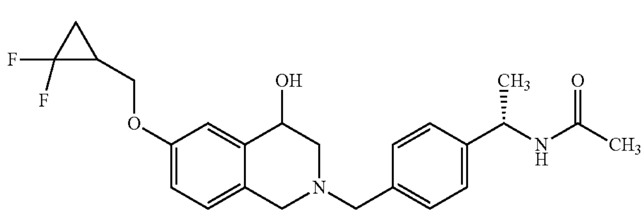 [SMILES: CC(=O)N[C@@H](C)c1ccc(CN2Cc3ccc(OCC4CC4(F)F)cc3C(O)C2)cc1] | 431 [M+H]+ | 0.84 (A) |

-continued
| Ex. | Starting materials | | Structure | ESI-MS | HPLC retention time (method) [min] |
|---|---|---|---|---|---|
| 1.92 | XLVII.7 | III | 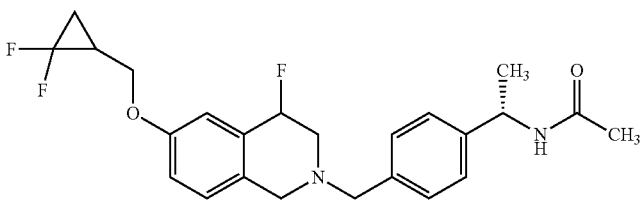 [SMILES: CC(=O)N[C@@H](C)c1ccc(CN2Cc3ccc(OCC4CC4(F)F)cc3C(F)C2)cc1] | 433 [M+H]+ | 0.92 (A) |
| 1.93 | XLVII.5 | III | 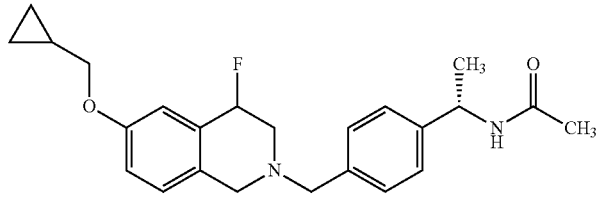 [SMILES: CC(=O)N[C@@H](C)c1ccc(CN2Cc3ccc(OCC4CC4)cc3C(F)C2)cc1] | 397 [M+H]+ | 0.88 (E) |
| 1.94 | XLVII.1 | III | 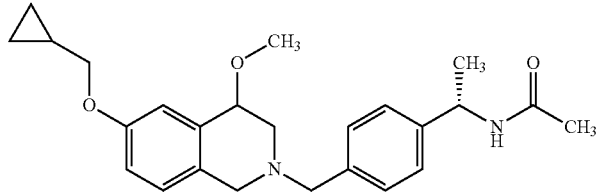 [SMILES: COC1CN(Cc2ccc([C@H](C)NC(C)=O)cc2)Cc2ccc(OCC3CC3)cc21] | 409 [M+H]+ | 0.56 (I) |
| 1.95 | XXVIII | III | 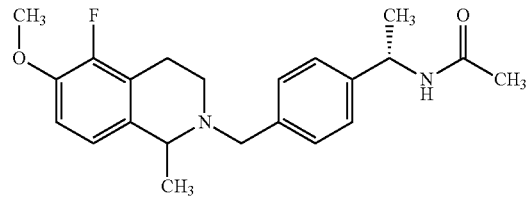 [SMILES: COc1ccc2c(c1F)CCN(Cc1ccc([C@H](C)NC(C)=O)cc1)C2C] | 371 [M+H]+ | 0.90 (A) |
| 1.96 | XLVII.2 | III | 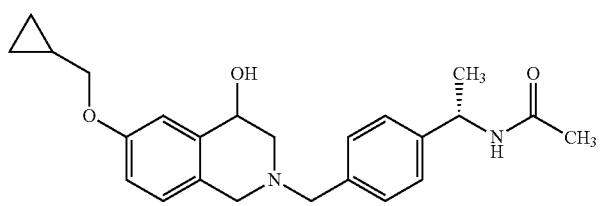 [SMILES: CC(=O)N[C@@H](C)c1ccc(CN2Cc3ccc(OCC4CC4)cc3C(O)C2)cc1] | 395 [M+H]+ | 0.77 (E) |
| 1.97 | XLVII.9 | III | 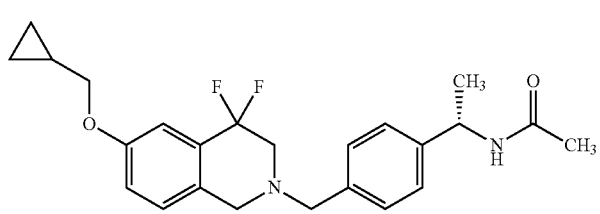 [SMILES: CC(=O)N[C@@H](C)c1ccc(CN2Cc3ccc(OCC4CC4)cc3C(F)(F)C2)cc1] | 415 [M+H]+ | 0.97 (J) |

-continued

| Ex. | Starting materials | | Structure | ESI-MS | HPLC retention time (method) [min] |
|---|---|---|---|---|---|
| 1.98* | XLVII.10 | III | 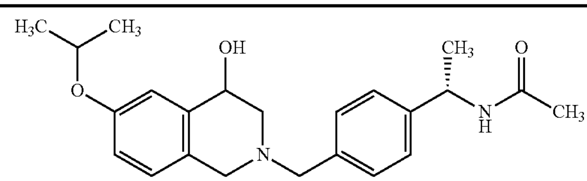 | 383 [M+H]+ | 0.93 (A) |
| 1.99* | XLVII.11 | III | 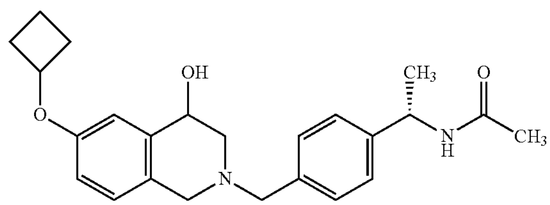 [SMILES: CC(=O)N[C@@H](C)c1ccc(CN2Cc3ccc(OC4CCC4)cc3C(O)C2)cc1] | 395 [M+H]+ | 0.97 (A) |
| 1.100* | XLVII.12 | III | 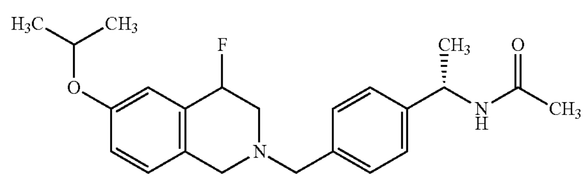 [SMILES: CC(=O)N[C@@H](C)c1ccc(CN2Cc3ccc(OC(C)C)cc3C(F)C2)cc1] | 385 [M+H]+ | 1.03 (A) |
| 1.101* | XLVII.13 | III | 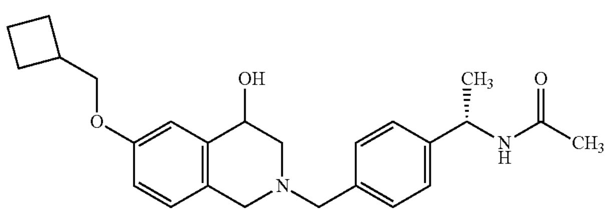 [SMILES: CC(=O)N[C@@H](C)c1ccc(CN2Cc3ccc(OCC4CCC4)cc3C(O)C2)cc1] | 409 [M+H]+ | 1.02 (A) |

* DMA used as solvent

Example 2

Example 2.1 (General Route)

Thiazole-5-carboxylic acid {(S)-1-[4-(5-methoxy-3,4-dihydro-1H-isoquinolin-2-ylmethyl)-phenyl]-ethyl}-amide

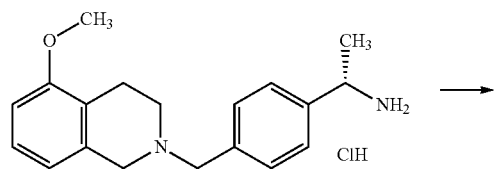

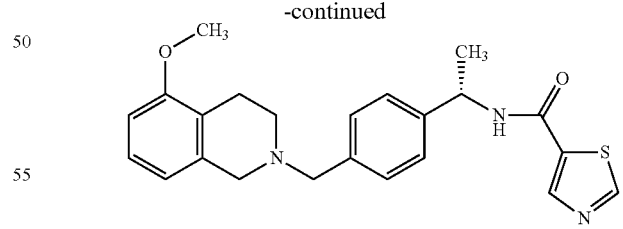

37 mg (0.29 mmol) Thiazole-5-carboxylic acid, 83 µl (0.48 mmol) DIPEA and 154 mg (0.481 mmol) TBTU in 0.5 mL DMF are stirred for 10 min at r.t. Then 80 mg (0.24 mmol) (S)-1-[4-(5-methoxy-3,4-dihydro-1H-isoquinolin-2-ylmethyl)-phenyl]-ethylamine hydrochloride (example XXXIII.2) in 1.0 mL DMF and 102 µl (0.601 mmol) DIPEA are added and the resulting mixture is stirred at r.t. for 2 h. After that time, the reaction is quenched by the addition of 200 µL water and purified by HPLC.

$C_{23}H_{25}N_3O_2S$ (M=407.5 g/mol)
ESI-MS: 408 [M+H]$^+$
$R_t$ (HPLC): 0.91 min (method A)

The following compounds are prepared according to the general procedure (example 2.1) described above:

| Ex. | Starting materials | | Structure | ESI-MS | HPLC retention time (method) [min] |
|---|---|---|---|---|---|
| 2.1 | Thiazole-5-carboxylic acid | XXXIII.2 | 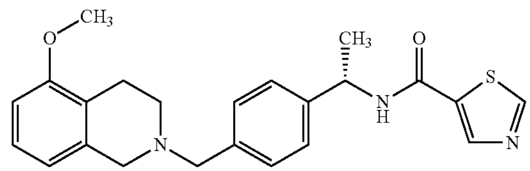 [SMILES: COc1cccc2c1CCN(Cc1ccc([C@H](C)NC(=O)c3cncs3)cc1)C2] | 408 [M + H]$^+$ | 0.91 (A) |
| 2.2 | Cyclopropane carboxylic acid | XXXIII.2 | 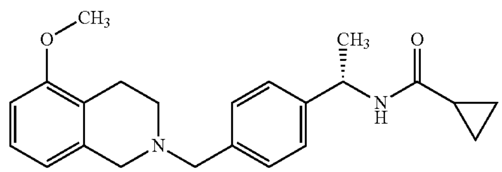 [SMILES: COc1cccc2c1CCN(Cc1ccc([C@H](C)NC(=O)C3CC3)cc1)C2] | 365 [M + H]$^+$ | 0.91 (A) |
| 2.3 | 2-(Acetylamino)-4-methyl-1,3-thiazole-5-carboxylic acid | XXXIII.2 | 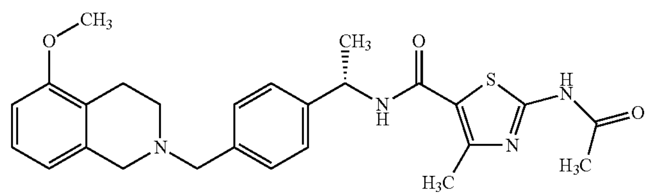 [SMILES: COc1cccc2c1CCN(Cc1ccc([C@H](C)NC(=O)c3sc(NC(C)=O)nc3C)cc1)C2] | 479 [M + H]$^+$ | 0.85 (A) |
| 2.4** | 1-Tetrahydropyran-2-ylpyrazole-4-carboxylic acid | XXXIII.2 | 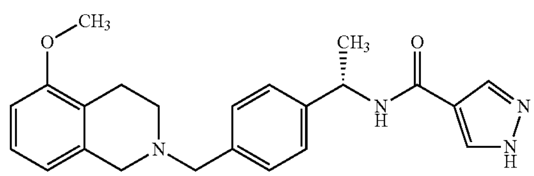 [SMILES: COc1cccc2c1CCN(Cc1ccc([C@H](C)NC(=O)c3cn[nH]c3)cc1)C2] | 391 [M + H]$^+$ | 0.84 (A) |
| 2.5 | 2-Acetylamino-4-methyl-1,3-thiazole-5-carboxylic acid | XXXIII.3 | 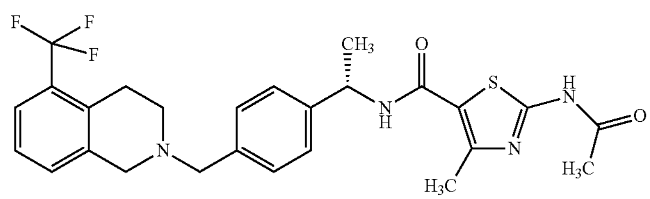 [SMILES: CC(=O)Nc1nc(C)c(C(=O)N[C@@H](C)c2ccc(CN3CCc4c(cccc4C(F)(F)F)C3)cc2)s1] | 517 [M + H]$^+$ | 0.95 (A) |
| 2.6 | Thiazole-5-carboxylic acid | XXXIII.3 | 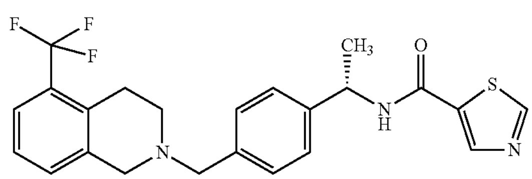 [SMILES: C[C@H](NC(=O)c1cncs1)c1ccc(CN2CCc3c(cccc3C(F)(F)F)C2)cc1] | 446 [M + H]$^+$ | 1.00 (A) |
| 2.7 | Cyclopropane carboxylic acid | XXXIII.3 | 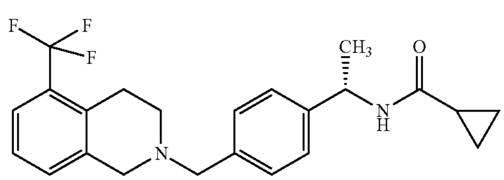 [SMILES: C[C@H](NC(=O)C1CC1)c1ccc(CN2CCc3c(cccc3C(F)(F)F)C2)cc1] | 403 [M + H]$^+$ | 1.01 (A) |
| 2.8** | 1-Tetrahydropyran-2-ylpyrazole-4-carboxylic acid | XXXIII.3 | 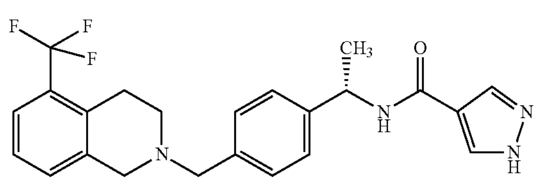 [SMILES: C[C@H](NC(=O)c1cn[nH]c1)c1ccc(CN2CCc3c(cccc3C(F)(F)F)C2)cc1] | 429 [M + H]$^+$ | 0.92 (A) |

-continued

| Ex. | Starting materials | | Structure | ESI-MS | HPLC retention time (method) [min] |
|---|---|---|---|---|---|
| 2.9 | Cyclopropane carboxylic acid | XXXIII.4 | 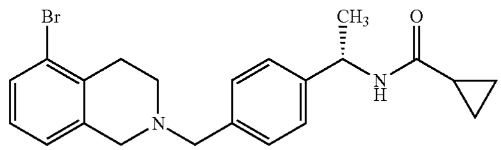 [SMILES: C[C@H](NC(=O)C1CC1)c1ccc(CN2CCc3c(Br)cccc3C2)cc1] | 413 [M + H]+ | 1.27 (G) |
| 2.10 | Thiazole-5-carboxylic acid | XXXIII.4 | 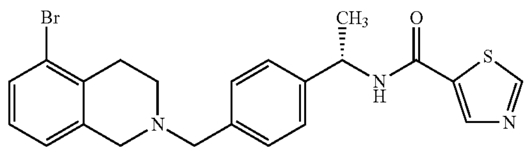 [SMILES: C[C@H](NC(=O)c1cncs1)c1ccc(CN2CCc3c(Br)cccc3C2)cc1] | 456 [M + H]+ | 0.65 (H) |
| 2.11 | Propionic acid | XXXIII.4 | 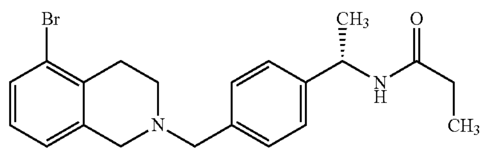 [SMILES: CCC(=O)N[C@@H](C)c1ccc(CN2CCc3c(Br)cccc3C2)cc1] | 401 [M + H]+ | 1.24 (G) |
| 2.12 | 2-(Acetylamino)-4-methyl-1,3-thiazole-5-carboxylic acid | XXXIII.5 | 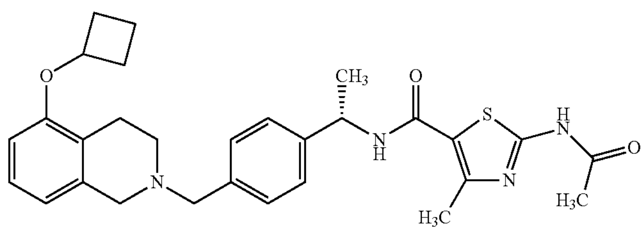 [SMILES: CC(=O)Nc1nc(C)c(C(=O)N[C@@H](C)c2ccc(CN3CCc4c(cccc4OC4CCC4)C3)cc2)s1] | 519 [M + H]+ | 0.86 (B) |
| 2.13 | Propionic acid | XXXIII.5 | 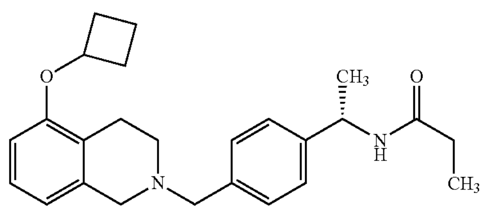 [SMILES: CCC(=O)N[C@@H](C)c1ccc(CN2CCc3c(cccc3OC3CCC3)C2)cc1] | 393 [M + H]+ | 0.84 (B) |
| 2.14 | Thiazole-5-carboxylic acid | XXXIII.5 | 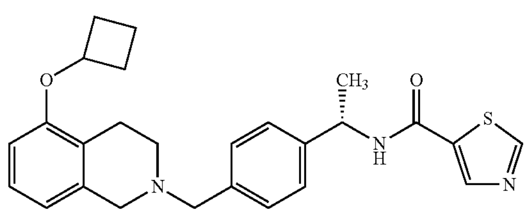 [SMILES: C[C@H](NC(=O)c1cncs1)c1ccc(CN2CCc3c(cccc3OC3CCC3)C2)cc1] | 448 [M + H]+ | 0.85 (B) |
| 2.15 | Cyclopropane carboxylic acid | XXXIII.6 | 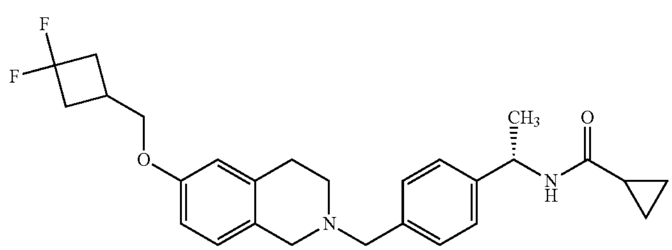 [SMILES: C[C@H](NC(=O)C1CC1)c1ccc(CN2CCc3cc(OCC4CC(F)(F)C4)ccc3C2)cc1] | 455 [M + H]+ | 0.90 (C) |

-continued

| Ex. | Starting materials | | Structure | ESI-MS | HPLC retention time (method) [min] |
|---|---|---|---|---|---|
| 2.16 | Cyclopropane carboxylic acid | XXXIII.7 | 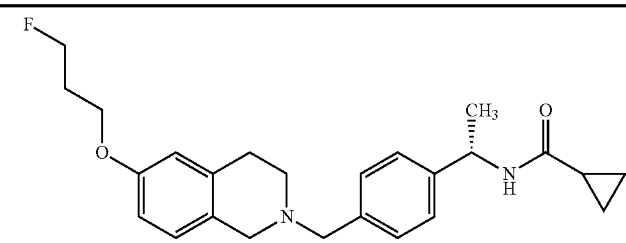 | 411 [M + H]⁺ | 0.82 (C) |
| 2.17 | Cyclopropane carboxylic acid | XXXIII.8 | 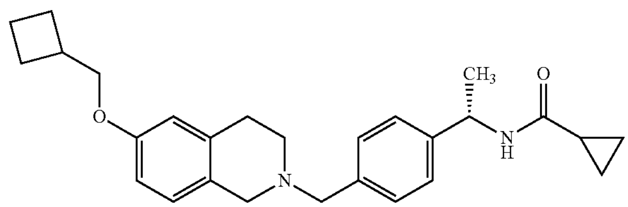 [SMILES: C[C@H](NC(=O)C1CC1)c1ccc(CN2CCc3cc(OCC4CCC4)ccc3C2)cc1] | 419 [M + H]⁺ | 0.98 (C) |
| 2.18 | Cyclopropane carboxylic acid | XXXIII.9 | 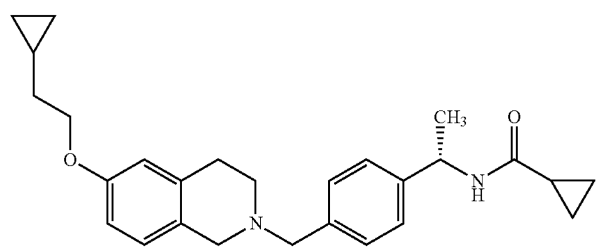 [SMILES: C[C@H](NC(=O)C1CC1)c1ccc(CN2CCc3cc(OCCC4CC4)ccc3C2)cc1] | 419 [M + H]⁺ | 0.96 (C) |
| 2.19 | Cyclopropane carboxylic acid | XXXIII.10 | 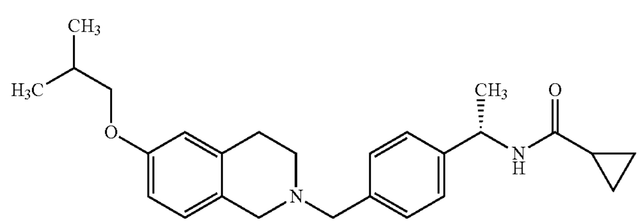 [SMILES: CC(C)COc1ccc2c(c1)CCN(Cc1ccc([C@H](C)NC(=O)C3CC3)cc1)C2] | 407 [M + H]⁺ | 0.96 (C) |
| 2.20 | 2-Acetylamino-4-methyl-1,3-thiazole-5-carboxylic acid | XXXIII.1 | 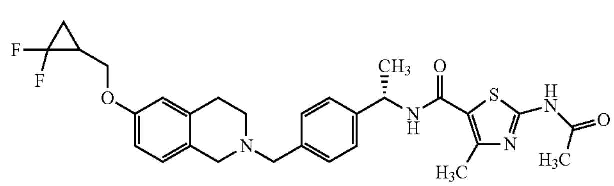 [SMILES: CC(=O)Nc1nc(C)c(C(=O)N[C@@H](C)c2ccc(CN3CCc4cc(OCC5CC5(F)F)ccc4C3)cc2)s1] | 555 [M + H]⁺ | 0.89 (A) |
| 2.21* | Lactic acid | XXXIII.11 | 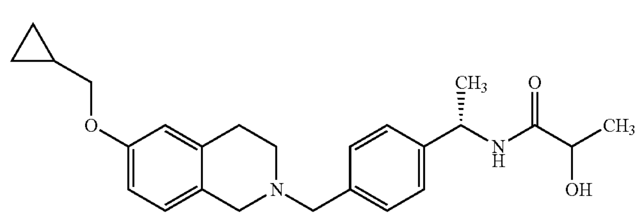 [SMILES: CC(O)C(=O)N[C@@H](C)c1ccc(CN2CCc3cc(OCC4CC4)ccc3C2)cc1] | 409 [M + H]⁺ | 0.81 (C) |
| 2.22* | Pyrimidin-5-yl-acetic acid | XXXIII.11 | 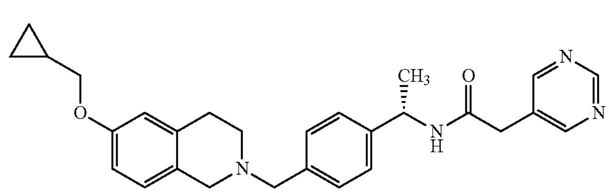 [SMILES: C[C@H](NC(=O)Cc1cncnc1)c1ccc(CN2CCc3cc(OCC4CC4)ccc3C2)cc1] | 457 [M + H]⁺ | 0.79 (C) |

-continued
| Ex. | Starting materials | | Structure | ESI-MS | HPLC retention time (method) [min] |
|---|---|---|---|---|---|
| 2.23* | Glycolic acid | XXXIII.11 | 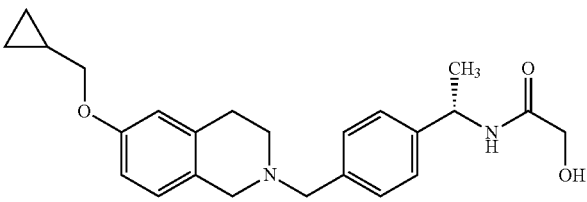 [SMILES: C[C@H](NC(=O)CO)c1ccc(CN2CCc3cc(OCC4CC4)ccc3C2)cc1] | 395 [M + H]+ | 0.78 (C) |
| 2.24* | 1-Hydroxy-1-cyclopropane carboxylic acid | XXXIII.11 | 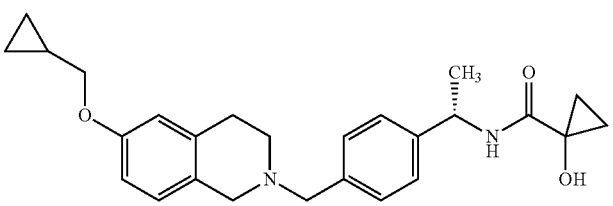 [SMILES: C[C@H](NC(=O)C1(O)CC1)c1ccc(CN2CCc3cc(OCC4CC4)ccc3C2)cc1] | 421 [M + H]+ | 0.83 (C) |
| 2.25* | Glycolic acid | XXXIII.12 | 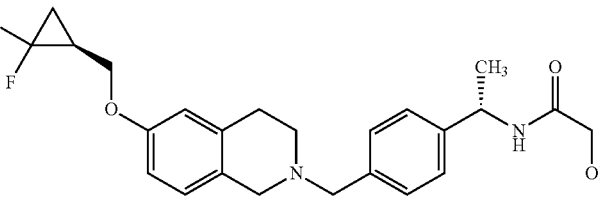 | 431 [M + H]+ | 0.90 (A) |
| 2.26* | Pyrimidin-5-yl-acetic acid | XXXIII.12 | 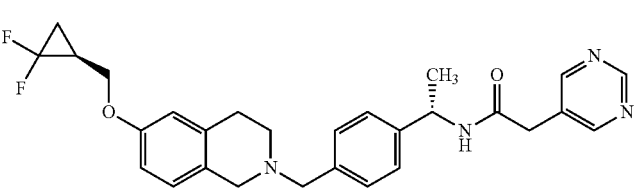 [SMILES: C[C@H](NC(=O)Cc1cncnc1)c1ccc(CN2CCc3cc(OC[C@@H]4CC4(F)F)ccc3C2)cc1] | 493 [M + H]+ | 0.57 (D) |
| 2.27* | Lactic acid | XXXIII.12 | 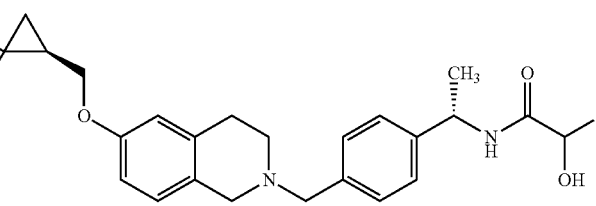 | 445 [M + H]+ | 0.56 (D) |
| 2.28* | 1-Hydroxy-1-cyclopropane carboxylic acid | XXXIII.12 | 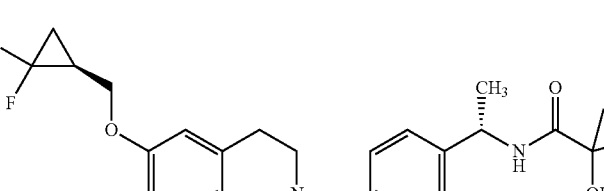 | 457 [M + H]+ | 0.58 (D) |
| 2.29* | 5-Oxo-pyrrolidine-2-carboxylic acid | XXXIII.12 | 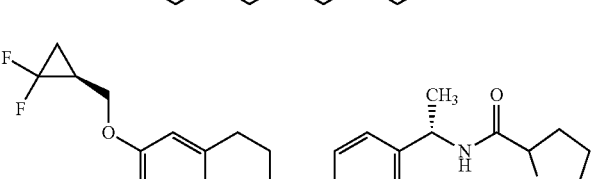 | 484 [M + H]+ | 0.55 (D) |

| Ex. | Starting materials | | Structure | ESI-MS | HPLC retention time (method) [min] |
|---|---|---|---|---|---|
| 2.30* | N,N-Dimethyl-malonamic acid | XXXIII.11 | 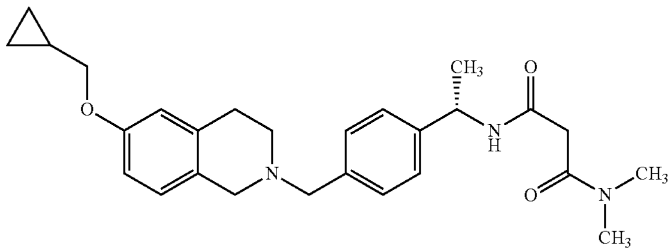 [SMILES: C[C@H](NC(=O)CC(=O)N(C)C)c1ccc(CN2CCc3cc(OCC4CC4)ccc3C2)cc1] | 450 [M + H]+ | 0.55 (D) |
| 2.31* | N,N-Dimethyl-malonamic acid | XXXIII.12 | 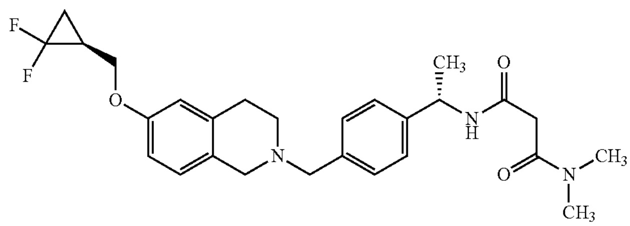 [SMILES: C[C@H](NC(=O)CC(=O)N(C)C)c1ccc(CN2CCc3cc(OC[C@@H]4CC4(F)F)ccc3C2)cc1] | 486 [M + H]+ | 0.55 (D) |
| 2.32* | 2-Acetylamino-4-methyl-1,3-thiazole-5-carboxylic acid | XXXIII.11 | 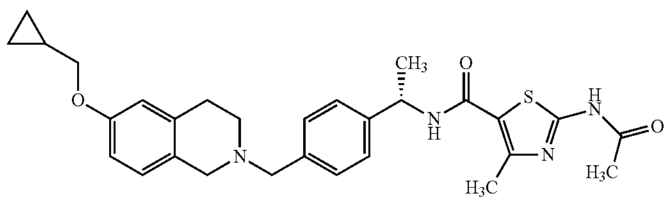 [SMILES: CC(=O)Nc1nc(C)c(C(=O)N[C@@H](C)c2ccc(CN3CCc4cc(OCC5CC5)ccc4C3)cc2)s1] | 519 [M + H]+ | 0.92 (E) |
| 2.33* | 4-Methyl-2-propionylamino-thiazole-5-carboxylic acid | XXXIII.11 | 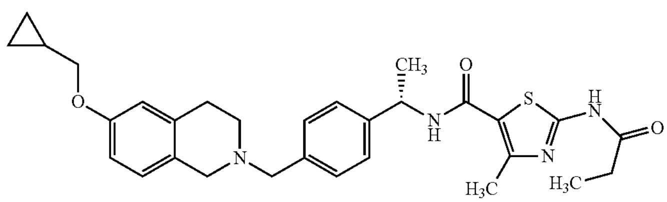 [SMILES: CCC(=O)Nc1nc(C)c(C(=O)N[C@@H](C)c2ccc(CN3CCc4cc(OCC5CC5)ccc4C3)cc2)s1] | 533 [M + H]+ | 0.98 (E) |
| 2.34* | Glycolic acid | XLVIII.2 | 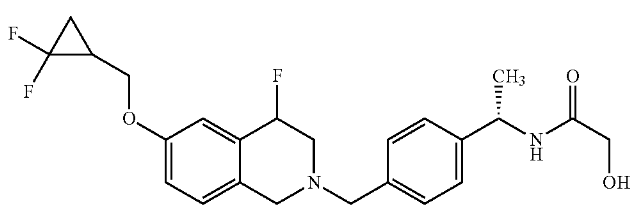 [SMILES: C[C@H](NC(=O)CO)c1ccc(CN2Cc3ccc(OCC4CC4(F)F)cc3C(F)C2)cc1] | 449 [M + H]+ | 0.78 (JJ) |
| 2.35*** | 2-Acetylamino-4-methyl-1,3-thiazole-5-carboxylic acid | XLVIII.4 | 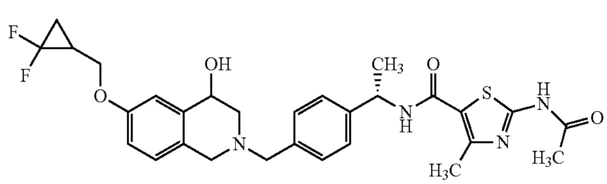 | 571 [M + H]+ | 0.83 (KK) |
| 2.36*** | 3-Fluorocyclo-butanecarboxylic acid | XLVIII.4 | 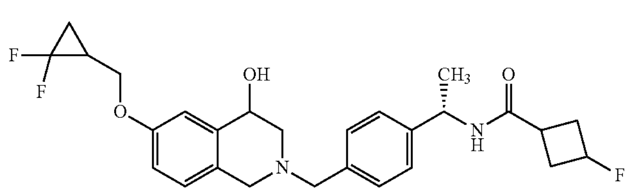 [SMILES: C[C@H](NC(=O)C1CC(F)C1)c1ccc(CN2Cc3ccc(OCC4CC4(F)F)cc3C(O)C2)cc1] | 489 [M + H]+ | 0.88 (KK) |

-continued

| Ex. | Starting materials | | Structure | ESI-MS | HPLC retention time (method) [min] |
|---|---|---|---|---|---|
| 2.37*** | Cyanoacetic acid | XLVIII.4 | 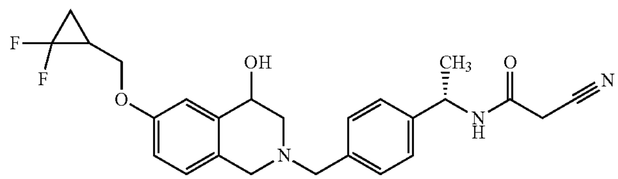 [SMILES: C[C@H](NC(=O)CC#N)c1ccc(CN2Cc3ccc(OCC4CC4(F)F)cc3C(O)C2)cc1] | 456 [M + H]⁺ | 0.52 (D) |
| 2.38*** | Pyrimidinyl-5-carboxylic acid | XLVIII.3 | 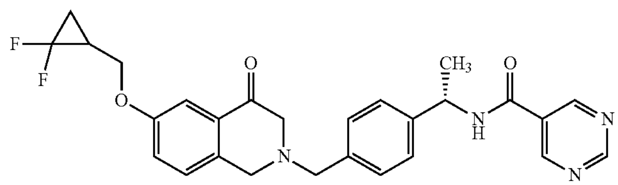 [SMILES: C[C@H](NC(=O)c1cncnc1)c1ccc(CN2CC(=O)c3cc(OCC4CC4(F)F)ccc3C2)cc1] | 493 [M + H]⁺ | 0.75 (C) |
| 2.39*** | Glycolic acid | XLVIII.3 | 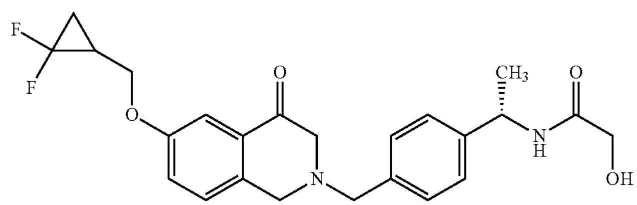 [SMILES: C[C@H](NC(=O)CO)c1ccc(CN2CC(=O)c3cc(OCC4CC4(F)F)ccc3C2)cc1] | 445 [M + H]⁺ | 0.70 (C) |
| 2.40*** | Cyanoacetic acid | XLVIII.3 | 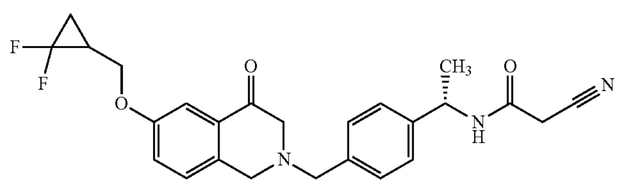 [SMILES: C[C@H](NC(=O)CC#N)c1ccc(CN2CC(=O)c3cc(OCC4CC4(F)F)ccc3C2)cc1] | 454 [M + H]⁺ | 0.55 (D) |
| 2.41*** | Glycolic acid | XLVIII.5 | 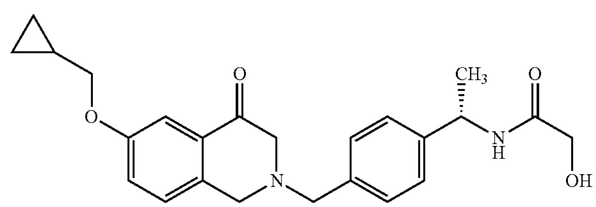 [SMILES: C[C@H](NC(=O)CO)c1ccc(CN2CC(=O)c3cc(OCC4CC4)ccc3C2)cc1] | 409 [M + H]⁺ | 0.82 (J) |
| 2.42*** | Lactic acid | XLVIII.5 | 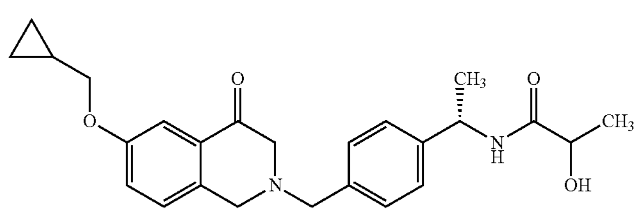 [SMILES: CC(O)C(=O)N[C@@H](C)c1ccc(CN2CC(=O)c3cc(OCC4CC4)ccc3C2)cc1] | 423 [M + H]⁺ | 0.83 (J) |
| 2.43*** | Cyanoacetic acid | XLVIII.5 | 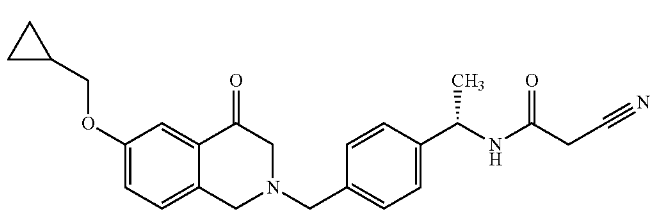 [SMILES: C[C@H](NC(=O)CC#N)c1ccc(CN2CC(=O)c3cc(OCC4CC4)ccc3C2)cc1] | 418 [M + H]⁺ | 0.85 (J) |

-continued

| Ex. | Starting materials | | Structure | ESI-MS | HPLC retention time (method) [min] |
|---|---|---|---|---|---|
| 2.44*** | Pyrimidin-5-yl-acetic acid | XLVIII.5 | 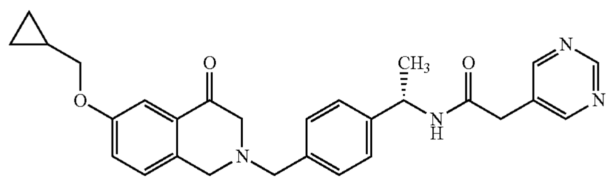 [SMILES: C[C@H](NC(=O)Cc1cncnc1)c1ccc(CN2CC(=O)c3cc(OCC4CC4)ccc3C2)cc1] | 471 [M + H]⁺ | 0.83 (J) |

*TEA is used as base and DMA as solvent
**After purification 2 mL MeOH and 20 μl aq. HCl solution (c = 1 mol/L) are added and the resulting mixture is stirred at r.t. for 1 h to remove the THP protecting group.
***HATU in DMA was used instead of TBTU

Example 3

Example 3.1 (General Route)

2-Cyano-N—((S)-1-{4-[6-(2,2-difluoro-cyclopropyl-methoxy)-3,4-dihydro-1H-isoquinolin-2-ylmethyl]-phenyl}-ethyl)-acetamide

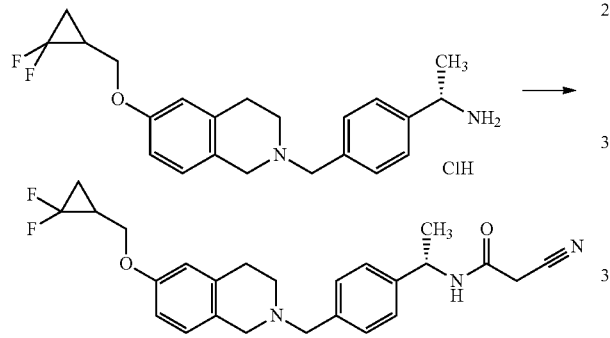

1.70 mg (20.0 μmol) Cyanoacetic acid, 4.09 mg (10.0 μmol) (S)-1-{4-[6-(2,2-difluoro-cyclopropylmethoxy)-3,4-dihydro-1H-isoquinolin-2-ylmethyl]-phenyl}-ethylamine hydrochloride (example XXXIII.1) and 6.88 μL (40.0 μmol) DIPEA in 0.5 mL ACN are stirred at r.t. Then 4.18 mg (15.0 μmol) CIP are added and the resulting mixture is stirred at r.t. over night. The reaction is quenched by the addition of 25 μL aq. $K_2CO_3$ solution (c=3 mol/L), filtered over basic aluminum oxide and concentrated by evaporation.

$C_{25}H_{27}F_2N_3O_2$ (M=439.5 g/mol)

ESI-MS: 440 [M+H]⁺

$R_t$ (HPLC): 0.81 min (method B)

The following compounds are prepared according to the general procedure (example 3.1) described above:

| Ex. | Starting materials | | Structure | ESI-MS | HPLC retention time (method) [min] |
|---|---|---|---|---|---|
| 3.1 | Cyano-acetic acid | XXXIII.1 | 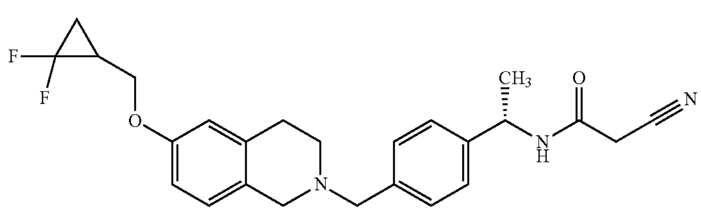 [SMILES: C[C@H](NC(=O)CC#N)c1ccc(CN2CCc3cc(OCC4CC4(F)F)ccc3C2)cc1] | 440 [M + H]⁺ | 0.81 (B) |
| 3.2 | 2,2-Difluoro-propionic acid | XXXIII.1 | 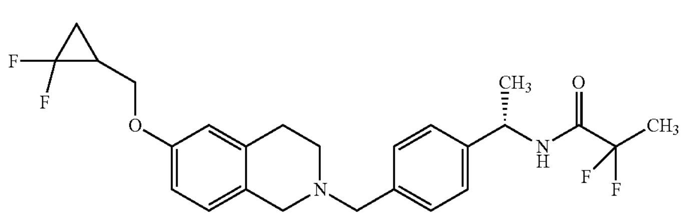 [SMILES: C[C@H](NC(=O)C(C)(F)F)c1ccc(CN2CCc3cc(OCC4CC4(F)F)ccc3C2)cc1] | 465 [M + H]⁺ | 0.90 (C) |

-continued

| Ex. | Starting materials | | Structure | ESI-MS | HPLC retention time (method) [min] |
|---|---|---|---|---|---|
| 3.3 | 2-Cyano-2-methyl-acetic acid | XXXIII.1 | 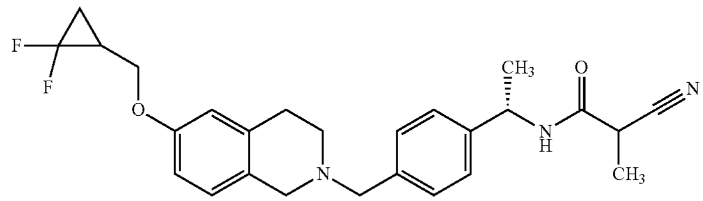 [SMILES: CC(C#N)C(=O)N[C@@H](C)c1ccc(CN2CCc3cc(OCC4CC4(F)F)ccc3C2)cc1] | 454 [M + H]+ | 0.84 (C) |
| 3.4 | 1-Methyl-1H-pyrazole-4-carboxylic acid | XXXIII.1 | 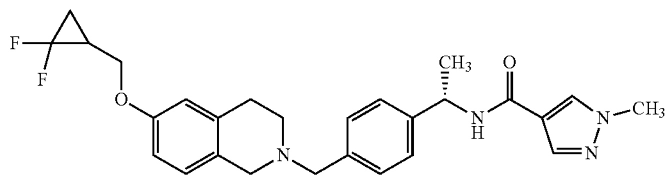 [SMILES: C[C@H](NC(=O)c1cnn(C)c1)c1ccc(CN2CCc3cc(OCC4CC4(F)F)ccc3C2)cc1] | 481 [M + H]+ | 0.79 (C) |
| 3.5 | 1-Trifluoro-methyl-cyclo-propane-1-carboxylic acid | XXXIII.1 | 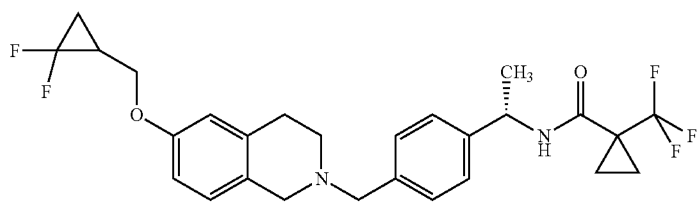 [SMILES: C[C@H](NC(=O)C1(C(F)(F)F)CC1)c1ccc(CN2CCc3cc(OCC4CC4(F)F)ccc3C2)cc1] | 509 [M + H]+ | 0.96 (C) |
| 3.6 | Cyclo-butane carboxylic acid | XXXIII.1 | 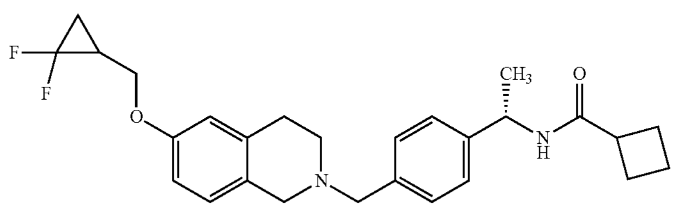 [SMILES: C[C@H](NC(=O)C1CCC1)c1ccc(CN2CCc3cc(OCC4CC4(F)F)ccc3C2)cc1] | 455 [M + H]+ | 0.89 (C) |
| 3.7 | 3-Fluoro-cyclo-butane-carboxylic acid | XXXIII.1 | 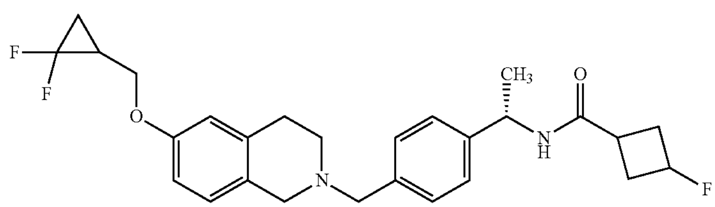 [SMILES: C[C@H](NC(=O)C1CC(F)C1)c1ccc(CN2CCc3cc(OCC4CC4(F)F)ccc3C2)cc1] | 473 [M + H]+ | 0.88 (C) |
| 3.8 | Isothiazole-5-carboxylic acid | XXXIII.1 | 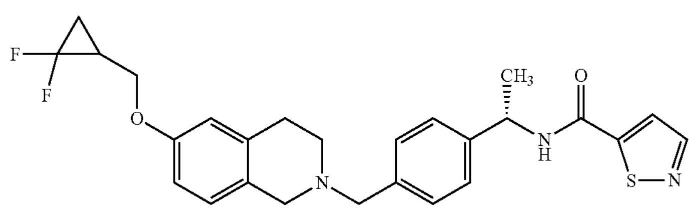 [SMILES: C[C@H](NC(=O)c1ccns1)c1ccc(CN2CCc3cc(OCC4CC4(F)F)ccc3C2)cc1] | 484 [M + H]+ | 0.88 (C) |
| 3.9 | Oxazole-5-carboxylic acid | XXXIII.1 | 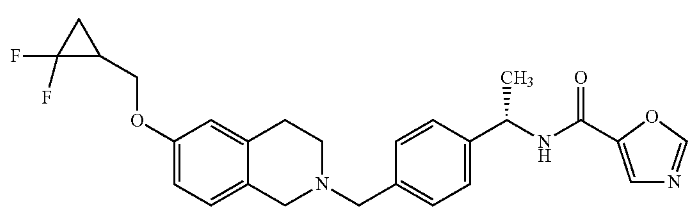 [SMILES: C[C@H](NC(=O)c1cnco1)c1ccc(CN2CCc3cc(OCC4CC4(F)F)ccc3C2)cc1] | 468 [M + H]+ | 0.81 (C) |

-continued

| Ex. | Starting materials | | Structure | ESI-MS | HPLC retention time (method) [min] |
|---|---|---|---|---|---|
| 3.10* | 1-Tetrahydro-pyran-2-ylpyrazole-4-carboxylic acid | XXXIII.1 | 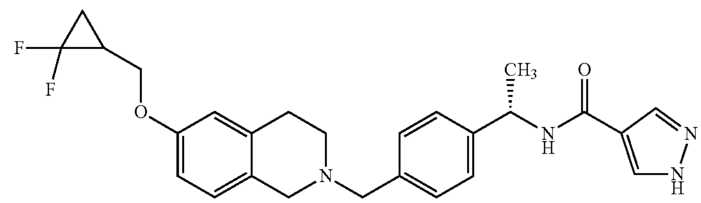 [SMILES: C[C@H](NC(=O)c1cn[nH]c1)c1ccc(CN2CCc3cc(OCC4CC4(F)F)ccc3C2)cc1] | 467 [M + H]+ | 0.76 (H) |
| 3.11 | 3-Isoxazole-carboxylic acid | XXXIII.1 | 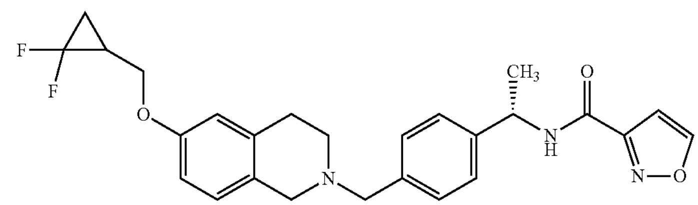 [SMILES: C[C@H](NC(=O)c1ccon1)c1ccc(CN2CCc3cc(OCC4CC4(F)F)ccc3C2)cc1] | 468 [M + H]+ | 0.88 (C) |
| 3.12 | 5-Methyl-1H-pyrazole-4-carboxylic acid | XXXIII.1 | 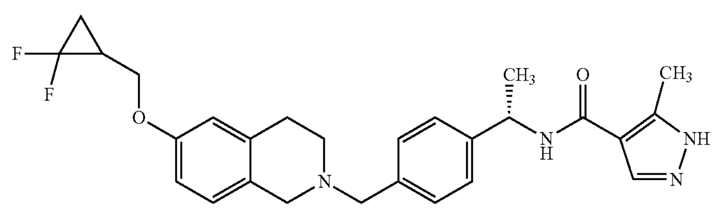 [SMILES: Cc1[nH]ncc1C(=O)N[C@@H](C)c1ccc(CN2CCc3cc(OCC4CC4(F)F)ccc3C2)cc1] | 481 [M + H]+ | 0.79 (C) |
| 3.13 | 1-Cyano-1-cyclo-propane-carboxylic acid | XXXIII.1 | 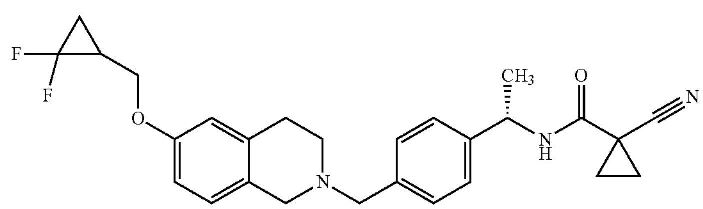 [SMILES: C[C@H](NC(=O)C1(C#N)CC1)c1ccc(CN2CCc3cc(OCC4CC4(F)F)ccc3C2)cc1] | 466 [M + H]+ | 0.89 (C) |
| 3.14 | Isoxazole-5-carboxylic acid | XXXIII.1 | 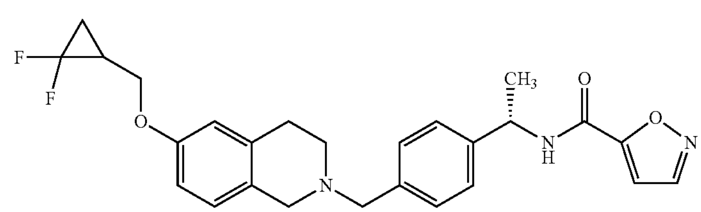 [SMILES: C[C@H](NC(=O)c1ccno1)c1ccc(CN2CCc3cc(OCC4CC4(F)F)ccc3C2)cc1] | 468 [M + H]+ | 0.86 (C) |
| 3.15 | 1-Methyl-cyclo-propane-carboxylic acid | XXXIII.1 | 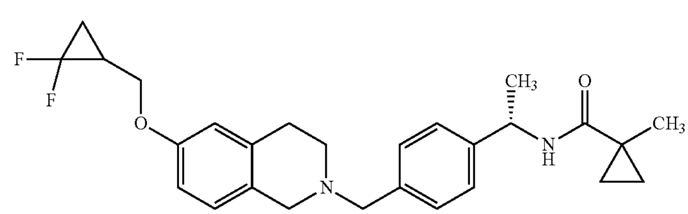 [SMILES: C[C@H](NC(=O)C1(C)CC1)c1ccc(CN2CCc3cc(OCC4CC4(F)F)ccc3C2)cc1] | 455 [M + H]+ | 0.90 (C) |
| 3.16 | 5-Chloro-1-methyl-1H-pyrazole-4-carboxylic acid | XXXIII.1 | 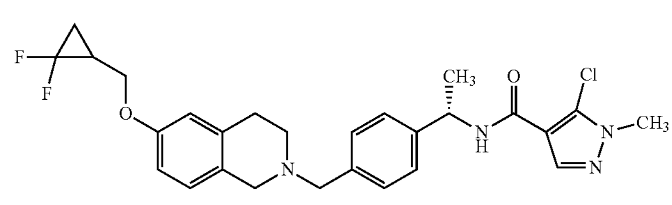 [SMILES: C[C@H](NC(=O)c1cnn(C)c1Cl)c1ccc(CN2CCc3cc(OCC4CC4(F)F)ccc3C2)cc1] | 515 [M + H]+ | 0.86 (C) |

-continued

| Ex. | Starting materials | | Structure | ESI-MS | HPLC retention time (method) [min] |
|---|---|---|---|---|---|
| 3.17 | V | XXXIII.1 | 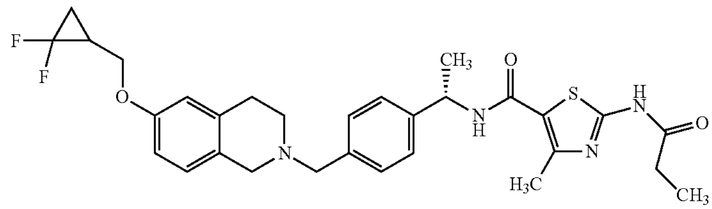 [SMILES: CCC(=O)Nc1nc(C)c(C(=O)N[C@@H](C)c2ccc(CN3CCc4cc(OCC5CC5(F)F)ccc4C3)cc2)s1] | 569 [M + H]⁺ | 0.85 (C) |
| 3.18 | 1,5-Dimethyl-1H-pyrazole-4-carboxylic acid | XXXIII.1 | 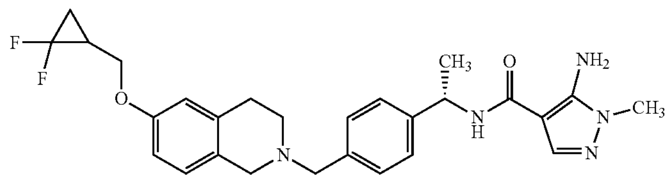 [SMILES: C[C@H](NC(=O)c1cnn(C)c1N)c1ccc(CN2CCc3cc(OCC4CC4(F)F)ccc3C2)cc1] | 496 [M + H]⁺ | 0.79 (C) |
| 3.19 | Thiazole-5-carboxylic acid | XXXIII.1 | 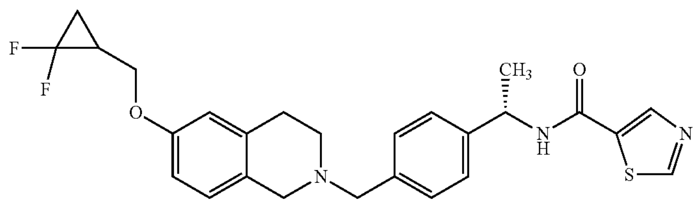 [SMILES: C[C@H](NC(=O)c1cncs1)c1ccc(CN2CCc3cc(OCC4CC4(F)F)ccc3C2)cc1] | 484 [M + H]⁺ | 0.84 (C) |
| 3.20 | 3-Methyl-isoxazole-4-carboxylic acid | XXXIII.1 | 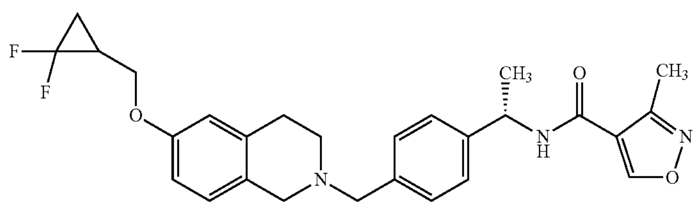 [SMILES: Cc1nocc1C(=O)N[C@@H](C)c1ccc(CN2CCc3cc(OCC4CC4(F)F)ccc3C2)cc1] | 482 [M + H]⁺ | 0.87 (C) |
| 3.21 | 3,3-Difluoro-cyclo-butane-carboxylic acid | XXXIII.1 | 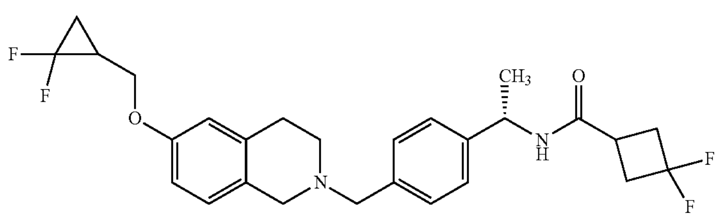 [SMILES: C[C@H](NC(=O)C1CC(F)(F)C1)c1ccc(CN2CCc3cc(OCC4CC4(F)F)ccc3C2)cc1] | 491 [M + H]⁺ | 0.88 (B) |
| 3.22 | trans-3-Fluoro-cyclo-butane-carboxylic acid | XLVIII.1 | 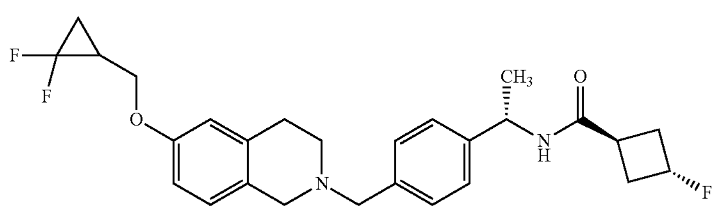 [SMILES: C[C@H](NC(=O)[C@H]1C[C@H](F)C1)c1ccc(CN2CCc3cc(OCC4CC4(F)F)ccc3C2)cc1] | 473 [M + H]⁺ | 0.86 (B) |
| 3.23 | trans-3-Fluoro-cyclo-butane-carboxylic acid | XLVIII.1 | 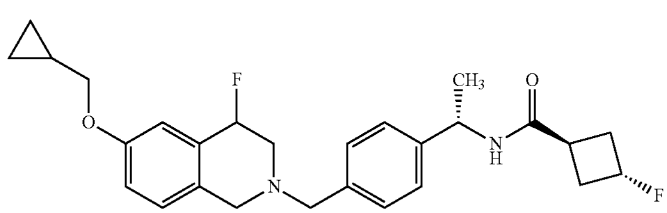 [SMILES: C[C@H](NC(=O)[C@H]1C[C@H](F)C1)c1ccc(CN2Cc3ccc(OCC4CC4)cc3C(F)C2)cc1] | 455 [M + H]⁺ | 0.97 (E) |

-continued
| Ex. | Starting materials | | Structure | ESI-MS | HPLC retention time (method) [min] |
|---|---|---|---|---|---|
| 3.24 | Propionic acid | XLVIII.1 | 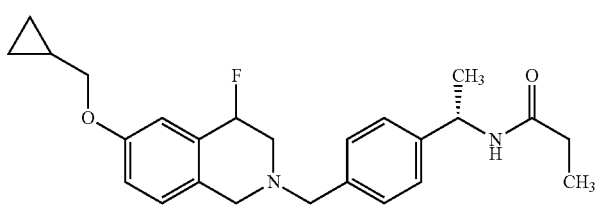 [SMILES: CCC(=O)N[C@@H](C)c1ccc(CN2Cc3ccc(OCC4CC4)cc3C(F)C2)cc1] | 411 [M + H]+ | 0.93 (E) |
| 3.25 | V | XLVIII.1 | 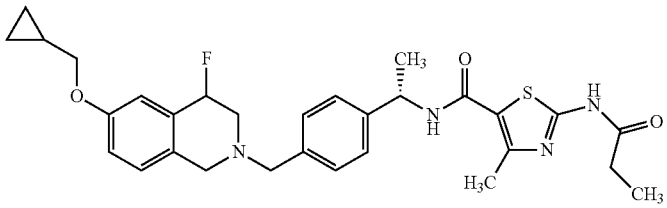 [SMILES: CCC(=O)Nc1nc(C)c(C(=O)N[C@@H](C)c2ccc(CN3Cc4ccc(OCC5CC5)cc4C(F)C3)cc2)s1] | 551 [M + H]+ | 0.96 (E) |
| 3.26 | Cyanoacetic acid | XLVIII.1 | 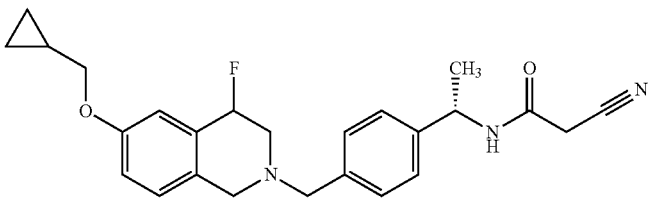 [SMILES: C[C@H](NC(=O)CC#N)c1ccc(CN2Cc3ccc(OCC4CC4)cc3C(F)C2)cc1] | 422 [M + H]+ | 0.58 (D) |
| 3.27 | Propionic acid | XLVIII.2 | 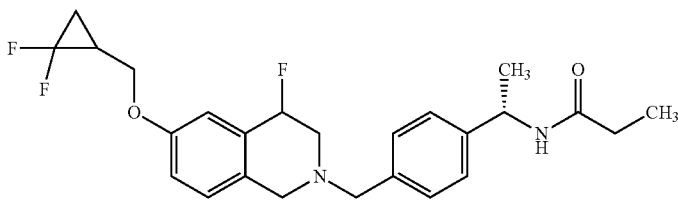 [SMILES: CCC(=O)N[C@@H](C)c1ccc(CN2Cc3ccc(OCC4CC4(F)F)cc3C(F)C2)cc1] | 447 [M + H]+ | 0.62 (I) |
| 3.28 | 1-Cyano-1-cyclopropane-carboxylic acid | XLVIII.2 | 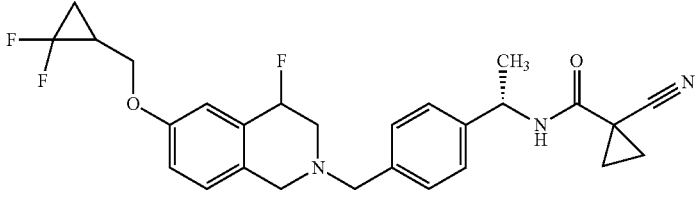 [SMILES: C[C@H](NC(=O)C1(C#N)CC1)c1ccc(CN2Cc3ccc(OCC4CC4(F)F)cc3C(F)C2)cc1] | 484 [M + H]+ | 0.63 (I) |
| 3.29 | Cyanoacetic acid | XLVIII.2 | 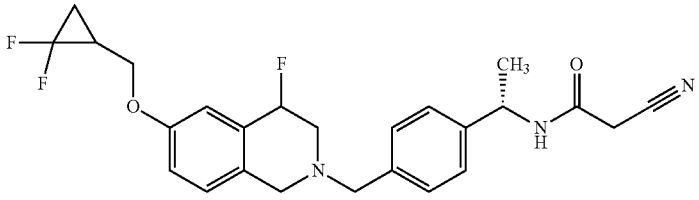 [SMILES: C[C@H](NC(=O)CC#N)c1ccc(CN2Cc3ccc(OCC4CC4(F)F)cc3C(F)C2)cc1] | 458 [M + H]+ | 0.81 (B) |
| 3.30 | Pyrimidin-5-yl-acetic acid | XLVIII.2 | 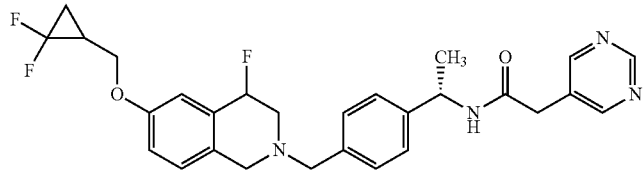 [SMILES: C[C@H](NC(=O)Cc1cncnc1)c1ccc(CN2Cc3ccc(OCC4CC4(F)F)cc3C(F)C2)cc1] | 511 [M + H]+ | 0.79 (JJ) |

-continued

| Ex. | Starting materials | | Structure | ESI-MS | HPLC retention time (method) [min] |
|---|---|---|---|---|---|
| 3.31 | trans-3-Fluoro-cyclobutane carboxylic acid | XLVIII.2 | 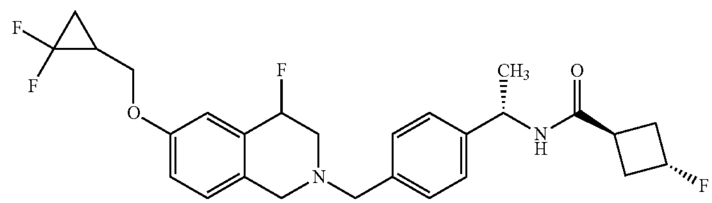 [SMILES: C[C@H](NC(=O)[C@H]1C[C@H](F)C1)c1ccc(CN2Cc3ccc(OCC4CC4(F)F)cc3C(F)C2)cc1] | 491 [M + H]+ | 0.84 (JJ) |
| 3.32 | 2-Acetyl-amino-4-methyl-1,3-thiazole-5-carboxylic acid | XLVIII.2 | 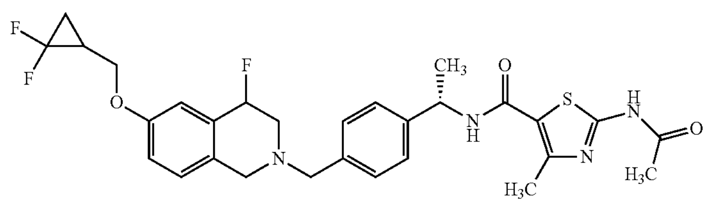 [SMILES: CC(=O)Nc1nc(C)c(C(=O)N[C@@H](C)c2ccc(CN3Cc4ccc(OCC5CC5(F)F)cc4C(F)C3)cc2)s1] | 573 [M + H]+ | 0.83 (JJ) |
| 3.33 | 1H-Imidazole-2-carboxylic acid | XLVIII.1 | 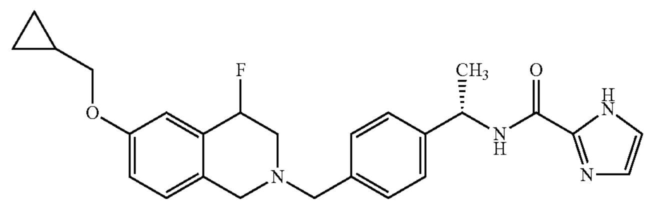 [SMILES: C[C@H](NC(=O)c1ncc[nH]1)c1ccc(CN2Cc3ccc(OCC4CC4)cc3C(F)C2)cc1] | 449 [M + H]+ | 0.51 (MM) |
| 3.34 | Malonamic acid | XLVIII.1 | 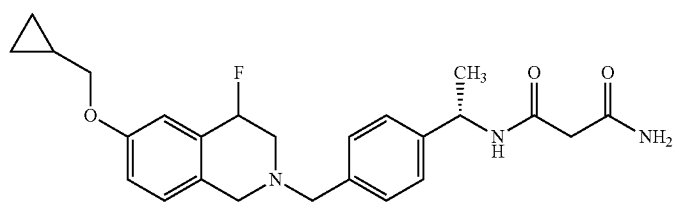 [SMILES: C[C@H](NC(=O)CC(N)=O)c1ccc(CN2Cc3ccc(OCC4CC4)cc3C(F)C2)cc1] | 440 [M + H]+ | 0.52 (MM) |
| 3.35 | 2-Oxo-pyrrolidine-2-carboxylic acid | XLVIII.1 | 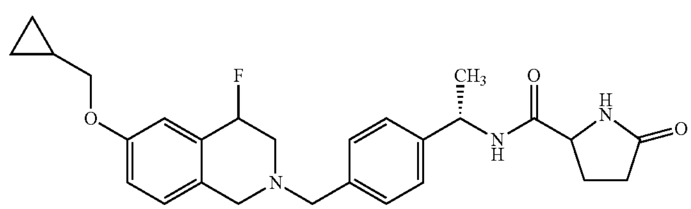 [SMILES: C[C@H](NC(=O)C1CCC(=O)N1)c1ccc(CN2Cc3ccc(OCC4CC4)cc3C(F)C2)cc1] | 466 [M + H]+ | 0.52 (MM) |
| 3.36 | 2-Acetyl-amino-4-methyl-oxazole-5-carboxylic acid | XLVIII.1 | 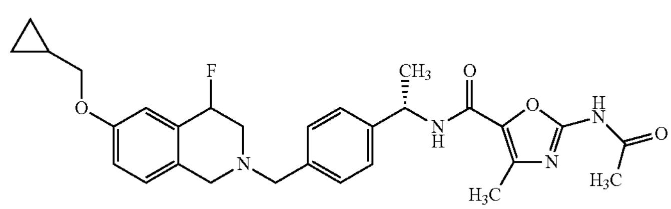 [SMILES: CC(=O)Nc1nc(C)c(C(=O)N[C@@H](C)c2ccc(CN3Cc4ccc(OCC5CC5)cc4C(F)C3)cc2)o1] | 521 [M + H]+ | 0.58 (MM) |
| 3.37 | Pyrazin-2-yl-acetic acid | XLVIII.1 | 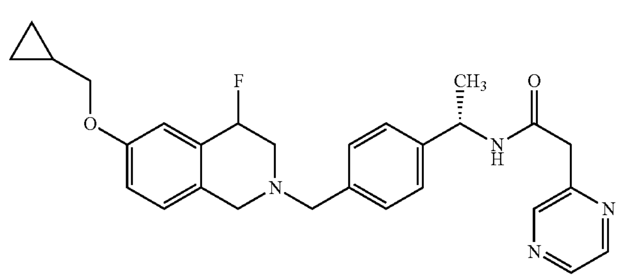 [SMILES: C[C@H](NC(=O)Cc1cnccn1)c1ccc(CN2Cc3ccc(OCC4CC4)cc3C(F)C2)cc1] | 475 [M + H]+ | 0.56 (MM) |

-continued

| Ex. | Starting materials | | Structure | ESI-MS | HPLC retention time (method) [min] |
|---|---|---|---|---|---|
| 3.38 | Cyclopropane-carboxylic acid | XLVIII.6 | 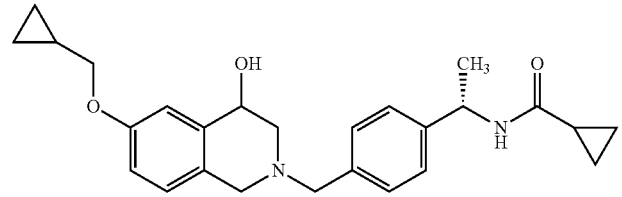 [SMILES: C[C@H](NC(=O)C1CC1)c1ccc(CN2Cc3ccc(OCC4CC4)cc3C(O)C2)cc1] | 421 [M + H]⁺ | 0.80 (JJ) |
| 3.39 | Propionic acid | XLVIII.6 | 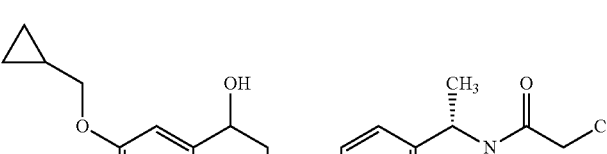 | 409 [M + H]⁺ | 0.78 (JJ) |
| 3.40 | 4-Methyl-2-propionyl-amino-thiazole-5-carboxylic acid | XLVIII.6 | 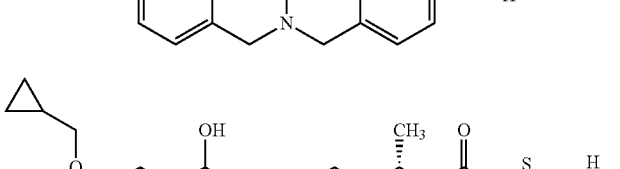 | 549 [M + H]⁺ | 1.01 (A) |
| 3.41 | Cyclobutane carboxylic acid | XLVIII.6 | 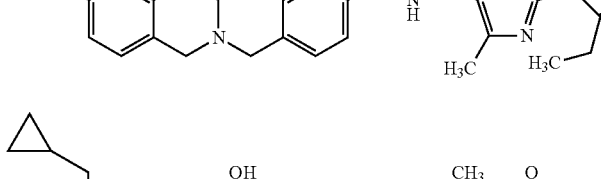 | 435 [M + H]⁺ | 1.05 (A) |
| 3.42 | Cyclobutane carboxylic acid | XLVIII.1 | 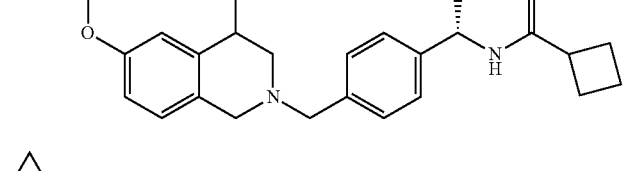 | 437 [M + H]⁺ | 1.13 (A) |
| 3.43 | 1-Cyano-cyclopropane-carboxylic acid | XLVIII.6 | 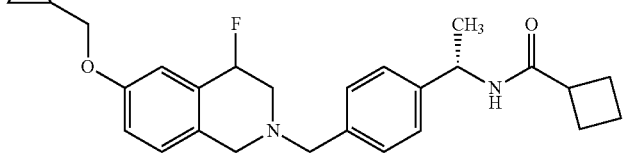 | 446 [M + H]⁺ | 1.04 (A) |
| 3.44 | 1-Cyano-cyclopropane-carboxylic acid | XLVIII.1 | 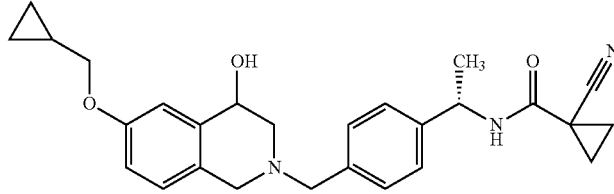 | 448 [M + H]⁺ | 1.13 (A) |

-continued

| Ex. | Starting materials | | Structure | ESI-MS | HPLC retention time (method) [min] |
|---|---|---|---|---|---|
| 3.45 | 2-Acetyl-amino-4-methyl-thiazole-5-carboxylic acid | XLVIII.6 | 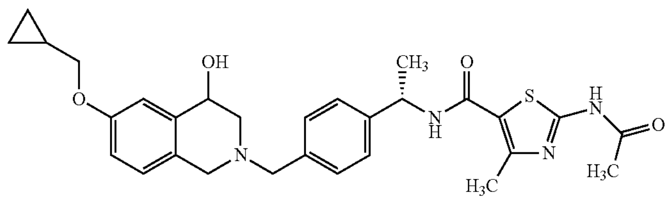 [SMILES: CC(=O)Nc1nc(C)c(C(=O)N[C@@H](C)c2ccc(CN3Cc4ccc(OCC5CC5)cc4C(O)C3)cc2)s1] | 535 [M + H]+ | 0.98 (A) |
| 3.46 | 2-Acetyl-amino-4-methyl-thiazol-5-carboxylic acid | XLVIII.1 | 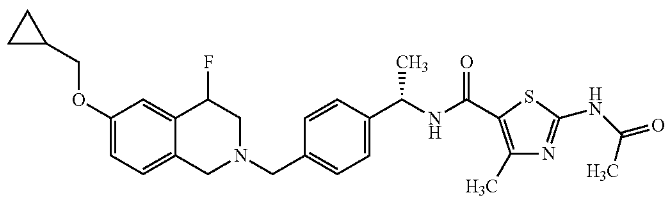 | 537 [M + H]+ | 1.07 (A) |
| 3.47 | Thiazole-5-carboxylic acid | XLVIII.6 | 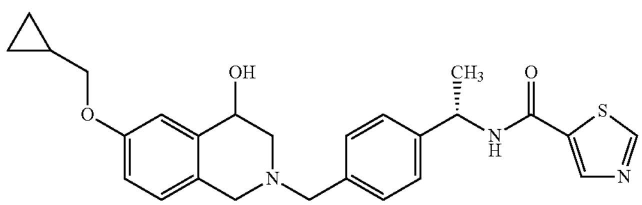 [SMILES: C[C@H](NC(=O)c1cncs1)c1ccc(CN2Cc3ccc(OCC4CC4)cc3C(O)C2)cc1] | 464 [M + H]+ | 1.00 (A) |
| 3.48 | Thiazole-5-carboxylic acid | XLVIII.1 | 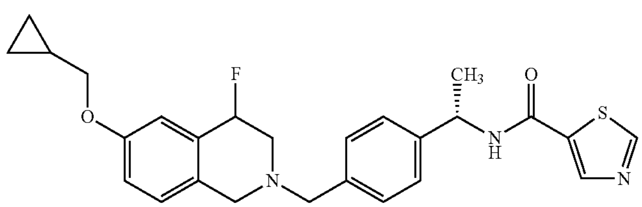 [SMILES: C[C@H](NC(=O)c1cncs1)c1ccc(CN2Cc3ccc(OCC4CC4)cc3C(F)C2)cc1] | 466 [M + H]+ | 1.08 (A) |
| 3.49 | trans-3-Fluoro-cyclobutane carboxylic acid | XLVIII.6 | 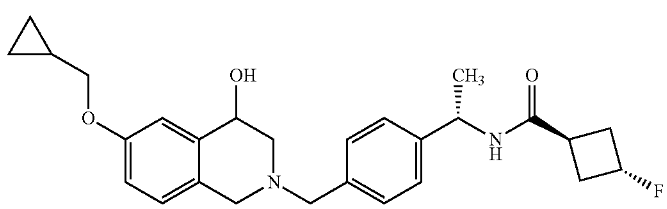 [SMILES: C[C@H](NC(=O)[C@H]1C[C@H](F)C1)c1ccc(CN2Cc3ccc(OCC4CC4)cc3C(O)C2)cc1] | 453 [M + H]+ | 1.04 (A) |
| 3.50 | cis-3-tert-Butoxy-carbonyl-amino-cyclo-pentane carboxylic acid | XLVIII.1 | 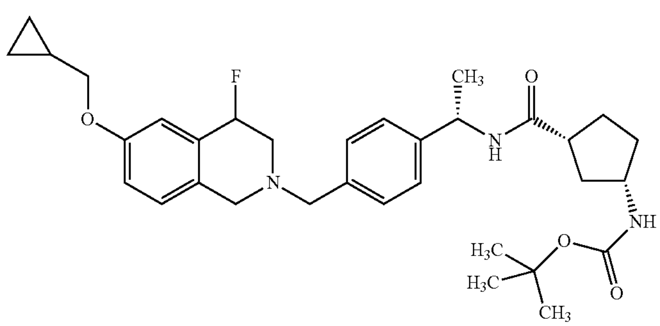 [SMILES: C[C@H](NC(=O)[C@@H]1CC[C@H](NC(=O)OC(C)(C)C)C1)c1ccc(CN2Cc3ccc(OCC4CC4)cc3C(F)C2)cc1] | 566 [M + H]+ | 1.18 (A) |

-continued

| Ex. | Starting materials | | Structure | ESI-MS | HPLC retention time (method) [min] |
|---|---|---|---|---|---|
| 3.51 | Cyano-acetic acid | XLVIII.6 | 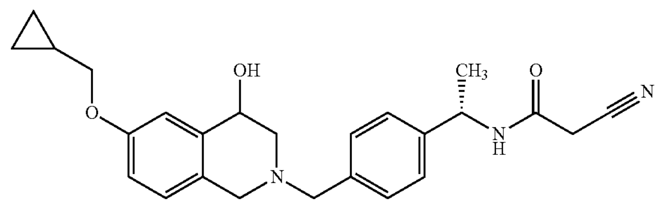 [SMILES: C[C@H](NC(=O)CC#N)c1ccc(CN2Cc3ccc(OCC4CC4)cc3C(O)C2)cc1] | 420 [M + H]⁺ | 0.96 (A) |
| 3.52 | (S)-5-Oxo-pyrrolidine-2-carboxylic acid | XLVIII.1 | 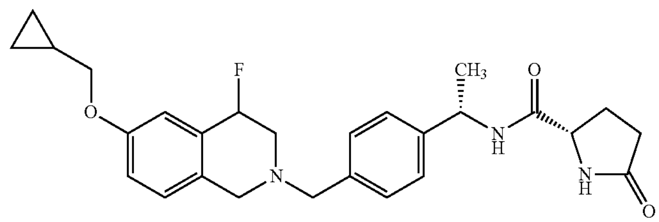 [SMILES: C[C@H](NC(=O)[C@@H]1CCC(=O)N1)c1ccc(CN2Cc3ccc(OCC4CC4)cc3C(F)C2)cc1] | 466 [M + H]⁺ | 1.00 (A) |
| 3.53 | (R)-5-Oxo-pyrrolidine-2-carboxylic acid | XLVIII.1 | 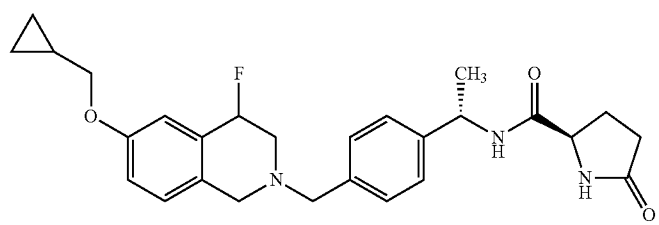 [SMILES: C[C@H](NC(=O)[C@H]1CCC(=O)N1)c1ccc(CN2Cc3ccc(OCC4CC4)cc3C(F)C2)cc1] | 466 [M + H]⁺ | 1.00 (A) |
| 3.54 | 5-Oxo-tetrahydro-furan-2-carboxylic acid | XLVIII.1 | 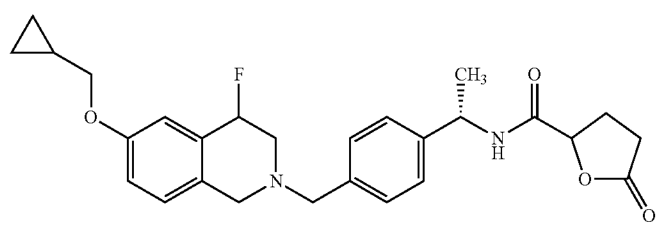 [SMILES: C[C@H](NC(=O)C1CCC(=O)O1)c1ccc(CN2Cc3ccc(OCC4CC4)cc3C(F)C2)cc1] | 467 [M + H]⁺ | 0.57 (MM) |
| 3.55** | 1-tert-Butoxy-carbonyl-amino-cyclo-propane-carboxylic acid | XLVIII.1 | 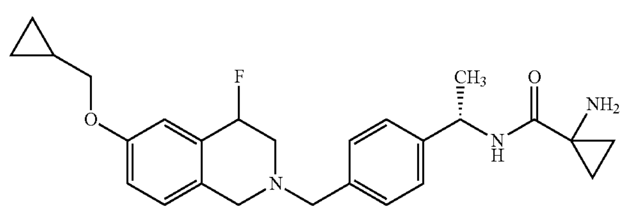 [SMILES: C[C@H](NC(=O)C1(N)CC1)c1ccc(CN2Cc3ccc(OCC4CC4)cc3C(F)C2)cc1] | 438 [M + H]⁺ | 0.46 (MM) |
| 3.56** | (1S,2S)-2-tert-Butoxy-carbonyl-amino-cyclo-pentane-carboxylic acid | XLVIII.1 | 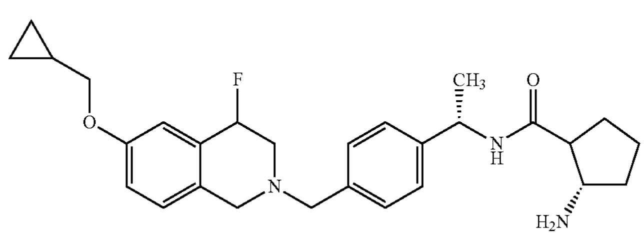 [SMILES: C[C@H](NC(=O)C1CCC[C@@H]1N)c1ccc(CN2Cc3ccc(OCC4CC4)cc3C(F)C2)cc1] | 466 [M + H]⁺ | 0.49 (MM) |

| Ex. | Starting materials | | Structure | ESI-MS | HPLC retention time (method) [min] |
|---|---|---|---|---|---|
| 3.57** | Morpholine-3,4-dicarboxylic acid 4-tert-butyl ester | XLVIII.1 | 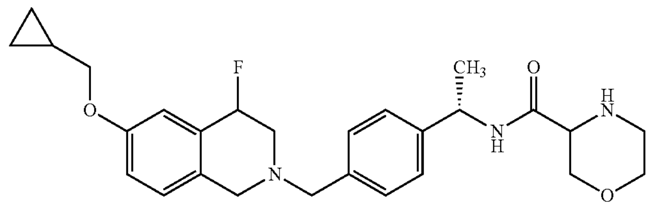 [SMILES: C[C@H](NC(=O)C1COCCN1)c1ccc(CN2Cc3ccc(OCC4CC4)cc3C(F)C2)cc1] | 468 [M + H]⁺ | 0.47 (MM) |
| 3.58** | tert-Butoxy-carbonyl-amino-acetic acid | XLVIII.1 | 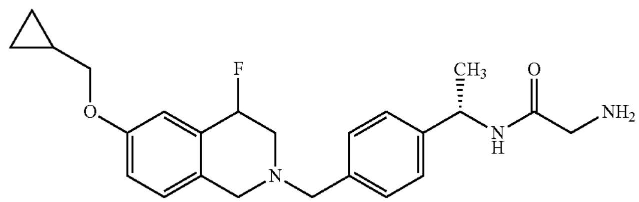 [SMILES: C[C@H](NC(=O)CN)c1ccc(CN2Cc3ccc(OCC4CC4)cc3C(F)C2)cc1] | 412 [M + H]⁺ | 0.45 (MM) |
| 3.59*** | Acetoxy-acetic acid | XLVIII.1 | 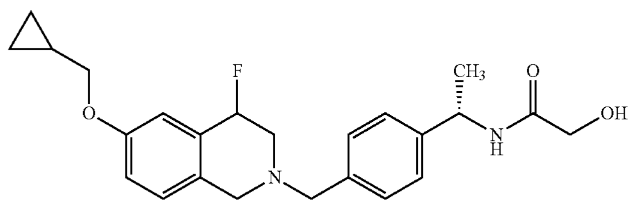 [SMILES: C[C@H](NC(=O)CO)c1ccc(CN2Cc3ccc(OCC4CC4)cc3C(F)C2)cc1] | 413 [M + H]⁺ | 1.02 (A) |
| 3.60*** | (S)-2-Acetoxy-propionic acid | XLVIII.1 | 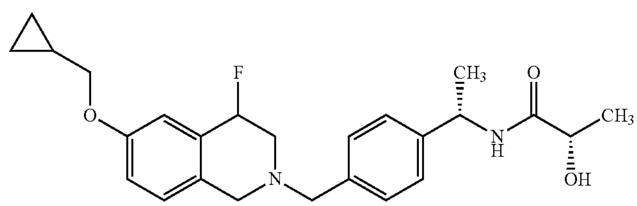 [SMILES: C[C@H](O)C(=O)N[C@@H](C)c1ccc(CN2Cc3ccc(OCC4CC4)cc3C(F)C2)cc1] | 427 [M + H]⁺ | 1.03 (A) |
| 3.61*** | (R)-2-Acetoxy-propionic acid | XLVIII.1 | 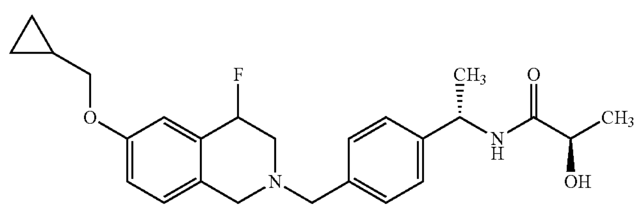 [SMILES: C[C@H](NC(=O)[C@@H](C)O)c1ccc(CN2Cc3ccc(OCC4CC4)cc3C(F)C2)cc1] | 427 [M + H]⁺ | 1.03 (A) |
| 3.62*** | 1-Acetoxy-cyclo-propane-carboxylic acid | XLVIII.1 | 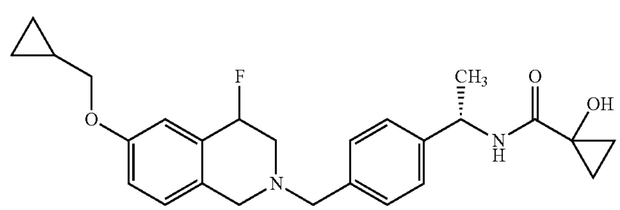 [SMILES: C[C@H](NC(=O)C1(O)CC1)c1ccc(CN2Cc3ccc(OCC4CC4)cc3C(F)C2)cc1] | 439 [M + H]⁺ | 1.05 (A) |
| 3.63* | 1-(Tetrahydro-pyran-2-yl)-1H-pyrazole-4-carboxylic acid | XLVIII.6 | 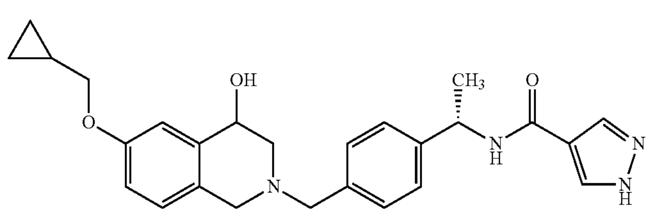 [SMILES: C[C@H](NC(=O)c1cn[nH]c1)c1ccc(CN2Cc3ccc(OCC4CC4)cc3C(O)C2)cc1] | 447 [M + H]⁺ | 0.94 (A) |

| Ex. | Starting materials | Structure | ESI-MS | HPLC retention time (method) [min] |
|---|---|---|---|---|
| 3.64* | 1-(Tetrahydro-pyran-2-yl)-1H-pyrazole-4-carboxylic acid | XLVIII.1 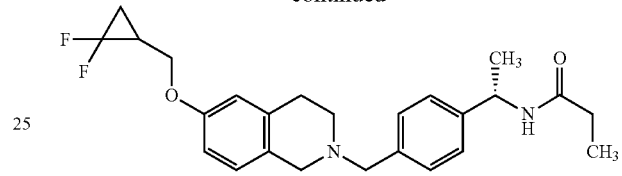 | 449 [M + H]⁺ | 1.02 (A) |

*After stirring over night, aq. HCl solution (c = 4 mol/L) is added. The resulting mixture is stirred at r.t. over night to remove the THP protecting group.
**After stirring over night, the solvent is removed and TFA in DCM is added. The resulting mixture is stirred at r.t. for 2 h to remove the BOC protecting group.
***After stirring over night, aq. NaOH solution (c = 1 mol/L) is added. The resulting mixture is stirred at 40° C. for 2 h to cleave the acetate protecting group.

Example 4

Example 4.1 (General Route)

N—((S)-1-{4-[6-(2,2-Difluoro-cyclopropyl-methoxy)-3,4-dihydro-1H-isoquinolin-2-ylmethyl]-phenyl}-ethyl)-propionamide

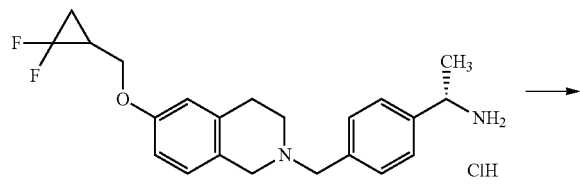

4.09 mg (10.0 μmol) (S)-1-{4-[6-(2,2-Difluoro-cyclopropylmethoxy)-3,4-dihydro-1H-isoquinolin-2-ylmethyl]-phenyl}-ethylamine hydrochloride (example XXXIII.1) and 5.58 μl (40.0 μmol) TEA in 0.5 mL THF are stirred at r.t. Then 3.87 μL (30.0 μmol) propionic anhydride are added and the resulting mixture is stirred at r.t. over night. The reaction is quenched by the addition of 25 μL aq. K₂CO₃ solution (c=3 mol/L), filtered over basic aluminum oxide and concentrated by evaporation.

$C_{25}H_{30}F_2N_2O_2$ (M=428.5 g/mol)
ESI-MS: 429 [M+H]⁺
$R_t$ (HPLC): 0.83 min (method C)

The following compounds are prepared according to the general procedure (example 4.1) described above:

| Ex. | Starting material | Structure | ESI-MS | HPLC retention time (method) [min] |
|---|---|---|---|---|
| 4.1 | Propionic anhydride | 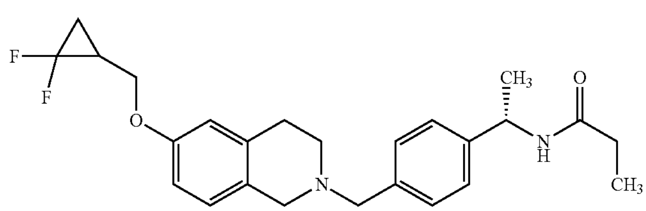 [SMILES: CCC(=O)N[C@@H](C)c1ccc(CN2CCc3cc(OCC4CC4(F)F)ccc3C2)cc1] | 429 [M + H]⁺ | 0.83 (C) |
| 4.2 | Trifluoroacetic anhydride | 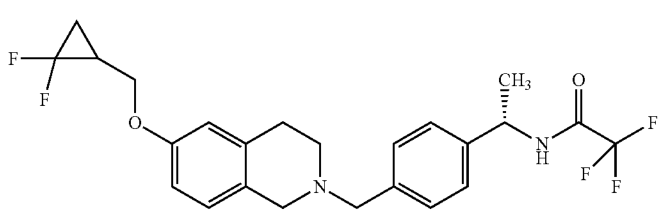 [SMILES: C[C@H](NC(=O)C(F)(F)F)c1ccc(CN2CCc3cc(OCC4CC4(F)F)ccc3C2)cc1] | 469 [M + H]⁺ | 0.92 (C) |

-continued

| Ex. | Starting material | Structure | ESI-MS | HPLC retention time (method) [min] |
|---|---|---|---|---|
| 4.3* | Difluoroacetic anhydride | 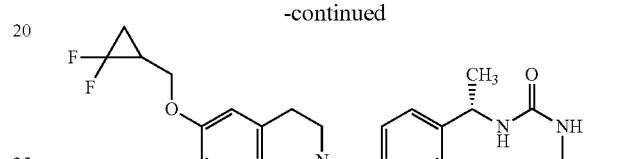 | 451 [M + H]⁺ | 0.86 (C) |

*DIPEA is used as base and ACN as solvent

Example 5

Example 5.1 (General Route)

1-((S)-1-{4-[6-(2,2-Difluoro-cyclopropylmethoxy)-3,4-dihydro-1H-isoquinolin-2-ylmethyl]-phenyl}-ethyl)-3-ethyl-urea

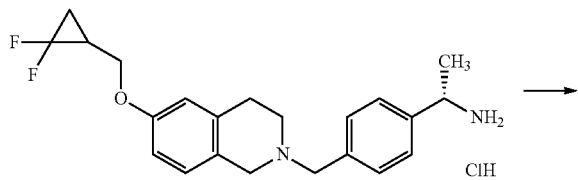

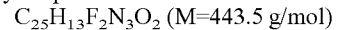

4.09 mg (10.0 μmol) (S)-1-{4-[6-(2,2-Difluoro-cyclopropylmethoxy)-3,4-dihydro-1H-isoquinolin-2-ylmethyl]-phenyl}-ethylamine hydrochloride (example XXXIII.1) and 5.62 μL (40.0 μmol) TEA in 250 μL THF are stirred at r.t. Then 3.91 μL (50.0 μmol) ethyl isocyanate are added and the resulting mixture is stirred at r.t. over night. The reaction is quenched by the addition of 25 μL aq. $K_2CO_3$ solution (c=3 mol/L), filtered over basic aluminum oxide and concentrated by evaporation.

$C_{25}H_{13}F_2N_3O_2$ (M=443.5 g/mol)
ESI-MS: 444 [M+H]⁺
$R_t$ (HPLC): 0.81 min (method C)

The following compounds are prepared according to the general procedure (example 5.1) described above:

| Ex. | Starting materials | | Structure | ESI-MS | HPLC retention time (method) [min] |
|---|---|---|---|---|---|
| 5.1 | Ethyl isocyanate | XXXII.1 | 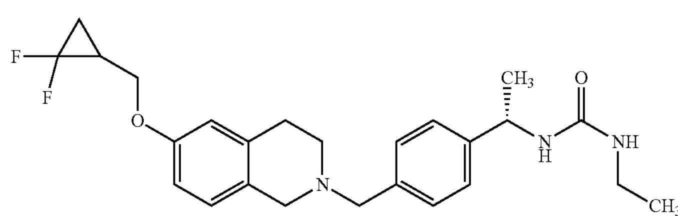 [SMILES: CCNC(=O)N[C@@H](C)c1ccc(CN2CCc3cc(OCC4CC4(F)F)ccc3C2)cc1] | 444 [M + H]⁺ | 0.81 (C) |
| 5.2 | N-Succinimidyl N-methylcarbamate | XXXII.1 | 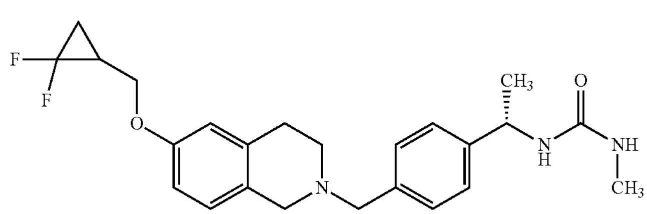 [SMILES: CNC(=O)N[C@@H](C)c1ccc(CN2CCc3cc(OCC4CC4(F)F)ccc3C2)cc1] | 430 [M + H]⁺ | 0.77 (C) |

-continued

| Ex. | Starting materials | | Structure | ESI-MS | HPLC retention time (method) [min] |
|---|---|---|---|---|---|
| 5.3* | Dimethylcarbamyl chloride | XXXII.1 | 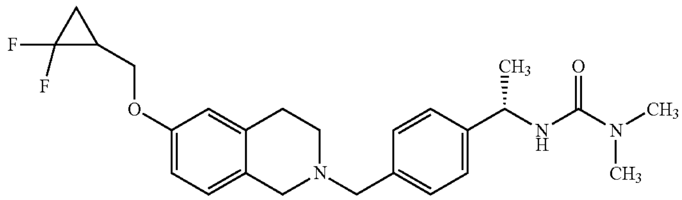 [SMILES: C[C@H](NC(=O)N(C)C)c1ccc(CN2CCc3cc(OCC4CC4(F)F)ccc3C2)cc1] | 444 [M + H]⁺ | 0.82 (C) |
| 5.4** | Dimethylcarbamyl chloride | XLVIII.2 | 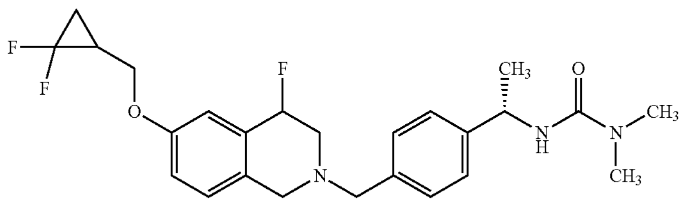 [SMILES: C[C@H](NC(=O)N(C)C)c1ccc(CN2Cc3ccc(OCC4CC4(F)F)cc3C(F)C2)cc1] | 462 [M + H]⁺ | 0.60 (I) |
| 5.5** | Dimethylcarbamyl chloride | XLVIII.6 | 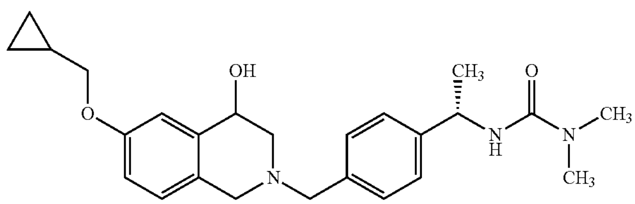 [SMILES: C[C@H](NC(=O)N(C)C)c1ccc(CN2Cc3ccc(OCC4CC4)cc3C(O)C2)cc1] | 424 [M + H]⁺ | 0.78 (JJ) |
| 5.6*** | Ethyl isocyanate | XLVIII.6 | 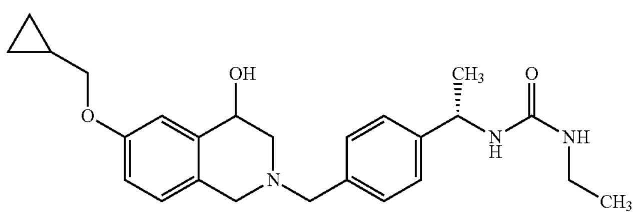 [SMILES: CCNC(=O)N[C@@H](C)c1ccc(CN2Cc3ccc(OCC4CC4)cc3C(O)C2)cc1] | 424 [M + H]⁺ | 0.98 (A) |
| 5.7*** | Ethyl isocyanate | XLVIII.1 | 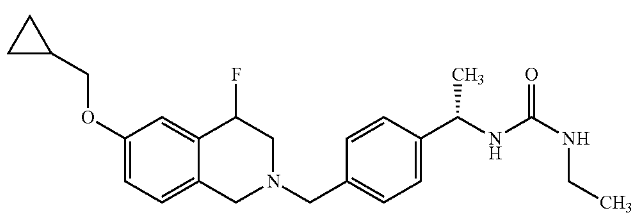 [SMILES: CCNC(=O)N[C@@H](C)c1ccc(CN2Cc3ccc(OCC4CC4)cc3C(F)C2)cc1] | 426 [M + H]⁺ | 1.06 (A) |
| 5.8* | Methylchloro formate | XLVIII.6 | 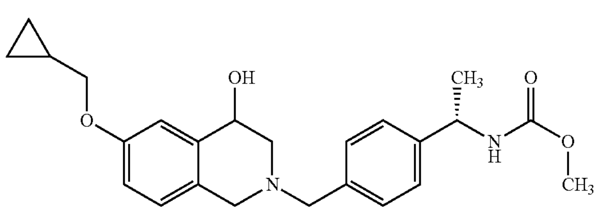 [SMILES: COC(=O)N[C@@H](C)c1ccc(CN2Cc3ccc(OCC4CC4)cc3C(O)C2)cc1] | 411 [M + H]⁺ | 1.02 (A) |

| Ex. | Starting materials | | Structure | ESI-MS | HPLC retention time (method) [min] |
|---|---|---|---|---|---|
| 5.9* | Methylchloro formate | XLVIII.1 | 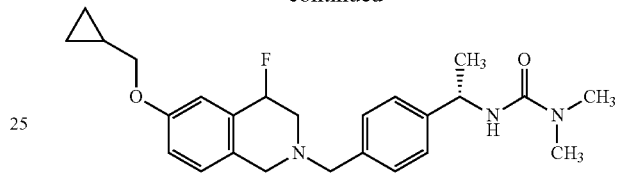 | 413 [M + H]⁺ | 1.12 (A) |

*DIPEA is used as base and ACN as solvent
**DIPEA is used as base and DCM as solvent
***DIPEA is used as base and DMF as solvent

Example 6

Example 6.1 (General Route)

3-{(S)-1-[4-(6-Cyclopropylmethoxy-3,4-dihydro-1H-isoquinolin-2-ylmethyl)-phenyl]-ethyl}-1,1-dimethyl-urea

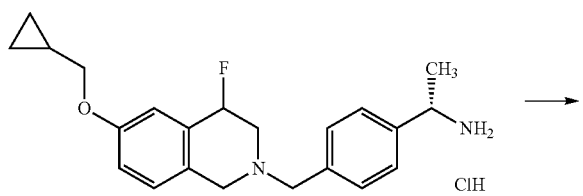

To 40 mg (0.10 mmol) (S)-1-[4-(6-cyclopropylmethoxy-4-fluoro-3,4-dihydro-1H-isoquinolin-2-ylmethyl)-phenyl]-ethylamine hydrochloride (example XLVIII.1) in 1.0 mL DCM are added 30 µL (0.21 mmol) TEA and 18 mg (0.11 mmol) CDT. The resulting mixture is stirred at r.t. for 1 h. Then 61 µL (0.12 mmol) dimethylamine solution (2.0 M in THF) are added and the mixture is stirred at 30° C. for 4 h. After that time the reaction mixture is purified by HPLC.

$C_{25}H_{32}FN_3O_2$ (M=425.5 g/mol)

ESI-MS: 426 [M+H]⁺

$R_t$ (HPLC): 0.92 min (method E)

The following compounds are prepared according to the general procedure (example 6.1) described above:

| Ex. | Starting materials | | Structure | ESI-MS | HPLC retention time (method) [min] |
|---|---|---|---|---|---|
| 6.1 | HNMe₂ | XLVIII.1 | 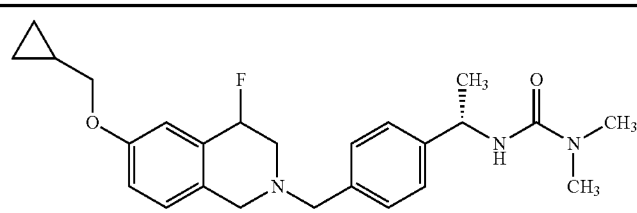 | 426 [M + H]⁺ | 0.92 (E) |
| 6.2* | HNMe₂ | XLVIII.4 | 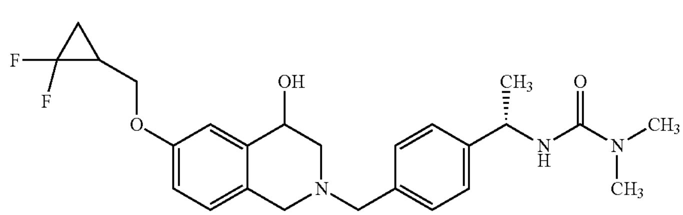 [SMILES: C[C@H](NC(=O)N(C)C)c1ccc(CN2Cc3ccc(OCC4CC4(F)F)cc3C(O)C2)cc1] | 460 [M + H]⁺ | 0.81 (KK) |

*CDI and DIPEA in DMA were used instead of CDT and TEA.

Example 7

Example 7.1 (General Route)

N-{(S)-1-[4-(5-Methoxy-3,4-dihydro-1H-isoquinolin-2-ylmethyl)-phenyl]-ethyl}-acetamide

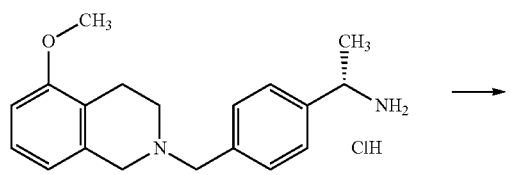

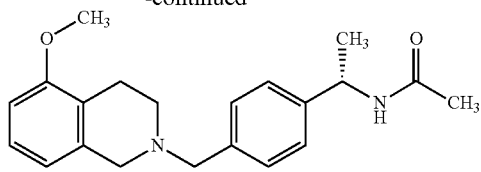

To 80 mg (0.24 mmol) (S)-1-[4-(5-methoxy-3,4-dihydro-1H-isoquinolin-2-ylmethyl)-phenyl]-ethylamine hydrochloride (example XXXIII.2) in 2.0 mL DCM are added 67 μL (0.48 mmol) TEA and 34 μL (0.26 mmol) acetic anhydride and the resulting mixture is stirred at r.t. over night. 200 μL MeOH are added and the reaction mixture is purified by HPLC.

$C_{21}H_{26}N_2O_2$ (M=338.4 g/mol)
ESI-MS: 339 [M+H]$^+$
$R_t$ (HPLC): 0.86 min (method A)

The following compounds are prepared according to the general procedure (example 7.1) described above:

| Ex. | Starting material | Structure | ESI-MS | HPLC retention time (method) [min] |
|---|---|---|---|---|
| 7.1 | XXXIII.2 | 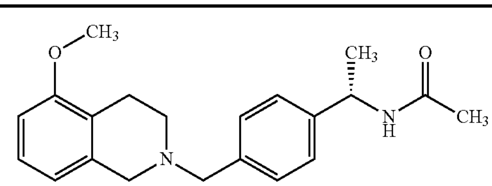 | 339 [M + H]$^+$ | 0.86 (A) |
| 7.2 | XXXIII.3 | 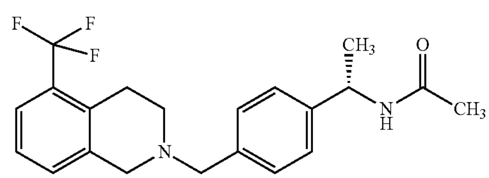 [SMILES: CC(=O)N[C@@H](C)c1ccc(CN2CCc3c(cccc3C(F)(F)F)C2)cc1] | 377 [M + H]$^+$ | 0.95 (A) |
| 7.3 | XXXIII.1 | 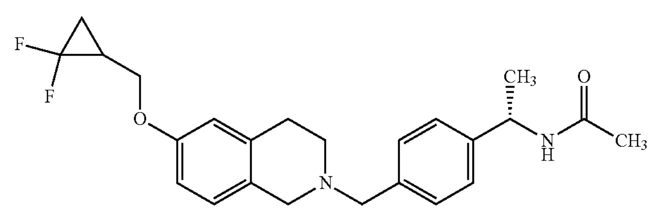 [SMILES: CC(=O)N[C@@H](C)c1ccc(CN2CCc3cc(OCC4CC4(F)F)ccc3C2)cc1] | 415 [M + H]$^+$ | 0.93 (A) |
| 7.4 | XXXIII.4 | 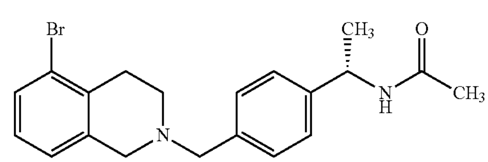 [SMILES: CC(=O)N[C@@H](C)c1ccc(CN2CCc3c(Br)cccc3C2)cc1] | 387 [M + H]$^+$ | 0.95 (A) |
| 7.5 | XXXIII.5 | 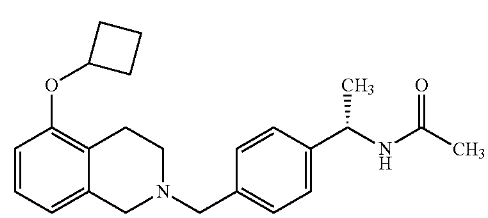 [SMILES: CC(=O)N[C@@H](C)c1ccc(CN2CCc3c(cccc3OC3CCC3)C2)cc1] | 379 [M + H]$^+$ | 0.83 (B) |

-continued

| Ex. | Starting material | Structure | ESI-MS | HPLC retention time (method) [min] |
|---|---|---|---|---|
| 7.6* | XLVIII.3 | 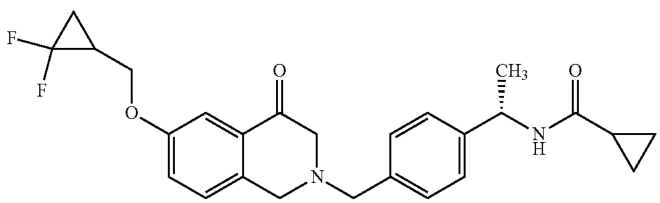 [SMILES: C[C@H](NC(=O)C1CC1)c1ccc(CN2CC(=O)c3cc(OCC4CC4(F)F)ccc3C2)cc1] | 455 [M + H]+ | 0.91 (KK) |
| 7.7** | XLVIII.3 | 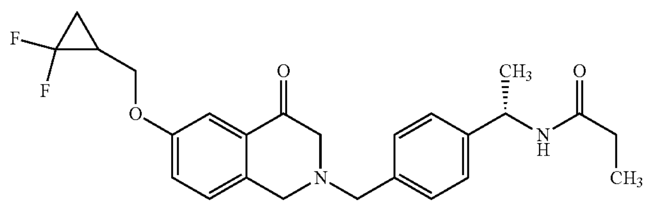 [SMILES: CCC(=O)N[C@@H](C)c1ccc(CN2CC(=O)c3cc(OCC4CC4(F)F)ccc3C2)cc1] | 443 [M + H]+ | 0.78 (C) |
| 7.8** | XLVIII.5 | 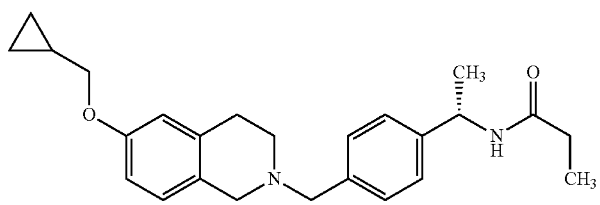 | 407 [M + H]+ | 0.87 (J) |
| 7.9*** | XLVIII.3 | 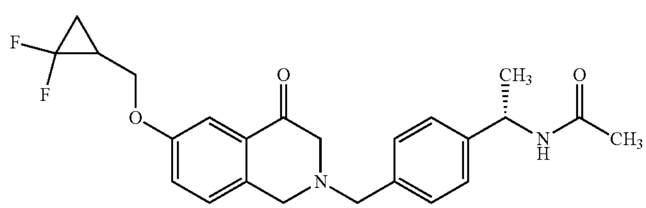 [SMILES: CC(=O)N[C@@H](C)c1ccc(CN2CC(=O)c3cc(OCC4CC4(F)F)ccc3C2)cc1] | 429 [M + H]+ | 0.82 (J) |

*Cyclopropanecarbonyl chloride in DIPEA/DMA was used as acylating agent.
**Propionyl chloride in DIPEA/DMA was used as acylating agent.
***DIPEA/DMA were used.

Example 8

2-[4-((S)-1-Acetylamino-ethyl)-benzyl]-1,2,3,4-tetrahydro-isoquinoline-5-carboxylic acid benzylamide

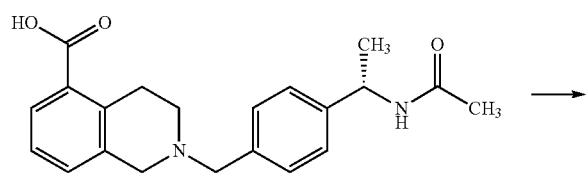

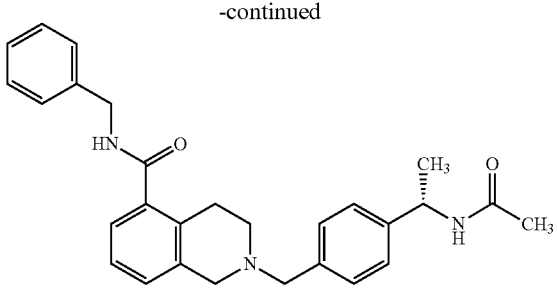

80 mg (0.15 mmol, 65%) 2-[4-((S)-1-Acetylamino-ethyl)-benzyl]-1,2,3,4-tetrahydro-isoquinoline-5-carboxylic acid (example XXXVII), 51 µL (0.30 mmol) DIPEA and 95 mg (0.30 mmol) TBTU in 1 mL DMF are stirred at r.t. for 10 min.

Then 16 mg (0.15 mmol) benzylamine and 63 µL (0.37 mmol) DIPEA are added and the resulting mixture is stirred at r.t. for 2 h. After that time, the reaction is quenched by the addition of 200 µL water and purified by HPLC.

C$_{28}$H$_{31}$N$_{3}$O$_{2}$ (M=441.6 g/mol)
ESI-MS: 442 [M+H]$^{+}$
R$_{t}$ (HPLC): 0.95 min (method G)

Example 9

2-[4-((S)-1-Acetylamino-ethyl)-benzyl]-6-cyclopropylmethoxy-1,2,3,4-tetrahydro-isoquinoline-1-carboxylic acid methyl ester

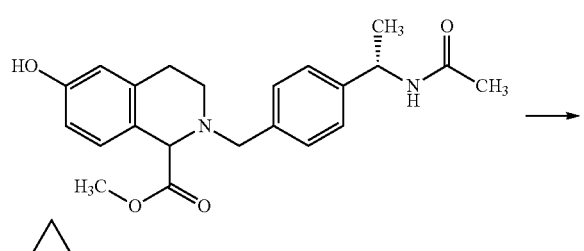

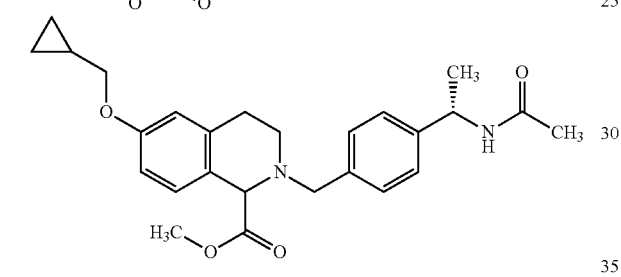

15 mg (39 µmol) 2-[4-((S)-1-Acetylamino-ethyl)-benzyl]-6-hydroxy-1,2,3,4-tetrahydro-isoquinoline-1-carboxylic acid methyl ester (example XXXVIII), 5.8 mg (43 µmol) (bromomethyl)cyclopropane and 10 mg (78 µmol) K$_{2}$CO$_{3}$ in 2 mL DMF are stirred at 80° C. over night. The reaction mixture is diluted with water and extracted with DCM. The organic layer is concentrated by evaporation and the residue is purified by HPLC.

C$_{26}$H$_{32}$N$_{2}$O$_{4}$ (M=436.5 g/mol)
ESI-MS: 437 [M+H]$^{+}$
R$_{t}$ (HPLC): 0.95 min (method A)

Example 10

2-[4-((S)-1-Acetylamino-ethyl)-benzyl]-6-cyclopropyl methoxy-1,2,3,4-tetrahydro-isoquinoline-1-carboxylic acid

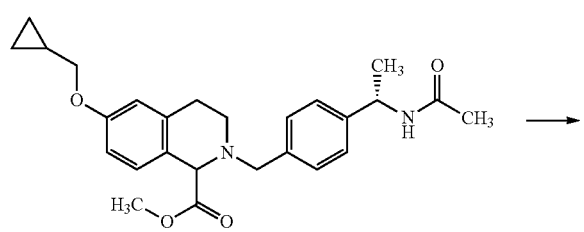

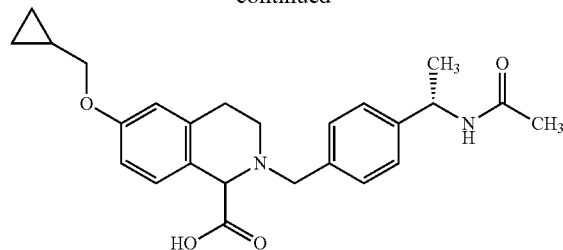

68 mg (0.16 mmol) 2-[4-((S)-1-Acetylamino-ethyl)-benzyl]-6-cyclopropylmethoxy-1,2,3,4-tetrahydro-isoquinoline-1-carboxylic acid methyl ester (example 9) and 0.50 mL (0.50 mmol) aq. NaOH solution (c=1 mol/L) in 2 mL MeOH are stirred at r.t. over night. Then 0.20 mL aq. NaOH solution (c=1 mol/L) are added and the mixture is stirred at r.t. for 3 h. The reaction mixture is concentrated by evaporation and purified by HPLC.

C$_{25}$H$_{30}$N$_{2}$O$_{4}$ (M=422.5 g/mol)
ESI-MS: 423 [M+H]$^{+}$
R$_{t}$ (HPLC): 0.80 min (method B)

Example 11

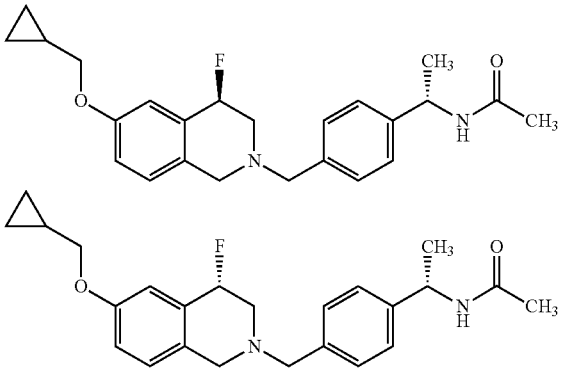

For example 1.93 separation of the diastereomers was performed using chiral SFC.

Column: Daicel Chiralcel® OZ-H 10×250 mm, 5 µm
Eluent: 80% scCO$_{2}$ (supercritical carbon dioxide); 20% MeOH+0.2% diethylamine
Flow: 10 mL/min
Temperature: 40° C.
Backpressure: 120 bar
Device Description: Thar MiniGram
Peak I: R$_{t}$ 4.72 min (method L)
Peak II: R$_{t}$ 5.56 min (method L)

Example 12

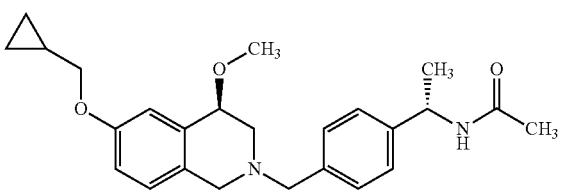

-continued

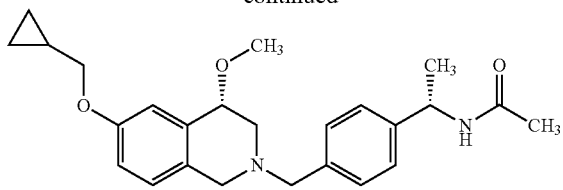

For example 1.94 separation of the diastereomers was performed using chiral SFC.
Column: Daicel Chiralpak® IB 10×250 mm, 5 μm
Eluent: 80% scCO$_2$ (supercritical carbon dioxide); 20% MeOH+0.2% diethylamine
Flow: 10 mL/min
Temperature: 40° C.
Backpressure: 120 bar
Device Description: Thar MiniGram
Peak I: R$_t$ 2.43 min (method M)
Peak II: R$_t$ 2.78 min (method M)

Example 13

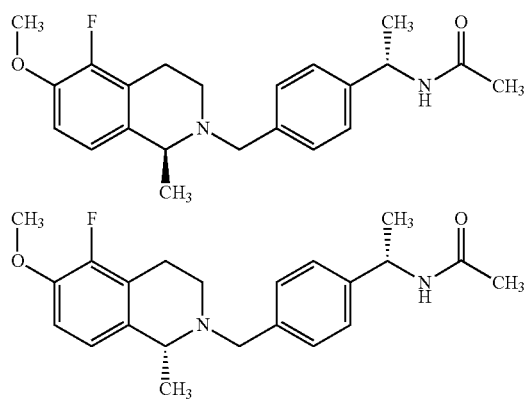

For example 1.95 separation of the diastereomers was performed using chiral SFC.
Column: Daicel Chiralcel® OJ-H 10×250 mm, 5 μm
Eluent: 85% scCO$_2$ (supercritical carbon dioxide); 15% MeOH+0.2% diethylamine
Flow: 10 mL/min
Temperature: 40° C.
Backpressure: 120 bar
Device Description: Thar MiniGram
Peak I: R$_t$ 1.83 min (method N)
Peak II: R$_t$ 2.07 min (method N)

Example 14

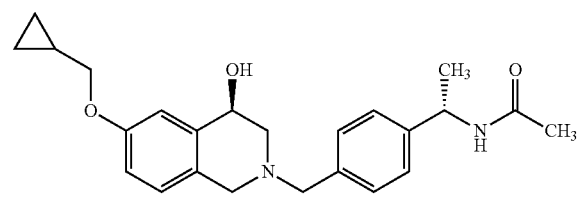

-continued

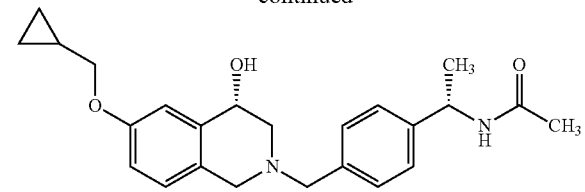

For example 1.96 separation of the diastereomers was performed using chiral SFC.
Column: Daicel Chiralpak® AD-H 20×250 mm, 5 μm
Eluent: 75% scCO$_2$ (supercritical carbon dioxide); 25% MeOH+20 mmol/L ammonia
Flow: 60 mL/min
Temperature: 40° C.
Backpressure: 150 bar
Device Description: Sepiatec Prep SFC 100
Peak I: R$_t$ 3.40 min (method O)
Peak II: R$_t$ 4.29 min (method O)

Example 15

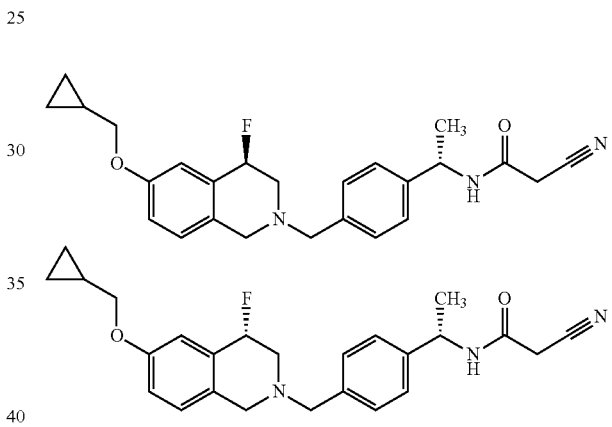

For example 3.26 separation of the diastereomers was performed using chiral SFC.
Column: Daicel Chiralpak® IC 10×250 mm, 5 μm
Eluent: 60% scCO$_2$ (supercritical carbon dioxide); 40% iPrOH+20 mmol/L ammonia
Flow: 10 mL/min
Temperature: 40° C.
Backpressure: 150 bar
Device Description: Thar MiniGram
Peak I: R$_t$ 3.51 min (method P)
Peak II: R$_t$ 5.17 min (method P)

Analytical HPLC Methods

Method A

| time (min) | Vol % water (incl. 0.1% NH$_4$OH) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: XBridge C18 (Waters) 2.5 μm; 3.0 × 30 mm; column temperature: 60° C.

Method B

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 μm; 3.0 × 30 mm; column temperature: 60° C.

Method C

| time (min) | Vol % water (incl. 0.1% NH$_4$OH) | Vol % ACN | Flow [mL/min] |
|---|---|---|---|
| 0.00 | 98 | 2 | 2.0 |
| 1.20 | 0 | 100 | 2.0 |
| 1.40 | 0 | 100 | 2.0 |

Analytical column: XBridge C18 (Waters) 2.5 μm; 3.0 × 30 mm; column temperature: 60° C.

Method D

| time (min) | Vol % water (incl. 0.1% TFA) | Vol % ACN | Flow [mL/min] |
|---|---|---|---|
| 0.00 | 98 | 2 | 2.0 |
| 1.20 | 0 | 100 | 2.0 |
| 1.40 | 0 | 100 | 2.0 |

Analytical column: Sunfire C18 (Waters) 2.5 μm; 3.0 × 30 mm; column temperature: 60° C.

Method E

| time (min) | Vol % water (incl. 0.1% NH$_4$OH) | Vol % ACN | Flow [mL/min] |
|---|---|---|---|
| 0.00 | 98 | 2 | 2.0 |
| 1.20 | 0 | 100 | 2.0 |
| 1.40 | 0 | 100 | 2.0 |

Analytical column: XBridge C18 (Waters) 2.5 μm; 3.0 × 30 mm; column temperature: 60° C.

Method F

| time (min) | Vol % water (incl. 0.1% TFA) | Vol % ACN (incl. 0.08% TFA) | Flow [mL/min] |
|---|---|---|---|
| 0.00 | 95 | 5 | 1.5 |
| 0.75 | 0 | 100 | 1.5 |
| 0.85 | 0 | 100 | 1.5 |

Analytical column: Sunfire C18 (Waters) 2.5 μm; 2.1 × 50 mm; column temperature: 60° C.

Method G

| time (min) | Vol % water (incl. 0.1% NH$_4$OH) | Vol % ACN | Flow [mL/min] |
|---|---|---|---|
| 0.00 | 98 | 2 | 2.5 |
| 1.50 | 0 | 100 | 2.5 |
| 1.80 | 0 | 100 | 2.5 |

Analytical column: XBridge C18 (Waters) 3.5 μm; 4.6 × 30 mm; column temperature: 60° C.

Method H

| time (min) | Vol % water (incl. 0.1% NH$_4$OH) | Vol % ACN | Flow [mL/min] |
|---|---|---|---|
| 0.00 | 95 | 5 | 1.5 |
| 0.70 | 0.1 | 99.9 | 1.5 |
| 0.80 | 0.1 | 99.9 | 1.5 |
| 0.81 | 95 | 5 | 1.5 |
| 1.1 | 95 | 5 | 1.5 |

Analytical column: XBridge BEH C18 (Waters) 1.7 μm; 3.0 × 30 mm; column temperature: 60° C.

Method I

| time (min) | Vol % water (incl. 0.1% NH$_4$OH) | Vol % ACN | Flow [mL/min] |
|---|---|---|---|
| 0.00 | 95 | 5 | 1.5 |
| 0.75 | 0.1 | 99.9 | 1.5 |
| 0.80 | 0.1 | 99.9 | 1.5 |
| 0.81 | 95 | 5 | 1.5 |
| 1.1 | 95 | 5 | 1.5 |

Analytical column: Triart C 18 (YMC) 1.9 μm; 2.0 × 30 mm; column temperature: 60° C.

Method J

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 μm; 3.0 × 30 mm; column temperature: 60° C.

Method JJ

| time (min) | Vol % water (incl. 0.1% TFA) | Vol % ACN | Flow [mL/min] |
|---|---|---|---|
| 0.00 | 50 | 50 | 2.2 |
| 0.20 | 50 | 50 | 2.2 |
| 1.20 | 0 | 100 | 2.2 |
| 1.25 | 0 | 100 | 3 |
| 1.40 | 0 | 100 | 3 |

Analytical column: Sunfire (Waters) 2.5 μm; 3.0 × 30 mm; column temperature: 60° C.

Method KK

| time (min) | Vol % water (incl. 0.1% NH$_4$OH) | Vol % ACN | Flow [mL/min] |
|---|---|---|---|
| 0.0 | 95.0 | 5.0 | 1.5 |
| 1.3 | 1.0 | 99.0 | 1.5 |
| 1.5 | 1.0 | 99.0 | 1.5 |
| 1.6 | 95.0 | 5.0 | 1.5 |

Analytical column: XBridge C18 (Waters) 2.5 μm; 3.0 × 30 mm; column temperature: 60° C.

Method LL

| time (min) | Vol % water (incl. 0.1% TFA) | Vol % ACN | Flow [mL/min] |
|---|---|---|---|
| 0.00 | 50 | 50 | 2.2 |
| 0.20 | 50 | 50 | 2.2 |

-continued

| time (min) | Vol % water (incl. 0.1% TFA) | Vol % ACN | Flow [mL/min] |
|---|---|---|---|
| 1.20 | 0 | 100 | 2.2 |
| 1.25 | 0 | 100 | 3 |
| 1.40 | 0 | 100 | 3 |

Analytical column: Stable Bond (Agilent) 1.8 µm; 3.0 × 30 mm; column temperature: 60° C.

Method MM

| time (min) | Vol % water (incl. 0.1% TFA) | Vol % ACN (incl. 0.08% TFA) | Flow [mL/min] |
|---|---|---|---|
| 0.0 | 95.0 | 5.0 | 1.5 |
| 1.3 | 0.0 | 100.0 | 1.5 |
| 1.5 | 0.0 | 100.0 | 1.5 |
| 1.6 | 95.0 | 5.0 | 1.5 |

Analytical column: Sunfire C18 (Waters) 2.5 µm; 3.0 × 30 mm; column temperature: 60° C.

Analytical GC Methods
Method K
  Type: GC 7890
  Carrier gas: helium
  Column: BGB-175; 50 m; 0.25 mm ID; 0.25 µm DF (30 m and 20 m column coupled)
  Injector temperature: 220° C.
  Flow: 5.0 mL/min
  Temperature program: 50° C. at 0 min; 3° C./min to 160° C.
Analytical SFC Methods
Method L
  Column: Daicel Chiralpak® OZ-H 4.6×250 mm, 5 µm
  Eluent: 80% scCO$_2$ (supercritical carbon dioxide); 20% MeOH+0.2% diethylamine
  Flow: 4 mL/min
  Backpressure regulator BPR: 150 bar
  Time: 10 min
Method M
  Column: Daicel Chiralpak® IB 4.6×250 mm, 5 µm
  Eluent: 80% scCO$_2$ (supercritical carbon dioxide); 20% MeOH+0.2% diethylamine
  Flow: 4 mL/min
  Backpressure regulator BPR: 150 bar
  Time: 10 min
Method N
  Column: Daicel Chiralcel® OJ-H 4.6×250 mm, 5 µm
  Eluent: 85% scCO$_2$ (supercritical carbon dioxide); 15% MeOH+0.2% diethylamine
  Flow: 4 mL/min
  Backpressure regulator BPR: 150 bar
  Time: 10 min
Method O
  Column: Daicel Chiralcel® AD-H 4.6×250 mm, 5 µm
  Eluent: 70% scCO$_2$ (supercritical carbon dioxide); 30% MeOH+0.2% diethylamine
  Flow: 4 mL/min
  Backpressure regulator BPR: 150 bar
Time: 10 min
Method P
  Column: Daicel Chiralpak® IC 4.6×250 mm, 5 µm
  Eluent: 70% scCO$_2$ (supercritical carbon dioxide); 30% MeOH+20 mmol/L ammonia
  Flow: 4 mL/min
  Backpressure regulator BPR: 150 bar
  Time: 10 min

The invention claimed is:
1. A compound of formula (I)

wherein
R$^1$ is selected from a group consisting of:
  halogen, CN, OH, C$_{1-6}$-alkyl, C$_{3-7}$-cycloalkyl, —(C$_{1-3}$-alkyl)-(C$_{3-7}$-cycloalkyl), —O—(C$_{1-6}$-alkyl), —O—(C$_{3-7}$-cycloalkyl), —O—(C$_{1-3}$-alkyl)-(C$_{3-7}$-cycloalkyl), —O-phenyl, —O—(C$_{1-3}$-alkyl)-phenyl, —COOH, —COO(C$_{1-4}$-alkyl), —CO—NH—(C$_{1-3}$-alkyl)-phenyl, —CO—NH—(C$_{1-6}$-alkyl), —NH—(C$_{1-6}$-alkyl), —NH—(C$_{3-7}$-cycloalkyl), —NH—[(C$_{1-3}$-alkyl)-(C$_{3-7}$-cycloalkyl)] and NH—(C$_{1-3}$-alkyl)-phenyl,
  wherein each alkyl and cycloalkyl is optionally substituted with one or more substituents selected from F and CF$_3$; and
  wherein the hydrogen atom in each NH group is optionally replaced with C$_{1-6}$-alkyl;
or, if two R$^1$-groups are attached to adjacent carbon atoms of the phenyl moiety of the tetrahydroisoquinolinyl group, they may be linked with each other and together form a C$_{3-5}$-alkylene bridging group in which 1 or 2 —CH$_2$-groups may independently of each other be replaced by —O—, —C(=O)—, —S—, —S(=O)—, —S(=O)$_2$—, —NH— or —N(C$_{1-4}$-alkyl)-;
n is 0, 1, 2 or 3;
R$^2$ is selected from a group consisting of: H, C$_{1-6}$-alkyl, C$_{3-7}$-cycloalkyl, NH$_2$, —NH—(C$_{1-6}$-alkyl), —N(C$_{1-6}$-alkyl)$_2$, —O—(C$_{1-6}$-alkyl), heterocyclyl, 5-membered heteroaryl containing 1 or 2 heteroatoms selected from O, S, N and NH, 6-membered heteroaryl containing one or two nitrogen atoms, and —(C$_{1-3}$-alkyl)-(6-membered heteroaryl containing one or two nitrogen atoms);
  wherein each alkyl group is optionally substituted with one or more substituents selected from F, CN, CONH$_2$, CONH(C$_{1-3}$-alkyl), CON(C$_{1-3}$-alkyl)$_2$, NH$_2$ and OH,
  wherein each cycloalkyl group is optionally substituted with one or more substituents selected from F, CN, OH, NH$_2$, NH(CO)OC$_{1-6}$-alkyl, C$_{1-3}$-alkyl and CF$_3$,
  wherein each heteroaryl group is optionally substituted with one or more substituents selected from F, Cl, C$_{1-3}$-alkyl, NH$_2$ and —NH—C(O)—(C$_{1-3}$-alkyl), and
  wherein the heterocyclyl group is selected from a group consisting of 2-oxo-pyrrolidinyl, 2-oxo-dihydrofuranyl and morpholinyl;
R$^3$ is H or C$_{1-4}$-alkyl;
R$^4$ is H or C$_{1-4}$-alkyl;
R$^5$ is H or C$_{1-3}$-alkyl;
R$^6$ is F, OH or —O—(C$_{1-4}$-alkyl),
or, if m is 2, both R$^6$ groups together with the carbon atom, to which they are attached, may form a carbonyl group; and $R^7$ is H, $C_{1-4}$-alkyl, —COOH or —COO($C_{1-4}$-alkyl), and
m is 0, 1 or 2;
wherein each of the above-mentioned alkyl and —O-alkyl
groups may be substituted by one or more F;
or a pharmaceutically acceptable salt thereof.

2. A compound according to claim 1, wherein
$R^3$ is H,
$R^4$ is $CH_3$ and
$R^5$ is H,
or a pharmaceutically acceptable salt thereof.

3. A compound according to claim 1, wherein
n is 1 or 2 and
$R^1$ is independently of one another selected from a group consisting of:
F, Cl, Br, $C_{1-3}$-alkyl, —O—($C_{1-6}$-alkyl), —O—($C_{3-7}$-cycloalkyl), —O—($C_{1-3}$-alkyl)-($C_{3-7}$-cycloalkyl), —O—($C_{1-3}$-alkyl)-phenyl, —COOH, —COO($C_{1-4}$-alkyl), and —CO—NH—($C_{1-3}$-alkyl)-phenyl,
wherein each alkyl and cycloalkyl is optionally substituted with one to three F or one $CF_3$; and
wherein the hydrogen atom in each NH group is optionally replaced with $C_{1-4}$-alkyl;
or, if two $R^1$-groups are attached to adjacent carbon atoms of the phenyl moiety of the tetrahydroisoquinolinyl group, they may be linked with each other and together form a $C_{3-5}$-alkylene bridging group in which 1 or 2 —$CH_2$-groups may independently of each other be replaced by —O—,
or a pharmaceutically acceptable salt thereof.

4. A compound according to claim 1, wherein
$R^2$ is selected from a group consisting of:
$C_{1-3}$-alkyl, $C_{3-5}$-cycloalkyl, —O—($C_{1-3}$-alkyl), $NH_2$, —NH—($C_{1-3}$-alkyl), —N($C_{1-3}$-alkyl)$_2$, —($C_{1-2}$-alkyl)-pyrimidinyl, pyrimidinyl, 2-oxo-pyrrolidinyl, 2-oxo-dihydrofuranyl, morpholinyl and a heteroaryl group selected from the group consisting of oxazolyl, isoxazolyl, thiazolyl, isothiatolyl, imidazolyl and 1H-pyrazolyl;
wherein each alkyl group is optionally substituted with one to three substituents selected from F, CN, —$CONH_2$, —$CONH(CH_3)$, —$CON(CH_3)_2$, $NH_2$ and OH;
wherein each cycloalkyl group is optionally substituted with one or two substituents selected from F, CN, OH, $NH_2$, —NH(CO)—O($C_{1-4}$-alkyl), $C_{1-3}$-alkyl and $CF_3$;
wherein each heteroaryl group is optionally substituted with one or more substituents selected from Cl, $CH_3$, $NH_2$ and —NH—C(O)—($C_{1-2}$-alkyl),
or a pharmaceutically acceptable salt thereof.

5. A compound according to claim 1, wherein
$R^2$ is $CH_3$, $CH_2CH_3$, $CH_2CN$, $CH_2OH$, cyclopropyl, cyclobutyl or

or a pharmaceutically acceptable salt thereof.

6. A compound according to claim 1, wherein
m is 0 or 1, and $R^6$ is F, OH, or $OCH_3$; or
m is 2 and $R^6$ is F; or
m is 2 and both $R^6$ together with the carbon atom, to which they are attached, form a carbonyl group, and
$R^7$ is H, $CH_3$, COOH or $COOCH_3$,
or a pharmaceutically acceptable salt thereof.

7. A compound according to claim 1 having the formula

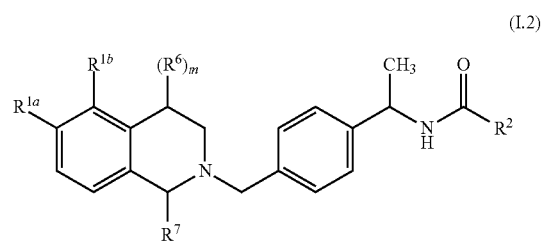

(I.2)

wherein
$R^{1a}$ is selected from the group consisting of Cl, $CF_3$, —O—($C_{3-4}$-alkyl), —O-cyclo-butyl, —O—($C_{1-2}$-alkyl)-($C_{3-4}$-cycloalkyl), —O—$CH_2$-phenyl, —$COOCH_3$, and —CO—NH—$CH_2$-phenyl,
wherein each alkyl and cycloalkyl is optionally substituted with one to three F or one $CF_3$;
$R^{1b}$ is H, F, Cl, Br or —$OCH_3$;
$R^2$ is selected from the group consisting of:
$C_{1-2}$-alkyl, $C_{3-4}$-cycloalkyl, —O—$CH_3$, —NH—($C_{1-2}$-alkyl), —N($C_{1-2}$-alkyl)$_2$, —$CH_2$-pyrimidinyl, pyrimidinyl, 2-oxo-pyrrolidinyl, 2-oxo-dihydrofuranyl, morpholinyl and a heteroaryl group selected from the group consisting of oxazolyl, isoxazolyl, thiazolyl, isothiatolyl, imidazolyl and 1H-pyrazolyl;
wherein each alkyl group is optionally substituted with one to three substituents selected from F, CN, —$CONH_2$, —$CONH(CH_3)$, —$CON(CH_3)_2$, $NH_2$ and OH;
wherein each cycloalkyl group is optionally substituted with one or two substituents selected from F, CN, OH, $NH_2$, —NH(CO)—O—C($CH_3$)$_3$, $CH_3$ and $CF_3$;
wherein each heteroaryl group is optionally substituted with one or more substituents selected from Cl, $CH_3$, $NH_2$ and —NH—C(O)—($C_{1-2}$-alkyl);
$R^6$ is selected from the group consisting of: F, OH, and —O—$CH_3$,
or, if m is 2, both $R^6$ groups together with the carbon atom, to which they are attached, may form a carbonyl group;
$R^7$ is selected from the group consisting of: H, $CH_3$, —COOH and —$COOCH_3$; and
m is 0, 1 or 2;
or a pharmaceutically acceptable salt thereof.

8. A compound according to claim 1 having one of the formula

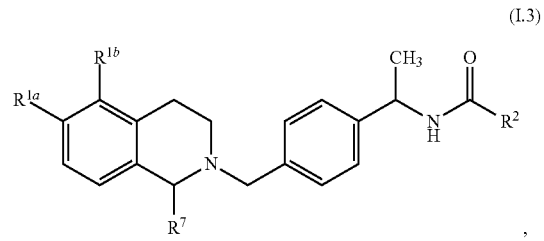

(I.3)

205

-continued

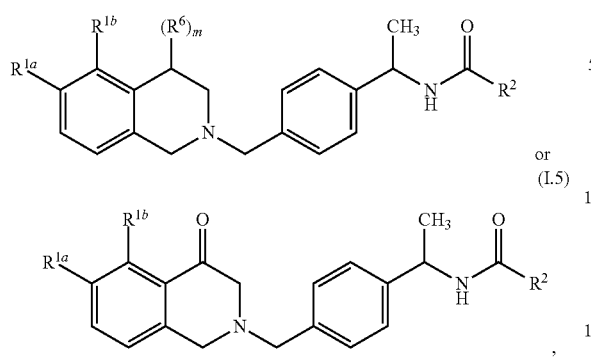

wherein
$R^{1a}$ is Cl, $CF_3$, —O—($C_{3-4}$-alkyl), —O-cyclobutyl, —O—($C_{1-2}$-alkyl)-($C_{3-4}$-cycloalkyl) or —O—$CH_2$-phenyl, wherein each alkyl and cycloalkyl is optionally substituted with one to three F or one $CF_3$;
$R^{1b}$ is H, Cl, Br or —$OCH_3$;
$R^2$ is selected from the group consisting of:

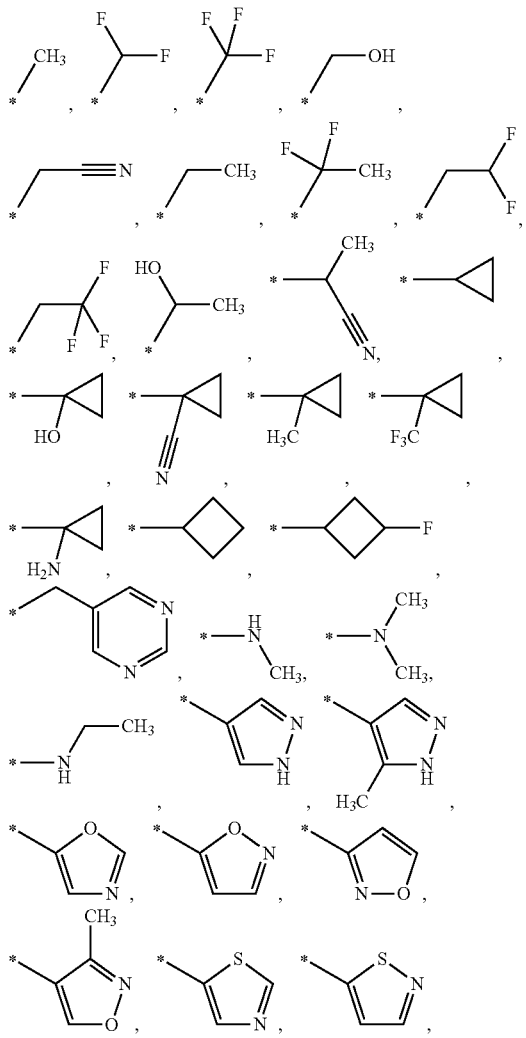

206

-continued

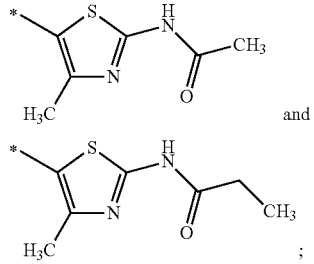

and
$R^6$ is H, F, —OH, or —$OCH_3$;
m is 0 or 1 or, if $R^6$ is F, m may also be 2;
$R^7$ is H or —$CH_3$;
or a pharmaceutically acceptable salt thereof.

9. A compound according to claim 1 selected from the group consisting of:

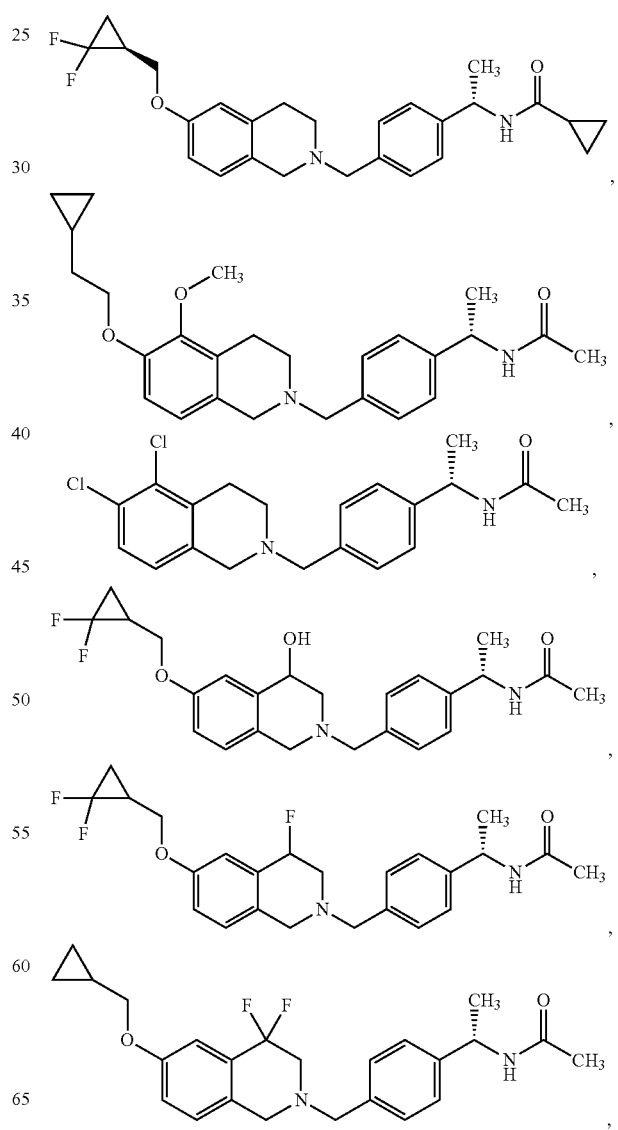

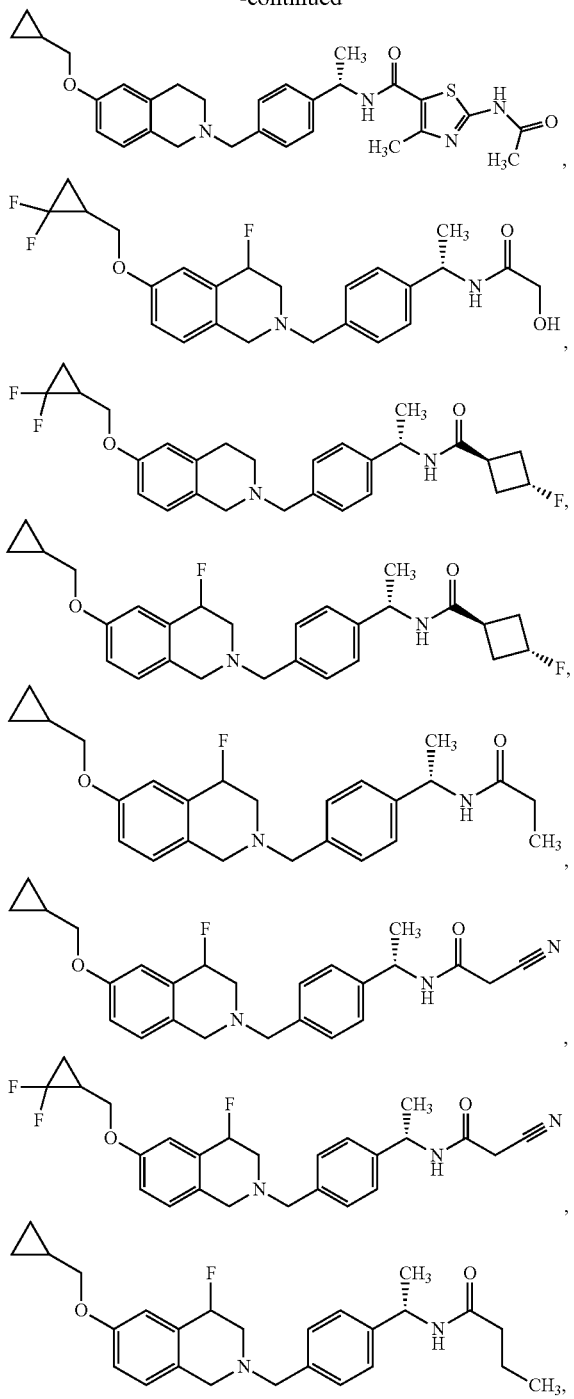

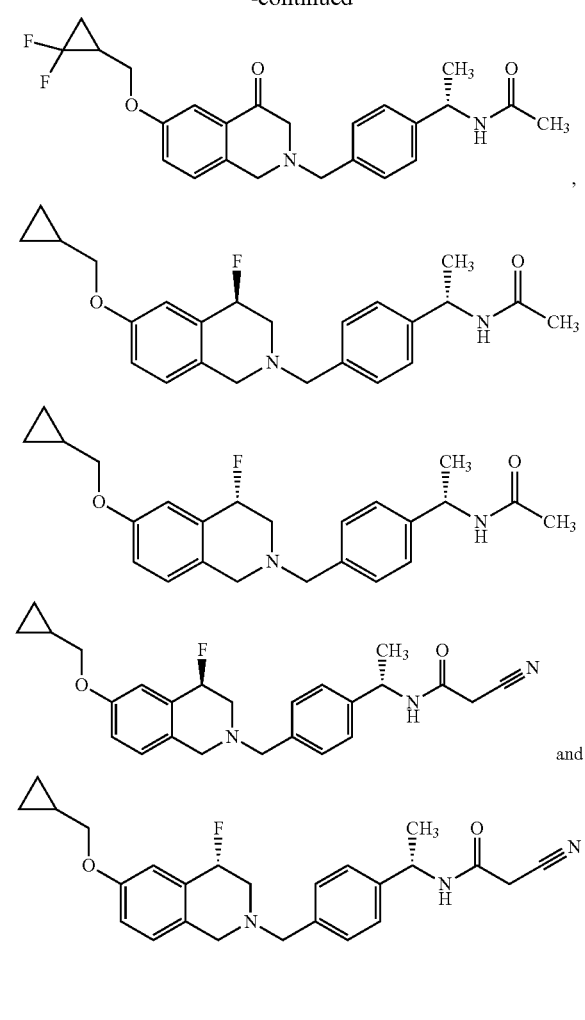

or a pharmaceutically acceptable salt thereof.

10. A method of treating obesity or type 2 diabetes which comprises administering to a host suffering from obesity or type 2 diabetes a therapeutically effective amount of a compound according to claim 1.

11. A pharmaceutical composition comprising a compound according to claim 1 and a pharmaceutically acceptable carrier or diluent.

* * * * *